US011001633B2

(12) United States Patent
Tesar et al.

(10) Patent No.: US 11,001,633 B2
(45) Date of Patent: May 11, 2021

(54) NK CELL ENGAGING ANTIBODY FUSION CONSTRUCTS

(71) Applicant: Affimed GmbH, Heidelberg (DE)

(72) Inventors: Michael Tesar, Heidelberg (DE); Kristina Ellwanger, Heidelberg (DE); Ivica Fucek, Heidelberg (DE); Uwe Reusch, Heidelberg (DE); Thorsten Ross, Heidelberg (DE); Joachim Koch, Heidelberg (DE); Erich Rajkovic, Heidelberg (DE); Martin Treder, Heidelberg (DE)

(73) Assignee: Affimed GmbH, Heidelberg (DE)

( * ) Notice: Subject to any disclaimer, the term of this patent is extended or adjusted under 35 U.S.C. 154(b) by 0 days.

(21) Appl. No.: 16/714,396

(22) Filed: Dec. 13, 2019

(65) Prior Publication Data

US 2020/0109202 A1 Apr. 9, 2020

Related U.S. Application Data

(63) Continuation of application No. PCT/IB2019/053040, filed on Apr. 12, 2019.

(30) Foreign Application Priority Data

Apr. 13, 2018 (EP) .................................... 18167384
Apr. 13, 2018 (EP) .................................... 18167385
Aug. 24, 2018 (EP) .................................... 18190661
Aug. 24, 2018 (EP) .................................... 18190662

(51) Int. Cl.
*C07K 16/00* (2006.01)
*C12P 21/08* (2006.01)
*A61K 39/395* (2006.01)
*A61K 39/40* (2006.01)
*C07K 16/28* (2006.01)
*A61P 35/00* (2006.01)
*C07K 1/00* (2006.01)
*A61K 39/00* (2006.01)

(52) U.S. Cl.
CPC ............ *C07K 16/283* (2013.01); *A61P 35/00* (2018.01); *C07K 16/2878* (2013.01); *A61K 2039/505* (2013.01); *C07K 2317/31* (2013.01); *C07K 2317/33* (2013.01); *C07K 2317/35* (2013.01); *C07K 2317/526* (2013.01); *C07K 2317/53* (2013.01); *C07K 2317/55* (2013.01); *C07K 2317/565* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 6,737,056 B1 * | 5/2004 | Presta ................ C07K 16/4291 424/133.1 |
| 2009/0214574 A1 * | 8/2009 | Hoffmann ................ A61P 37/00 424/173.1 |
| 2010/0111967 A1 * | 5/2010 | Baehner .................... A61P 1/00 424/158.1 |
| 2013/0156770 A1 * | 6/2013 | Kufer ...................... A61P 37/06 424/136.1 |
| 2016/0009824 A1 * | 1/2016 | Lo ...................... C07K 16/2893 424/136.1 |

FOREIGN PATENT DOCUMENTS

| EP | 2 361 936 A1 | 8/2011 |
| EP | 3 091 031 A1 | 11/2016 |
| EP | 3 156 417 A1 | 4/2017 |
| WO | WO 2014/144357 A1 | 9/2014 |
| WO | WO 2015/109131 A2 | 7/2015 |
| WO | WO 2016/177846 A1 | 11/2016 |
| WO | WO 2016/207278 A1 | 12/2016 |
| WO | WO 2018/158349 A1 | 9/2018 |
| WO | WO-2018158349 A1 * | 9/2018 ......... C07K 16/2878 |

OTHER PUBLICATIONS

Lu et al. Journal of Immunological Methods, 2002, 267:213-223. (Year: 2002).*
Gantke et al. Abstract 5671: AFM26—A novel CD16A-directed bispecific TandAb targeting BCMA for multiple myeloma, presented at AACR meeting Apr. 1-5, 2017. (Year: 2017).*
Ellwanger et al., "Redirected optimized cell killing (ROCK®): A highly versatile multispecific fit-for-purpose antibody platform for engaging innate immunity," MABS 11(5):899-918 (2019).
Evaluate: "Affimed Provides Update on NK-Cell Immuno-Oncology Platform," Internet Citation, Jan. 11, 2017 (Jan. 11, 2017), XP002772984, Retrieved from the Internet: 5 pages URL:http://www.evaluategroup.com/Universal/View.aspx?type=Story&id=684070.
Gantke et al., "AFM26—Targeting B Cell Maturation Antigen (BCMA) for NK cell-Mediated Immunotherapy of Multiple Myeloma," Blood 130:3082 (2017) 2 pages.
Gantke et al., "Trispecific Antibodies for Selective CD16A-Directed NK-Cell Engagement in Multiple Myeloma," Internet Citation, Dec. 5, 2016 (Dec. 5, 2016), XP002772986, 1 page, Retrieved from the Internet: URL:https://ash.confex.com/ash/2016/webprogram/Paper96043.html.

(Continued)

*Primary Examiner* — Chun W Dahle
(74) *Attorney, Agent, or Firm* — Baker Botts L.L.P.

(57) ABSTRACT

The invention relates to multispecific antigen-binding proteins for engaging natural killer (NK) cells for triggering NK cell cytotoxicity by engaging the CD16A (FcγRIIIA) expressed on NK cells, wherein the antigen-binding protein comprises at least two CD16A antigen-binding moieties and at least a further target antigen-binding moiety. The CD16A antigen-binding moiety comprises light chain and heavy chain variable regions linked one after another in a polypeptide chain and the variable region at the N-terminus of the polypeptide chain comprising the CD16A antigen-binding moiety is a light chain variable region.

14 Claims, 81 Drawing Sheets

Specification includes a Sequence Listing.

(56) References Cited

OTHER PUBLICATIONS

International Search Report dated Oct. 18, 2019 in International Application No. PCT/IB2019/053040.

Reusch et al., "A novel tetravalent bispecific TandAb (CD30/CD16A) efficiently recruits NK cells for the lysis of CD30 + tumor cells," MABS 6(3):727-738 (2014).

Rothe et al., "A phase 1 study of the bispecific anti-CD30/CD16A antibody construct AFM13 in patients with relapsed or refractory Hodgkin lymphoma," Blood 125(26):4024-4031 (2015).

Schoonjans et al., "Fab Chains as an Efficient Heterodimerization Scaffold for the Production of Recombinant Bispecific and Trispecific Antibody Derivatives," The Journal of Immunology 165:7050-7057 (2000).

Spiess et al., "Alternative molecular formats and therapeutic applications for bispecific antibodies," Molecular Immunology 67:95-106 (2015).

* cited by examiner

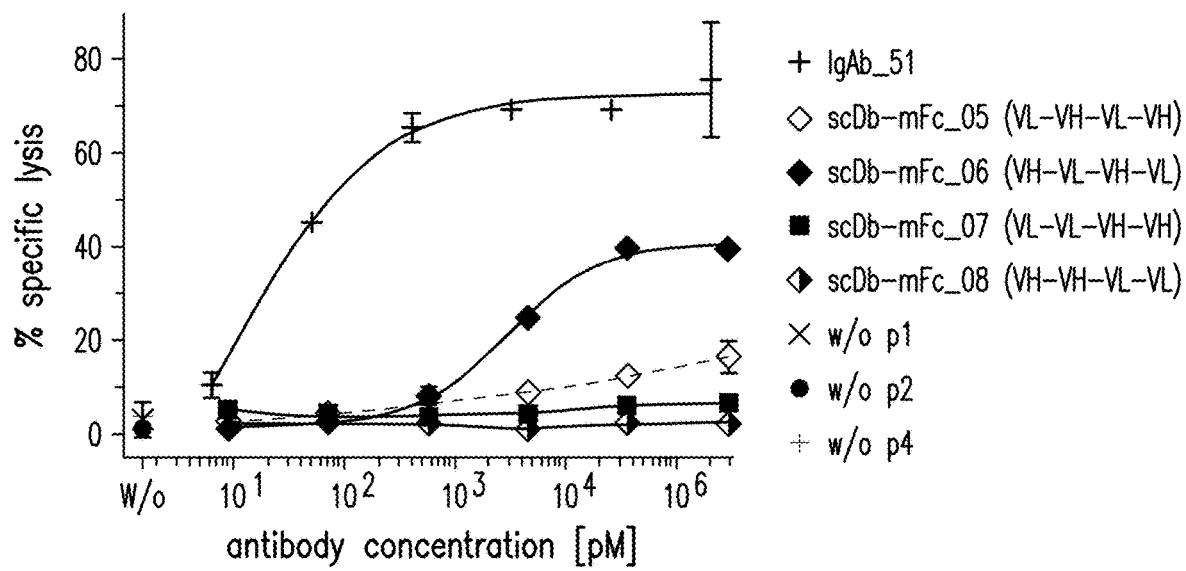
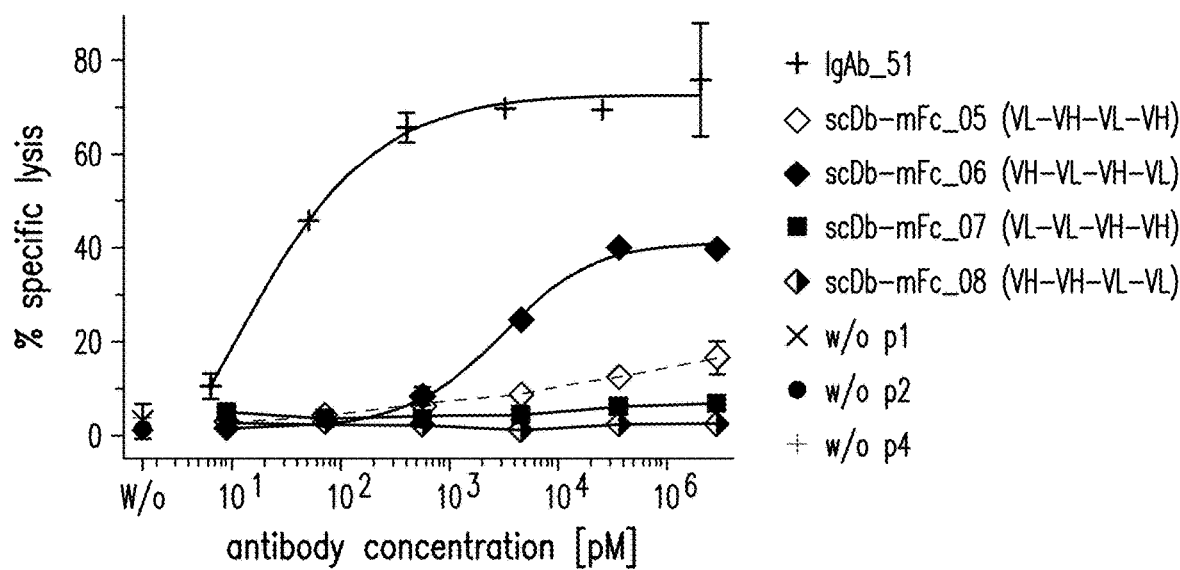
FIG. 17B

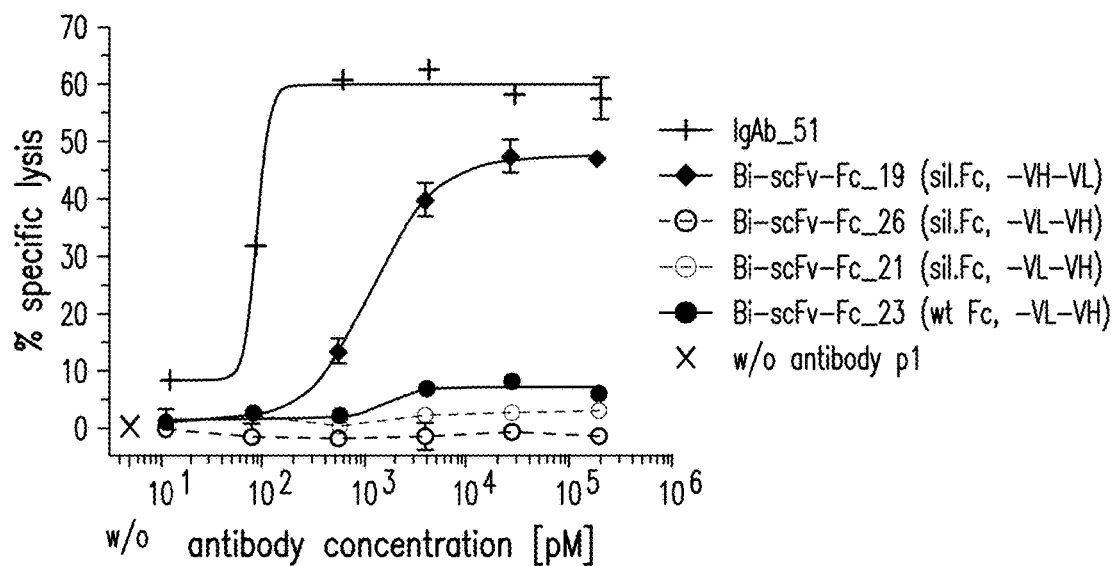
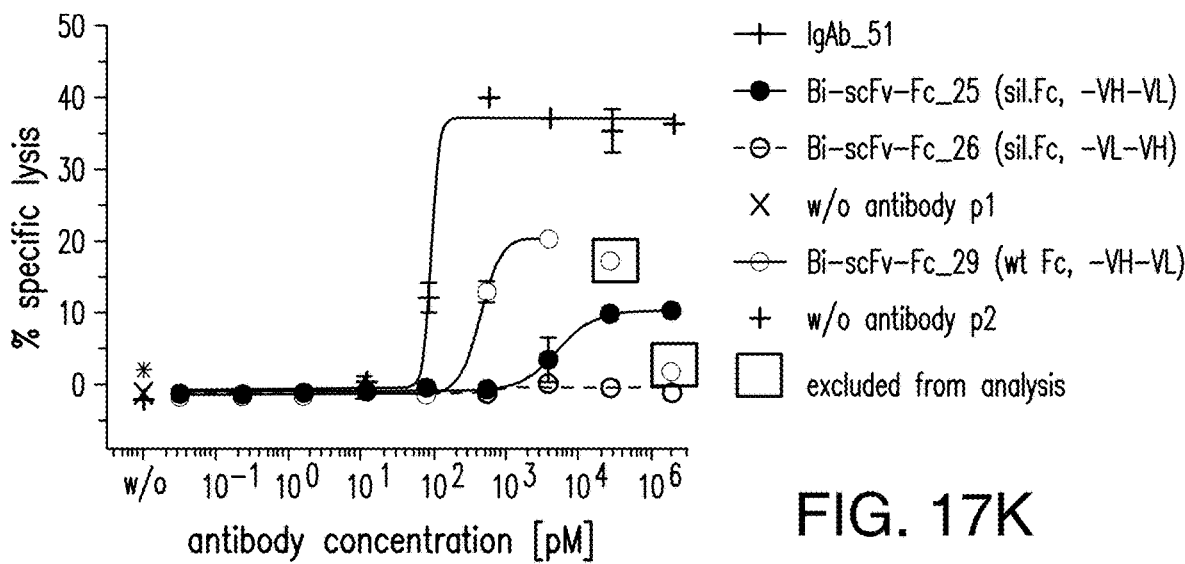
FIG. 17K
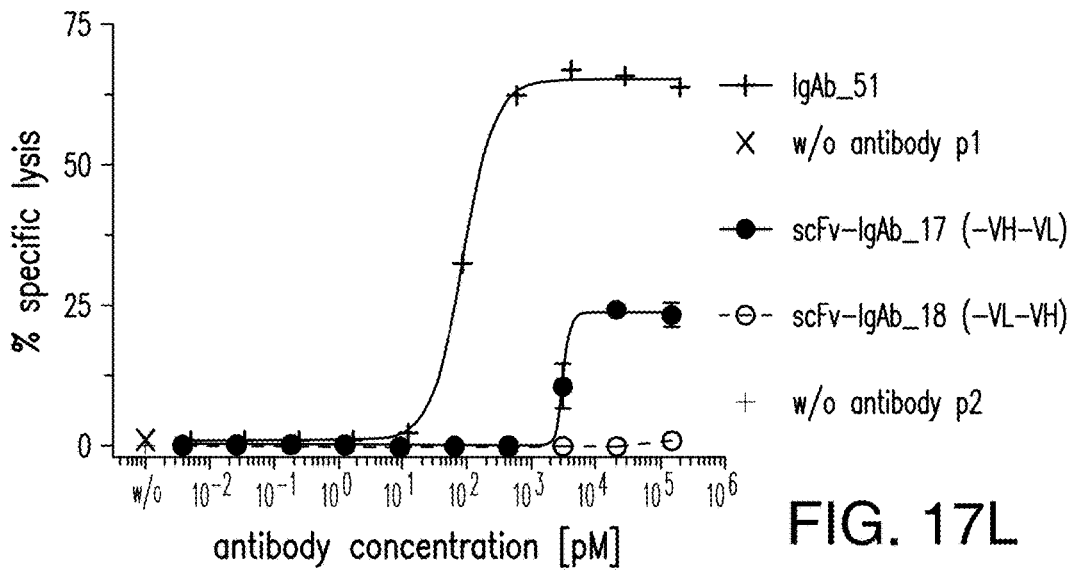
FIG. 17L

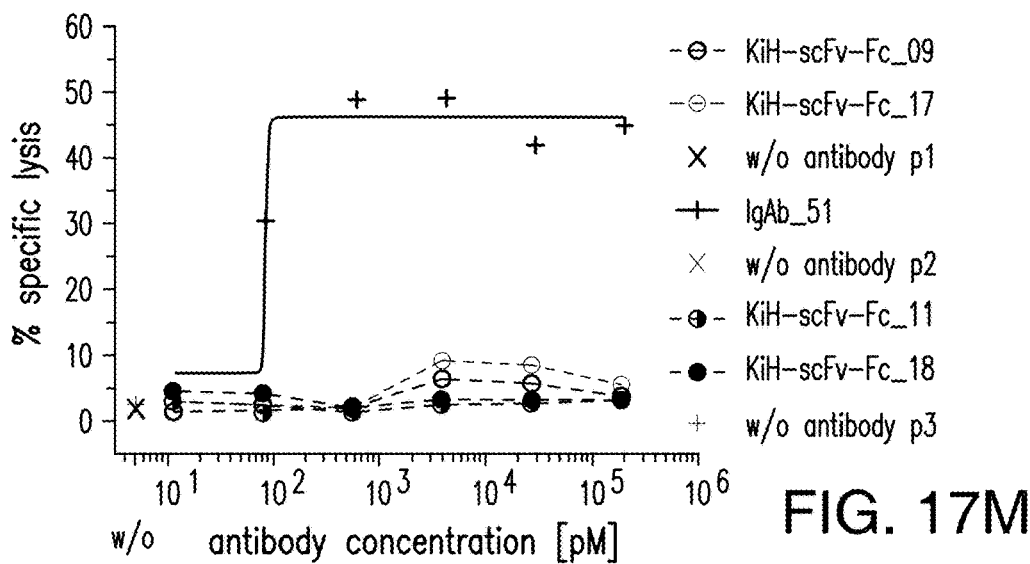
FIG. 17M
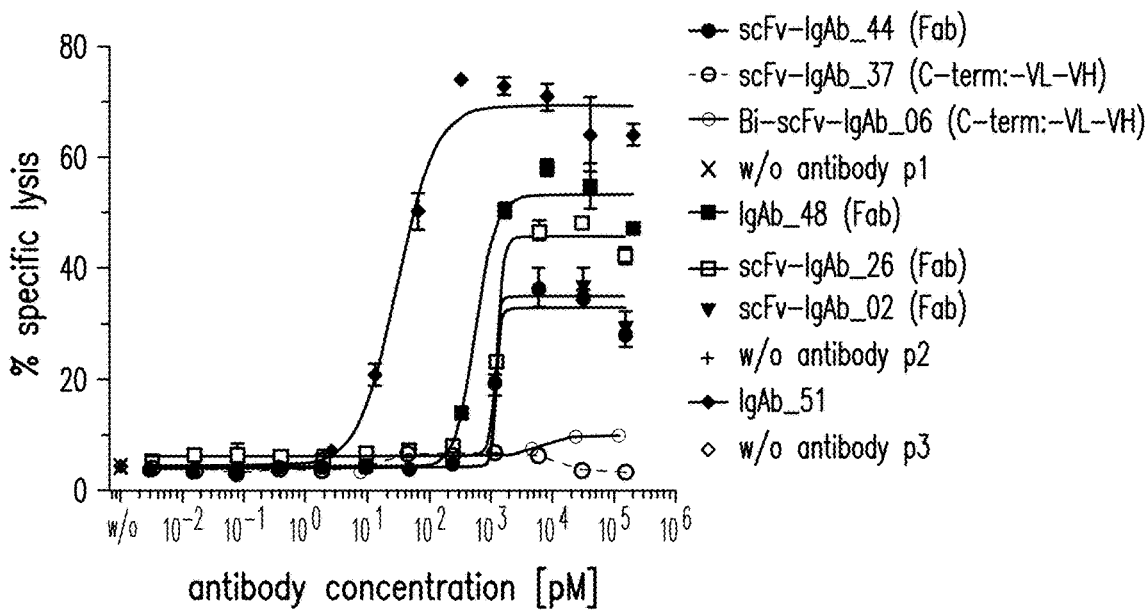
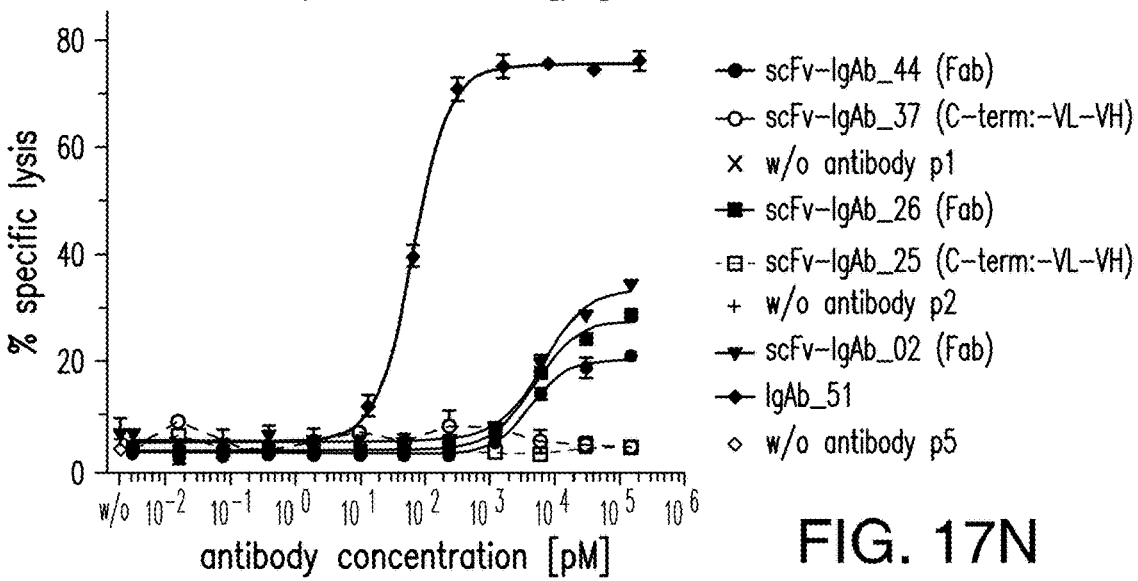
FIG. 17N

FIG. 19A

```
                                   ↓                        ↓↓                    58
Human CD16A(158V)    GMRTEDLPKAVVFLEPQWYRVLEKDSVTLKCQGAYSPEDNSTQWFHNESRISSQASSYFI 58
Human CD16A(158F)    GMRTEDLPKAVVFLEPQWYRVLEKDSVTLKCQGAYSPEDNSTQWFHNESRISSQASSYFI 58
Cynomolgus CD16      GMRAEDLPKAVVFLEPQWYRVLEKDRVTLKCQGAYSPEDNSTRWFHNESLISSQTSSYFI 58
Human CD16B(NA1)pr   GMRTEDLPKAVVFLEPQWYRVLEKDSVTLKCQGAYSPEDNSTQWFHNENLISSQASSYFI 58
Human CD16B(NA2)pr   GMRTEDLPKAVVFLEPQWYSVLEKDSVTLKCQGAYSPEDNSTQWFHNESLISSQASSYFI 58
Human CD16B(SH)pr    GMRTEDLPKAVVFLEPQWYSVLEKDSVTLKCQGAYSPEDNSTQWFHNESLISSQASSYFI 58
                     ***:************ ***** ******************:*****.****:*****

↓ ↓                 ↓                                       118
Human CD16A(158V)    DAATVDDSGEYRCQTNLSTLSDPVQLEVHIGWLLLQAPRWVFKEEDPIHLRCHSWKNTAL 118
Human CD16A(158F)    DAATVDDSGEYRCQTNLSTLSDPVQLEVHIGWLLLQAPRWVFKEEDPIHLRCHSWKNTAL 118
Cynomolgus CD16      AAARVNNSGEYRCQTSLSTLSDPVQLEVHIGWLLLQAPRWVFKEEESIHLRCHSWKNTLL 118
Human CD16B(NA1)pr   DAATVDDSGEYRCQTNLSTLSDPVQLEVHVGWLLLQAPRWVFKEEDPIHLRCHSWKNTAL 118
Human CD16B(NA2)pr   DAATVNDSGEYRCQTNLSTLSDPVQLEVHVGWLLLQAPRWVFKEEDPIHLRCHSWKNTAL 118
Human CD16B(SH)pr    DDATVNDSGEYRCQTNLSTLSDPVQLEVHVGWLLLQAPRWVFKEEDPIHLRCHSWKNTAL 118
                     * *::**********.*************:*************:********** *

↓                  178
Human CD16A(158V)    HKVTYLQNGKGRKYFHHNSDFIPKATLKDSGSYFCRGLVGSKNVSSETVNITITQGLAV 178
Human CD16A(158F)    HKVTYLQNGKGRKYFHHNSDFIPKATLKDSGSYFCRGLFGSKNVSSETVNITITQGLAV 178
Cynomolgus CD16      HKVTYLQNGKGRKYFHQNSDFIPKATLKDSGSYFCRGLIGSKNVSSETVNITITQDLAV 178
Human CD16B(NA1)pr   HKVTYLQNGKDRKYFHHNSDFIPKATLKDSGSYFCRGLVGSKNVSSETVNITITQGLAV 178
Human CD16B(NA2)pr   HKVTYLQNGKDRKYFHHNSDFIPKATLKDSGSYFCRGLVGSKNVSSETVNITITQGLAV 178
Human CD16B(SH)pr    HKVTYLQNGKDRKYFHHNSDFIPKATLKDSGSYFCRGLVGSKNVSSETVNITITQGLAV 178
                     ********.:.********.************.* dddddd    188
Human CD16A(158V)    STISSFFPPG  188   SEQ ID NO: 131
Human CD16A(158F)    STISSFFPPG  188   SEQ ID NO: 132
Cynomolgus CD16      SSISSFFPPG  188   SEQ ID NO: 133
Human CD16B(NA1)pr   STISSFSPPG  188   SEQ ID NO: 134
Human CD16B(NA2)pr   STISSFSPPG  188   SEQ ID NO: 135
Human CD16B(SH)pr    STISSFSPPG  188   SEQ ID NO: 136
                     *:**** ***
```

Human PBMC

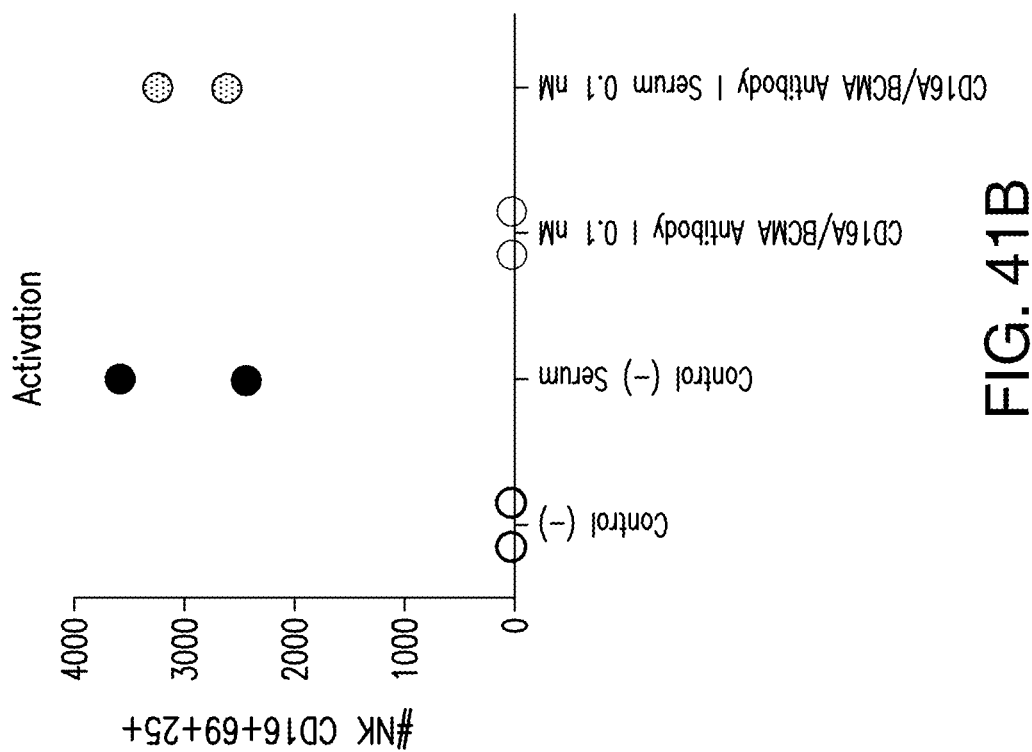
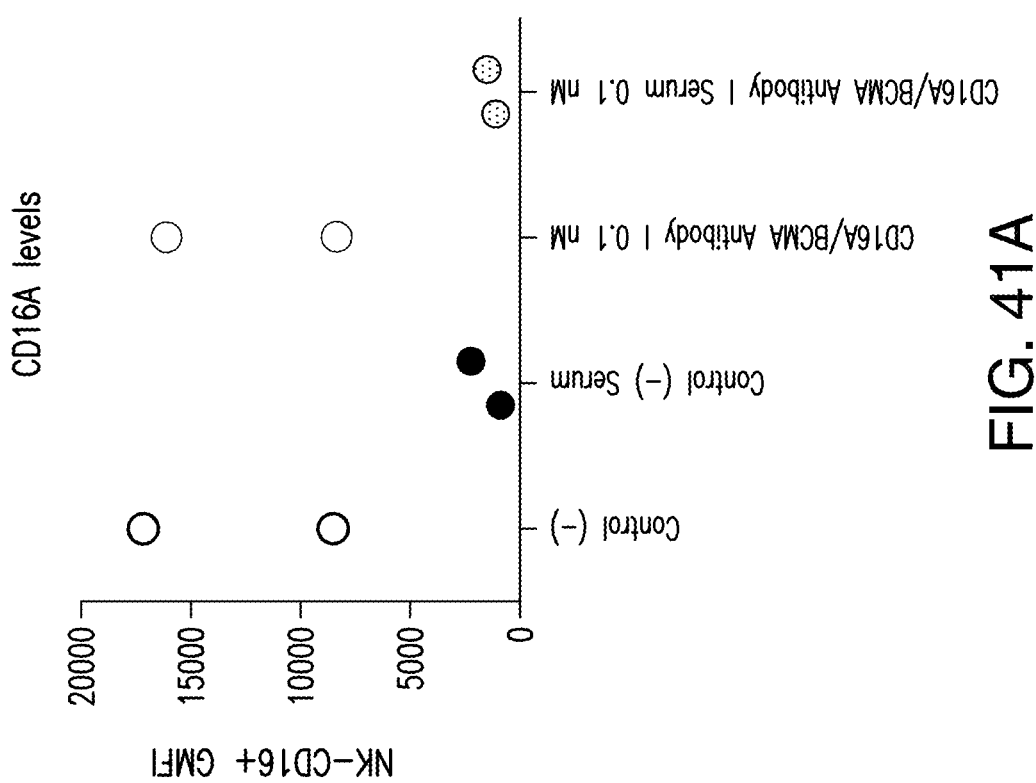
FIG. 41A
FIG. 41B

CDR sequences according to Kabat definition are underlined

Light chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 |
|---|---|
| CD16A/BCMA Antibody I BCMA-binding moiety | A I Q M T Q S P S S L S A S V G D R V T I T C R A S E D I Y N G L A W Y Q Q K P G K |

| Kabat number | 43 44 45 46 47 48 49 50 51 52 53 54 55 56 57 58 59 60 61 62 63 64 65 66 67 68 69 70 71 72 73 74 75 76 77 78 79 80 81 82 83 84 |
|---|---|
| CD16A/BCMA Antibody I BCMA-binding moiety | A P K L L I Y G A S S L Q D G V P S R F S G S G S G T E F T L T I S S L Q P E D E A |

| Kabat number | 85 86 87 88 89 90 91 92 93 94 95 96 97 98 99 100 101 102 103 104 105 106 107 |
|---|---|
| CD16A/BCMA Antibody I BCMA-binding moiety | T Y Y C A G P H K Y P L T F G G G T K V E I K |

Heavy chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 |
|---|---|
| CD16A/BCMA Antibody I BCMA-binding moiety | E V Q L L E S G G G L V Q P G G S L R L S C A A S G F T F S N Y D M A W V R Q A P G |

FIG. 53A

Light Chain Variable Region of the BCMA-targeting moiety of CD16A/BCMA Antibody I AIQMTQSPSSLSASVGDRVTITCRASEDIYNGLAWYQQKPGKAPKLLIYGASSLQDGVPSRFSGSGSGTEFTLT
ISSLQPEDEATYYCAGPHKYPLTFGGGTKVEIK     (SEQ ID NO: 66)

Heavy Chain Variable Region of the BCMA-targeting moiety of CD16A/BCMA Antibody I EVQLLESGGGLVQPGGSLRLSCAASGFTFSNYDMAWVRQAPGKGLEWVSSISTRGDITSYRDSVKGRFTISR
DNSKNTLYLQMNSLRAEDTAVYYCARQDYYTDYMGFAYWGQGTLVTVSS (SEQ ID NO: 65)

FIG. 53B

CDR sequences according to Kabat definition are underlined

Light chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 43 |
|---|---|
| CD16A/BCMA Antibody I CD16A antigen-binding moiety | S Y V L T Q P S S V S V A P G Q T A T I S C G G H N I G S K N V H W Y Q Q R P G Q S |

| Kabat number | 44 45 46 47 48 49 50 51 52 53 54 55 56 57 58 59 60 61 62 63 64 65 66 67 68 69 70 71 72 73 74 75 76 77 78 79 80 81 82 83 84 85 |
|---|---|
| CD16A/BCMA Antibody I CD16A antigen-binding moiety | P V L V I Y Q D N K R P S G I P E R F S G S N S G N T A T L T I S G T Q A M D E A D |

| Kabat number | 86 87 88 89 90 91 92 93 94 95 96 97 98 99 100 101 102 103 104 105 106 107 |
|---|---|
| CD16A/BCMA Antibody I CD16A antigen-binding moiety | Y Y C Q V W D N Y S V L F G G G T K L T V L |

Heavy chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 |
|---|---|
| CD16A/BCMA Antibody I CD16A antigen-binding moiety | Q V Q L V Q S G A E V K K P G E S L K V S C K A S G Y T F T S Y Y M H W V R Q A P G |

FIG. 53C

Kabat number 43 44 45 46 47 48 49 50 51 52 52a 53 54 55 56 57 58 59 60 61 62 63 64 65 66 67 68 69 70 71 72 73 74 75 76 77 78 79 80 81 82 82a
CD16A/BCMA Antibody I
CD16A antigen-binding moiety    Q G L E W M G A I E P M Y G S T S Y A Q K F Q G R V T M T R D T S T S T V Y M E L S CDR H2-Contact: positions 47–59
CDR H2-Chothia: positions 52–56
CDR H2-Kabat: positions 50–65

Kabat number 82b 82c 83 84 85 86 87 88 89 90 91 92 93 94 95 96 97 98 99 100 100a 100b 100c 101 102 103 104 105 106 107 108 109 110 111 112 113
CD16A/BCMA Antibody I
CD16A antigen-binding moiety    S L R S E D T A V Y Y C A R G S A Y Y Y D F A D Y W G Q G T L V T V S S CDR H3-Contact: positions 93–101
CDR H3-Chothia: positions 96–100c
CDR H3-Kabat: positions 95–100c

| Antibody | CDR L1 | CDR L2 | CDR L3 | CDR H1 | CDR H2 | CDR H3 |
|---|---|---|---|---|---|---|
| CD16A/BCMA Antibody I CD16A antigen-binding moiety | GGHNIGSKNVH | QDNKRPS | QVWDNYSVL | SYYMH | AIEPMYGSTSYAQKFQG | GSAYYYDFADY |
| SEQ ID NO. | 76 | 77 | 78 | 73 | 74 | 75 |

FIG. 53C continued

Light Chain Variable Region of the CD16A antigen-binding moiety of CD16A/BCMA Antibody I SYVLTQPSSVSVSVAPGQTATISCGGHNIGSKNVHWYQQRPGQSPVLVIYQDNKRPSGIPERFSGSNSGNTATL
TISGTQAMDEADYYCQVWDNYSVLFGGGTKLTVL  (SEQ ID NO: 2)

Heavy Chain Variable Region of the CD16A antigen-binding moiety of CD16A/BCMA Antibody I QVQLVQSGAEVKKPGESLKVSCKASGYTFTSYYMHWVRQAPGQGLEWMGAIEPMYGSTSYAQKFQGRVT
MTRDTSTSTVYMELSSLRSEDTAVYYCARGSAYYYDFADYWGQGTLVTVSS  (SEQ ID NO: 3)

FIG. 53D

SEQUENCE LISTING

<160> NUMBER OF SEQ ID NOS: 136

<210> SEQ ID NO 1
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 2
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ser Tyr Val Leu Thr Gln Pro Ser Ser Val Ser Val Ala Pro Gly Gln
1               5                   10                  15

Thr Ala Thr Ile Ser Cys Gly Gly His Asn Ile Gly Ser Lys Asn Val
            20                  25                  30

His Trp Tyr Gln Gln Arg Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 3

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ala Ile Glu Pro Met Tyr Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Asn Tyr
            20                  25                  30

Tyr Met Gln Trp Val Arg Gln Ala Pro Gly Gln Gly Leu Glu Trp Met
        35                  40                  45

Gly Val Ile Asn Pro Gly Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 5
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ser Tyr Val Leu Thr Gln Pro Ser Ser Val Ser Val Ala Pro Gly Gln
1               5                   10                  15

```
Thr Ala Arg Ile Thr Cys Gly Gly His Asn Ile Gly Ser Gln Ser Val
             20                  25                  30

His Trp Tyr Gln Gln Lys Pro Gly Gln Ala Pro Val Leu Val Ile Tyr
             35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Val
                 85                  90                  95

Phe Gly Gly Gly Thr Lys Leu Thr Val Leu
            100                 105

<210> SEQ ID NO 6
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Val Gln Ser Gly Ala Glu Val Lys Lys Pro Gly Glu
1               5                  10                  15

Ser Leu Lys Val Ser Cys Lys Ala Ser Gly Tyr Ser Phe Ser Asp Phe
             20                  25                  30

Tyr Ile Gln Trp Val Arg Gln Ala Pro Gly Gln Gly Leu Glu Trp Met
             35                  40                  45

Gly Ile Ile Asn Pro Gly Gly Ala Ser Thr Thr Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 7
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ser Tyr Val Leu Thr Gln Pro Ser Ser Val Ser Val Ala Pro Gly Gln
1               5                  10                  15

Thr Ala Arg Ile Thr Cys Gly Gly Tyr Asn Ile Gly Arg Gln Ser Val
             20                  25                  30

His Trp Tyr Gln Gln Lys Pro Gly Gln Ala Pro Val Leu Val Ile Tyr
             35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
```

```
                65                  70                  75                  80
Asp Glu Ala Asp Tyr Tyr Cys Gln Val Trp Asp Asn Tyr Thr Val Val
                            85                  90                  95

Phe Gly Gly Gly Thr Lys Leu Thr Val Leu
                100                 105

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Ser Ser Tyr
                20                  25                  30

Tyr Met His Trp Val Arg Gln Ala Pro Gly Gln Gly Leu Glu Trp Met
            35                  40                  45

Gly Ala Ile Glu Pro Arg Gly Val Arg Ile Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Asp Phe Ala Asp Tyr Trp Gly Gln
                100                 105                 110

Gly Thr Leu Val Thr Val Ser Ser
            115                 120

<210> SEQ ID NO 9
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ser Tyr Val Leu Thr Gln Pro Ser Ser Val Ser Val Ala Pro Gly Gln
1               5                   10                  15

Thr Ala Arg Ile Thr Cys Gly Gly His Asn Ile Gly Ser Thr Asn Val
                20                  25                  30

His Trp Tyr Gln Gln Lys Pro Gly Gln Ala Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Gln
                85                  90                  95

Phe Gly Gly Gly Thr Lys Leu Thr Val Leu
                100                 105

<210> SEQ ID NO 10
```

```
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10
```

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Asn Tyr
            20                  25                  30

Tyr Met Gln Trp Val Arg Gln Ala Pro Gly Gln Gly Leu Glu Trp Met
        35                  40                  45

Gly Ile Ile Asn Pro Ser Gly Gly Val Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Asp Phe Ala Asp Tyr Trp Gly Gln
            100                 105                 110

Gly Thr Leu Val Thr Val Ser Ser
        115                 120

```
<210> SEQ ID NO 11
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

Ser Tyr Val Leu Thr Gln Pro Ser Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Tyr Ile Val Leu
                85                  90                  95

Phe Gly Gly Gly Thr Lys Leu Thr Val Leu
            100                 105

```
<210> SEQ ID NO 12
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Val Ile Glu Pro Asp Gly Gly Arg Arg Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
            115                 120

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Gly His Gln Gly Val Ser Gly Asp
            20                  25                  30

Val His Trp Tyr Gln Gln Lys Pro Gly Gln Ala Pro Arg Leu Leu Ile
        35                  40                  45

Tyr Gln Ala Asn Lys Arg Ala Ser Gly Ile Pro Ala Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Trp Asp Asn Tyr Ser Val
                85                  90                  95

Thr Phe Gly Gln Gly Thr Lys Val Glu Ile Lys
            100                 105

<210> SEQ ID NO 14
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys

```
                50                   55                  60
Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Thr Val Pro Gly Tyr Ser Thr Ala Pro Tyr Phe Asp Leu Trp Gly
                100                 105                 110

Gln Gly Thr Leu Val Thr Val Ser Ser
            115                 120

<210> SEQ ID NO 15
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Ser Val Ser Ala Ser Val Gly
  1               5                  10                  15

Asp Arg Val Thr Ile Thr Cys Gln Ser Ser Pro Ser Val Trp Ser Asn
                 20                  25                  30

Phe Leu Ser Trp Tyr Gln Gln Lys Pro Gly Lys Ala Pro Lys Leu Leu
             35                  40                  45

Ile Tyr Glu Ala Ser Lys Leu Thr Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gly Gly Tyr Ser Ser Ile
                 85                  90                  95

Ser Asp Thr Thr Phe Gly Gly Gly Thr Lys Val Glu Ile Lys
                100                 105                 110

<210> SEQ ID NO 16
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Gly Ser Gly Gly Ser
 1               5

<210> SEQ ID NO 17
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Gly Ser Gly Gly Ser Gly Gly Ser Gly Gly Ser Gly Gly Ser Gly
 1               5                  10                  15

Gly Ser
```

<210> SEQ ID NO 18
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Gly Gly Gly Gly Ser
1               5

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

Gly Gly Gly Gly Ser Gly Gly Gly Gly Ser
1               5                   10

<210> SEQ ID NO 21
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

Gly Gly Gly Gly Ser Gly Gly Gly Gly Ser Gly Gly Gly Gly Ser Gly
1               5                   10                  15

Gly Gly Gly Ser
            20

<210> SEQ ID NO 22
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

Gly Gly Gly Gly Ser Gly Gly Gly Gly Ser Gly Gly Gly Gly Ser Gly

```
                1               5                   10                  15
Gly Gly Gly Ser Gly Gly Gly Ser Gly Gly Gly Ser
                20                  25                  30

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Glu Pro Lys Ser Cys Asp Lys Thr His Thr Cys Pro Pro Cys Pro
1               5                   10                  15

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Lys Thr His Thr Cys Pro Pro Cys Pro
1               5                   10

<210> SEQ ID NO 25
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 26
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 27
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 28
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
                35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 29
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ala Pro Glu Phe Glu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Ala Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 30
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30
```

Ala Pro Glu Phe Glu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ala Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Lys Pro Pro Ser Arg Asp Glu Leu
        115                 120                 125

Thr Lys Asn Gln Val Ser Leu Ser Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175

Ala Ser Tyr Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro
    210                 215

<210> SEQ ID NO 31
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ala Pro Glu Phe Glu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ala Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Tyr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
                195                 200                 205

Lys Ser Leu Ser Leu Ser Pro Gly
    210                 215

<210> SEQ ID NO 32
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ala Pro Glu Phe Glu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ala Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Thr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 33
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 34
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Ser Ser
            100                 105

<210> SEQ ID NO 35
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 36
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 37
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Val Gln Leu Val Gln Ser Gly Ala Glu Val Lys Thr Pro Gly Glu

```
                1               5                  10                 15
Pro Leu Lys Ile Ser Cys Lys Gly Ser Gly Tyr Ser Phe Thr Asp Ser
                20                 25                 30

Trp Ile Gly Trp Val Arg Gln Met Pro Gly Lys Gly Leu Glu Trp Met
                35                 40                 45

Gly Ile Ile Tyr Ala Gly Asp Ser Asp Ala Arg Tyr Ser Pro Ser Phe
        50                 55                 60

Gln Gly Gln Val Thr Ile Ser Ala Asp Thr Ser Thr Ser Thr Val Tyr
65                  70                 75                     80

Leu Gln Trp Ser Ser Leu Lys Ala Ser Asp Thr Ala Met Tyr Tyr Cys
                85                 90                 95

Ala Arg Asn Phe Gly Asp His Trp Gly Gln Gly Thr Leu Val Thr Val
                100                105                110

Ser Ser

<210> SEQ ID NO 38
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ser Tyr Glu Leu Thr Gln Ser Pro Ser Val Ser Val Ala Pro Gly Gln
1               5                  10                 15

Thr Ala Arg Ile Phe Cys Gly Gly Asp Asn Ile Gly Ser Lys Asn Val
                20                 25                 30

His Trp Tyr Gln Gln Lys Pro Gly Gln Ala Pro Val Leu Val Ile Tyr
                35                 40                 45

Arg Asp Ser Asn Arg Pro Ser Gly Ile Pro Glu Arg Phe Ser Gly Ala
        50                 55                 60

Asn Ser Glu Asn Thr Ala Thr Leu Thr Ile Ser Arg Ala Gln Ala Gly
65                  70                 75                     80

Asp Glu Ala Asp Tyr Tyr Cys Gln Val Trp Asp Ser Arg Thr Tyr Val
                85                 90                 95

Phe Gly Thr Gly Thr Lys Leu Thr Val Leu
                100                105

<210> SEQ ID NO 39
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Val Gln Ser Gly Ala Glu Val Lys Thr Pro Gly Glu
1               5                  10                 15

Pro Leu Lys Ile Ser Cys Lys Gly Ser Gly Tyr Ser Phe Thr Asp Ser
                20                 25                 30

Trp Ile Gly Trp Val Arg Gln Met Pro Gly Lys Gly Leu Glu Trp Met
                35                 40                 45

Gly Ile Ile Tyr Ala Gly Asp Ser Asp Ala Arg Tyr Ser Pro Ser Phe
        50                 55                 60
```

Gln Gly Gln Val Thr Ile Ser Ala Asp Thr Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Asn Phe Gly Asp His Trp Gly Gln Gly Thr Leu Val Thr Val
            100                 105                 110

Ser Ser Gly Gly Ser Gly Gly Ser Gly Gly Ser Gly Gly Ser Gly Gly
        115                 120                 125

Ser Gly Gly Ser Ser Tyr Glu Leu Thr Gln Ser Pro Ser Val Ser Val
130                 135                 140

Ala Pro Gly Gln Thr Ala Arg Ile Phe Cys Gly Gly Asp Asn Ile Gly
145                 150                 155                 160

Ser Lys Asn Val His Trp Tyr Gln Gln Lys Pro Gly Gln Ala Pro Val
                165                 170                 175

Leu Val Ile Tyr Arg Asp Ser Asn Arg Pro Ser Gly Ile Pro Glu Arg
            180                 185                 190

Phe Ser Gly Ala Asn Ser Glu Asn Thr Ala Thr Leu Thr Ile Ser Arg
        195                 200                 205

Ala Gln Ala Gly Asp Glu Ala Asp Tyr Tyr Cys Gln Val Trp Asp Ser
210                 215                 220

Arg Thr Tyr Val Phe Gly Thr Gly Thr Lys Leu Thr Val Leu Ala Ala
225                 230                 235                 240

Ala Gly Ser His His His His His His
            245

<210> SEQ ID NO 40
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asn Pro Ile Ser Ile Pro Ala Phe Asp Ile Trp Gly Gln
            100                 105                 110

Gly Thr Met Val Thr Val Ser Ser
        115                 120

<210> SEQ ID NO 41
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Pro Val Leu Thr Gln Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Val Leu Phe Gly Gly Gly Thr Lys Leu Thr Val Leu
            100                 105

<210> SEQ ID NO 42
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Ser Val Ser Ser Gly Ser Tyr Tyr
1               5                   10

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Tyr Tyr Ser Gly Ser Thr
1               5

<210> SEQ ID NO 44
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ala Arg Asn Pro Ile Ser Ile Pro Ala Phe Asp Ile
1               5                   10

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:

```
            Synthetic peptide"

<400> SEQUENCE: 45

Asn Ile Gly Ser Lys Ser
1               5

<210> SEQ ID NO 46
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Asp Ser
1

<210> SEQ ID NO 47
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gln Val Trp Asp Thr Ser Ser Asp His Val Leu
1               5                   10

<210> SEQ ID NO 48
<211> LENGTH: 192
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Phe
145                 150                 155                 160
```

```
Gly Ser Lys Asn Val Ser Ser Glu Thr Val Asn Ile Thr Ile Thr Gln
                165                 170                 175

Gly Leu Ala Val Ser Thr Ile Ser Phe Phe Pro Pro Gly Tyr Gln
        180                 185                 190
```

<210> SEQ ID NO 49
<211> LENGTH: 192
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Gly Met Arg Ala Glu Asp Leu Pro Lys Ala Val Val Phe Leu Glu Pro
1               5                   10                  15

Gln Trp Tyr Arg Val Leu Glu Lys Asp Arg Val Thr Leu Lys Cys Gln
            20                  25                  30

Gly Ala Tyr Ser Pro Glu Asp Asn Ser Thr Arg Trp Phe His Asn Glu
        35                  40                  45

Ser Leu Ile Ser Ser Gln Thr Ser Ser Tyr Phe Ile Ala Ala Ala Arg
50                  55                  60

Val Asn Asn Ser Gly Glu Tyr Arg Cys Gln Thr Ser Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Glu Ser Ile His Leu Arg Cys
            100                 105                 110

His Ser Trp Lys Asn Thr Leu Leu His Lys Val Thr Tyr Leu Gln Asn
        115                 120                 125

Gly Lys Gly Arg Lys Tyr Phe His Gln Asn Ser Asp Phe Tyr Ile Pro
    130                 135                 140

Lys Ala Thr Leu Lys Asp Ser Gly Ser Tyr Phe Cys Arg Gly Leu Ile
145                 150                 155                 160

Gly Ser Lys Asn Val Ser Ser Glu Thr Val Asn Ile Thr Ile Thr Gln
                165                 170                 175

Asp Leu Ala Val Ser Ser Ile Ser Ser Phe Phe Pro Pro Gly Tyr Gln
            180                 185                 190
```

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

```
Gly Tyr Thr Phe Thr Ser Tyr Tyr
1               5
```

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 51

Ile Glu Pro Met Tyr Gly Ser Thr
1               5

<210> SEQ ID NO 52
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Arg Gly Ser Ala Tyr Tyr Tyr Asp Phe Ala Asp Tyr
1               5                   10

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Asn Ile Gly Ser Lys Asn
1               5

<210> SEQ ID NO 54
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Asp Asn
1

<210> SEQ ID NO 55
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gln Val Trp Asp Asn Tyr Ser Val Leu
1               5

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ile Asn Pro Ser Gly Gly Ser Thr
1               5
```

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Phe Phe Pro Pro Gly Tyr Gln
1               5

<210> SEQ ID NO 58
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 58

His His His His His His
1               5

<210> SEQ ID NO 59
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Glu Pro Glu Ala
1

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Gly Ser Gly Gly Ser Gly Gly Ser
1               5

<210> SEQ ID NO 61
<211> LENGTH: 727
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

```
Asp Met Ala Trp Val Arg Gln Ala Pro Gly Lys Gly Leu Glu Trp Val
        35                  40                  45

Ser Ser Ile Ser Thr Arg Gly Asp Ile Thr Ser Tyr Arg Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Tyr Tyr Thr Asp Tyr Met Gly Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Gly Ser Gly Gly Gly Gly
```

```
                    450                 455                 460
Ser Gly Gly Gly Ser Gly Gly Gly Ser Gly Gly Gly Ser
465                 470                 475                 480

Ser Tyr Val Leu Thr Gln Pro Ser Ser Val Ser Val Ala Pro Gly Gln
                    485                 490                 495

Thr Ala Thr Ile Ser Cys Gly Gly His Asn Ile Gly Ser Lys Asn Val
                500                 505                 510

His Trp Tyr Gln Gln Arg Pro Gly Gln Ser Pro Val Leu Val Ile Tyr
            515                 520                 525

Gln Asp Asn Lys Arg Pro Ser Gly Ile Pro Glu Arg Phe Ser Gly Ser
        530                 535                 540

Asn Ser Gly Asn Thr Ala Thr Leu Thr Ile Ser Gly Thr Gln Ala Met
545                 550                 555                 560

Asp Glu Ala Asp Tyr Tyr Cys Gln Val Trp Asp Asn Tyr Ser Val Leu
                565                 570                 575

Phe Gly Gly Gly Thr Lys Leu Thr Val Leu Gly Gly Ser Gly Gly Ser
                580                 585                 590

Gly Gly Ser Gly Gly Ser Gly Gly Ser Gly Gly Ser Gln
            595                 600                 605

Val Gln Leu Val Gln Ser Gly Ala Glu Val Lys Lys Pro Gly Glu Ser
        610                 615                 620

Leu Lys Val Ser Cys Lys Ala Ser Gly Tyr Thr Phe Thr Ser Tyr Tyr
625                 630                 635                 640

Met His Trp Val Arg Gln Ala Pro Gly Gln Gly Leu Glu Trp Met Gly
                645                 650                 655

Ala Ile Glu Pro Met Tyr Gly Ser Thr Ser Tyr Ala Gln Lys Phe Gln
                660                 665                 670

Gly Arg Val Thr Met Thr Arg Asp Thr Ser Thr Ser Thr Val Tyr Met
            675                 680                 685

Glu Leu Ser Ser Leu Arg Ser Glu Asp Thr Ala Val Tyr Tyr Cys Ala
        690                 695                 700

Arg Gly Ser Ala Tyr Tyr Tyr Asp Phe Ala Asp Tyr Trp Gly Gln Gly
705                 710                 715                 720

Thr Leu Val Thr Val Ser Ser
                725

<210> SEQ ID NO 62
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Ala Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Gly
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Asp Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80
```

```
Glu Asp Glu Ala Thr Tyr Tyr Cys Ala Gly Pro His Lys Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 729
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Ala Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Thr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220
Pro Gly Gly Gly Gly Ser Gly Gly Gly Ser Ser Tyr Val Leu
225                 230                 235                 240
Thr Gln Pro Ser Ser Val Ser Val Ala Pro Gly Gln Thr Ala Thr Ile
                245                 250                 255
Ser Cys Gly Gly His Asn Ile Gly Ser Lys Asn Val His Trp Tyr Gln
            260                 265                 270
Gln Arg Pro Gly Gln Ser Pro Val Leu Val Ile Tyr Gln Asp Asn Lys
        275                 280                 285
Arg Pro Ser Gly Ile Pro Glu Arg Phe Ser Gly Ser Asn Ser Gly Asn
290                 295                 300
Thr Ala Thr Leu Thr Ile Ser Gly Thr Gln Ala Met Asp Glu Ala Asp
305                 310                 315                 320
Tyr Tyr Cys Gln Val Trp Asp Asn Tyr Ser Val Leu Phe Gly Gly Gly
                325                 330                 335
Thr Lys Leu Thr Val Leu Gly Ser Gly Gly Ser Gln Val Gln Leu
            340                 345                 350
Val Gln Ser Gly Ala Glu Val Lys Lys Pro Gly Glu Ser Leu Lys Val
        355                 360                 365
Ser Cys Lys Ala Ser Gly Tyr Thr Phe Thr Ser Tyr Tyr Met His Trp
370                 375                 380
Val Arg Gln Ala Pro Gly Gln Gly Leu Glu Trp Met Gly Ala Ile Glu
385                 390                 395                 400
Pro Met Tyr Gly Ser Thr Ser Tyr Ala Gln Lys Phe Gln Gly Arg Val
                405                 410                 415
Thr Met Thr Arg Asp Thr Ser Thr Ser Thr Val Tyr Met Glu Leu Ser
            420                 425                 430
Ser Leu Arg Ser Glu Asp Thr Ala Val Tyr Tyr Cys Ala Arg Gly Ser
        435                 440                 445
Ala Tyr Tyr Tyr Asp Phe Ala Asp Tyr Trp Gly Gln Gly Thr Leu Val
450                 455                 460
Thr Val Ser Ser Gly Gly Ser Gly Gly Ser Gly Gly Ser Gly Gly Ser
465                 470                 475                 480
Gly Gly Ser Gly Gly Ser Ser Tyr Val Leu Thr Gln Pro Ser Ser Val
                485                 490                 495
Ser Val Ala Pro Gly Gln Thr Ala Thr Ile Ser Cys Gly Gly His Asn
            500                 505                 510
Ile Gly Ser Lys Asn Val His Trp Tyr Gln Gln Arg Pro Gly Gln Ser
        515                 520                 525
Pro Val Leu Val Ile Tyr Gln Asp Asn Lys Arg Pro Ser Gly Ile Pro
530                 535                 540
Glu Arg Phe Ser Gly Ser Asn Ser Gly Asn Thr Ala Thr Leu Thr Ile
545                 550                 555                 560
Ser Gly Thr Gln Ala Met Asp Glu Ala Asp Tyr Tyr Cys Gln Val Trp
                565                 570                 575
Asp Asn Tyr Ser Val Leu Phe Gly Gly Gly Thr Lys Leu Thr Val Leu
            580                 585                 590
Gly Gly Ser Gly Gly Ser Gln Val Gln Leu Val Gln Ser Gly Ala Glu
        595                 600                 605
Val Lys Lys Pro Gly Glu Ser Leu Lys Val Ser Cys Lys Ala Ser Gly
610                 615                 620
Tyr Thr Phe Thr Ser Tyr Tyr Met His Trp Val Arg Gln Ala Pro Gly
```

```
            625                 630                 635                 640

Gln Gly Leu Glu Trp Met Gly Ala Ile Glu Pro Met Tyr Gly Ser Thr
                        645                 650                 655

Ser Tyr Ala Gln Lys Phe Gln Gly Arg Val Thr Met Thr Arg Asp Thr
                    660                 665                 670

Ser Thr Ser Thr Val Tyr Met Glu Leu Ser Ser Leu Arg Ser Glu Asp
                675                 680                 685

Thr Ala Val Tyr Tyr Cys Ala Arg Gly Ser Ala Tyr Tyr Asp Phe
        690                 695                 700

Ala Asp Tyr Trp Gly Gln Gly Thr Leu Val Thr Val Ser Ser Ala Ala
    705                 710                 715                 720

Ala Gly Ser His His His His His His
                        725

<210> SEQ ID NO 64
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Val Gln Leu Leu Glu Ser Gly Gly Gly Leu Val Gln Pro Gly Gly
    1               5                   10                  15

Ser Leu Arg Leu Ser Cys Ala Ala Ser Gly Phe Thr Phe Ser Asn Tyr
                    20                  25                  30

Asp Met Ala Trp Val Arg Gln Ala Pro Gly Lys Gly Leu Glu Trp Val
                35                  40                  45

Ser Ser Ile Ser Thr Arg Gly Asp Ile Thr Ser Tyr Arg Asp Ser Val
            50                  55                  60

Lys Gly Arg Phe Thr Ile Ser Arg Asp Asn Ser Lys Asn Thr Leu Tyr
    65                  70                  75                  80

Leu Gln Met Asn Ser Leu Arg Ala Glu Asp Thr Ala Val Tyr Tyr Cys
                    85                  90                  95

Ala Arg Gln Asp Tyr Tyr Thr Asp Tyr Met Gly Phe Ala Tyr Trp Gly
                100                 105                 110

Gln Gly Thr Leu Val Thr Val Ser Ser Gly Gly Gly Ser Gly Gly
                115                 120                 125

Gly Gly Ser Gly Gly Gly Ser Ala Ile Gln Met Thr Gln Ser Pro
    130                 135                 140

Ser Ser Leu Ser Ala Ser Val Gly Asp Arg Val Thr Ile Thr Cys Arg
    145                 150                 155                 160

Ala Ser Glu Asp Ile Tyr Asn Gly Leu Ala Trp Tyr Gln Gln Lys Pro
                    165                 170                 175

Gly Lys Ala Pro Lys Leu Leu Ile Tyr Gly Ala Ser Ser Leu Gln Asp
                180                 185                 190

Gly Val Pro Ser Arg Phe Ser Gly Ser Gly Ser Gly Thr Glu Phe Thr
                195                 200                 205

Leu Thr Ile Ser Ser Leu Gln Pro Glu Asp Ala Thr Tyr Tyr Cys
            210                 215                 220

Ala Gly Pro His Lys Tyr Pro Leu Thr Phe Gly Gly Gly Thr Lys Val
    225                 230                 235                 240

Glu Ile Lys Asp Lys Thr His Thr Cys Pro Pro Cys Pro Ala Pro Glu
                    245                 250                 255
```

```
Phe Glu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Ala
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Tyr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465

<210> SEQ ID NO 65
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ala Trp Val Arg Gln Ala Pro Gly Lys Gly Leu Glu Trp Val
        35                  40                  45

Ser Ser Ile Ser Thr Arg Gly Asp Ile Thr Ser Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Tyr Tyr Thr Asp Tyr Met Gly Phe Ala Tyr Trp Gly
            100                 105                 110

Gln Gly Thr Leu Val Thr Val Ser Ser
        115                 120
```

```
<210> SEQ ID NO 66
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ala Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Gly
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Glu Ala Thr Tyr Tyr Cys Ala Gly Pro His Lys Tyr Pro Leu
                85                  90                  95

Thr Phe Gly Gly Gly Thr Lys Val Glu Ile Lys
            100                 105

<210> SEQ ID NO 67
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Asn Tyr Asp Met Ala
1               5

<210> SEQ ID NO 68
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ser Ile Ser Thr Arg Gly Asp Ile Thr Ser Tyr Arg Asp Ser Val Lys
1               5                   10                  15

Gly

<210> SEQ ID NO 69
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gln Asp Tyr Tyr Thr Asp Tyr Met Gly Phe Ala Tyr
1               5                   10
```

```
<210> SEQ ID NO 70
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Arg Ala Ser Glu Asp Ile Tyr Asn Gly Leu Ala
1               5                   10

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Ala Ser Ser Leu Gln Asp
1               5

<210> SEQ ID NO 72
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ala Gly Pro His Lys Tyr Pro Leu Thr
1               5

<210> SEQ ID NO 73
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ser Tyr Tyr Met His
1               5

<210> SEQ ID NO 74
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ala Ile Glu Pro Met Tyr Gly Ser Thr Ser Tyr Ala Gln Lys Phe Gln
1               5                   10                  15

Gly
```

<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gly Ser Ala Tyr Tyr Tyr Asp Phe Ala Asp Tyr
1               5                   10

<210> SEQ ID NO 76
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Gly His Asn Ile Gly Ser Lys Asn Val His
1               5                   10

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gln Asp Asn Lys Arg Pro Ser
1               5

<210> SEQ ID NO 78
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gln Val Trp Asp Asn Tyr Ser Val Leu
1               5

<210> SEQ ID NO 79
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ala Pro Glu Phe Glu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Ala Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
            50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 80
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Thr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 81
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Gly Gln Pro Arg Glu Pro Gln Val Tyr Thr Leu Pro Pro Ser Arg Glu
1               5                   10                  15

Glu Met Thr Lys Asn Gln Val Ser Leu Tyr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Tyr Thr Phe Thr Asn Tyr Tyr
1               5

<210> SEQ ID NO 83
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ile Asn Pro Gly Gly Gly Ser Thr
1               5

<210> SEQ ID NO 84
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Asn Ile Gly Ser Gln Ser
1               5

<210> SEQ ID NO 85
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gln Asp Ser
1

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gln Val Trp Asp Asn Tyr Ser Val Val
1               5

<210> SEQ ID NO 87
<211> LENGTH: 8
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Gly Tyr Ser Phe Ser Asp Phe Tyr
1               5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Ile Asn Pro Gly Gly Ala Ser Thr
1               5

<210> SEQ ID NO 89
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Asn Ile Gly Arg Gln Ser
1               5

<210> SEQ ID NO 90
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gln Val Trp Asp Asn Tyr Thr Val Val
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Tyr Thr Phe Ser Ser Tyr Tyr
1               5

<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 92

Ile Glu Pro Arg Gly Val Arg Ile
1               5

<210> SEQ ID NO 93
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Asn Ile Gly Ser Thr Asn
1               5

<210> SEQ ID NO 94
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gln Val Trp Asp Asn Tyr Ser Val Gln
1               5

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ile Asn Pro Ser Gly Gly Val Thr
1               5

<210> SEQ ID NO 96
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Asn Ile Gly Ser Lys Ser
1               5

<210> SEQ ID NO 97
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

```
Gln Asp Lys
 1
```

<210> SEQ ID NO 98
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

```
Gln Val Trp Asp Asp Tyr Ile Val Leu
 1               5
```

<210> SEQ ID NO 99
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

```
Ile Glu Pro Asp Gly Gly Arg Arg
 1               5
```

<210> SEQ ID NO 100
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

```
Gln Gly Val Ser Gly Asp
 1               5
```

<210> SEQ ID NO 101
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

```
Gln Ala Asn
 1
```

<210> SEQ ID NO 102
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

```
Gln Gln Trp Asp Asn Tyr Ser Val Thr
 1               5
```

```
<210> SEQ ID NO 103
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ile Glu Pro Ser Gly Gly Ser Thr
1               5

<210> SEQ ID NO 104
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gln Val Trp Asp Ser Tyr Ser Val Leu
1               5

<210> SEQ ID NO 105
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gln Val Trp Asp Asn Tyr Asn Val Leu
1               5

<210> SEQ ID NO 106
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 107
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Gly Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 108
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Gly Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 109
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
```

<210> SEQ ID NO 110
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 111

```
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 112
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys
        100                 105                 110

<210> SEQ ID NO 113
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gly Phe Thr Phe Ser Asn Tyr Asp
1               5

<210> SEQ ID NO 114
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ile Ser Thr Arg Gly Asp Ile Thr
1               5

<210> SEQ ID NO 115
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ala Arg Gln Asp Tyr Tyr Thr Asp Tyr Met Gly Phe Ala Tyr
1               5                   10

<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Glu Asp Ile Tyr Asn Gly
1               5

<210> SEQ ID NO 117
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gly Ala Ser

```
<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Gly Phe Thr Phe Ser Asn Phe Asp
1               5

<210> SEQ ID NO 119
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ile Thr Thr Gly Gly Gly Asp Thr
1               5

<210> SEQ ID NO 120
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Val Arg His Gly Tyr Tyr Asp Gly Tyr His Leu Phe Asp Tyr Trp Gly
1               5                   10                  15

<210> SEQ ID NO 121
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gln Gly Ile Ser Asn Asn
1               5

<210> SEQ ID NO 122
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Tyr Thr Ser
1

<210> SEQ ID NO 123
```

<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 123

Gln Gln Phe Thr Ser Leu Pro Tyr Thr
1               5

<210> SEQ ID NO 124
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Asp Met Ala Trp Val Arg Gln Ala Pro Gly Lys Gly Leu Val Trp Val
        35                  40                  45

Ser Ser Ile Thr Thr Gly Gly Gly Asp Thr Tyr Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Val Tyr Tyr Cys
                85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser
        115                 120

<210> SEQ ID NO 125
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Gly Ile Ser Asn Asn
            20                  25                  30

Leu Asn Trp Tyr Gln Gln Lys Pro Gly Lys Ala Pro Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Thr Ser Leu Pro Tyr
                85                  90                  95

```
Thr Phe Gly Gln Gly Thr Lys Leu Glu Ile Lys
            100                 105
```

<210> SEQ ID NO 126
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Asp Met Ala Trp Val Arg Gln Ala Pro Gly Lys Gly Leu Glu Trp Val
            35                  40                  45

Ser Ser Ile Ser Thr Arg Gly Asp Ile Thr Ser Tyr Arg Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Tyr Tyr Thr Asp Tyr Met Gly Phe Ala Tyr Trp Gly
            100                 105                 110

Gln Gly Thr Leu Val Thr Val Ser Ser Gly Ser Gly Gly Ser Gly
        115                 120                 125

Gly Ser Gly Gly Ser Ser Tyr Val Leu Thr Gln Pro Ser Ser Val Ser
130                 135                 140

Val Ala Pro Gly Gln Thr Ala Thr Ile Ser Cys Gly Gly His Asn Ile
145                 150                 155                 160

Gly Ser Lys Asn Val His Trp Tyr Gln Gln Arg Pro Gly Gln Ser Pro
                165                 170                 175

Val Leu Val Ile Tyr Gln Asp Asn Lys Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Thr Gln Ala Met Asp Glu Ala Asp Tyr Tyr Cys Gln Val Trp Asp
    210                 215                 220

Asn Tyr Ser Val Leu Phe Gly Gly Gly Thr Lys Leu Thr Val Leu Gly
225                 230                 235                 240

Gly Ser Gln Val Gln Leu Val Gln Ser Gly Ala Glu Val Lys Lys Pro
                245                 250                 255

Gly Glu Ser Leu Lys Val Ser Cys Lys Ala Ser Gly Tyr Thr Phe Thr
            260                 265                 270

Ser Tyr Tyr Met His Trp Val Arg Gln Ala Pro Gly Gln Gly Leu Glu
        275                 280                 285

Trp Met Gly Ala Ile Glu Pro Met Tyr Gly Ser Thr Ser Tyr Ala Gln
    290                 295                 300

Lys Phe Gln Gly Arg Val Thr Met Thr Arg Asp Thr Ser Thr Ser Thr
305                 310                 315                 320

Val Tyr Met Glu Leu Ser Ser Leu Arg Ser Glu Asp Thr Ala Val Tyr
                325                 330                 335

Tyr Cys Ala Arg Gly Ser Ala Tyr Tyr Tyr Asp Phe Ala Asp Tyr Trp
```

```
                    340                 345                 350
Gly Gln Gly Thr Leu Val Thr Val Ser Ser Gly Gly Ser Gly Gly Ser
            355                 360                 365

Gly Gly Ser Gly Gly Ser Ala Ile Gln Met Thr Gln Ser Pro Ser Ser
    370                 375                 380

Leu Ser Ala Ser Val Gly Asp Arg Val Thr Ile Thr Cys Arg Ala Ser
385                 390                 395                 400

Glu Asp Ile Tyr Asn Gly Leu Ala Trp Tyr Gln Gln Lys Pro Gly Lys
                405                 410                 415

Ala Pro Lys Leu Leu Ile Tyr Gly Ala Ser Ser Leu Gln Asp Gly Val
            420                 425                 430

Pro Ser Arg Phe Ser Gly Ser Gly Ser Gly Thr Glu Phe Thr Leu Thr
        435                 440                 445

Ile Ser Ser Leu Gln Pro Glu Asp Glu Ala Thr Tyr Tyr Cys Ala Gly
    450                 455                 460

Pro His Lys Tyr Pro Leu Thr Phe Gly Gly Gly Thr Lys Val Glu Ile
465                 470                 475                 480

Lys

<210> SEQ ID NO 127
<211> LENGTH: 721
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Ser Tyr Val Leu Thr Gln Pro Ser Ser Val Ser Val Ala Pro Gly Gln
1               5                   10                  15

Thr Ala Thr Ile Ser Cys Gly Gly His Asn Ile Gly Ser Lys Asn Val
            20                  25                  30

His Trp Tyr Gln Gln Arg Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu Gly Gly Ser Gly Gly Ser
            100                 105                 110

Gln Val Gln Leu Val Gln Ser Gly Ala Glu Val Lys Lys Pro Gly Glu
        115                 120                 125

Ser Leu Lys Val Ser Cys Lys Ala Ser Gly Tyr Thr Phe Thr Ser Tyr
    130                 135                 140

Tyr Met His Trp Val Arg Gln Ala Pro Gly Gln Gly Leu Glu Trp Met
145                 150                 155                 160

Gly Ala Ile Glu Pro Met Tyr Gly Ser Thr Ser Tyr Ala Gln Lys Phe
                165                 170                 175

Gln Gly Arg Val Thr Met Thr Arg Asp Thr Ser Thr Ser Thr Val Tyr
            180                 185                 190

Met Glu Leu Ser Ser Leu Arg Ser Glu Asp Thr Ala Val Tyr Tyr Cys
        195                 200                 205
```

```
Ala Arg Gly Ser Ala Tyr Tyr Tyr Asp Phe Ala Asp Tyr Trp Gly Gln
    210                 215                 220
Gly Thr Leu Val Thr Val Ser Ser Gly Gly Gly Gly Ser Gly Gly Gly
225                 230                 235                 240
Gly Ser Asp Lys Thr His Thr Cys Pro Pro Cys Pro Ala Pro Glu Phe
            245                 250                 255
Glu Gly Gly Pro Ser Val Phe Leu Phe Pro Pro Lys Pro Lys Asp Thr
                260                 265                 270
Leu Met Ile Ser Arg Thr Pro Glu Val Thr Cys Val Val Val Ala Val
            275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Glu Glu Met Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Gly Gly Gly Ser Gly Gly Gly Gly Ser Glu Val
465                 470                 475                 480
Gln Leu Leu Glu Ser Gly Gly Gly Leu Val Gln Pro Gly Gly Ser Leu
                485                 490                 495
Arg Leu Ser Cys Ala Ala Ser Gly Phe Thr Phe Ser Asn Tyr Asp Met
            500                 505                 510
Ala Trp Val Arg Gln Ala Pro Gly Lys Gly Leu Glu Trp Val Ser Ser
        515                 520                 525
Ile Ser Thr Arg Gly Asp Ile Thr Ser Tyr Arg Asp Ser Val Lys Gly
    530                 535                 540
Arg Phe Thr Ile Ser Arg Asp Asn Ser Lys Asn Thr Leu Tyr Leu Gln
545                 550                 555                 560
Met Asn Ser Leu Arg Ala Glu Asp Thr Ala Val Tyr Tyr Cys Ala Arg
                565                 570                 575
Gln Asp Tyr Tyr Thr Asp Tyr Met Gly Phe Ala Tyr Trp Gly Gln Gly
            580                 585                 590
Thr Leu Val Thr Val Ser Gly Gly Gly Gly Ser Gly Gly Gly Gly
        595                 600                 605
Ser Gly Gly Gly Gly Ser Ala Ile Gln Met Thr Gln Ser Pro Ser Ser
    610                 615                 620
Leu Ser Ala Ser Val Gly Asp Arg Val Thr Ile Thr Cys Arg Ala Ser
```

```
            625                 630                 635                 640
Glu Asp Ile Tyr Asn Gly Leu Ala Trp Tyr Gln Gln Lys Pro Gly Lys
                    645                 650                 655

Ala Pro Lys Leu Leu Ile Tyr Gly Ala Ser Ser Leu Gln Asp Gly Val
                660                 665                 670

Pro Ser Arg Phe Ser Gly Ser Gly Ser Gly Thr Glu Phe Thr Leu Thr
            675                 680                 685

Ile Ser Ser Leu Gln Pro Glu Asp Glu Ala Thr Tyr Tyr Cys Ala Gly
        690                 695                 700

Pro His Lys Tyr Pro Leu Thr Phe Gly Gly Gly Thr Lys Val Glu Ile
705                 710                 715                 720

Lys

<210> SEQ ID NO 128
<211> LENGTH: 960
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ala Trp Val Arg Gln Ala Pro Gly Lys Gly Leu Glu Trp Val
        35                  40                  45

Ser Ser Ile Ser Thr Arg Gly Asp Ile Thr Ser Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Tyr Tyr Thr Tyr Met Gly Phe Ala Tyr Trp Gly
            100                 105                 110

Gln Gly Thr Leu Val Thr Val Ser Gly Gly Gly Gly Ser Gly Gly
        115                 120                 125

Gly Gly Ser Gly Gly Gly Ser Ala Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Glu Asp Ile Tyr Asn Gly Leu Ala Trp Tyr Gln Gln Lys Pro
                165                 170                 175

Gly Lys Ala Pro Lys Leu Leu Ile Tyr Gly Ala Ser Ser Leu Gln Asp
            180                 185                 190

Gly Val Pro Ser Arg Phe Ser Gly Ser Gly Ser Gly Thr Glu Phe Thr
        195                 200                 205

Leu Thr Ile Ser Ser Leu Gln Pro Glu Asp Glu Ala Thr Tyr Tyr Cys
    210                 215                 220

Ala Gly Pro His Lys Tyr Pro Leu Thr Phe Gly Gly Gly Thr Lys Val
225                 230                 235                 240

Glu Ile Lys Gly Gly Gly Gly Ser Gly Gly Gly Gly Ser Ala Pro Glu
                245                 250                 255
```

-continued

```
Phe Glu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Ala
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Lys Pro Pro Ser Arg Asp Glu Leu Thr Lys Asn
    370                 375                 380

Gln Val Ser Leu Ser Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Val Pro Val Leu Asp Ser Asp Gly Ser Phe Arg Leu Ala Ser Tyr
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Gly Gly Ser Gly Gly Gly Ser Ser Tyr
465                 470                 475                 480

Val Leu Thr Gln Pro Ser Ser Val Ser Val Ala Pro Gly Gln Thr Ala
                485                 490                 495

Thr Ile Ser Cys Gly Gly His Asn Ile Gly Ser Lys Asn Val His Trp
            500                 505                 510

Tyr Gln Gln Arg Pro Gly Gln Ser Pro Val Leu Val Ile Tyr Gln Asp
        515                 520                 525

Asn Lys Arg Pro Ser Gly Ile Pro Glu Arg Phe Ser Gly Ser Asn Ser
    530                 535                 540

Gly Asn Thr Ala Thr Leu Thr Ile Ser Gly Thr Gln Ala Met Asp Glu
545                 550                 555                 560

Ala Asp Tyr Tyr Cys Gln Val Trp Asp Asn Tyr Ser Val Leu Phe Gly
                565                 570                 575

Gly Gly Thr Lys Leu Thr Val Leu Gly Gly Ser Gly Gly Ser Gln Val
            580                 585                 590

Gln Leu Val Gln Ser Gly Ala Glu Val Lys Lys Pro Gly Glu Ser Leu
        595                 600                 605

Lys Val Ser Cys Lys Ala Ser Gly Tyr Thr Phe Thr Ser Tyr Tyr Met
    610                 615                 620

His Trp Val Arg Gln Ala Pro Gly Gln Gly Leu Glu Trp Met Gly Ala
625                 630                 635                 640

Ile Glu Pro Met Tyr Gly Ser Thr Ser Tyr Ala Gln Lys Phe Gln Gly
                645                 650                 655

Arg Val Thr Met Thr Arg Asp Thr Ser Thr Ser Thr Val Tyr Met Glu
            660                 665                 670

Leu Ser Ser Leu Arg Ser Glu Asp Thr Ala Val Tyr Tyr Cys Ala Arg
```

```
            675                 680                 685
Gly Ser Ala Tyr Tyr Asp Phe Ala Asp Tyr Trp Gly Gln Gly Thr
    690                 695                 700
Leu Val Thr Val Ser Ser Gly Ser Gly Gly Ser Gly Gly Ser Gly
705                 710                 715                 720
Gly Ser Gly Gly Ser Gly Ser Ser Tyr Val Leu Thr Gln Pro Ser
                725                 730                 735
Ser Val Ser Val Ala Pro Gly Gln Thr Ala Thr Ile Ser Cys Gly
            740                 745                 750
His Asn Ile Gly Ser Lys Asn Val His Trp Tyr Gln Gln Arg Pro
        755                 760                 765
Gln Ser Pro Val Leu Val Ile Tyr Gln Asp Asn Lys Arg Pro Ser
770                 775                 780
Ile Pro Glu Arg Phe Ser Gly Ser Asn Ser Gly Asn Thr Ala Thr Leu
785                 790                 795                 800
Thr Ile Ser Gly Thr Gln Ala Met Asp Glu Ala Asp Tyr Tyr Cys Gln
                805                 810                 815
Val Trp Asp Asn Tyr Ser Val Leu Phe Gly Gly Gly Thr Lys Leu Thr
            820                 825                 830
Val Leu Gly Gly Ser Gly Gly Ser Gln Val Gln Leu Val Gln Ser Gly
        835                 840                 845
Ala Glu Val Lys Lys Pro Gly Glu Ser Leu Lys Val Ser Cys Lys Ala
850                 855                 860
Ser Gly Tyr Thr Phe Thr Ser Tyr Tyr Met His Trp Val Arg Gln Ala
865                 870                 875                 880
Pro Gly Gln Gly Leu Glu Trp Met Gly Ala Ile Glu Pro Met Tyr Gly
                885                 890                 895
Ser Thr Ser Tyr Ala Gln Lys Phe Gln Gly Arg Val Thr Met Thr Arg
            900                 905                 910
Asp Thr Ser Thr Ser Thr Val Tyr Met Glu Leu Ser Ser Leu Arg Ser
        915                 920                 925
Glu Asp Thr Ala Val Tyr Tyr Cys Ala Arg Gly Ser Ala Tyr Tyr Tyr
930                 935                 940
Asp Phe Ala Asp Tyr Trp Gly Gln Gly Thr Leu Val Thr Val Ser Ser
945                 950                 955                 960

<210> SEQ ID NO 129
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Gly Ser Gly Gly Ser Gly Gly Ser Gly Gly Ser
1               5                   10

<210> SEQ ID NO 130
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130
```

Gly Gly Ser
1

<210> SEQ ID NO 131
<211> LENGTH: 190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Arg Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly
            180                 185                 190

<210> SEQ ID NO 132
<211> LENGTH: 190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Arg Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Gln
            85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
            115                 120                 125

Gly Lys Gly Arg Lys Tyr Phe His His Asn Ser Asp Phe Tyr Ile Pro
            130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
            165                 170                 175

Gly Leu Ala Val Ser Thr Ile Ser Ser Phe Phe Pro Pro Gly
            180                 185                 190

<210> SEQ ID NO 133
<211> LENGTH: 190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Gly Met Arg Ala Glu Asp Leu Pro Lys Ala Val Phe Leu Glu Pro
1               5                   10                  15

Gln Trp Tyr Arg Val Leu Glu Lys Asp Arg Val Thr Leu Lys Cys Gln
            20                  25                  30

Gly Ala Tyr Ser Pro Glu Asp Asn Ser Thr Arg Trp Phe His Asn Glu
            35                  40                  45

Ser Leu Ile Ser Ser Gln Thr Ser Ser Tyr Phe Ile Ala Ala Ala Arg
        50                  55                  60

Val Asn Asn Ser Gly Glu Tyr Arg Cys Gln Thr Ser Leu Ser Thr Leu
65                  70                  75                  80

Ser Asp Pro Val Gln Leu Glu Val His Ile Gly Trp Leu Leu Gln
            85                  90                  95

Ala Pro Arg Trp Val Phe Lys Glu Glu Glu Ser Ile His Leu Arg Cys
            100                 105                 110

His Ser Trp Lys Asn Thr Leu Leu His Lys Val Thr Tyr Leu Gln Asn
            115                 120                 125

Gly Lys Gly Arg Lys Tyr Phe His Gln Asn Ser Asp Phe Tyr Ile Pro
            130                 135                 140

Lys Ala Thr Leu Lys Asp Ser Gly Ser Tyr Phe Cys Arg Gly Leu Ile
145                 150                 155                 160

Gly Ser Lys Asn Val Ser Ser Glu Thr Val Asn Ile Thr Ile Thr Gln
            165                 170                 175

Asp Leu Ala Val Ser Ser Ile Ser Ser Phe Phe Pro Pro Gly
            180                 185                 190

<210> SEQ ID NO 134
<211> LENGTH: 190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 134

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Asn Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Val Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Asp Arg Lys Tyr Phe His His Asn Ser Asp Phe His Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Ser Pro Pro Gly
            180                 185                 190

<210> SEQ ID NO 135
<211> LENGTH: 190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Gly Met Arg Thr Glu Asp Leu Pro Lys Ala Val Val Phe Leu Glu Pro
1               5                   10                  15

Gln Trp Tyr Ser Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asn Asp Ser Gly Glu Tyr Arg Cys Gln Thr Asn Leu Ser Thr Leu
65                  70                  75                  80

Ser Asp Pro Val Gln Leu Glu Val His Val Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Asp Arg Lys Tyr Phe His His Asn Ser Asp Phe His Ile Pro
    130                 135                 140

Lys Ala Thr Leu Lys Asp Ser Gly Ser Tyr Phe Cys Arg Gly Leu Val
145                 150                 155                 160
```

-continued

```
Gly Ser Lys Asn Val Ser Ser Glu Thr Val Asn Ile Thr Ile Thr Gln
                165                 170                 175
Gly Leu Ala Val Ser Thr Ile Ser Ser Phe Ser Pro Pro Gly
            180                 185                 190

<210> SEQ ID NO 136
<211> LENGTH: 190
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Gly Met Arg Thr Glu Asp Leu Pro Lys Ala Val Val Phe Leu Glu Pro
1               5                   10                  15
Gln Trp Tyr Ser Val Leu Glu Lys Asp Ser Val Thr Leu Lys Cys Gln
            20                  25                  30
Gly Ala Tyr Ser Pro Glu Asp Asn Ser Thr Gln Trp Phe His Asn Glu
        35                  40                  45
Ser Leu Ile Ser Ser Gln Ala Ser Ser Tyr Phe Ile Asp Asp Ala Thr
    50                  55                  60
Val Asn Asp Ser Gly Glu Tyr Arg Cys Gln Thr Asn Leu Ser Thr Leu
65                  70                  75                  80
Ser Asp Pro Val Gln Leu Glu Val His Val Gly Trp Leu Leu Leu Gln
                85                  90                  95
Ala Pro Arg Trp Val Phe Lys Glu Glu Asp Pro Ile His Leu Arg Cys
            100                 105                 110
His Ser Trp Lys Asn Thr Ala Leu His Lys Val Thr Tyr Leu Gln Asn
        115                 120                 125
Gly Lys Asp Arg Lys Tyr Phe His His Asn Ser Asp Phe His Ile Pro
    130                 135                 140
Lys Ala Thr Leu Lys Asp Ser Gly Ser Tyr Phe Cys Arg Gly Leu Val
145                 150                 155                 160
Gly Ser Lys Asn Val Ser Ser Glu Thr Val Asn Ile Thr Ile Thr Gln
                165                 170                 175
Gly Leu Ala Val Ser Thr Ile Ser Ser Phe Ser Pro Pro Gly
            180                 185                 190
```

NK CELL ENGAGING ANTIBODY FUSION CONSTRUCTS

CROSS-REFERENCE TO RELATED APPLICATIONS

This application is a continuation application of International Application No. PCT/IB2019/053040, filed Apr. 12, 2019, which claims priority to European Provisional Patent Application No. EP18167384.9, filed Apr. 13, 2018, European Provisional Patent Application No. EP18167385.6, filed Apr. 13, 2018, European Provisional Patent Application No. EP18190661.1, filed Aug. 24, 2018, European Provisional Patent Application No. EP18190662.9, filed Aug. 24, 2018, the contents of each of which are incorporated by reference in their entirety.

SEQUENCE LISTING

The instant application contains a Sequence Listing which has been submitted electronically in ASCII format and is hereby incorporated by reference in its entirety. Said ASCII copy, created on Dec. 13, 2019, is named 087353_0106_SL.txt and is 137,682 bytes in size.

FIELD OF THE INVENTION

The invention relates to multispecific antigen-binding proteins for engaging natural killer (NK) cells for triggering NK cell cytotoxicity by engaging the CD16A (FcγRIIIA) expressed on NK cells, wherein the antigen-binding protein comprises at least two CD16A antigen-binding moieties and at least a further target antigen-binding moiety.

BACKGROUND

WO 2006/125668 and Reusch et al., MABS, 2014, 6:3: 728-739 describe a bispecific tandem diabody for engaging the CD16A and its use for NK cell immunotherapy.

Natural Killer (NK) cells are cytotoxic, IFN-γ-producing innate lymphocytes that are considered to constitute the first line of defense against virus-infected cells and cancer cells (Cerwenka and Lanier, *Nat Rev Immunol.* 2001; 1(1):41-9). The cytotoxic potential of NK cells can be utilized in cancer immunotherapy by redirecting NK cell lysis to tumor cells and stimulating the activating receptor CD16A, also known as FcγRIIIA, expressed on the cell surface of NK cells.

Directing NK cells for tumor cell lysis using multispecific antibodies is considered a potent immunotherapeutic approach with low toxicity and well acceptable safety profile.

CD16A is an activating receptor triggering the cytotoxic activity of NK cells. The affinity of antibodies for CD16A directly correlates with their ability to trigger NK cell activation, thus reducing the antibody dose required for activation.

The cytotoxic activity of NK cells can be increased by increasing the avidity through multivalent binding to CD16A, e.g., bivalent binding to CD16A.

However, bivalency and multivalency for CD16A may result in antibody-mediated cross-linking of CD16A-expressing cells, including NK cells, γδ T cells and subsets of monocytes, macrophages and dendritic cells. Such interactions are expected to result in undesired cellular stimulation via CD16A. For example, cross-linking of NK cells with CD16A-expressing immune cells results in NK cell activation, cytokine release and induction of cell-directed cytotoxicity, which reduces NK cell activity and accelerates NK cell exhaustion that is independent of the desired anti-tumor effect. Hence, NK cell cross-linking with CD16A-expressing immune cells is expected to reduce therapeutic efficacy of NK cell-engagement. Most importantly, cross-linking of two or more NK cells through bivalent or multivalent interaction with CD16A can cause NK cell activation and induction of fratricide (NK-NK cell lysis) ultimately resulting in efficient NK cell depletion in vivo, as previously described using a CD16-directed murine IgG antibody (3G8) that is bivalent for CD16A in rhesus macaques and tamarins (Choi et al., Immunology 2008; 124:215-222; Yoshida et al., Frontier in Microbiology (2010); 1:128). Hence, induction of NK lysis reduces the number of effector cells available to mediate ADCC and impairs therapeutic antibody efficacy.

Thus, there is need for antibodies capable for enhanced NK cell engagement which is not diminished by fratricide (NK-NK cell lysis).

SUMMARY OF THE INVENTION

The invention provides a CD16A-engaging antibody capable of at least bivalent interaction with CD16A on NK cells and, hence, with increased binding affinity and cytotoxic potency but, preferably, incapable of inducing NK-NK cell lysis.

The invention refers to:

A multivalent and multispecific antigen-binding protein comprising at least one target antigen-binding moiety and at least two CD16A antigen-binding moieties, wherein the two CD16A antigen-binding moieties are fused to a constant domain, for example a Fab fragment or a Fc portion. Preferably, the target antigen-binding moiety is also fused to the Fab fragment or the Fc portion.

For example, each of the antigen-binding moieties may be selected from the group consisting of a single-chain diabody (scDb), a diabody (Db), a single chain Fv (scFv) or a Fab fragment.

In some embodiments the light chain and heavy chain variable regions of the CD16A antigen-binding moiety are linked one after another in a polypeptide such that the variable region at the N-terminus of the polypeptide chain is the light chain variable region, thereby preventing induction of fratricide (NK-NK cell lysis).

A multitude of protein architectures is available by fusing the antigen-binding moieties N-terminally or C-terminally to various units comprising constant domains, such as F(ab)', F(ab)$_2$', CH2-CH3, Hinge-CH2-CH3, Fc, CH1-Hinge-CH2-CH3 or IgG.

In some embodiments the antigen-binding protein comprises a silenced Fc portion that does not bind to the Fc-gammaR, but retains binding to FcRn and, optionally, at least one further Fc-functionality.

In some embodiments the antigen-binding protein comprises a Fc portion which on the one hand is silenced so that it does not bind to the Fc-γR and which on the other hand may include further mutation to increase or decrease its ability to bind to FcRn which does correlate with different in vivo pharmacokinetics based on different abilities for transcytosis and recycling.

In certain embodiments the antigen-binding protein comprises at least an HSA antigen-binding moiety. For example, the antigen-binding protein may comprise 2, 3 or 4 HSA antigen-binding moieties.

In certain embodiments the antigen-binding protein comprises at least two different target antigen-binding moieties, i.e. a first and a second target antigen-binding moiety.

In certain embodiments CD16A antigen-binding moieties with increased or decreased affinity to CD16A are applied.

Among others the invention is characterized by:
1. An enhanced NK cell engaging functionality, because of
   Two CD16A antigen-binding moieties fused to a Fab fragment or a Fc portion, thereby increasing the cytotoxic potency due to the bivalent binding to CD16A.
   Utilizing anti-CD16A antigen-binding moieties with high affinity binding to CD16A.
   Avoiding induction of fratricide (NK-NK cell lysis) by arranging the CD16A antigen-binding in a particular order which does not induce fratricide and thereby prevents weakening of the cytotoxic activity of NK cells towards target cells.
   Avoiding fratricide is independent from the binding affinity of the CD16A antigen-binding moiety.
   Using a silenced Fc portion for avoiding additional binding to Fc-gammaR-positive monocytes or other cells expressing Fc-gammaR, while maintaining binding to FcRn and thereby prolonged serum half-life.
2. This enhanced NK cell engaging functionality can be attributed due to the modularity of the antigen-binding moieties to a multitude of protein architectures achieving tunable cytotoxicity, target affinities, CD16A functionalities, target biology, tissue penetration and distribution, half-life and exposure.

The use of diverse antibody formats specifically described herein and functionalities including varying half-lives and different exposures allow tailoring new therapeutics to different indications with high medical need, offering targeted product development to the respective setting.

Furthermore, the lack of NK cell fratricide is an important feature for high-affinity, at least bivalent immune cell engager formats that are characterized by longer cell retention times and that are either to be used for the engagement of endogenous NK cells or that are to be combined with NK cellular therapeutic approaches. These include NK cells derived from different sources, such as for example those from cord blood, from peripheral blood of healthy donors, from patients for autologous treatment or from stem cells. These engagers can be co-infused or pre-mixed with such NK cells.

Protein formats are presented herein which further enable increase of target binding affinity by at least bivalent binding to the target and/or increase of target selectivity by dual-targeting of the target by two different, first and second target antigen-binding moieties.

Further functionalities may be incorporated into the antigen-binding protein, such as, for example a human serum albumin (HSA) binding moiety.

BRIEF DESCRIPTION OF THE FIGURES

FIG. 4 the scDb consisting of two CD16A antigen-binding moieties is fused to the Hinge or middle Hinge at the N-terminus of one of the two polypeptides of the Fc portion which consists of a CH2-CH3 heterodimer and a scFv comprising a single target antigen-binding moiety is fused to the Hinge at the N-terminus of the other polypeptide of the CH2-CH3 heterodimeric (KiH) Fc portion; FIG. 5 the scDb consisting of two CD16A antigen-binding moieties is fused to the C-terminus of the Fc portion which consists of a CH2-CH3 heterodimer and a scFv comprising a single target antigen-binding moiety is fused to the Hinge or middle Hinge at the N-terminus of the other polypeptide of the CH2-CH3 heterodimeric (KiH) Fc portion; and FIG. 6 the scDb consisting of two CD16A antigen-binding moieties is fused to the C-terminus of the Fc portion which consists of a CH2-CH3 heterodimer and a first scFv comprising a first target antigen-binding moiety is fused to the Hinge or middle Hinge at the N-terminus of the Fc portion and a second scFv comprising a second (and different from the first) target antigen-binding moiety is fused to the Hinge or middle Hinge at the N-terminus of the other polypeptide of the CH2-CH3 heterodimeric (KiH) Fc portion. The first and second targets are two different tumor associated targets.

FIG. 8 a bivalent scDb consisting of two CD16A antigen-binding moieties is fused to the C-terminus of one of the two polypeptides of the Fab fragment and a scFv consisting of a single target antigen-binding moiety is fused to the C-terminus of the other polypeptide of the Fab fragment and the Fv at the N-terminus of the Fab fragment provides a HSA antigen-binding moiety. The target is a tumor associated target.

FIG. 15A shows a KiH-scFv-Fc with two CD16A antigen-binding moieties, each fused to the Hinge at the N-terminus of one of the CH2-CH3 polypeptides and a scFv comprising a first target antigen-binding moiety is fused to the C-terminus of one of the CH2-CH3 polypeptides and another scFv comprising a second target antigen-binding moiety is fused to the C-terminus of the other CH2-CH3 polypeptide. FIG. 15B shows a KiH-scFv-Fc with two CD16A antigen-binding moieties, each fused to the C-terminus of one of the CH2-CH3 polypeptides and a scFv comprising a first target antigen-binding moiety is fused to the Hinge at the N-terminus of one of the CH2-CH3 polypeptides and another scFv comprising a second target antigen-binding moiety is fused to the Hinge at the N-terminus of the other CH2-CH3 polypeptide.

FIGS. 17A-17N show the antibody-mediated NK-NK cell lysis results in Example 6. FIG. 17A shows two anti-CD16A moieties in Diabody format (scDb) fused to monomeric Fc at N-terminus (and scFvs targeting TAA to C-terminus), as shown in FIG. 1. FIG. 17B shows two anti-CD16A moieties in Diabody format (scDb) fused to monomeric Fc at C-terminus (and scFvs targeting TAA to N-terminus), as shown in FIG. 2. FIG. 17K shows two anti-CD16A moieties in scFv format fused to Fc at C-terminus (and scFvs targeting TAA to N-terminus), as shown in FIG. 12. FIG. 17L shows two anti-CD16A moieties in scFv format fused to Fc at C-terminus (and Fab arms targeting TAA at N-terminus), as shown in FIG. 13. FIG. 17M shows two anti-CD16A moieties in scFv format fused to asymmetric Fc at N-terminus (and 2 scFvs targeting 2 TAAs at C-terminus) and two anti-CD16A moieties in scFv format fused to asymmetric Fc at C-terminus (and 2 scFvs targeting 2 TAAs at N-terminus), as shown in FIGS. 15a and 15b. FIG. 17N shows two anti-CD16A moieties in Fab arms of an IgG with two scFv targeting an TAA fused to Fc at C-terminus (as shown in FIG. 16) in comparison to two anti-CD16A moieties in scFv format fused to Fc at C-terminus (and Fab arms targeting TAA at N-terminus; as shown in FIG. 13.

FIG. 18A shows enhanced binding to human CD16A-158V. FIG. 18B shows the binding to human CD16A-158F. Analytes were measured at a single concentration of 312.5 nM.

FIG. 19A-19C show Tyrosine (Y) in position 140 is crucial for formation of a conformational epitope and CD16A-specific reactivity of scFv antibodies. Different recombinant CD16 variants expressed as fusion proteins of ECD sequences with monomeric Fc or membrane anchor were analyzed. FIG. 19A shows protein spots containing defined CD16 antigen variants on Nitrocellulose membranes were tested for their reactivity with the indicated CD16 binding scFvs. FIG. 19B shows reactivity of different anti-CD16 scFv, control scFv, or mAbs with CD16 antigen variants or EGFR antigen expressed on CHO cells anchored via fusion to the EGFR transmembrane domain or GPI, was analyzed by antibody staining and flow cytometry. FIG. 19C shows binding of different anti-CD16 antibodies to CD16 antigen variants after separation by SDS-PAGE and Western blotting.

FIG. 21 shows sequence alignment of ECD sequences of human and cynomolgus CD16A and human CD16B variants used as recombinant antigens in certain experiments described herein. Positions with polymorphisms in human CD16A or CD16B are marked with thin and thick arrows, respectively. Symbol '#' marks position connecting human CD16B to GPI membrane anchor, positions marked with are cleaved from the mature CD16B antigen sequence. Variations in the cynomolgus CD16A ECD sequence are in bold. Positions with sequence variations between human CD16A and human CD16B are in brackets (crucial for CD16A-specific binding of the tested anti-CD16 antibodies). CLUSTAL O(1.2.4) multiple sequence alignment tool was used for the alignment.

FIG. 23 shows the ROCK® platform overview.

FIG. 24A shows the SPR sensograms on immobilized human CD16A-158V. FIG. 24B shows the SPR sensograms on cynomolgus CD16. FIG. 24C shows the legend and percentage of antibodies remaining on the receptor after 3 h of dissociation. Analytes were measured at a single concentration of 50 nM.

FIG. 26A shows the summary of CD16A apparent affinity by Fab or scFv-based CD16 engagement. FIG. 26B shows the summary of CD16A apparent affinity by diabody (Db)-based CD16 engagement. FIG. 26C shows the summary of CD16A apparent affinity by C-terminal scFv-based CD16 engagement comprising different connector lengths (10aa or 30aa) and domain orders of anti-CD16 Fv (HL: scFv domain order VH-VL, LH: scFv domain order VL-VH). All analyzed antibodies contain silenced Fc or lack Fc in the case of fusion to C-terminus of Fab. Binding specificities depicted in black or shaded comprised antibody domains targeting BCMA, CD19, CD20, EGFR, HSA or RSV.

FIG. 27A shows primary human NK cells were stained with increasing concentrations of the indicated Fc-less ROCK® in the presence or absence of 10 mg/mL polyclonal human IgG at 37° C. FIG. 27B shows primary human NK cells were stained with increasing concentrations of the indicated Fc fusion ROCK® in the presence or absence of 10 mg/mL polyclonal human IgG at 37° C. FIG. 27C shows primary human NK cells were stained with increasing concentrations of the indicated IgG-like ROCK® constructs in the presence or absence of 10 mg/mL polyclonal human IgG at 37° C. Cell bound antibodies were detected by flow cytometry, and median fluorescence intensities (MFI) were used for calculation of apparent affinities ($K_D$) by non-linear regression.

FIG. 29A shows representative sigmoidal dose-response curves of the indicated BCMA-targeting ROCK® antibodies in 4 h calcein-release cytotoxicity assays with NK cells and target cell lines NCI-H929 expressing differential levels of BCMA as indicated by the SABC values (mean of ≥3 assays) at an E:T ratio of 5:1. FIG. 29B shows representative sigmoidal dose-response curves of the indicated BCMA-targeting ROCK® antibodies in 4 h calcein-release cytotoxicity assays with NK cells and target cell lines MM.1S expressing differential levels of BCMA as indicated by the SABC values (mean of ≥3 assays) at an E:T ratio of 5:1. FIG. 29C shows representative sigmoidal dose-response curves of the indicated BCMA-targeting ROCK® antibodies in 4 h calcein-release cytotoxicity assays with NK cells and target cell lines MC/CAR expressing differential levels of BCMA as indicated by the SABC values (mean of ≥3 assays) at an E:T ratio of 5:1. FIG. 29D shows representative sigmoidal dose-response curves of the indicated EGFR-targeting ROCK® antibodies, comparators, or monovalently binding controls in 4 h calcein-release cytotoxicity assays with NK cells and SW-982 target cells at an E:T ratio of 5:1. FIG. 29E shows correlation of ROCK® antibodies regarding NK cell binding affinity and cytotoxic potency towards tumor target cells in vitro. Apparent affinities (KD) of ROCK® antibody formats on primary human NK cells are shown. $EC_{50}$ values of the same ROCK® antibodies were determined in 3 h calcein-release cytotoxicity measurements with NK cells and BCMA-expressing RPMI-8226 target cells at an E:T ratio of 2:1 (left) or in 4 h calcein-release cytotoxicity assays with NK cells and BCMA-expressing NCI-H929 target cells at an E:T ratio of 5:1 (right). SABC, specific antibody-binding capacity.

FIG. 31A shows the results for NCI-H929 cell lines. FIG. 31B shows the results for MM.1S cell lines.

FIG. 32A shows human PBMCs that were isolated from a healthy human blood donor and frozen for later experimentation. PBMC upon thaw were ~85% viable by trypan blue staining and later confirmed by FACS with 7AAD. PBMC (~165K) were co-cultured with BCMA+ multiple myeloma tumor cell lines (~20K) and exposed to 3-fold serial diluted test articles from 0.1-3000 pM for approximately 20 hours at 37 C with 5% $CO_2$. The approximate number of $CD56^+CD3e-$ NK cells per 165K of PBMC was about 8000 cells, thus the NK:Tumor ratio was ~0.4 (similar to clinical data estimating MM patient NK to tumor cell ratio; data not shown). As shown in FIG. 32B-32E, antibody staining and FACS were used to determine BCMA expression on MM tumor cells and monitor cytotoxicity of multiple myeloma target cells. Data were analyzed with the software programs FlowJo and GraphPad Prism 6: FIG. 32B shows NCI-H929 cell lines, FIG. 32C shows RPMI-8226 cell lines, FIG. 32D shows MM.1S cell lines, and FIG. 32E shows MOLP-2 cell lines. A non-BCMA targeting/CD16a negative control is shown with open symbols. CD16A/BCMA antibody I is shown with filled symbols.

FIG. 33A shows NCI-H929 cell lines, FIG. 33B shows RPMI-8226 cell lines, and FIG. 33C shows MM.1S cell lines. A non-BCMA targeting/CD16a negative control is shown with unfilled squares. CD16A/BCMA antibody I is shown with solid circles. Daratumumab ("Dara") is shown with filled squares.

FIG. 34A shows depletion of $BCMA^+$ target cells for donor A. FIG. 34B shows depletion of SK-MM-2 for donor B. FIG. 34C shows depletion of MOLP-2 for donor B. For FIGS. 34B and 34C, non-BCMA targeting/CD16a negative control is shown with open symbols, and CD16A/BCMA antibody I is shown with filled symbols.

FIG. 35A shows lysis of Raji cell lines. FIG. 35B shows cytotoxicity of Raji cell lines. FIG. 35C shows BCMA expression detected by commercially available anti-BCMA antibodies and isotype. FIG. 35D shows BCMA expression detected by CD16A/BCMA Antibody I, CD16A/BCMA Antibody II, CD16A/BCMA Antibody III, BCMA (Fc silenced), and isotype.

FIG. 36A shows BCMA expression on Raji cells. FIG. 36B shows BCMA expression on NCI-H929 (MM positive control) cells. For (A) and (B), a commercial anti-BCMA conjugated to APC was used for the quantitation of BCMA expression on Raji and NCI-H929 (MM positive control) cells. (C) Cytotoxicity of Raji cells and H929 cells. CD16A/BCMA antibody I is shown with filled symbols, and a non-BCMA targeting/CD16a negative control is shown with open symbols.

FIG. 37A shows allogeneic cells as positive control. FIG. 37B shows autologous BCMA+ normal human plasma cells. CD16A/BCMA antibody I is shown with filled symbols, and a non-BCMA targeting/CD16a negative control is shown with open symbols.

FIG. 38A shows the number of $NK-CD16^+$ cells. FIG. 38B shows the number of $NKCD69^+CD25^+$ cells. FIG. 38C shows the number of target cells.

FIG. 39A shows the number of NK-CD16+ cells. FIG. 39B shows the number of $NKCD69^+CD25^+$ cells.

FIG. 40A shows the binding of anti-BCMA/CD16a in the presence of exogenous human Ig. Fresh prepared human NK cells were pre-incubated for 1-hours at 37 C with and without 10 mg/mL of SCIG (Hizentra), then stained with DyLight650 labeled anti-AFM26/CD16a at indicted concentrations. FIG. 40B shows anti-BCMA/CD16 induced target cell lysis in the presence of 100% of autologous human serum. Multiple Myeloma cell line NCI-H929 was treated with CD16A/BCMA antibody I at indicated concentration, using fresh prepared human NK cells as effector cells. Before adding the CD16A/BCMA antibody I, cells were pre-incubated with heat inactivated autologous human serum from the same healthy donor at 37 C for half hour. FIGS. 40C and 40D show that anti-BCMA/CD16a depletes BCMA+ target cells in the presence of 50% autologous human serum without loss of NK cells. In FIGS. 40C and 40D, the CD16A/BCMA antibody I is used by example. In FIGS. 40C and 40D, human NK cells were isolated from a healthy human blood donor. NK (FIG. 40D) and MM.1S cells (FIG. 40C) were preincubated separately in 50% human autologous serum for 2 hours prior to assay setup. NK cells were co-cultured with MM.1S tumor cell line at an approximate E:T ration of 5, and exposed to 10-fold serial diluted test articles from 0.1-100 nM for approximately 20 hours at 37 C with 5% $CO_2$. Antibody staining with CD138 and CD56 followed by FACS were used to monitor cytotoxicity of MM.1S target cells and NK survival. Data were analyzed with the software programs FlowJo and GraphPad Prism 6. Ab-1, non-BCMA Targeting/CD16a negative control, is shown with open symbols. BCMA/CD16a antibody I is shown with filled symbols. FIG. 40E shows that second line R/R MM is a target indication for treatment with an anti-BCMA/CD16A antibody. In this example, the BCMA/CD16A antibody I is used by example. Specifically, the data in this figure shows that anti-BCMA/CD16A antibodies (the BCMA/CD16A antibody I used for exemplary purposes) is differentiated from the anti-CD38 antibody (daratumumab). Daratumumab has complement dependent cytotoxicity activity in MM (de Weers, M. et al. 2011. J. Immun. 186(3):1840-1848) and the ability to induce apoptosis by signaling through cross linking of CD38 (Overdijk, M. B., et al., 2016 J. Immun. 197(3):807-813) while the BCMA/CD16A antibody I does not have these activities. Furthermore, unlike daratumumab, the activity of the BCMA/CD16A antibody I is unaffected by CD16A polymorphisms that reduce activity of Fc mediated drugs as shown in FIGS. 41A and 41B. In all, FIG. 40E shows that the BCMA/CD16A antibody I does not deplete NK cells (which are CD38 positive) but daratumumbab does.

FIGS. 41A and 41B show the impact of serum on CD16A expression and activation of NK cells in the absence of BCMA+ target cells. Furthermore, low CD16 expression in the presence of serum suggests a non-CD1A mediated activation of NK cells. FIG. 41A shows a lower CD16A detection with serum. FIG. 41B shows higher non-target mediated activation with serum.

FIG. 42A shows the percent lysis of tumor cells that were treated with either a) no antibody, b) negative control 1, c) negative control 2, d) the BCMA/CD16A antibody I, e) an anti-BCMA/CD19 antibody, and f) daratumumab. FIG. 42B shows the percent lysis of tumor cells that were treated with either a) no antibody+IL-15, b) negative control 1+IL-15, c) negative control 2+IL-15, d) the BCMA/CD16A antibody I+IL-15, e) an anti-BCMA/CD19 antibody+IL-15, and f) daratumumab+IL-15. FIG. 42C shows the structures of negative control #1, negative control #2, and BCMA/CD19 shown in FIGS. 42A and 42B.

FIG. 43 shows NK flow data in peripheral blood (absolute counts/uL) at baseline for atezolizumab trials. The NK cells were gated as CD56/CD16+ lymphocytes: CD45×SSC low population (standard gating), then subgated into a CD56/CD16+ population. In atezolizumab, the NK levels in Dara refractory patients were lower than Dara naïve and lower than the healthy donor range (area between dotted lines).

In FIG. 45A, E:T was 0.05. In FIG. 45B, E:T was 0.5.

FIG. 46A shows cytotoxicity of fresh prepared NK cells on NCI-H929 cells. FIG. 46B shows cytotoxicity of fresh prepared NK cells on MM.1S cells. FIG. 46C shows cytotoxicity of $2^{nd}$ day NK cells on NCI-H929 cells. FIG. 46D shows cytotoxicity of $2^{nd}$ day NK cells on MM.1S cells.

FIG. 48A shows the expression of BCMA on normal human plasma cells. FIG. 48B shows an example of BCMA expression in a frozen primary myeloma BMMC. For both FIGS. 48A and 48B, the cells were stained and gated according to the protocol described above in FIG. 47 with BCMA then the % of Max was plotted in FlowJo. The grey shaded peak is the Fluorescence Minus One (FMO) control and red peak is the BCMA expression.

FIGS. 49A-49C show percentages of CD69+ NK cells in PBMC cultures at increasing concentrations of BCMA/CD16A ROCK engagers TandAb_A, scFv-IgAb_D and KiH-scDb-Fc_A in presence and absence of BCMA+ RPMI-8226 target cells. FIG. 49A is for TandAb_A, FIG. 49B is for scFv-IgAb_D, and FIG. 49C is for KiH-scDb-Fc_A. Human PBMC were cultured with (filled symbols) or without (open symbols) RPMI-8226 target cells (E:T ratio: 50:1) in presence of increasing concentrations of antibody (squares) or without antibody (triangles). Following 22 h incubation, CD69 surface expression on CD56+ NK cells was analyzed by flow cytometry. FIGS. 49D-49F show freshly isolated human PBMC were cultured in presence or absence of BCMA+ NCI-H929 cells at an E:T ratio of 50:1 with or without 10 μg/mL TandAb_A, scFv-IgAb_D or KiH-scDb-Fc_A. FIG. 49D is for TandAb_A, FIG. 49E is for scFv-IgAb_D, and FIG. 49F is for KiH-scDb-Fc_A. Following 24 h incubation, IFN-γ concentration in supernatants were quantified. *: below lower limited of detection.

FIG. 52A shows RPMI 1640 medium. FIG. 52B shows medium supplemented with 10 mg/mL polyclonal human IgG. FIG. 52C shows 10 mg/mL monoclonal human anti-EGFR IgG1. FIG. 52D shows 10 mg/mL Fc-enhanced monoclonal human anti-EGFR IgG1.

FIGS. 53A-53D show the sequences of the BCMA-targeting moiety and CD16A antigen-binding moiety of CD16A/BCMA Antibody I. FIG. 53A shows the CDR sequences of the BCMA-targeting moiety of CD16A/BCMA Antibody I. FIG. 53B shows the heavy and light chain variable region sequences of the BCMA-targeting moiety of CD16A/BCMA Antibody I. FIG. 53C shows the CDR sequences of the CD16A antigen-binding moiety of CD16A/BCMA Antibody I. FIG. 53D shows the heavy and light chain variable region sequences of the CD16A antigen-binding moiety of CD16A/BCMA Antibody I.

DETAILED DESCRIPTION OF THE INVENTION

I. Definitions

Figure 1:
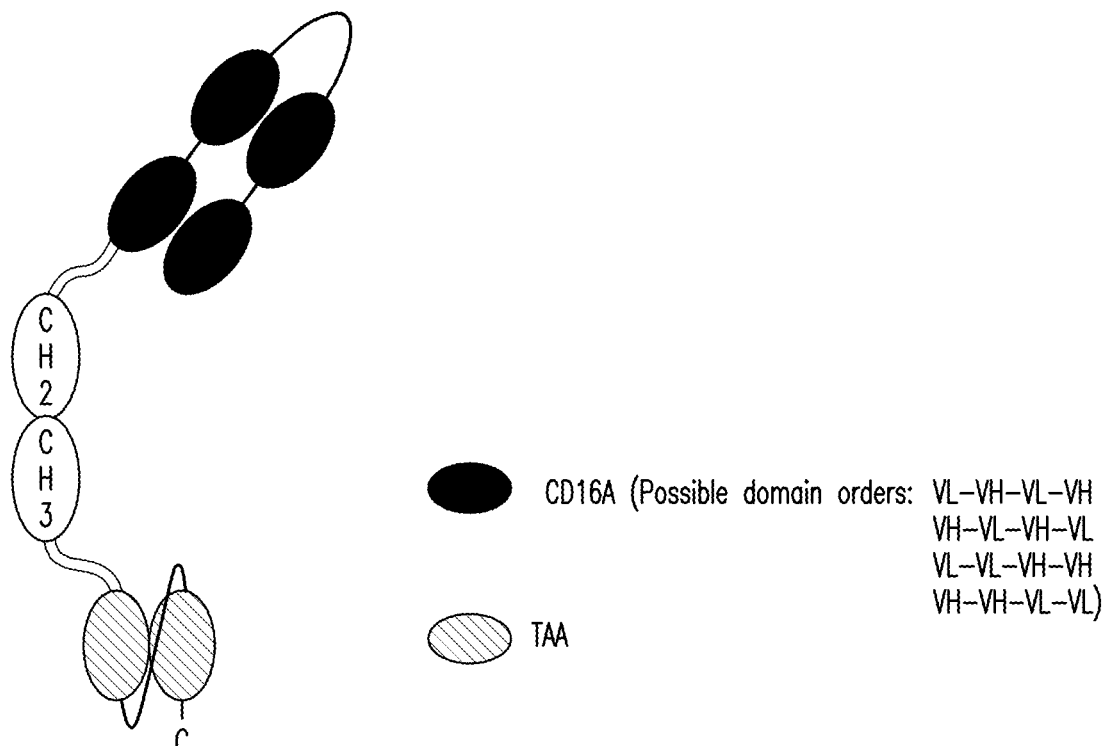
FIGS. 1-2 show a scDb-mFc antigen-binding protein which is monomeric and comprises a bivalent CD16A antigen-binding moiety in the format of a scDb fused to a monomeric Fc portion, wherein in FIG. 1 the scDb consisting of two CD16A antigen-binding moieties is fused to the N-terminus of the Fc portion which consists of a variant CH2-CH3 polypeptide and a scFv comprising a single target antigen-binding moiety fused to the C-terminus of the Fc portion, and in FIG. 2 the scDb consisting of two CD16A antigen-binding moieties is fused to the C-terminus of the Fc portion which consists of a variant CH2-CH3 polypeptide and a scFv comprising a single target antigen-binding moiety is fused to the N-terminus of the Fc portion. The target is a tumor associated target.

The term "multispecific" refers to an antigen-binding molecule, comprising antigen-binding sites that bind to at least two different epitopes, in particular epitopes of different antigens. "Multispecific" includes, but is not limited to, bispecific, trispecific and tetraspecific.

The term "valent" denotes the presence of a determined number of antigen-binding moieties in the antigen-binding protein. A natural IgG has two antigen-binding moieties and is bivalent. The antigen-binding proteins according to the invention are at least trivalent. Examples of tetra-, penta- and hexavalent antigen-binding proteins are described herein.

The term "polypeptide" refers to a polymer of amino acid residues consecutively linked by amide bonds. In certain embodiments, the term "polypeptide" refers to a group of molecules, which usually consist of more than 30 amino acids. Polypeptides may further form multimers such as dimers, trimers and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "peptide," "polypeptide," and "protein" also refer to naturally modified peptides/polypeptides/proteins wherein the modification is affected e.g., by post-translational modifications like glycosylation, acetylation, phosphorylation and the like. A "peptide," "polypeptide," or "protein" when referred to herein may also be chemically modified such as pegylated. Such modifications are well known in the art and described herein below.

"Fv polypeptide" denotes a fusion polypeptide wherein antibody variable (Fv) domains are linked one after another. The polypeptide may have contiguous amino acid residues in addition to N-terminal and/or C-terminal sequence extensions. For example, the polypeptide may contain a Tag sequence, preferably at the C-terminus which might be useful for the purification as well as detection of the polypeptide. Examples of Tag sequences are a Histidine-Tag, e.g., a His-Tag consisting of six His-residues (SEQ ID NO:58), or a C-Tag, e.g., an EPEA tetrapeptide (SEQ ID NO:59). For a multimeric antigen-binding molecule, different Tag sequences may be used for different polypeptides, e.g., a His-Tag for a first polypeptide and a C-Tag for a second polypeptide of a heterodimeric molecule. In certain embodiments the polypeptide comprises variable domains providing the antigen-binding sites and constant antibody domains, for example $C_L$, $C_H1C_H$ and/or Fc portions (CH2-CH3) connected into the polypeptide. For example, such embodiments comprise an Fv polypeptide fused to at least one constant antibody domain, for example a Fc portion. In further embodiments the polypeptide may be connected to another agent, e.g., a toxin, an immune-modulating agent or a signal generating agent.

The term "Fc portion" refers to a polypeptide comprising a C-terminal part of an immunoglobulin H chain and retaining at least one functionality of a Fc-region of an IgG region, in particular the function of binding to FcRn. The antibody effector functions are determined by sequences in the Fc region. A Fc portion can comprise a CH2 domain, a CH3 domain or a CH2-CH3 polypeptide chain. The CH2-CH3 polypeptide chain assembles with another CH2-CH3 polypeptide chain to a dimer of two CH2-CH3 polypeptides combined with one another, wherein the dimerization is promoted by covalent linkage in the Hinge region NC-terminal to the CH2 domain. Hence, in some embodiments the Fc portion comprises a dimer of two CH2-CH3 polypeptide chains and a Hinge region. Preferably, the Fc portion comprises constant domains of the Ig class, e.g., IgA, IgD, IgE, IgM, preferably IgG1, IgG2, IgG2, IgG4, in particular IgG1 constant domains. The light chain constant regions (CL) can be selected from kappa (η), lambda (λ), and sigma (σ), wherein the human lambda class has the subclasses lambda 1-4.

The "hinge" domain may be of the same or different IgG class as the Fc portion or an engineered, not naturally occurring Hinge domain. An example of an IgG Hinge region has the amino acid sequence as depicted in SEQ ID NO:23. Included are also variants of wild-type Hinge regions, such as shortened Hinge regions, for example a Hinge designated as middle. hinge having the amino acid sequence of SEQ ID NO:24.

The terms "antigen-binding protein" and "antigen-binding molecule" (with and without a hyphen) are used interchangeably herein to refer to an immunoglobulin derivative with antigen binding properties; i.e. the binding protein is an antigen binding molecule. The binding protein comprises an immunologically functional immunoglobulin portion capable of binding to a target antigen. The immunologically functional immunoglobulin portion may comprise immunoglobulins, or portions thereof, fusion peptides derived from immunoglobulin portions or conjugates combining immunoglobulin portions that form an antigen binding site. Each antigen binding moiety comprises at least the CDRs of the immunoglobulin heavy or light chains from which the antigen binding moiety was derived. The terms "antigen binding protein" and "antigen-binding molecule" (with and without a hyphen) are used interchangeably herein to refer to antibody fragments, antibody derivatives or antibody-like binding proteins that retain specificity and affinity for their antigen including, for example, IgG-like fusion polypeptides based on Fv domains with additional constant domains. Dependent on desired features, such as valency, multispecificity, pharmacokinetic and pharmacodynamic properties Fv and constant domains and/or additional functional domains are modularly assembled in different molecule formats or protein scaffolds, such as, for example, described in Brinkmann and Kontermann, mAbs, 2017, 9(2):182-192 or in Spiess et al., Molecular Immunology 2015; 67:95-106.

In some embodiments the antigen-binding protein consists of a single polypeptide chain. Such an antigen-binding protein is a monomer. In other embodiments the antigen-binding protein comprises at least two polypeptide chains. Such an antigen-binding protein is a multimer, e.g., dimer, trimer or tetramer.

Preferably, the antigen-binding protein is human, most preferably fully human.

The term "antigen-binding moiety" refers to an antibody-antigen combining site or paratope of the antigen-binding protein that binds, in particular specifically, to an antigenic determinant (epitope) of an antigen. The antigen-binding site is the binding portion of the antigen-binding protein which is capable of recognizing the antigen and binds specifically to the antigen.

"Fv" as described herein denotes an antigen-binding moiety comprising the variable domains of both the light ($V_L$) and heavy ($V_H$) chains of an antibody that recognize the antigen, i.e. bind to the epitope of the antigen. In certain embodiments the antigen-binding site may be a single domain (sdAb), e.g., $V_HH$ fragments from camelids or $V_{NAR}$ fragments from cartilaginous fishes.

Each antigen-binding moiety is formed by an antibody, i.e. immunoglobulin, variable heavy chain domain ($V_H$) and an antibody variable light chain domain ($V_L$) binding to the same epitope, whereas the variable heavy chain domain ($V_H$) comprises three heavy chain complementarity determining regions (CDR): HCDR1, HCDR2 and HCDR3; and the variable light chain domain ($V_L$) comprises three light chain complementary determining regions (CDR): LCDR1, LCDR2 and LCDR3. The variable heavy and light chain domains of an antigen-binding site may be covalently linked with one another, e.g., by a peptide linker, or non-covalently associate with one another to form an antigen-binding site.

"Linker" refers to a sequence of amino acids comprising a linker peptide joining two juxtaposed variable domains forming an antigen-binding moiety with the C-terminus of one domain linked to the N-terminus of the other juxtaposed domain or vice versa. Regarding the amino acid composition a peptide linker sequence is selected that does not interfere with the formation of Fv, i.e. $V_H/V_L$, antigen binding- and recognition sites as well as does not interfere with the multimerization, e.g., dimerization of the polypeptides of the multispecific antigen-binding protein. For example, a linker comprising glycine and serine residues generally provides protease resistance. In some embodiments (G2S)$_x$ peptide linkers are used, wherein, for example, x=1-20, e.g., (G$_2$S), (G$_2$S)$_2$, (G$_2$S)$_3$, (G$_2$S)$_4$, (G$_2$S)$_5$, (G$_2$S)$_6$, (G$_2$S)$_7$ or (G$_2$S)$_8$, or (G$_3$S)$_x$ peptide linkers are used, wherein, for example, x=1-15 or (G$_4$S)$_x$ peptide linkers are used, wherein, for example, x=1-10, preferably 1-6. The amino acid sequence of the linker can be optimized, for example, by phage-display methods to improve the formation of the antigen binding site and production yield of the polypeptide.

"Connector" refers to a peptide joining an antigen-binding moiety to a Fab fragment, to a Hinge or a Fc portion. By definition a connector is not a peptide joining two variable domains.

The length of the linkers and connectors can influence the folding and flexibility of the Fv polypeptide of the antigen-binding moiety. The desired flexibility of the Fv polypeptide depends on the target antigen density and the accessibility of the target antigen, i.e. epitopes on the target antigen. Longer linkers or connectors can provide more flexible Fv polypeptides with more agile antigen-binding sites. The effect of linker lengths on the formation of dimeric antigen-binding polypeptides is described, for example, in Todorovska et al., Journal of Immunological Methods 2001; 248:47-66; Perisic et al., Structure 1994; 2:1217-1226; Le Gall et al., Protein Engineering 2004; 17:357-366 and WO 94/13804.

A "single-chain variable antibody fragment" or "scFv" comprises an antigen binding site consisting of a heavy chain variable domain ($V_H$), which is optionally fused via a peptide linker to a light chain variable domain ($V_L$). The scFv can be a polypeptide chain: $V_L$-Linker-$V_H$ or $V_H$-Linker-$V_L$ from the N- to the C-terminus of the polypeptide chain, (Huston et al., Proc. Natl. Acad.Sci. USA, 1988, 85:5879-83). The linker between the $V_H$ and $V_L$ domains enables the formation of a desired structure that allows for antigen binding.

The "antigen-binding (Fab) fragment" or "Fab" comprises one constant (CH1, CL) and one variable domain ($V_H$, $V_L$) formed by dimerization of each of the heavy (H) chain derived and the light (L) chain derived sequences, wherein the variable domains $V_H$ and $V_L$ constitute an antigen-binding site. Two Fab' fragments are joined as a F(ab')$_2$ fragment N-terminally to the Fc portion via the Hinge-region.

A "Diabody" (Db) denotes a bivalent Fv-molecule consisting of two pairs of variable heavy ($V_H$) and variable light ($V_L$) chain domains, a first pair and a second pair, which associate to two $V_L/V_H$ antigen binding sites. Each pair of variable domains is connected one after another in a polypeptide. In certain embodiments the bivalent Fv-molecule consists of a first and a second pair of two juxtaposed variable domains, wherein in each pair the two variable domains are fused by a short peptide linker that precludes intramolecular association between the variable domains connected by the short linker. The first pair of variable domains is forced to associate with the second pair of variable domains cross-over to form two Fv antigen binding sites. Hence, each of the two antigen binding moieties is formed by one variable domain of the first pair of variable domains and one variable domain of the second pair of variable domains. Therefore, such diabody comprises at least one antigen binding site composed of two variable domains which are not directly connected by a short linker. In the diabody the variable domains of a first antigen-binding moiety is connected by a linker with a variable domain of a second antigen-binding moiety. For example, the $V_H$ of a first antigen-binding moiety is linked by a first linker to a $V_L$ of a second antigen-binding moiety in a first polypeptide and the $V_L$ of the first antigen-binding moiety is linked by second linker to the $V_H$ of the second antigen-binding moiety in a second polypeptide. In each pair of juxtaposed variable domains the short first or second linker connects the C-terminus of one variable domain with the N-terminus of the other variable domain or vice versa. In each pair the variable domains can be oriented from the N- to the C-terminus as $V_L$-$V_H$, $V_H$-$V_L$, $V_H$-$V_H$ and $V_L$-$V_L$, wherein the two variable domains of the pair can have different antigen epitope specificities or the same antigen epitope specificity. In certain instances the two variable domains are directly linked by a peptide bond between the C-terminus of one variable domain and the N-terminus of the other variable domain of the pair. The length of the short peptide linker connecting the two variable domains in each of the first and second pair of variable domains of the diabody is such that an intramolecular association between the variable domains connected by the linker is precluded. Such linker is "short", i.e. consists of 0, 1, 2, 3, 4, 5, 6, 7, 8, 9, 10, 11 or about 12 amino acid residues In the case of 0 amino acid residues the linker is a peptide bond. Such short linker favors the correct dimerization between the two pairs of variable domains and formation of two Fv antigen binding sites. Shortening the linker to about 12 or less amino acid residues generally prevents adjacent domains on the same polypeptide chain from interacting with each other. In an embodiment of the invention these linkers consist of about 3 to about 12, for example 5 to 10, in particular 7 to 9 contiguous amino acid residues. The linker length may be adjusted to the particular domain orientation within the polypeptide of the diabody. Besides, it is in principle possible that two polypeptides having a linker with more than 12 amino acid residues between the variable antibody domains of the pair correctly dimerize with one another (see for example Le Gall et al., Protein Engineering 2004; 17:357-366).

"Single-chain diabody (scDb)" denotes a diabody derivative converted into a single polypeptide chain by adding a further linker fusing the first and second polypeptide (Kontermann et al., Immunol. Methods, 1999; 226: 179-188). Hence, the further linker connects the C-terminus of the first polypeptide comprising variable domains of the first and second antigen binding moieties connected by a first linker with the N-terminus of the second polypeptide comprising the cognate variable domains of the first and second antigen-binding moieties connected by a second linker. Hence, a scDb consists of a single polypeptide chain, i.e., Fv polypeptide, wherein four variable domains of two antigen-binding moieties are arranged from the N- to the C-terminus:

VL-linker1-VH-linker3-VL-linker2-VH, or
VL-linker1-VL-linker3-VH-linker2-VH, or
VH-linker1-VL-linker3-VH-linker2-VL, or
VH-linker1-VH-linker3-VL-linker2-VL Linker1 and linker2 are "short" linkers as used in diabodies, e.g., consist of less than 13, e.g., 1, 2, 3, 4, 5, 6, 7, 8, 9, 10, 11, or 12 amino acid residues.

Linker3 is a more flexible linker as used for i.e. a scFv that promotes intramolecular folding back and association of the two N-terminal variable domains with the two C-terminal variable domains to two antigen-binding moieties. Linker3 consists of 13 or more amino acid residues, e.g., 13, 14, 15, 16, 17, 18, 19, 20, 21, 22, 23, 24, 25, 26, 27, 28, 29 or 30 amino acid residues. In some embodiments linker3 is from 15 to 25, preferable from 15 to 20 or from 13 to 18 amino acids.

The term "tandem diabody" refers to an antigen-binding molecule constructed by linking at least four variable domains (two heavy chain variable domains (VH) and two light chain variable domains (VL)) in a single gene construct enabling homo-dimerization of two of the translated polypeptide chains. In such tandem diabodies the linker length is such that it prevents intramolecular pairing of the variable domains so that the molecule cannot fold back upon itself to form a monomeric single-chain molecule, but rather is forced to pair with the complementary domains of another chain. The variable domains are also arranged such that the corresponding variable domains pair during this dimerization (Weichel et al., European Pharmaceutical Review 2015; 20(1):27-32; Reusch et al., mAbs 2014; 6:3, 728-739).

"Dual-affinity retargeting molecule (DARTs)" refers to a protein scaffold wherein the VH of a first antigen-binding moiety is linked to a VL of a second antigen-binding moiety on a second polypeptide, and the VH of the second antigen-binding moiety is linked to the VL on the first polypeptide in an arrangement VL(A)-VH(B)+VL(B)-VH(A), wherein an interchain disulfide bond is introduced to stabilize the molecule.

The term "target" or "target antigen" refers to an antigen which is expressed by or associated with a type of cell, i.e. target cell, or virus-infected cell to which the NK cells should be directed to induce or trigger the NK cell cytotoxicity. Examples of a target antigen may be tumor antigen or Tumor-Associated Antigen (TAA). The tumor antigen or TAA may be expressed on the surface of the target cell or displayed by a MHC complex as a MHC-restricted peptide. Examples of tumor antigens include but are not limited to CD5, CD19, CD20, CD22, CD30, CD33, CD38, CD123, CD138, CCR4, CS-1, GD2, matrix metalloproteinase 1 (MMP1), the laminin receptor precursor protein, BCMA, EGFR, EGFRvIII, Ep-CAM, gpA33, AMHRII, PDGFRα, SLAMF7, PLAP, Thomsen-Friedenreich (TF) antigen, MUC-1 (mucin), IGFR, IL4-R alpha, IL13-R, HER2/neu, HER3, PSMA, CEA, TAG-72, HPV E6, HPV E7, BING-4, Cyclin-$B_1$, 9D7, EphA2, EphA3, Telomerase, Mesothelin, SAP-1, Survivin, Cancer Testis antigens (BAGE family, CAGE family, GAGE family, MAGE family, SAGE family, XAGE family), NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, MART-2, p53, Ras, TGF-βRII and TCR (from Categories of Tumor Antigens, Holland-Frei Cancer Medicine. $6^{th}$ edition. Kufe D W, Pollock R E, Weichselbaum R R. et al., editors Hamilton (ON):Becker; 2003). "target" and "target antigen" also includes serum albumin, in particular human serum albumin (HSA). In certain embodiments, the target antigen is BCMA.

In other embodiments the target antigen may be an infectious agent such as viral or bacterial pathogens, for example from a dengue virus, herpes simplex, cytomegalovirus, hepatitis viruses, human T-cell lymphotropic viruses, influenza virus, RSV, papilloma viruses (including antigens in addition to E6 and E7 mentioned above) influenza virus or HIV. Included are also peptide targets displayed by a MHC complex as a MHC-restricted peptide "CD16A" refers to the activating receptor CD16A, also known as FcγRIIIA, expressed on the cell surface of NK cells. CD16A is an activating receptor triggering the cytotoxic activity of NK cells. The affinity of antibodies for CD16A directly correlates with their ability to trigger NK cell activation, thus higher affinity towards CD16A reduces the antibody dose required for activation. The antigen-binding site of the antigen-binding protein binds to CD16A, but not to CD16B. For example, an antigen-binding site comprising heavy (VH) and light (VL) chain variable domains binding to CD16A, but not binding to CD16B, may be provided by an antigen-binding site which specifically binds to an epitope of CD16A which comprises amino acid residues of the C-terminal sequence SFFPPGYQ (SEQ ID NO:57) and/or residues G130 and/or Y141 of CD16A (SEQ ID NO:48)) which are not present in CD16B.

"Myeloma cell" is a malignant (cancerous) plasma cell arising from a plasma cell in the bone marrow by neoplastic transformation. In myeloma, malignant plasma cells produce large amounts of abnormal antibodies that lack the capability to fight infection. These abnormal antibodies are the socalled monoclonal protein, or M-protein, that functions as a tumor marker for myeloma. The myeloma cell has the phenotype $CD19^-/CD38^+/CD138^+/BCMA^+$. Hence, CD38, CD138 and BCMA represent antigens expressed on a myeloma cell. Also included are malignant phenotypes in the B cell lineage that are positive for CD19/CD20/CD22/BCMA and other antigens (this should include phenotypes that are not classically understood as plasma cells, but may be evolutions from memory B cells or the pre-plasma cell lineage).

"EGFR" refers to the epidermal growth factor receptor (EGFR; ErbB-1; HER1 in humans, including all isoforms or variants described with activation, mutations and implicated in pathophysiological processes. The EGFR antigen-binding site recognizes an epitope in the extracellular domain of the EGFR. In certain embodiments the antigen-binding site specifically binds to human and cynomolgus EGFR.

The epidermal growth factor receptor (EGFR) is a member of the HER family of receptor tyrosine kinases and consists of four members: EGFR (ErbB1/HER1), HER2/neu (ErbB2), HER3 (ErbB3) and HER4 (ErbB4). Stimulation of the receptor through ligand binding (e.g., EGF, TGFa, HB-EGF, neuregulins, betacellulin, amphiregulin) activates the intrinsic receptor tyrosine kinase in the intracellular domain through tyrosine phosphorylation and promotes receptor homo- or heterodimerization with HER family members. These intracellular phospho-tyrosines serve as docking sites for various adaptor proteins or enzymes including MAPK and PI(3)K/Akt, which simultaneously initiate many signaling cascades that influence cell proliferation, angiogenesis, apoptosis resistance, invasion and metastasis.

"EGFRvIII" refers to an extracellular domain mutant of EGFR resulting from in-frame deletion of base pairs spanning exons 2-7 of the EGFR coding sequence (Gan H K et al., FEBS 2013, 280:5350-5370).

The term "binding domain" characterizes in connection with the present invention a domain which (specifically) binds to/interacts with/recognizes a given target epitope or a given target side on the target molecules (antigens), e.g., CD16 and a target cell surface antigen, respectively. The structure and function of the first binding domain (recognizing e.g., CD16), and preferably also the structure and/or function of the second binding domain (recognizing the target cell surface antigen), is/are based on the structure and/or function of an antibody, e.g., of a full-length or whole immunoglobulin molecule and/or is/are drawn from the variable heavy chain ($V_H$) and/or variable light chain ($V_L$) domains of an antibody or fragment thereof. Preferably the first binding domain is characterized by the presence of three light chain CDRs (i.e. CDR1, CDR2 and CDR3 of the $V_L$ region) and/or three heavy chain CDRs (i.e. CDR1, CDR2 and CDR3 of the $V_H$ region). The second binding domain preferably also comprises the minimum structural requirements of an antibody which allow for the target binding. More preferably, the second binding domain comprises at least three light chain CDRs (i.e., CDR1, CDR2 and CDR3 of the $V_L$ region) and/or three heavy chain CDRs (i.e., CDR1, CDR2 and CDR3 of the $V_H$ region). It is envisaged that the first and/or second binding domain is produced by or obtainable by phage-display or library screening methods rather than by grafting CDR sequences from a pre-existing (monoclonal) antibody into a scaffold.

The term "(specifically) binds to", "(specifically) recognizes," "is (specifically) directed to," or "(specifically) reacts with" means in accordance with this invention that a binding domain interacts or specifically interacts with a given epitope or a given target side on the target molecules (antigens), e.g. CD16a, and the target cell surface antigen, e.g., BCMA, respectively.

The term "does not essentially/substantially bind" or "is not capable of binding" means that a binding domain of the present invention does not bind a protein or antigen other than CD16a, and the target cell surface antigen, i.e., does not show reactivity of more than about 30%, preferably not more than about 20%, more preferably not more than about 10%, particularly preferably not more than about 9%, about 8%, about 7%, about 6% or about 5% with proteins or antigens other than CD16a, and the target cell surface antigen, whereby binding to CD16a, and the target cell surface antigen, respectively, is set to be about 100%.

Specific binding is believed to be affected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-side with its specific antigen may result in a simple binding of said side to the antigen. Moreover, the specific interaction of the antigen-interaction-side with its specific antigen may alternatively or additionally result in the initiation of a signal, e.g., due to the induction of a change of the conformation of the antigen, an oligomerization of the antigen, etc.

The term "variable" refers to the portions of the antibody or immunoglobulin domains that exhibit variability in their sequence and that are involved in determining the specificity and binding affinity of a particular antibody (i.e., the "variable domain(s)"). The pairing of a variable heavy chain (VH) and a variable light chain (VL) together forms a single antigen-binding side.

Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding side (see Kabat et al., loc. cit.).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so-called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), MacCallum, Honegger, and IMGT (Wu and Kabat, J. Exp. Med. 1970; 132:211-250; Chothia et al., J. Mol. Biol, 1987, 196: 901-917; MacCallum et al., J. Mol. Biol, 1996, 262: 732; Lefranc et al., Dev. Comp. Immunol. 2003; 27:55-77; Honegger et al., J. Mol. Bol. (2001); 309:657-670). Still another standard for characterizing the antigen binding side is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred. In certain embodiments, the CDRs disclosed herein are identified according to the Kabat numbering system. In certain embodiments, the CDRs disclosed herein are identified according to the IMGT approach. In certain embodiments, the CDRs disclosed herein are identified according to the Honegger approach.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding side. H3, for example, can be as short as two amino acid residues or greater than 26 amino acids.

In a classical full-length antibody or immunoglobulin, each light (L) chain is linked to a heavy (H) chain by one covalent disulfide bond, while the two H chains are linked to each other by one or more disulfide bonds depending on the H chain isotype. The CH domain most proximal to VH is usually designated as CH1. The constant ("C") domains are not directly involved in antigen binding, but exhibit various effector functions, such as antibody-dependent, cell-mediated cytotoxicity and complement activation. The Fc region of an antibody is comprised within the heavy chain constant domains and is for example able to interact with cell surface located Fc receptors.

Amino acid sequence modifications of the antibody binding molecules described herein are also contemplated. For example, it may be desirable to improve the binding affinity and/or other biological properties of the antibody construct. Amino acid sequence variants of the antibody constructs are prepared by introducing appropriate nucleotide changes into the antibody constructs nucleic acid, or by peptide synthesis. All of the below described amino acid sequence modifications should result in an antibody construct which still retains the desired biological activity (binding to CD16a and the target cell surface antigen) of the unmodified parental molecule.

Amino acid modifications include, for example, deletions from, and/or insertions into, and/or substitutions of, residues within the amino acid sequences of the antibody binding molecules. Any combination of deletion, insertion, and substitution is made to arrive at the final molecule, provided that the final molecule possesses the desired characteristics. The amino acid changes also may alter post-translational processes of the antibody binding molecules, such as changing the number or position of glycosylation sites.

For example, 1, 2, 3, 4, 5, or 6 amino acids may be inserted, substituted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted, substituted or deleted in each of the FRs. Preferably, amino acid sequence insertions into the antibody construct include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. Corresponding modifications may also be performed within a third domain of the antibody construct defined in the context of the invention. An insertional variant of the antibody construct defined in the context of the invention includes the fusion to the N-terminus or to the C-terminus of the antibody binding molecule of an enzyme or the fusion to a polypeptide.

The sites of greatest interest for substitutional mutagenesis include (but are not limited to) the CDRs of the heavy and/or light chain, in particular the hypervariable regions, but FR alterations in the heavy and/or light chain are also contemplated. The substitutions are preferably conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs of the heavy and/or light chain, it is preferred that the then-obtained "substituted" sequence is at least about 60% or about 65%, more preferably about 70% or about 75%, even more preferably about 80% or about 85%, and particularly preferably about 90% or about 95% identical to the "original" CDR sequence. This means that it is dependent of the length of the CDR to which degree it is identical to the "substituted" sequence. For example, a CDR having 5 amino acids is preferably about 80% identical to its substituted sequence in order to have at least one amino acid substituted. Accordingly, the CDRs of the antibody construct may have different degrees of identity to their substituted sequences, e.g., CDRL1 may have about 80%, while CDRL3 may have about 90%.

Preferred substitutions (or replacements) are conservative substitutions. However, any substitution (including non-conservative substitution or one or more from the "exemplary substitutions" listed in Table A, below) is envisaged as long as the antibody construct retains its capability to bind to CD16a via the first domain and to the target cell surface antigen via the second domain and/or its CDRs have an identity to the then substituted sequence (at least about 60% or about 65%, more preferably about 70% or about 75%, even more preferably about 80% or about 85%, and particularly preferably about 90% or about 95% identical to the "original" CDR sequence).

Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened for a desired characteristic.

TABLE A

Amino acid substitutions

| Original | Exemplary Substitutions | Preferred Substitutions |
|---|---|---|
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | ala | ala |
| His (H) | asn, gln, lys, arg | arg |
| Ile(I) | leu, val, met, ala, phe | leu |
| Leu (L) | norleucine, ile, val, met, ala | Iie |
| Lys (K) | arg, gln, asn | arg |
| Met (M) | leu, phe, ile | leu |
| Phe (F) | leu, val, ile, ala, tyr | tyr |
| Pro (P) | ala | ala |
| Ser (S) | thr | thr |
| Thr (T) | ser | ser |
| Trp (W) | tyr, phe | tyr |
| Tyr (Y) | trp, phe, thr, ser | phe |
| Val (V) | ile, leu, met, phe, ala | leu |

Substantial modifications in the biological properties of the antibody construct of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr, asn, gin; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the antibody construct may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

For amino acid sequences, sequence identity and/or similarity is determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, Nucl. Acid Res. 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, J. Mol. Evol. 35:351-360; the method is similar to that described by Higgins and Sharp, 1989, CABIOS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, J. Mol. Biol. 215:403-410; Altschul et al., 1997, Nucleic Acids Res. 25:3389-3402; and Karin et al., 1993, Proc. Natl. Acad. Sci. U.S.A. 90:5873-5787. A particularly useful BLAST program is the WU-BLAST-2 program which was obtained from Altschul et al., 1996, Methods in Enzymology 266: 460-480. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, Nucl. Acids Res. 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs or $V_H/V_L$ sequences are at least about 60% to the sequences depicted herein, and more typically with preferably increasing homologies or identities of at least about 65% or about 70%, more preferably at least about 75% or about 80%, even more preferably at least about 85%, about 90%, about 91%, about 92%, about 93%, about 94%, about 95%, about 96%, about 97%, about 98%, about 99%, and almost about 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs or VH VL sequences and the nucleotide sequences depicted herein are at least about 60%, and more typically with preferably increasing homologies or identities of at least about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and almost 100%. Thus, a "variant CDR" or a "variant $V_H/V_L$ region" is one with the specified homology, similarity, or identity to the parent CDR/VH/VL defined in the context of the invention, and shares biological function, including, but not limited to, at least about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the specificity and/or activity of the parent CDR or $V_H/V_L$.

In one embodiment, the percentage of identity to human germline of the antibody constructs according to the invention is ≥ about 70% or ≥ about 75%, more preferably ≥ about 80% or ≥ about 85%, even more preferably ≥ about 90%, and most preferably ≥ about 91%, ≥ about 92%, ≥ about 93%, ≥ about 94%, ≥ about 95% or even ≥ about 96%. Identity to human antibody germline gene products is thought to be an important feature to reduce the risk of therapeutic proteins to elicit an immune response against the drug in the patient during treatment. Hwang & Foote ("Immunogenicity of engineered antibodies"; Methods 36 (2005) 3-10) demonstrate that the reduction of non-human portions of drug antibody constructs leads to a decrease of risk to induce anti-drug antibodies in the patients during treatment. By comparing an exhaustive number of clinically evaluated antibody drugs and the respective immunogenicity data, the trend is shown that humanization of the V-regions of antibodies makes the protein less immunogenic (average about 5.1% of patients) than antibodies carrying unaltered non-human V regions (average about 23.59% of patients). A higher degree of identity to human sequences is hence desirable for V-region based protein therapeutics in the form of antibody constructs. For this purpose of determining the germline identity, the V-regions of $V_L$ can be aligned with the amino acid sequences of human germline V segments and J segments (http://vbase.mrc-cpe.cam.ac.uk/) using Vector NTI software and the amino acid sequence calculated by dividing the identical amino acid residues by the total number of amino acid residues of the VL in percent. The same can be for the VH segments (http://vbase.mrc-cpe.cam.ac.uk/) with the exception that the $V_H$ CDR3 may be excluded due to its high diversity and a lack of existing human germline $V_H$ CDR3 alignment partners. Recombinant techniques can then be used to increase sequence identity to human antibody germline genes.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the singular forms "a," "an," and "the," include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and," "or," and "all or any other combination of the elements connected by said term".

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

II. CD16A Antigen-Binding Proteins

In a first aspect the invention provides CD16A antigen-binding proteins for a natural killer (NK) cell-based targeting approach, namely:

A multispecific antigen-binding protein comprising
at least a first target antigen-binding moiety;
at least two CD16A antigen-binding moieties; and
at least one antibody constant domain.

In some embodiments the constant domain is a part of a Fab fragment or a Fc portion.

In some embodiments the CD16A antigen-binding moieties are fused to a constant domain, wherein the constant domain can be a part of a Fab fragment (CH1 or CL) or a Fc portion.

Hence, in a further embodiment the multispecific antigen-binding protein comprises:
at least a first target antigen-binding moiety;
at least two CD16A antigen-binding moieties fused to a constant domain, for example of a Fab fragment or a Fc portion.

This antigen-binding protein engages NK cell to redirect NK cell mediated cytotoxicity towards a target, for example tumor antigen positive cells, virus infected cells or pathogens.

Due to the bivalent binding by two CD16A binding moieties the avidity of NK cell binding strength via CD16A is increased and NK cell effector functions, such as, for example, antibody-dependent cell-mediated cytotoxicity (ADCC) can be enhanced compared to monoclonal antibodies or antibody fragments.

The NK cell is engaged via its CD16A receptor by the multispecific antigen-binding protein and, thereby, redirected towards a target, e.g., tumor associated antigen (TAA) expressing target cell. Thus, such multispecific antigen-binding protein is able to selectively redirect NK cells and mediate lysis to tumor cells, virus infected cells or pathogens. In contrast, full-length antibodies of the IgG isotype bind through their Fc region to activating and inhibitory Fcγ receptors, including CD16A, CD16B (FcγRIIIB), CD32A (FcγRIIA), CD32B (FcγRIIB) and CD64 (FcγRI). However, the antigen-binding protein having specificity for CD16A selectively targets the activating subtype CD16A, which is found i.e. on NK cells and macrophages, but not on neutrophils. Furthermore, the NK cell engaging antigen-binding protein interacts bivalently with CD16A resulting in approximately 1,000-fold higher affinity compared with regular antibodies.

CD16A is an activating receptor triggering the cytotoxic activity of NK cells. The affinity of antibodies for CD16A directly correlates with their ability to trigger NK cell activation. Antigen-binding proteins are provided binding bivalently to CD16A, i.e. with two antigen-binding moieties, thereby increasing affinity due to the higher avidity for CD16A.

Further, serum half-life can be extended compared to scFv-based antigen-binding scaffolds by fusing the antigen-binding moiety to a Fc portion or an IgG-based antibody capable of FcRn binding, which makes therapeutic application in vivo more convenient. Thereby, such Fc portion may be modified for increased or decreased binding to FcRn which further modulates the serum half-life and/or the transport of the bound IgG across cells. The latter also being described as transcytosis (Dickinson et al., 1999).

Further, serum half-life can be extended by fusion of the antigen-binding protein with human serum albumin (HSA) or an HSA binding-moiety. For example, serum half-life of a Fab fragment can be extended by a HSA binding-moiety in the Fv region of the Fab fragment, while CD16A- and target antigen-binding moieties are fused to the C-terminus of the Fab fragment. Alternatively, the HSA binding moiety may be fused to the C-terminus of the Fab fragment and the Fv region of the Fab fragment may provide a target antigen or CD16A binding-moiety.

The antigen-binding moieties can be fused to a Fab fragment or to a Fc portion in many ways and the modular structure of the antigen-binding protein described herein makes numerous scaffolds available which can be readily designed and selected depending on the desired application.

Preferably, the $V_H$ and $V_L$ variable regions are connected by a peptide linker which enables the variable regions to associate in the desired conformation for antigen binding. The polypeptide comprising extra variable domain regions are fused by a connector to a constant domain of a Fab fragment or to a Fc portion.

The antigen-binding moiety is provided by an antigen-binding molecule format comprising one or more Fv polypeptides, for example, a single-chain Fv (scFv), tandem single-chain Fv ((scFv)$_2$) consisting of two scFvs connected in a single polypeptide, diabody (Db), single chain diabody (scDb), tandem diabody (TandAb®), Fab, F(ab')$_2$ or dual affinity retargeting antibodies (DART™). Particularly preferred for the CD16A antigen-binding protein are scFv, Db or scDb. While each scFv provides a single antigen-binding moiety, the bivalent Db, scDb and (scFv)$_2$ provide two antigen-binding moieties to the antigen-binding protein. Preferably, the bivalent Db, scDb or (scFv)$_2$ or two scFvs are monospecific and provide two antigen-binding moieties of the same antigen specificity, i.e. CD16A or target antigen.

Each antigen-binding moiety is joined to a constant domain of a Fab or to a Fc portion by a "connector" or a peptide bond. Preferably, the connector is a peptide. Particularly, the connector is a peptide consisting of a continuous chain of 1 to 30 amino acid residues, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acid residues. More particularly, the connector consists of 3 to 30, 6 to 20, 6 to 18 or 6 to 15 amino acid residues. In some embodiments the connector is composed of G and S amino acid residues, for example the connector is a $(G_2S)_x$ peptide, wherein x=1-10 or $(G_4S)_y$, wherein y=1-6, e.g., a connector having an amino acid sequence as depicted in SEQ ID NOs: 19, 20, 21 or 22.

In certain embodiments an antigen-binding moiety is fused via the Hinge region to the N-terminus of a CH2 domain of a Fc portion. The Hinge region may be of the same or different IgG class as the Fc portion or an engineered, not naturally occurring Hinge domain. An example of an IgG wild-type Hinge region has the amino acid sequence as depicted in SEQ ID NO:23. An example of a modified (shortened) Hinge region (middle.hinge) has the amino acid sequence as depicted in SEQ ID NO:24.

In some embodiments the two CD16A antigen-binding moieties are fused to the N-terminus of the Fc portion, while one or two target antigen binding moieties are fused to the C-terminus of the Fc portion; or the two CD16A antigen-binding moieties are fused to the C-terminus of the Fc portion and the one or two target antigen-binding moieties are fused to the N-terminus of the Fc portion (e.g., KiH-scDb-Fc; FIGS. 3-6; Db-Fc, FIGS. 9-10; Bi-scFv-Fc, FIGS. 11-12 and KiH-scFv-Fc, FIGS. 15A and 15B).

In a further embodiment, the antigen-binding moieties are integrated or fused to an Ig antibody, e.g., IgG. Each of the CD16A antigen-binding moieties may be fused as scFv to the C-terminus of the Fc portion and target antigen-binding moieties integrated into each of the two Fab arms (scFv-IgAb, FIG. 13). Alternatively, each of the CD16A antigen-binding moieties can be integrated as a Fv domain in each of the Fab arms, while one or two target antigen-binding moieties can be fused to the C-terminus of the Fc portion (scFv-IgAb, FIG. 16). In a certain embodiment additional target antigen-binding moieties may be fused to the C-terminus of each of the CL domains (Bi-scFv-IgAb, FIG. 14).

Figure 7:
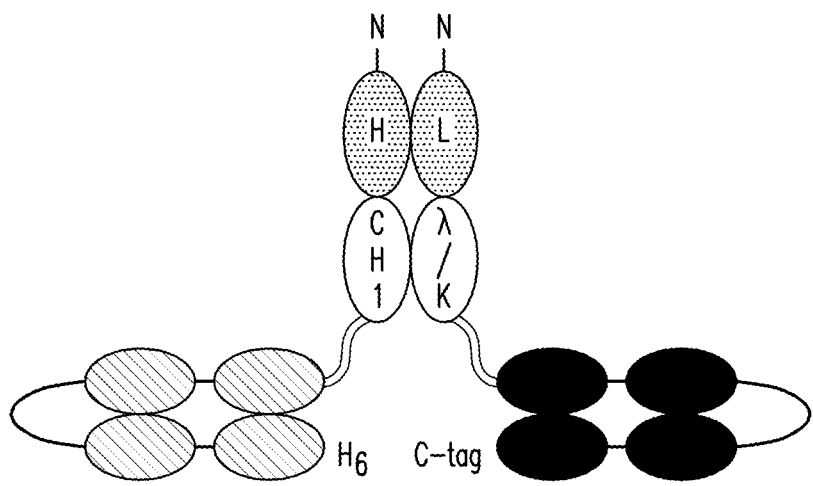
FIGS. 7-8 show a trispecific scDb-TriB antigen-binding protein which is a heterodimeric Fab fragment-scDb fusion comprising CD16A, target and HSA antigen-binding moieties, wherein in FIG. 7 a bivalent scDb consisting of two CD16A antigen-binding moieties is fused to the C-terminus of one of the two polypeptides of the Fab fragment and a bivalent scDb consisting of two target antigen-binding moieties is fused to the C-terminus of the other polypeptide of the Fab fragment and the Fv at the N-terminus of the Fab fragment provides a HSA antigen-binding moiety.
Figure 8:
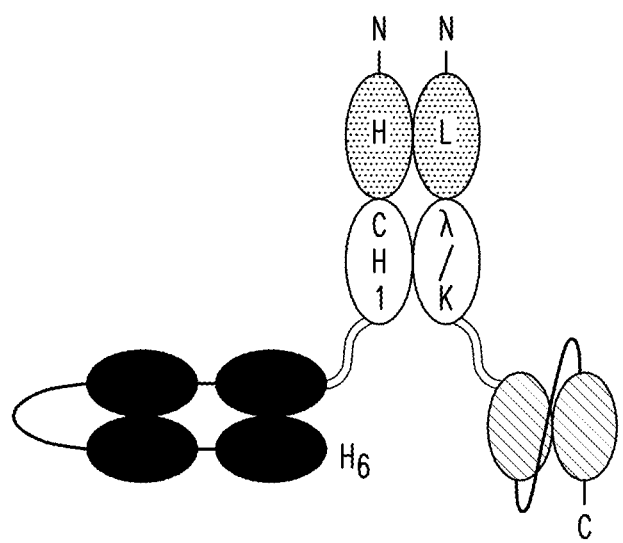

In a further embodiment the two CD16A antigen-binding moieties and the target antigen-moieties are fused to the C-terminus of a Fab, while the Fv domain of the Fab provides a second or third target antigen-binding moiety (scDb-TriBs(-scFv), FIGS. 7 and 8). Alternatively, the two CD16A antigen-binding moieties may be fused to the C-terminus of a Fab and a target antigen-binding moiety is integrated into the Fv domain of the Fab.

The antigen-binding protein is at least bivalent for CD16A, i.e. comprises at least two CD16A antigen-binding moieties.

In some embodiments the antigen-binding protein is tetravalent and bispecific comprising at least two target antigen-binding moieties for the same antigen and two CD16A antigen-binding moieties.

In a further embodiment the antigen-binding moiety is tetravalent and trispecific comprising a first and a second target antigen-binding moiety and wo CD16A antigen-binding moieties. Such antigen-binding protein can be used for co- or dual-targeting. For example, such antigen-binding protein comprises a first tumor antigen-binding moiety (TAA1) and a second tumor antigen-binding moiety (TAA2) and two CD16A antigen-binding moieties for redirecting NK cell cytotoxicity towards a cell displaying the first (TAA1) and second (TAA2) tumor antigens. Alternatively, such trispecific antigen-binding protein comprising a first (TAA1) tumor antigen-binding moiety and a second (TAA2) tumor antigen-binding moiety and two CD16A antigen-binding moieties may be used to redirect NK cell cytotoxicity to phenotypically distinct cell types expressing either the first (TAA1) or the second (TAA2) tumor antigen.

In certain embodiments the antigen-binding protein may be trivalent and bispecific, trivalent and trispecific, tetravalent and bispecific, tetravalent and trispecific, tetravalent and tetraspecific, hexavalent and trispecific or hexavalent and bispecific.

In a second aspect the invention provides particular antigen-binding protein formats with at least two CD16A antigen-binding moieties and a determined anti-CD16A domain arrangement within the polypeptide of the CD16A antigen-binding moiety which prevents NK cell fratricide and enables efficient NK cell binding and recruitment for enhanced immune effector functions, such as, for example, enhanced ADCC.

The CD16A antigen-binding protein is considered as negative for inducing NK-NK lysis, when there is no or only minimal lysis below 10% measurable at antibody concentrations up to 30 µg/mL in assays in which daratumumab induced more than 50% NK lysis.

The effects of preventing NK cell fratricide, while NK cell binding and recruitment for effector functions are enhanced, should be associated with intrinsic properties of the particular 3D structure of the antigen-binding protein described herein.

CD16A engagement at the N-terminus of the antigen-binding proteins disclosed herein (e.g., those described in Example 7) generally resulted less NK cell fratricide than CD16A engagement at the C-terminus. The instant disclosure, however, encompasses antigen-binding proteins engaging CD16A at either the N- or C-terminus (e.g., see Examples 7, 8, and 9 for examples of engagement at either terminus). With respect to N-terminal CD16 engagement in detail, more pronounced NK cell depletion was observed, as disclosed in Example 8, using Fab based CD16A engagement. Moreover, by analyzing the domain order of the CD16 Fv, a clearly reduced occurrence of NK cell fratricide is induced by antibody formats containing the VL-VH domain order, as compared to those containing the VH-VL order.

In certain embodiments, the proportion of NK cell fratricide inducing antibodies as well as the potency of NK cell killing is ameliorated by avoiding Fab-based CD16A engagement and focusing on the beneficial VL-VH order of a CD16 binding Fv domain.

In certain embodiments, the variable regions within the polypeptide of the CD16A antigen-binding moiety have to be linked one after another such that at the N-terminus of the polypeptide, i.e., Fv polypeptide, a light chain variable region ($V_L$) is positioned. The variable region next to the $V_L$ positioned at the N-terminus may be a $V_L$ or a $V_H$. Noteworthy, fratricide can be avoided independent from the binding affinity of the CD16A antigen-binding moiety, if the variable regions of the CD16A antigen-binding moiety are positioned such that a $V_L$ is at the N-terminus of the polypeptide of the CD16A antigen-binding moiety.

Particularly, if the CD16A antigen-binding moiety is a scFv, the variable regions are positioned from the N- to the C-terminus of the polypeptide: $V_L$-$V_H$.

Particularly, if the CD16A antigen-binding moiety is a Db, the variable regions are positioned from the N- to the C-terminus in each of the two polypeptides forming the Db: $V_L$-$V_H$.

Particularly, if the CD16A antigen-binding moiety is a scDb the variable regions are positioned from the N- to the C-terminus of the polypeptide either (i) $V_L$-$V_H$-$V_L$-$V_H$ or (ii) $V_L$-$V_L$-$V_H$-$V_H$, or (iii) $V_H$-$V_H$-$V_L$-$V_L$.

Particularly, if the CD16A antigen-binding moiety is a (scFv)$_2$ the variable regions are positioned from the N- to the C-terminus of the polypeptide: $V_L$-$V_H$-$V_L$-$V_H$ This polypeptide of the CD16A antigen-binding moiety, e.g., scFv, Db or scDb, is fused via connectors either (i) by its C-terminus to the N-terminus of a CH2 domain of a Fc portion or to a Hinge/middle Hinge region, or (ii) by its N-terminus to the C-terminus of a CH3 domain of a Fc portion or to the C-terminus of a CL or a CH1 domain.

Preferably, both CD16A antigen-binding moieties are positioned in the antigen-binding protein either N-terminally or C-terminally.

In some embodiments the CD16A antigen-binding moiety is fused to a Fc portion. Preferably, both CD16A binding-moieties are fused either N-terminally or C-terminally to the Fc portion. The Fc portion contains a portion of the constant region retaining at least one functionality of an IgG Fc region. "Fc portion" includes native sequence Fc regions and variant Fc regions.

Preferably, the Fc portion is "silenced". "Silenced Fc portion" refers to a modified Fc portion which does per se not bind to Fc-gamma receptor (Fcγ) Receptors (FcγRs) including CD16A (FcγRIIIA), but retains binding to the neonatal Fc receptor (FcRn). FcRn binding enables transcytosis across epithelial barriers and recycling to protect IgGs or fusion proteins containing FcRn binding Fc portions from lysosomal degradation resulting in extended serum half-life and longer persistence in the circulation. The antigen-binding protein is designed to engage CD16A on NK cells specifically via the CD16A antigen-binding moieties and, thus, in preferred embodiments Fc binding to other Fc-gamma receptors should be prevented. Hence, modifications in the Fc portion of Fc-fusion antigen-binding proteins which retain or enhance FcRn binding are preferred.

Several sets of mutations or changes to generate an IgG1 Fc portion with reduced or no binding to Fc-gamma receptor (referred to as "silencing mutations" or "effector-less mutations") have been described which are selected from the mutations of the group consisting of: C220S, C229S, E233P, L234A, L234V, L234F, L235A, L235E, P238S, D265A, N297A, N297Q, P331S; or mutations for generating an IgG2 Fc portion with reduced binding to Fc-gamma receptor which can be selected from the group consisting of: H268Q, V309L, A330S, A331S or mutations for generating an IgG4 Fc portion with reduced binding to Fc-gamma receptor which can be selected from the group consisting of: L235A, G237A, E318A (Strohl W., *Current Opinion in Biotechnology* (2009); 20:1-7; Kaneko E and Niwa R, *Biodrugs* (2011); 25(1):1-11; Baudino L., *J. Immunology* (2008); 181:6664-6669).

Further, the Fc portion may be engineered to modulate serum half-life, e.g., increase or decrease. The following mutations in the IgG1 Fc portion that increase serum half-life of the antigen-binding protein have been described: T250Q, M252Y, S254T, T256E, T307A, E380A, M428L, H433K, N434A, N434Y (Srohl W., Current Opinion in Biotechnology (2009); 20:1-7; Borrok M J, et al., J. Pharmaceutical Sciences 2017; 106(4):1008-1017).

In some embodiments the IgG, in particular IgG1, Fc portion comprises a set of mutations at positions 234, 235 and 265 according to the Kabat EU numbering, in particular the set of mutations is selected from L234F/V/A, L235A/E and D265A. Particularly preferred is an IgG1 Fc portion comprising the set of mutations L234F, L235E and D265A. Accordingly, in some embodiments the antigen-binding protein comprises a silenced IgG1 Fc portion with the set of mutations L234F, L235E and D265A. All recited mutations correspond to the Kabat EU numbering system (Kabat, E. A. et al., Sequences of proteins of immunological interest. 5th Edition—US Department of Health and Human Services, NIH publication n° 91-3242, pp 662,680,689 (1991). In certain embodiments the antigen-binding protein comprises a silenced IgG1 Fc portion with the set of mutations L234F and L235E.

In some embodiments the CD16A antigen-binding moiety is fused to a homodimeric Fc portion comprising two identical CH2-CH3 polypeptides assembled with one another, wherein the covalent dimerization is promoted by the Hinge region N-terminal to the CH2 domain.

The antigen-binding moiety can be fused either N-terminally via the Hinge region to the Fc portion or C-terminally to a CH3 domain. When the CD16A antigen-binding moieties are N-terminally fused, the first target antigen-binding moiety is preferably fused C-terminally to the Fc region.

Figure 9:
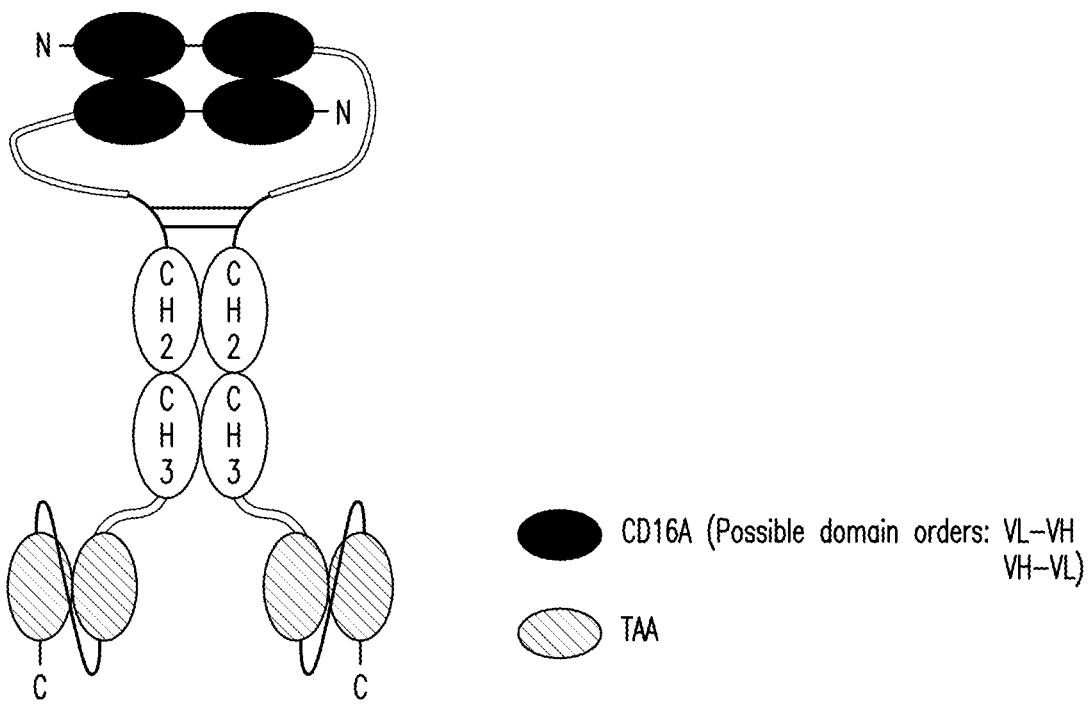
FIGS. 9-10 show a Db-Fc antigen-binding protein which is homodimeric and comprises a bivalent CD16A antigen-binding moiety in the format of a Db fused to the middle Hinge at the N-terminus or to the C-terminus of a homodimeric Fc portion and two target antigen-binding moieties in the format of scFvs, wherein in FIG. 9 the scFv are fused to the C-terminus of the homodimerizing CH2-CH3 polypeptide and the polypeptides comprising the Db are fused to the middle Hinge at the N-terminus of a CH2-CH3 polypeptide, wherein the two polypeptides of the Db non-covalently associate to a Db comprising two CD16A antigen-binding moieties. The target is a tumor associated target, and in FIG. 10 the scFv target antigen-binding moieties are fused to the middle Hinge at the N-terminus of the homodimerizing CH2-CH3 polypeptide and the polypeptides comprising the Db comprising two CD16A antigen-binding moieties is fused to the C-terminus of the Fc homodimer. The target is a tumor associated target.
Figure 10:
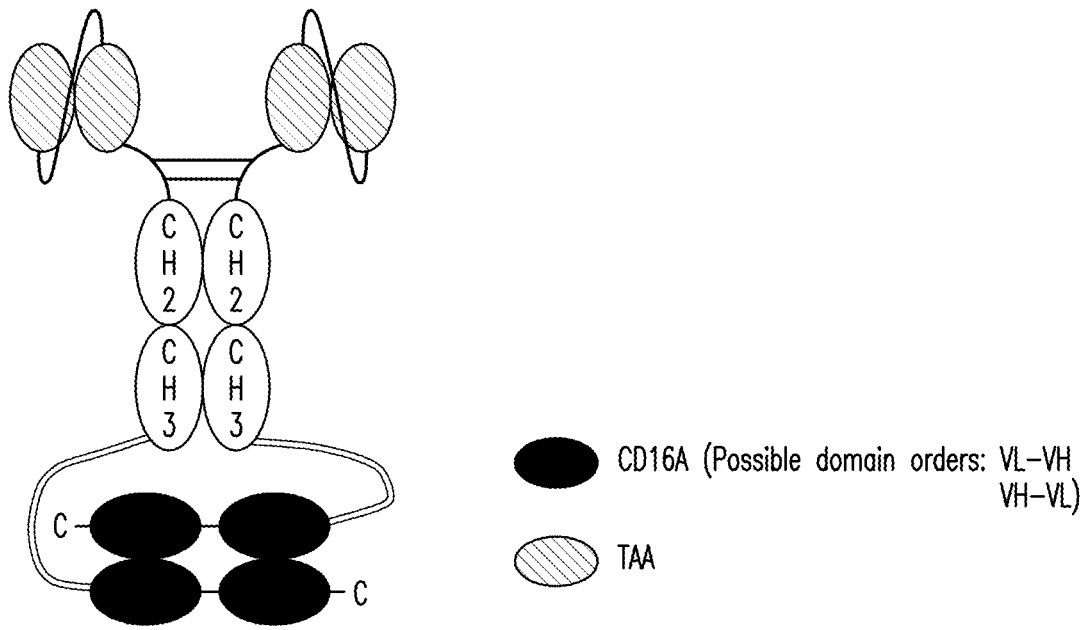

In a particular embodiment the two CD16A antigen-binding moieties are fused such that a Db is formed at the N-terminus or C-terminus of the Fc portion (Db-Fc) by dimerization, wherein a CD16A antigen-binding VL-VH-polypeptide is fused via connector and Hinge-region to a CH2-CH3 polypeptide at the N-terminus or to the C-terminus of CH3 and target antigen-binding moieties are fused as scFv to the respective opposite terminus (FIGS. 9, 10). Preferably, the Hinge is a middle.hinge (SEQ ID NO: 24). For example, such antigen-binding protein comprises two polypeptide chains dimerized in the Fc region, wherein each polypeptide chain comprises from the N- to the C-terminus:
(i) $V_L$(CD16A)-$V_H$(CD16A)-Hinge-CH2-CH3-$V_H$(target)-$V_L$(target) (FIG. 9);
(ii) $V_L$(CD16A)-$V_H$(CD16A)-Hinge-CH2-CH3-$V_L$(target)-$V_H$(target) (FIG. 9);
(iii) $V_L$(target)-$V_H$(target)-Hinge-CH2-CH3-$V_L$(CD16A)-$V_H$(CD16A) (FIG. 10; or
(iv) $V_H$(target)-$V_L$(target)-Hinge-CH2-CH3-$V_L$(CD16A)-$V_H$(CD16A) (FIG. 10).

Figure 11:
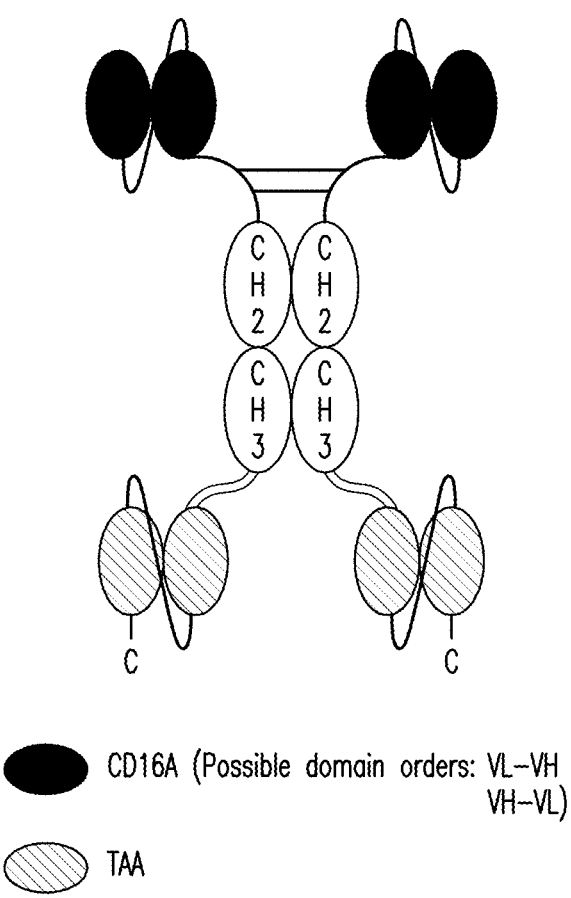
FIGS. 11-12 show a B1-scFv-Fc antigen-binding protein which is homodimeric and tetravalent comprising two CD16A antigen-binding moieties and two target antigen-binding moieties, each in the format of a scFv, fused to a Fc homodimer, wherein in FIG. 11 two CD16A antigen-binding scFv fused to a Hinge at the N-terminus of one of the CH2-CH3 polypeptides and two target antigen-binding scFv are fused to the C-terminus of the CH2-CH3 polypeptides; and in FIG. 12 the CD16A antigen-binding moieties are scFv C-terminally fused to the Fc homodimer, while the target antigen-binding scFv are fused to the Hinge at the N-terminus of the Fc homodimer. The target is a tumor associated target.
Figure 12:
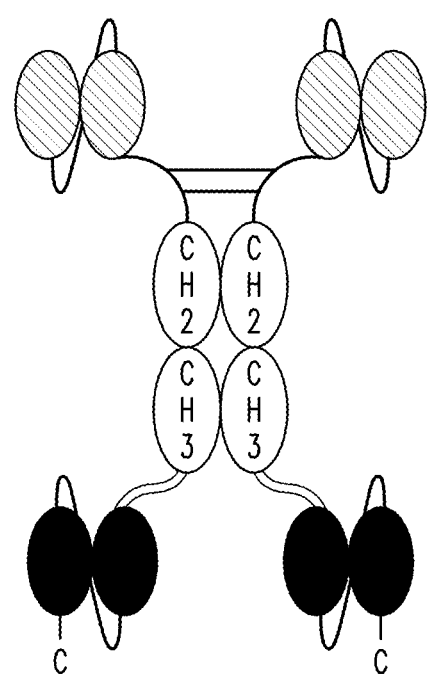

In another embodiment the two CD16A antigen-binding moieties are fused as scFvs to the Fc portion (Bi-scFv-Fc), wherein scFvs of a first specificity (target- or CD16A-binding) are fused to one terminus of the CH2-CH3 polypeptide and scFvs of the second specificity (CD16A- or target-binding) are fused to the other terminus of the CH2-CH3 polypeptide forming the dimeric Fc portion. Thereby, each of the two target antigen-binding moieties are fused as scFv to the respective opposite terminus of each of the two CH2-CH3 polypeptides (FIGS. 11, 12). For example, such antigen-binding protein comprises two polypeptide chains homodimerizing in the Hinge and Fc region, wherein each polypeptide chain comprises a scFv at the N-terminus and at the C-terminus each of the CH2-CH3 polypeptide and the domains are positioned from the N- to the C-terminus:
(i) $V_L$(CD16A)-$V_H$(CD16A)-Hinge-CH2-CH3-$V_H$(target)-$V_L$(target) (FIG. 11);
(ii) $V_L$(CD16A)-$V_H$(CD16A)-Hinge-CH2-CH3-$V_L$(target)-$V_H$(target) (FIG. 11);
(iii) $V_L$(target)-$V_H$(target)-Hinge-CH2-CH3-$V_L$(CD16A)-$V_H$(CD16A) (FIG. 12; or
(iv) $V_H$(target)-$V_L$(target)-Hinge-CH2-CH3-$V_L$(CD16A)-$V_H$(CD16A) (FIG. 12).

In some embodiments the CD16A antigen-binding moiety is fused to a heterodimeric (asymmetric) Fc portion. Such heterodimeric Fc portion comprises modifications of each of the two CH2-CH3 polypeptides of the Fc region that promote (hetero)dimerization of the two polypeptides. These include separate modifications in each of the polypeptides which are complementary to each other to promote assembling of the two CH2-CH3 polypeptides. The modifications may be nucleic acid mutations, being translated into amino acid substitution. Such modifications are known as "knobs-into-holes" (KiH) and construction of a number of variants has been described, for example by Ridgway et al. (Protein Engineering, vol. 9, no.7, pp. 617-621, 1996): For example, the substitution T366Y in one CH2-CH3 polypeptide and the substitution Y407T in the other polypeptide according to the EU numbering system (Kabat et al., Sequences of Proteins of Immunological Interest, 5$^{th}$ edn. NIH, 1991). An example for a Fc portion containing knobs-into-holes substitutions T366Y in a first IgG1 CH2-CH3 polypeptide and the Y407T substitution in a second IgG1 CH2-CH3 polypeptide has the amino acid sequences as depicted in SEQ ID NOs:31,32. In addition, further strategies to generate complementary interfaces promoting heterodimerization have been developed (reviewed in Brinkmann and Kontermann, MABS 2017; 9(2):182-212). In a further embodiment, a disulfide bridge may be incorporated to further stabilize the heterodimer and increase the yield (Merchant et al., Nature Biotech. 1998; 16: 677-681; Atwell et al.; J. Mol. Biol. 270 (1997) 26-35).

Figure 3:
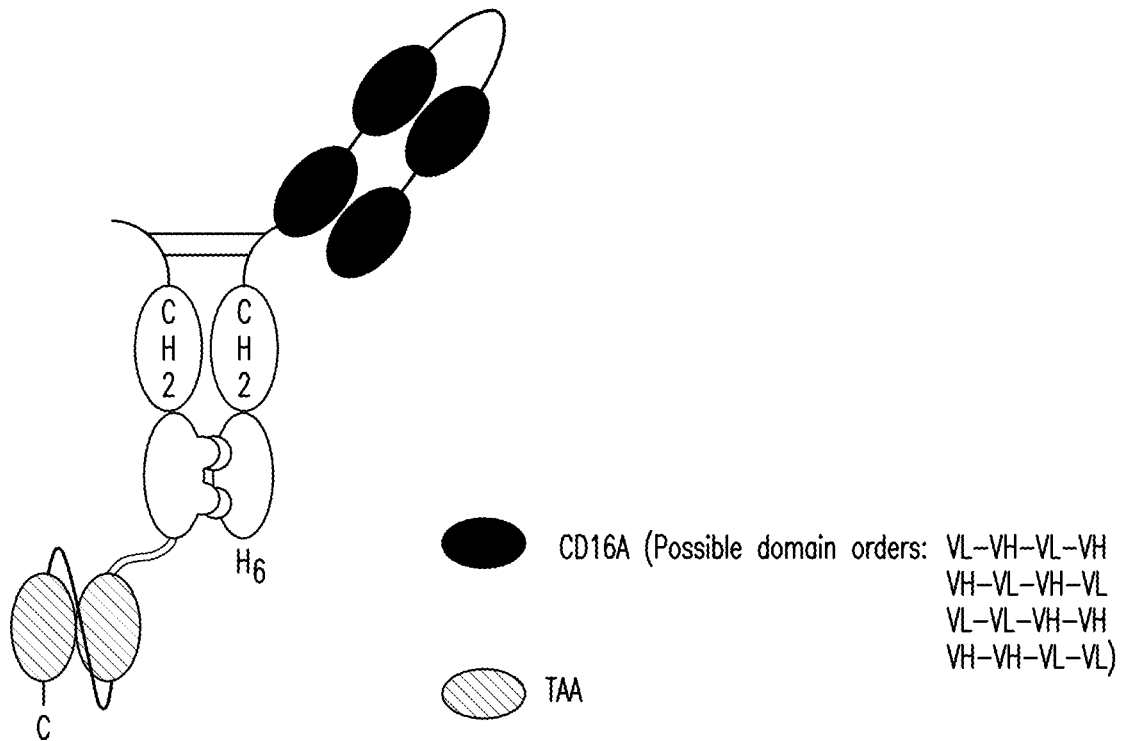
FIGS. 3-6 show KiH-scDb-Fc antigen-binding proteins which are heterodimeric and comprise a bivalent CD16A antigen-binding moiety in the format of a scDb fused to a heterodimeric (KiH) Fc portion, wherein in FIG. 3 the scDb consisting of two CD16A antigen-binding moieties is fused to the Hinge or middle Hinge at the N-terminus of the Fc portion which consists of a CH2-CH3 heterodimer and a scFv comprising a single target antigen-binding moiety is fused to the C-terminus of the Fc portion.
Figure 4:
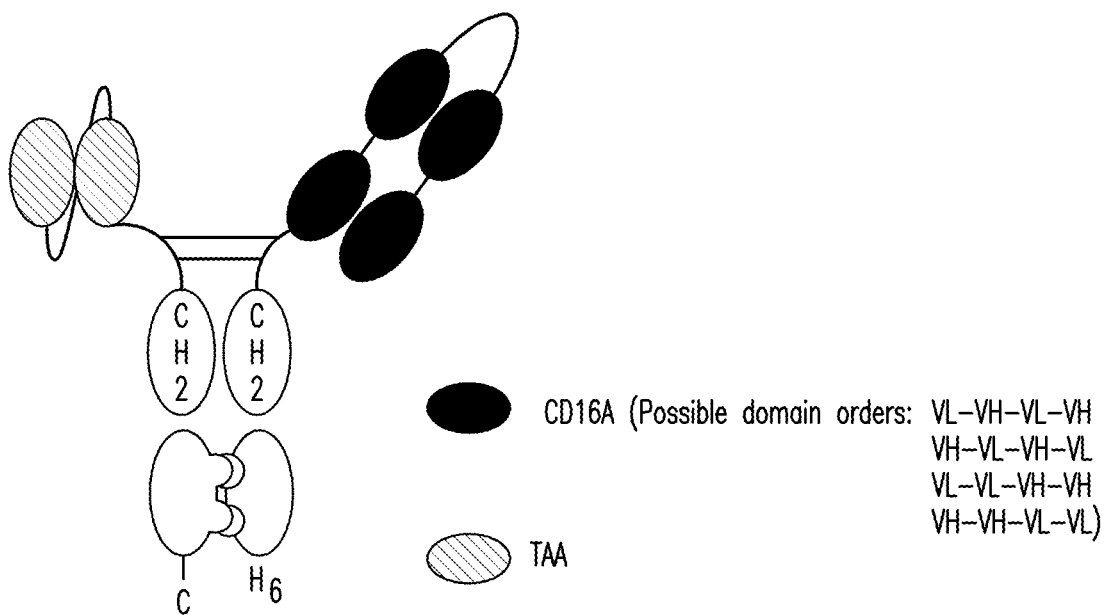
Figure 5:
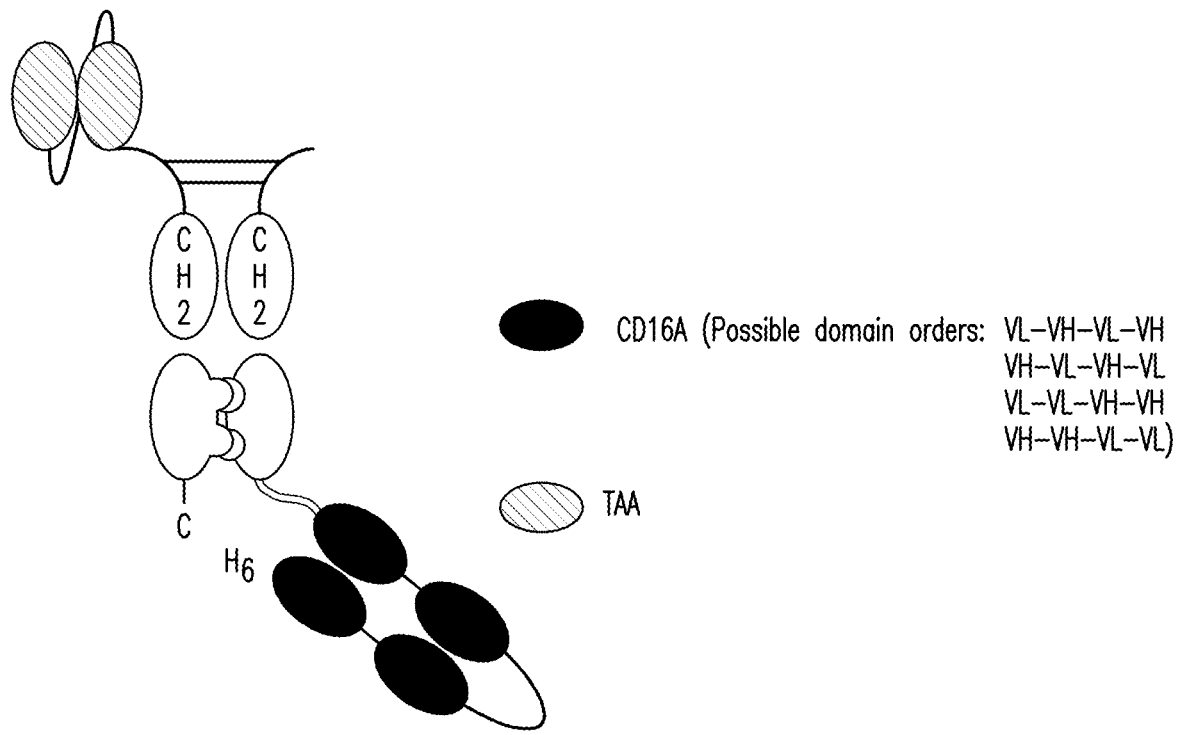

In a particular embodiment two CD16A antigen-binding moieties are fused as a scDb to the heterodimeric Fc portion (KiH-scDb-Fc), wherein the single polypeptide of the scDb is fused to a first CH2-CH3 polypeptide and a single target antigen-binding moiety is fused as a scFv to the respective opposite terminus of the same or the second CH2-CH3 polypeptide (FIGS. 3, 5). For example, such antigen-binding protein comprises two polypeptide chains heterodimerized in the middle. Hinge or Hinge and Fc region, wherein a first polypeptide chain comprises from the N- to the C-terminus: $V_L$(CD16A)-$V_H$(CD16A)-$V_L$(CD16A)-$V_H$(CD16A)-Hinge-CH2-CH3 or $V_L$(CD16A)-$V_L$(CD16A)-$V_H$(CD16A)-$V_H$(CD16A)-Hinge-CH2-CH3 and the second polypeptide comprises from the N- to the C-terminus: Hinge-CH2-CH3-$V_H$(target)-$V_L$(target) or Hinge-CH2-CH3-$V_L$(target)-$V_H$(target) (FIG. 3); or a first polypeptide chain comprises from the N- to the C-terminus: Hinge-CH2-CH3-$V_L$(CD16A)-$V_H$(CD16A)-$V_L$(CD16A)-$V_H$(CD16A) or Hinge-CH2-CH3-$V_L$(CD16A)-$V_L$(CD16A)-$V_H$(CD16A)-$V_H$(CD16A) and the second polypeptide comprises from the N- to the C-terminus: $V_H$(target)-$V_L$(target)-Hinge-CH2-CH3 or $V_L$(target)-$V_H$(target)-Hinge-CH2-CH3 (FIG. 5); or the single polypeptide of the scDb is fused to a first CH2-CH3 polypeptide and a single target antigen-binding moieties is fused as a scFv to the same terminus of the second CH2-CH3 polypeptide (FIG. 4). For example, such antigen-binding protein comprises two polypeptide chains, wherein a first polypeptide chain comprises from the N- to the C-terminus: $V_L$(CD16A)-$V_H$(CD16A)-$V_L$ (CD16A)-V$_H$(CD16A)-Hinge-CH2-CH3 or V$_L$(CD16A)-V$_L$(CD16A)-V$_H$(CD16A)-V$_H$(CD16A)-Hinge-CH2-CH3 and the second polypeptide comprises from the N- to the C-terminus: V$_H$(target)-V$_L$(target)-Hinge-CH2-CH3 or V$_L$(target)-V$_H$(target)-Hinge-CH2-CH3 (FIG. 4).

Figure 6:
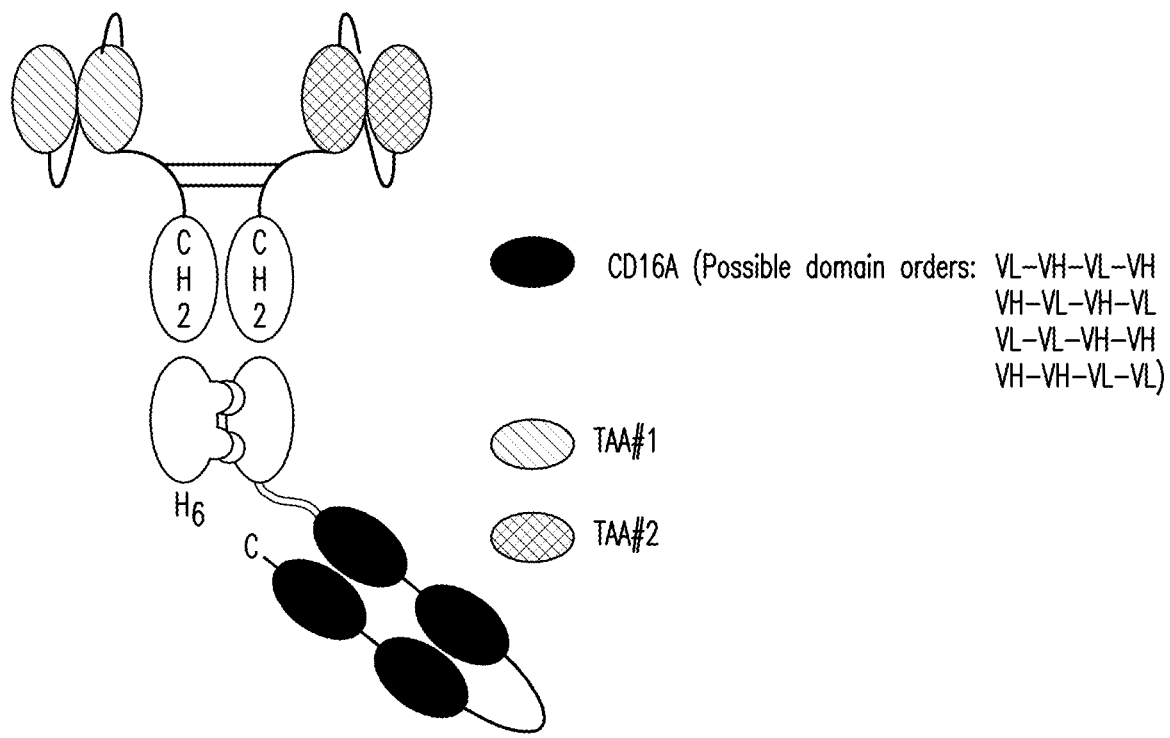

In another embodiment the two CD16A antigen-binding moieties are fused as a scDb to the heterodimeric Fc portion and the single polypeptide of the scDb is fused to a first CH2-CH3 polypeptide and a single first target antigen-binding moiety (TAA1) is fused as a scFv to the respective opposite terminus of this first CH2-CH3 polypeptide and a second target antigen-binding moiety (TAA2) is fused as a scFv to a second CH2-CH3 polypeptide at the same terminus as the first target antigen-binding moiety (FIG. 6). For example, such antigen-binding protein comprises two polypeptide chains heterodimerizing in the Hinge or middle hinge and the Fc region, wherein a first polypeptide chain comprises from the N- to the C-terminus: V$_H$(target1)-V$_L$(target1)-Hinge-CH2-CH3-V$_L$(CD16A)-V$_H$(CD16A)-V$_L$(CD16A)-V$_H$(CD16A)) or V$_H$(target1)-V$_L$(target1)-Hinge-CH2-CH3-V$_L$(CD16A)-V$_L$(CD16A)-V$_H$(CD16A)-V$_H$(CD16A) or V$_L$(target1)-V$_H$(target1)-Hinge-CH2-CH3-V$_L$(CD16A)-V$_H$(CD16A)-V$_L$(CD16A)-V$_H$(CD16A) or V$_L$(target1)-V$_H$(target1)-Hinge-CH2-CH3-V$_L$(CD16A)-V$_L$(CD16A)-V$_H$(CD16A)-V$_H$(CD16A) and the second polypeptide comprises from the N- to the C-terminus: V$_H$(target2)-V$_L$(target2)-Hinge-CH2-CH3 or V$_L$(target2)-V$_H$(target2)-Hinge-CH2-CH3 (FIG. 6).

Figure 15A:
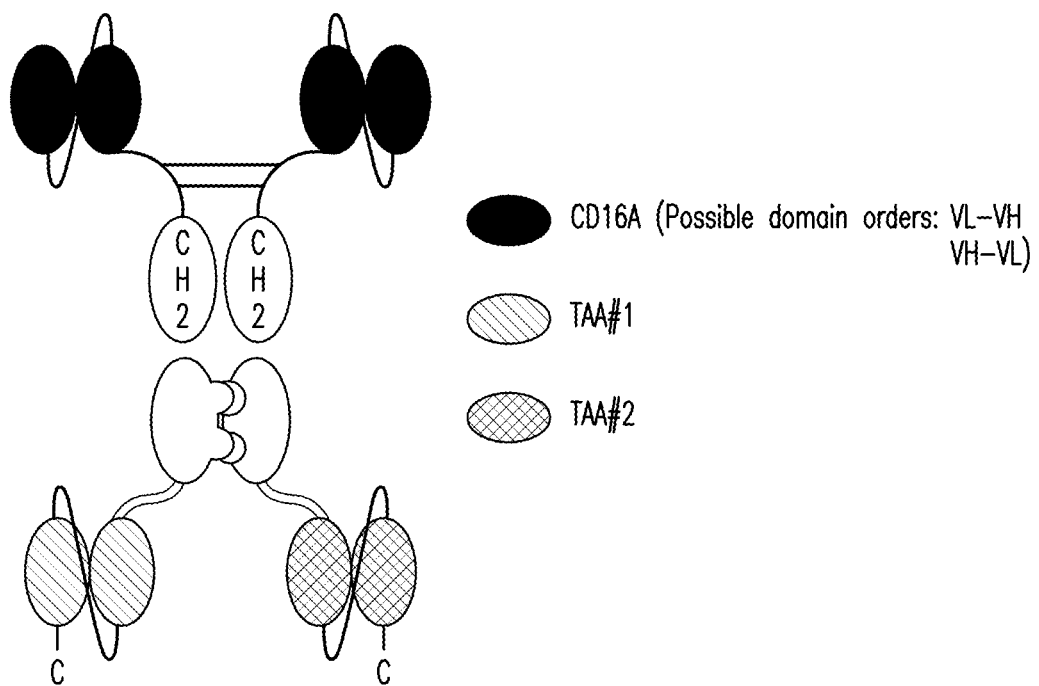
FIGS. 15A and 15B show a KiH-scFv-Fc antigen-binding protein wherein four antigen-binding scFvs are fused to a heterodimeric (KiH) Fc portion, wherein two CD16A antigen-binding moieties are fused either N- or C-terminally to the Fc portion.
Figure 15B:
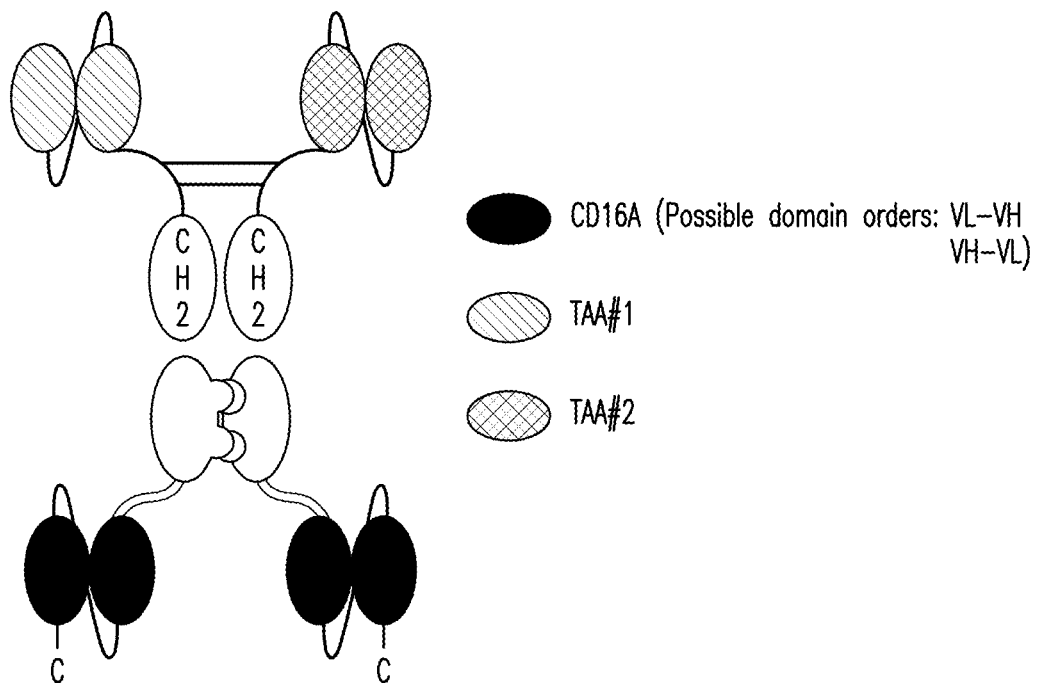

In a further embodiment the two CD16A antigen-binding moieties are each fused as a scFv to the heterodimeric Fc portion (KiH-scFv-Fc) and each of the two scFvs is fused to one of the first and second CH2-CH3 polypeptides and a single first target antigen-binding moiety (TAA1) is fused as a scFv to the respective opposite terminus of a first CH2-CH3 polypeptide and a second target antigen-binding moiety (TAA2) is fused as a scFv to a second CH2-CH3 polypeptide at the same terminus as the first target antigen-binding moiety (FIG. 15). For example, such antigen-binding protein comprises two polypeptide chains heterodimerized in the Fc region, wherein a first polypeptide chain comprises from the N- to the C-terminus: V$_H$(target1)-V$_L$(target1)-Hinge-CH2-CH3-V$_L$(CD16A)-V$_H$(CD16A) or V$_L$(target1)-V$_H$(target1)-Hinge-CH2-CH3-V$_L$(CD16A)-V$_H$(CD16A) and the second polypeptide comprises from the N- to the C-terminus: V$_H$(target2)-V$_L$(target2)-Hinge-CH2-CH3-V$_L$(CD16A)-V$_H$(CD16A) or V$_L$(target2)-V$_H$(target2)-Hinge-CH2-CH3-V$_L$(CD16A)-V$_H$(CD16A) (FIG. 15b); alternatively, such antigen-binding protein comprises two polypeptide chains heterodimerized in the Fc region, wherein a first polypeptide chain comprises from the N- to the C-terminus: V$_L$(CD16A)-V$_H$(CD16A)-Hinge-CH2-CH3-V$_H$(target1)-V$_L$(target1) or V$_L$(CD16A)-V$_H$(CD16A)-Hinge-CH2-CH3-V$_L$(target1)-V$_H$(target1) and the second polypeptide comprises from the N- to the C-terminus: V$_L$(CD16A)-V$_H$(CD16A)-Hinge-CH2-CH3-V$_H$(target2)-V$_L$(target2) or V$_L$(CD16A)-V$_H$(CD16A)-Hinge-CH2-CH3-V$_L$(target2)-V$_H$(target2) (FIG. 15a).

Figure 2:
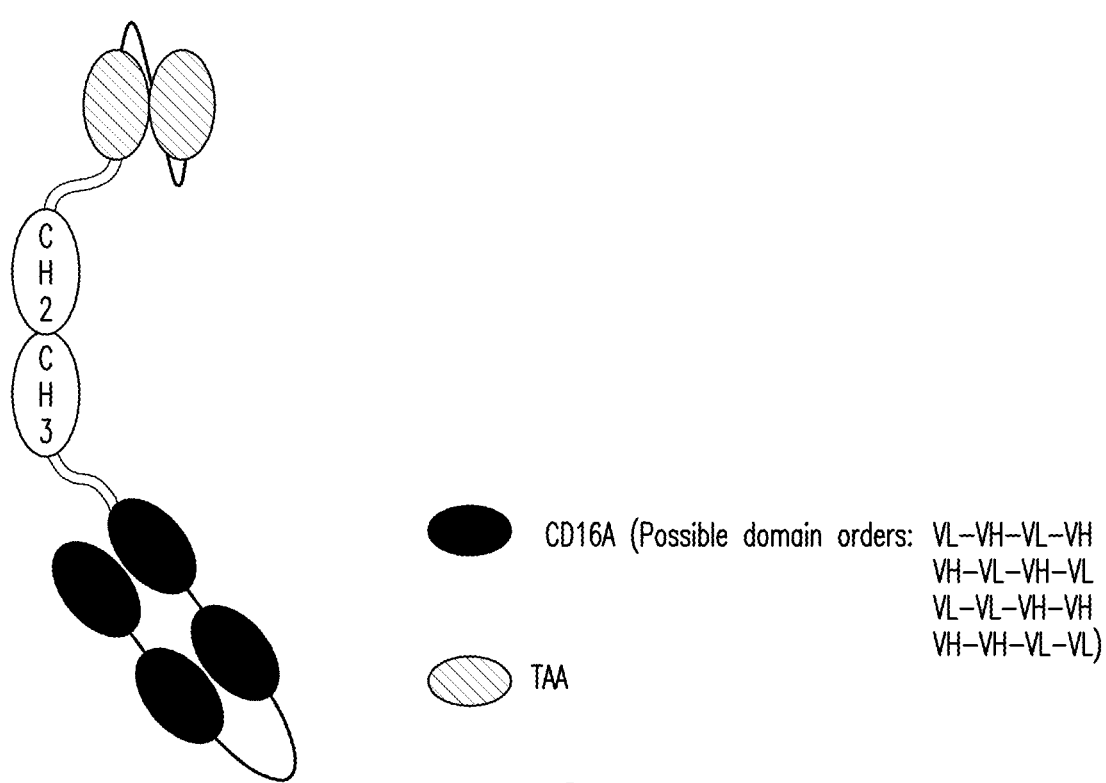

In a further embodiment the two CD16A antigen-binding moieties are fused as a scDb to a monomeric Fc portion (scDb-mFc, FIGS. 1, 2). Such monomeric Fc portion (mFc) contains mutations in the CH3 domain that prevent dimerization with another CH2-CH3 polypeptide and lacks a Hinge region, but retains binding to the FcRn receptor and does not bind to other Fc-gammaR. Such mutations are described in Ying et al. (MABS, 2014; 6(5):1201-1210; or WO 2013/138643). An example for such a monomeric Fc portion has the amino acid sequence as depicted in SEQ ID NO:30. Such antigen-binding protein consists of a single polypeptide chain, wherein a scDb comprising the two CD16A antigen-binding moieties is fused to one terminus of the monomeric Fc portion and the target antigen-binding moiety is fused to the other terminus of the monomeric Fc portion. Such antigen-binding protein consists of a single polypeptide chain comprising from the N- to the C-terminus: V$_L$(CD16A)-V$_H$(CD16A)-V$_L$(CD16A)-V$_H$(CD16A)-CH2-CH3-V$_H$(target)-V$_L$(target) or V$_L$(CD16A)-V$_H$(CD16A)-V$_L$(CD16A)-V$_H$(CD16A)-CH2-CH3-V$_L$(target)-V$_H$(target), or V$_L$(CD16A)-V$_L$(CD16A)-V$_H$(CD16A)-V$_H$(CD16A)-CH2-CH3-V$_H$(target)-V$_L$(target), or V$_L$(CD16A)-V$_L$(CD16A)-V$_H$(CD16A)-V$_H$(CD16A)-CH2-CH3-V$_L$(target)-V$_H$(target) (FIG. 1), or V$_H$(target)-V$_L$(target)-CH2-CH3-V$_L$(CD16A)-V$_H$(CD16A)-V$_L$(CD16A)-V$_H$(CD16A), or V$_L$(target)-V$_H$(target)-CH2-CH3-V$_L$(CD16A)-V$_H$(CD16A)-V$_L$(CD16A)-V$_H$(CD16A), or V$_H$(target)-V$_L$(target)-CH2-CH3-V$_L$(CD16A)-V$_L$(CD16A)-V$_H$(CD16A)-V$_H$(CD16A), or V$_L$(target)-V$_H$(target)-CH2-CH3-V$_L$(CD16A)-V$_L$(CD16A)-V$_H$(CD16A)-V$_H$(CD16A) (FIG. 2).

In other embodiments the N-terminus of the polypeptide of the antigen-binding moiety is fused to a C-terminus of a Fab fragment. For example, a Db, scDb or two scFvs comprising the two CD16A antigen-binding moieties are fused to the C-terminus of the Fab fragment and the Fv of the Fab fragment comprises the target antigen-binding moiety.

In other embodiments the antigen-binding protein is trispecific (scDb-TriBs(-scFv), wherein a scDb comprising the two CD16A antigen-binding moieties is fused C-terminally to a first of the two polypeptides of the Fab fragment and a first target antigen-binding moiety (TAA1) is fused C-terminally either as a scFv or as a bivalent scDb to a second polypeptide of the Fab fragment and the Fv of the Fab fragment provides a second target antigen-binding moiety (TAA2). In a particular embodiment the second target antigen-binding moiety of the Fv is a human serum albumin (HSA) antigen-binding moiety. Such antigen-binding protein comprises two polypeptide chains heterodimerized to a Fab fragment-fusion with two scDbs fused C-terminally to the Fab, wherein a first polypeptide chain comprises from the N- to the C-terminus: V$_L$(HSA)-CL-V$_L$(CD16A)-V$_H$(CD16A)-V$_L$(CD16A)-V$_H$(CD16A) the second polypeptide comprises from the N- to the C-terminus: V$_H$(HSA)-CH1-V$_H$(target1)-V$_L$(target1)-V$_H$(target1)-V$_L$(target1) (FIG. 7). In another embodiment a scDb comprising the two CD16A antigen-binding moieties and a scFv comprising the first target antigen-binding moiety are fused C-terminally to the Fab fragment, wherein a first polypeptide chain comprises from the N- to the C-terminus: V$_L$(HSA)-CL-V$_H$(target1)-V$_L$(target1) and the second polypeptide comprises from the N- to the C-terminus: V$_H$(HSA)-CH1-V$_L$(CD16A)-V$_H$(CD16A)-V$_L$(CD16A)-V$_H$(CD16A) (FIG. 8).

Figure 13:
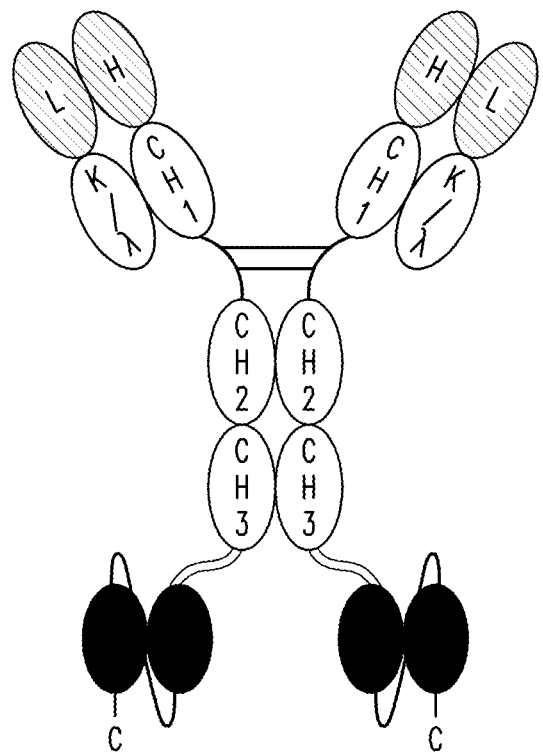
FIG. 13 shows a scFv-IgAb antigen-binding protein which comprises an IgG antibody-fusion with two CD16A antigen-binding moieties in the format of scFvs fused to the C-terminus of the H chain, whereas two target antigen-binding moieties are provided by each Fv in the Fab arms of the IgG. The target is a tumor associated target.

In a further embodiment the two CD16A antigen-binding moieties are fused C-terminally to an IgG, wherein the two Fab arms of the IgG provide two further antigen-binding moieties (scFv-IgAb, FIG. 13). In such an antigen-binding protein a first scFv comprising a CD16A antigen-binding moiety is fused C-terminally to a CH3 of a first H chain and a second scFv comprising a CD16A antigen-binding moiety is fused to a CH3 of a second H chain and the two Fab arms provide target antigen-binding moieties with each Fv. Both Fv's can have the same target antigen-binding moiety or the two Fv's may provide a first and a second target antigen-binding moiety. For example, such antigen-binding protein comprises two identical H and two identical L chains, wherein the H chain comprises from the N- to the C-terminus: V$_H$(target)-CH1-Hinge-CH2-CH3-V$_L$(CD16A)-V$_H$(CD16A) and the L chain comprises from the N- to the C-terminus: V$_L$(target)-CL (FIG. 13).

Alternatively, a scFv-IgAb the two CD16A antigen-binding moieties are provided by the two Fv's of the Fab arms of the IgG and one or two further antigen-binding moieties are fused C-terminally to the IgG. In such an antigen-binding protein each of the two Fab arms provide a CD16A antigen-binding moiety with each Fv and a first scFv comprising a target antigen-binding moiety is fused C-terminally to a CH3 of a first H chain and, optionally, a second scFv comprising a further first or a second target antigen-binding moiety is fused to a CH3 of a second H chain. For example, such antigen-binding protein comprises two identical H and two identical L chains, wherein the H chain comprises from the N- to the C-terminus: V$_H$(CD16A)-CH1-Hinge-CH2-CH3-V$_L$(target)-V$_H$(target) and the L chain comprises from the N- to the C-terminus: V$_L$(CD16A)-CL (FIG. 16) or the H chain comprises from the N- to the C-terminus: V$_H$(CD16A)-CH1-Hinge-CH2-CH3-V$_H$(target)-V$_L$(target) and the L chain comprises from the N- to the C-terminus: V$_L$(CD16A)-CL.

Figure 14:
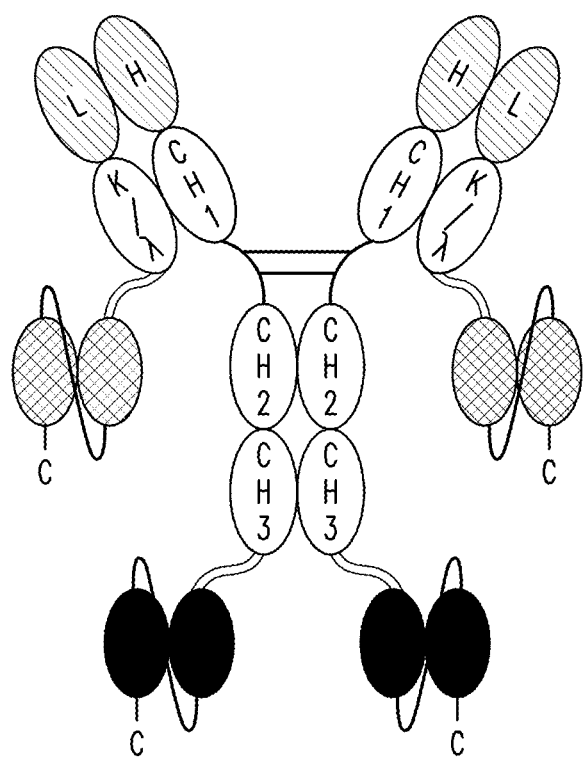
FIG. 14 shows a Bi-scFv-IgAb antigen-binding protein which comprises an IgG antibody-fusion with four scFv antigen-binding moieties fused thereto, wherein each of two CD16A antigen-binding moieties in the format of scFv are fused to the C-terminus of the H chains, whereas two antigen-binding moieties binding to the first target are provided by each Fv in the Fab arms of the IgG and each of the two antigen-binding moieties binding to the second target is fused to the C-terminus of the two CL chains.

In a further embodiment the two CD16A antigen-binding moieties are fused C-terminally to an IgG, the two Fab arms of the IgG provide two first target antigen-binding moieties (TAA1) and a further scFv second target antigen-binding moiety (TAA2) is fused C-terminally to each of the two CL domains (Bi-scFv-IgAb, FIG. 14). In such an antigen-binding protein a first scFv comprising a CD16A antigen-binding moiety is fused C-terminally to a CH3 of a first H chain and a second scFv comprising a CD16A antigen-binding moiety is fused to a CH3 of a second H chain, the two Fab arms provide a first target antigen-binding moiety (TAA1) with each Fv and two further second target antigen-binding moieties (TAA2) are provided by each of the scFv second target antigen-binding moiety fused to each of the CL domains. For example, such antigen-binding protein comprises two identical H and two identical L chains, wherein the H chain comprises from the N- to the C-terminus: V$_H$(target1)-CH1-Hinge-CH2-CH3-V$_L$(CD16A)-V$_H$(CD16A) and the L chain comprises from the N- to the C-terminus: V$_L$(target1)-CL-V$_L$(target2)-V$_H$(target2) or V$_L$(target1)-CL-V$_H$(target2)-V$_L$(target2)(FIG. 14).

According to the invention the multispecific antigen-binding protein comprises CD16A antigen-binding moieties specifically binding to CD16A and at least a target antigen (TA) different from CD16A.

In some embodiments, the CD16A binding moiety binds to human and cynomolgus CD16A.

In some embodiments, the CD16A antigen-binding moiety comprises a heavy and a light chain variable domain specific for CD16A, wherein (i) the heavy chain variable domain (V$_H$) specific for CD16A comprises a heavy chain CDR1 having the amino acid sequence set forth in SEQ ID NO:50; a heavy chain CDR2 having the amino acid sequence set forth in SEQ ID NO:51 or SEQ ID NO:56; a heavy chain CDR3 having the amino acid sequence set forth in SEQ ID NO:52 and the light chain variable domain (VL) specific for CD16A comprises a light chain CDR1 having the amino acid sequence set forth in SEQ ID NO:53; a light chain CDR2 having the amino acid sequence set forth in SEQ ID NO:54; and a light chain CDR3 having the amino acid sequence set forth in SEQ ID NOs:55; or
  (ii) the heavy chain variable domain (VH) specific for CD16A has the amino acid sequence set forth in SEQ ID NOs:1 or SEQ ID NO:3; and/or
  (iii) the light chain variable domain (VL) specific for CD16A has the amino acid sequence set forth in SEQ ID NO:2.

In some embodiments, the CD16A antigen-binding moiety comprises a heavy chain variable domain (V$_H$) and a light chain variable domain (V$_L$), wherein (a) the V$_H$ comprises a CDR1 comprising or having the amino acid sequence set forth in SEQ ID NO:73, a CDR2 comprising or having the amino acid sequence set forth in SEQ ID NO:74, and a CDR3 comprising or having the amino acid sequence set forth in SEQ ID NO:75; and (b) the V$_L$ comprises a CDR1 comprising or having the amino acid sequence set forth in SEQ ID NO:76, a light chain CDR2 comprising or having the amino acid sequence set forth in SEQ ID NO:77, and a CDR3 comprising or having the amino acid sequence set forth in SEQ ID NOs:78.

In certain embodiments, the V$_H$ of the CD16A antigen-binding moiety comprises or has the amino acid sequence set forth in SEQ ID NO: 3. In certain embodiments, the V$_L$ of the CD16A antigen-binding moiety comprises or has the amino acid sequence set forth in SEQ ID NO: 2.

In some embodiments, the CD16A antigen-binding moiety comprises a V$_H$ and a V$_L$, wherein (a) the V$_H$ comprises a CDR1 comprising or having the amino acid sequence set forth in SEQ ID NO:82, a CDR2 comprising or having the amino acid sequence set forth in SEQ ID NO:83, and a CDR3 comprising or having the amino acid sequence set forth in SEQ ID NO:52; and (b) the V$_L$ comprises a CDR1 comprising or having the amino acid sequence set forth in SEQ ID NO:84, a CDR2 comprising or having the amino acid sequence set forth in SEQ ID NO:85, and a CDR3 comprising or having the amino acid sequence set forth in SEQ ID NOs:86.

In certain embodiments, the V$_H$ of the CD16A antigen-binding moiety comprises or has the amino acid sequence set forth in SEQ ID NO: 4. In certain embodiments, the V$_L$ of the CD16A antigen-binding moiety comprises or has the amino acid sequence set forth in SEQ ID NO: 5.

In some embodiments, the CD16A antigen-binding moiety comprises a V$_H$ and a V$_L$, wherein (a) the V$_H$ comprises a CDR1 comprising or having the amino acid sequence set forth in SEQ ID NO:87, a CDR2 comprising or having the amino acid sequence set forth in SEQ ID NO:88, and a CDR3 comprising or having the amino acid sequence set forth in SEQ ID NO:52; and (b) the V$_L$ comprises a CDR1 comprising or having the amino acid sequence set forth in SEQ ID NO:89, a CDR2 comprising or having the amino acid sequence set forth in SEQ ID NO:95, and a CDR3 comprising or having the amino acid sequence set forth in SEQ ID NOs:90.

In certain embodiments, the V$_H$ of the CD16A antigen-binding moiety comprises or has the amino acid sequence set forth in SEQ ID NO: 6. In certain embodiments, the V$_L$ of the CD16A antigen-binding moiety comprises or has the amino acid sequence set forth in SEQ ID NO: 7.

In some embodiments, the CD16A antigen-binding moiety comprises a V$_H$ and a V$_L$, wherein (a) the V$_H$ comprises a CDR1 comprising or having the amino acid sequence set forth in SEQ ID NO:91, a CDR2 comprising or having the amino acid sequence set forth in SEQ ID NO:92, and a CDR3 comprising or having the amino acid sequence set forth in SEQ ID NO:52; and (b) the V$_L$ comprises a CDR1 comprising or having the amino acid sequence set forth in SEQ ID NO:93, a CDR2 comprising or having the amino acid sequence set forth in SEQ ID NO:85, and a CDR3 comprising or having the amino acid sequence set forth in SEQ ID NOs:94.

In certain embodiments, the $V_H$ of the CD16A antigen-binding moiety comprises or has the amino acid sequence set forth in SEQ ID NO: 8. In certain embodiments, the $V_L$ of the CD16A antigen-binding moiety comprises or has the amino acid sequence set forth in SEQ ID NO:9.

In some embodiments, the CD16A antigen-binding moiety comprises a $V_H$ and a $V_L$, wherein (a) the $V_H$ comprises a CDR1 comprising or having the amino acid sequence set forth in SEQ ID NO:82, a CDR2 comprising or having the amino acid sequence set forth in SEQ ID NO:95, and a CDR3 comprising or having the amino acid sequence set forth in SEQ ID NO:52; and (b) the $V_L$ comprises a CDR1 comprising or having the amino acid sequence set forth in SEQ ID NO:96, a CDR2 comprising or having the amino acid sequence set forth in SEQ ID NO:97, and a CDR3 comprising or having the amino acid sequence set forth in SEQ ID NOs:98.

In certain embodiments, the $V_H$ of the CD16A antigen-binding moiety comprises or has the amino acid sequence set forth in SEQ ID NO: 10. In certain embodiments, the $V_L$ of the CD16A antigen-binding moiety comprises or has the amino acid sequence set forth in SEQ ID NO: 11.

In some embodiments, the CD16A antigen-binding moiety comprises a $V_H$ and a $V_L$, wherein (a) the $V_H$ comprises a CDR1 comprising or having the amino acid sequence set forth in SEQ ID NO:82, a CDR2 comprising or having the amino acid sequence set forth in SEQ ID NO:99, and a CDR3 comprising or having the amino acid sequence set forth in SEQ ID NO:52; and (b) the $V_L$ comprises a CDR1 comprising or having the amino acid sequence set forth in SEQ ID NO:100, a CDR2 comprising or having the amino acid sequence set forth in SEQ ID NO:101, and a CDR3 comprising or having the amino acid sequence set forth in SEQ ID NOs:102.

In certain embodiments, the $V_H$ of the CD16A antigen-binding moiety comprises or has the amino acid sequence set forth in SEQ ID NO: 12. In certain embodiments, the $V_L$ of the CD16A antigen-binding moiety comprises or has the amino acid sequence set forth in SEQ ID NO: 13.

In some embodiments, the CD16A antigen-binding moiety comprises a $V_H$ and a $V_L$, wherein (a) the $V_H$ comprises a CDR1 comprising or having the amino acid sequence set forth in SEQ ID NO:50, a CDR2 comprising or having the amino acid sequence set forth in SEQ ID NO:103, and a CDR3 comprising or having the amino acid sequence set forth in SEQ ID NO:52; and (b) the $V_L$ comprises a CDR1 comprising or having the amino acid sequence set forth in SEQ ID NO:53, a CDR2 comprising or having the amino acid sequence set forth in SEQ ID NO:54, and a CDR3 comprising or having the amino acid sequence set forth in SEQ ID NOs:104.

In some embodiments, the CD16A antigen-binding moiety comprises a $V_H$ and a $V_L$, wherein (a) the $V_H$ comprises a CDR1 comprising or having the amino acid sequence set forth in SEQ ID NO:50, a CDR2 comprising or having the amino acid sequence set forth in SEQ ID NO:103, and a CDR3 comprising or having the amino acid sequence set forth in SEQ ID NO:52; and (b) the $V_L$ comprises a CDR1 comprising or having the amino acid sequence set forth in SEQ ID NO:53, a CDR2 comprising or having the amino acid sequence set forth in SEQ ID NO:54, and a CDR3 comprising or having the amino acid sequence set forth in SEQ ID NOs:105.

This CD16A antigen-binding moiety for CD16A does not bind to CD16B and binds to the known CD16A allotypes F158 and V158 with similar affinity. Two allelic single nucleotide polymorphisms have been identified in human CD16A altering the amino acid in position 158, which is important for interaction with the hinge region of IgG. The allelic frequencies of the homozygous 158 F/F and the heterozygous 158 V/F alleles are similar within the Caucasian population, ranging between 35 and 52% or 38 and 50%, respectively, whereas the homozygous 158 V/V allele is only found in 10-15% (Lopez-Escamez J A et al.; BMC Med Genet 2011; 12:2). Engagement and activation of NK cells by this anti-CD16A domain in all patient populations due to the similar affinity is therefore advantageous. This, CD16A antigen-binding moiety binds to human and cynomolgus CD16A. Further, CD16A antigen-binding moieties comprising heavy and light variable chain domains that bind to CD16A, but not to CD16B are described in WO 2006/125668.

In some embodiments the multispecific antigen-binding molecule comprises an anti-CD16A Fv domain having improved binding to CD16A compared to an anti-CD16A having SEQ ID NOs:1 and 2 and that does not bind to CD16B and recognizes the known CD16A allotypes F158 and V158 with similar affinity. In certain embodiments the affinity improved anti-CD16A Fv domain comprises the VCDRs having the sequence as depicted in SEQ ID NOs:53, 54, 55 or consists of a $V_L$ having the sequence as depicted in SEQ ID NO:2 and a VH having at least one variation in the sequence as depicted in SEQ ID NO:1.

Such an improved binder can be an affinity matured CD16A Fv antigen-binding moiety.

Hence, in some embodiments the CD16A antigen-binding moiety comprises an Fv domain showing higher affinity (e.g., improvements by affinity maturation) and/or selectivity to human CD16A than the anti-CD16A Fv of SEQ ID NOs:1 and 2, if tested in ELISA on wells coated with 0.16 μg/ml human CD16A (SEQ ID NO:48) measured with purified scFv molecules in a Biacore T200 system. For example, such higher affinity to human CD16A may be more than 2, 3, 4, 5, 6, 7, 8, 9, 10, 50, 100, 150-fold. For example, the monovalent binding affinity measured on a Biacore T200 system may be $K_D$=0.27 nM to 1.91 nM, which is a 21- to 150-fold higher affinity than 40.5 nM measured for binding of SEQ ID NOs: 1 and 2 to human CD16A.

Preferably, such affinity matured Fv domain further shows similarly improved affinity to cynomolgus CD16A, if tested in ELISA on wells coated with 0.16 μg/ml cynomolgus CD16A (SEQ ID NO:49) measured with purified scFv molecules in a Biacore T200 system.X100. For example, such higher affinity to cynomolgus CD16A may be more than 2, 3, 4, 5, 6, 7, 8, 9, 10, 50, 100, 150, 200, 250, 300, 400, 500, 541-fold. For example, the monovalent binding affinity measured on a Biacore T200 system may be $K_D$=0.24 to 3.63 nM, which is 36- to 541-fold higher affinity than 132 nM measured for binding of SEQ ID NOs: 1,2 to cynomolgus CD16A.

In the anti-CD16 Fv of SEQ ID NOs:1,2 certain sequence positions have been identified (X37, X44, X46) in which amino acid substitutions are beneficial for specific CD16A binding in the $V_L$ domain (SEQ ID NO:2). See Table 1.

TABLE 1

Summary of the strongest effects of amino acid substitution. Residues encoded in the germline sequences and in the reference sequences of SEQ ID NOs: 1-2 are given for comparison.

| Position | Location | Selected amino acid | Deselected amino acid | Germline residue | |
|---|---|---|---|---|---|
| | | | | | SEQ ID NO: 1 |
| X9 | HCDR1 | Q | H | H | H |
| X11 | HCDR2 | V | I | I | I |
| | | | | | SEQ ID NO: 2 |
| X37 | LCDR2 | K | D | D | K |
| X44 | LCDR3 | Y | | S | Y |
| X46 | LCDR3 | V | | D | V |

Not all amino acid substitutions shown in Table 1 are equally important for binding to CD16A. Substitutions in positions X44 and X46 might be of higher importance and, preferably, affinity maturated clones preserve the amino acids of SEQ ID NO:2.

Further responsible for CD16A binding, in certain embodiments, is the sequence of LCDR3 and also the N-terminal residues NI of LCDR1 or the QDX sequence motif in LCDR2.

In certain embodiments, the $V_L$ of the CD16A antigen-binding moiety comprises a light chain CDR1, a light chain CDR2 and a light chain CDR3 comprising 1, 2, 3, 4 or 5 amino acid substitutions compared with the sequences set forth in SEQ ID NOs:53, 54 and 55, and the $V_L$ retains binding specificity to CD16A. In certain embodiments, the one or more substitutions in the sequence of SEQ ID NO:53 are from position 3 to 6. In certain embodiments, the substitution in the sequence of SEQ ID NO:54 is in position 3. In certain embodiments, residues Y at position 6 and V at position 8 the sequence of SEQ ID NO:55 are not substituted and the. Preferably, LCDR3 has the sequence as depicted in SEQ ID NO:55.

In a further embodiment the $V_L$ of the CD16A antigen-binding moiety has a sequence identity of at least 99%, 98%, 97%, 96%, 95%, 94%, 93%, 92%, 91%, 90%, 89%, 88%, 87%, 86%, 85%, 84%, 83%, 82%, 81% or 80% compared to the sequence of SEQ ID NO:2, wherein the residues GGHNI from position 23 to 27 in SEQ ID NO:2, the sequence motif QDXK from position 49 to 52 in SEQ ID NO:2 are not mutated and the VL retains binding specificity to CD16A.

In the $V_H$ of the CD16A antigen-binding moiety a substitution at position 9 in HCDR1 and/or position 11 in HCDR2 compared to the sequence of SEQ ID NO:1 is beneficial for improving the binding to CD16A. In particular the residue at position 9 in HCDR1 is Q and/or the residue at position 11 of HCDR2 is V.

Thus, in a further embodiment the $V_H$ of the CD16A antigen-binding moiety has a sequence identity of at least 99%, 98%, 97%, 96%, 95%, 94%, 93%, 92%, 91%, 90%, 89%, 88%, 87%, 86%, 85%, 84%, 83%, 82%, 81% or 80% compared to the sequence of SEQ ID NO:1, the residue at position 9 in HCDR1 is Q and/or the residue at position 11 of HCDR2 is V.

Therefore, in a certain embodiment the CD16A antigen-binding moiety comprises a $V_L$ and a $V_H$, wherein the $V_L$ of the CD16A has a sequence identity of at least 99%, 98%, 97%, 96%, 95%, 94%, 93%, 92%, 91%, 90%, 89%, 88%, 87%, 86%, 85%, 84%, 83%, 82%, 81% or 80% compared to the sequence of SEQ ID NO:2, wherein the residues GGHNI from position 23 to 27 in SEQ ID NO:2, the sequence motif QDXK from position 49 to 52 in SEQ ID NO:2 are not mutated and the VL retains binding specificity to CD16A and the VH of the CD16A antigen-binding moiety has a sequence identity of at least 99%, 98%, 97%, 96%, 95%, 94%, 93%, 92%, 91%, 90%, 89%, 88%, 87%, 86%, 85%, 84%, 83%, 82%, 81% or 80% compared to the sequence of SEQ ID NO:1, the residue at position 9 in HCDR1 is Q and/or the residue at position 11 of HCDR2 is V.

In a further embodiment, the $V_L$ of the CD16A antigen-binding moiety has a sequence identity of at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% compared to the sequence of SEQ ID NO:2, wherein the residues GGHNI from position 23 to 27 in SEQ ID NO:2, the sequence motif QDXK from position 49 to 52 in SEQ ID NO:2 are not mutated and the $V_L$ retains binding specificity to CD16A.

In the $V_H$ of the CD16A antigen-binding moiety a substitution at position 9 in HCDR1 and/or position 11 in HCDR2 compared to the sequence of SEQ ID NO:1 is beneficial for improving the binding to CD16A. In particular the residue at position 9 in HCDR1 is Q and/or the residue at position 11 of HCDR2 is V.

Thus, in a further embodiment the $V_H$ of the CD16A antigen-binding moiety has a sequence identity of at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% compared to the sequence of SEQ ID NO:1, the residue at position 9 in HCDR1 is Q and/or the residue at position 11 of HCDR2 is V.

Therefore, in certain embodiments, the CD16A antigen-binding moiety comprises a $V_L$ and a $V_H$, wherein the $V_L$ of the CD16A antigen-binding moiety has a sequence identity of at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% compared to the sequence of SEQ ID NO:2, wherein the residues GGHNI from position 23 to 27 in SEQ ID NO:2, the sequence motif QDXK from position 49 to 52 in SEQ ID NO:2 are not mutated and the $V_L$ retains binding specificity to CD16A and the $V_H$ of the CD16A antigen-binding moiety has a sequence identity of at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% compared to the sequence of SEQ ID NO:1, the residue at position 9 in HCDR1 is Q and/or the residue at position 11 of HCDR2 is V.

In certain embodiments, the $V_H$ of the CD16A antigen-binding moiety has a sequence identity of at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% compared to the sequence set forth in SEQ ID NO:3.

In certain embodiments, the CD16A antigen-binding moiety comprises a $V_H$ comprising an amino acid sequence that is at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% identical or homologous to the amino acid sequence set forth in SEQ ID NO:2, and a $V_L$ comprising an amino acid sequence that is at least about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81% or about 80% identical or homologous to the amino acid sequence set forth in SEQ ID NO:3.

In a particular embodiment, the CD16A antigen-binding moiety comprises a $V_L$ and a $V_H$, wherein the $V_L$ is selected from the group consisting of regions having SEQ ID NO:2, 5, 7, 9, 11 and 13, and the $V_H$ is selected from the group consisting of SEQ ID NOs:1, 3, 4, 6, 8, 10 and 12.

III. Target Antigen-Binding Moiety

In certain embodiments, the target antigen of the target antigen-binding moiety is an antigen displayed on a myeloma cell or plasma cell. A myeloma cell is a malignant (cancerous) plasma cell arising from a plasma cell in the bone marrow. In myeloma, malignant plasma cells produce large amounts of abnormal antibodies that lack the capability to fight infection. These abnormal antibodies are the monoclonal protein, or M-protein, that functions as a tumor marker for myeloma. The myeloma cell has the phenotype $CD19^-/CD38^+/CD138^+/BCMA^+$. Hence, CD38, CD138 and BCMA represent antigens expressed on a myeloma cell.

A. BCMA

B-cell maturation antigen (BCMA, CD269 or TNFRSF17) is a protein of the TNF receptor superfamily which is crucial for long term survival of plasma cells through its binding of B-cell activating (BAFF) and A proliferation-inducing ligand (APRIL) (O'Connor, B. P. et al. BCMA is essential for the survival of long-lived bone marrow plasma cells. J. Exp. Med. 2004, 199, 91-96). Human BCMA is a 184 amino acid (aa) protein consisting of a 54 aa extracellular domain, a 23 aa transmembrane domain, and a 107 aa intracellular domain (Entrez Gene IDs: 608 (Human) 102145399 (Cynomolgous Monkey); UniProt Q02223 (Human)).

BCMA plays a role in the long-term cell survival of plasma cells (O'Connor, JEM 2004; 199(1):91-98). BCMA is expressed in normal plasma cells and up-regulated and high prevalence in multiple myeloma.

In certain embodiments the target antigen-binding moiety specifically binds to BCMA, e.g., the extracellular domain of BCMA.

Preferably, such anti-BCMA Fv employed in the antigen binding protein of the invention interacts with BCMA with an equilibrium dissociation constant ($K_D$) (measured by Biacore) of less than $10^{-7}$ M, preferably less than $10^{-8}$M, less than $10^{-9}$M most preferably less than $10^{-10}$ M. Such anti-BCMA Fv domains incorporated in the target antigen-binding moiety is capable of redirecting CD16A engaged NK cells and inducing ADCC in the presence of $BCMA^+$ MM (multiple myeloma) cells. Proof-of-concept for bispecific antibodies engaging T cells via CD3 towards $BCMA^+$ myeloma cells in vitro and in vivo has been reported (e.g., Hipp S. et al., Leukemia. 2017 August; 31(8):1743-1751. Epub 2016 Dec. 27). In certain embodiments, the target antigen-binding moiety binds to BCMA with a $K_D$ of between about $1\times10^{-9}$ M and about $5\times10^{-9}$ M. In certain embodiments, the target antigen-binding moiety binds to BCMA with a $K_D$ of about $2\times10^{-9}$ M.

Such BCMA antigen-binding moiety is obtainable, for example, by phage or ribosome library screening methods or immunization of a non-human animal with the extracellular domain of BCMA as described, for example, in Ryan M. C, et al., Antibody targeting of B-cell maturation antigen on malignant plasma cells. Mol Cancer Ther. (2007); 6:3009-3018.

Ryan et al. describes the production of anti-BCMA antibodies with cytotoxic activity either as IgG or antibody drug conjugates. Ryan M. C, et al., which is incorporated by reference, describes the generation of human BCMA-selective antibodies for tumor cell targeting. The antibodies were generated against the human BCMA extracellular domain (ECD, amino acids 5-51; NP_001183). The antibody induced potent ADCC towards MM cells in vitro which was increased with Fc mutations that enhance CD16A binding. The binding affinity $K_D$ of SG1 towards H929 cells was 51 nmol/L by saturation binding. These antibodies demonstrated in vitro antitumor activity against MM cell lines and their and, thus, their Fv-domain can be employed as BCMA antigen-binding moiety in the antigen binding protein according to the invention.

Further, WO 02/066516 describes BCMA antibodies cross-reactive with TACI. Anti-BCMA/TACI bispecific antibodies are described binding to residues 1-48 of BCMA and residues 30-67 and 68-154 of TACI. The variable heavy and light chain domains thereof could be employed as BCMA antigen-binding moiety in the antigen-binding protein of the invention and are incorporated by reference.

Ramadoss et al., J. Am. Chem. Soc. 2015; 137:5288-5291, incorporated by reference, describes a bispecific (Bi-Fab-BCMA) antibody which redirects T cells to lyse malignant MM cells. It is described that bispecific antibodies can be useful for the treatment of MM, as they target quiescent cancer stem cells as well as with low numbers of tumor-associated antigens.

WO 2014/122144 describes a bispecific antibody specifically binding to human BCMA and CD3 in a bispecific format. The disclosed anti-BCMA variable domains are suitable for a BCMA antigen-binding moiety according to the invention.

WO 2013/072406 discloses anti-BCMA Fv domains designated as BCMA-1 to BCMA-108 in bispecific single-chain antibodies having a second specificity for CD3 for engaging T cells. Anti-tumor efficacy of these BCMA/CD3 bispecific single chain antibodies in human tumor xenograft model is described and, thus, these anti-BCMA Fv domains can be employed in a BCMA antigen-binding moiety of the invention.

Further anti-BCMA antibodies that can be employed in bispecific antibodies engaging immune effector cells such as T- or NK cells have been disclosed in, WO 2010/104949, WO 2012/163805, WO 2013/072415, WO 2014/140248, and WO 2014/068079. Also these references describe anti-BCMA Fv-domains specifically targeting BCMA with high affinity and bispecific antibodies employing such anti-BCMA Fv-domains which induce potent and efficacious myeloma cell lysis. Therefore, proof-of-concept has been shown for anti-BCMA Fv-domains in bispecific antibodies for redirecting T cell to lyse MM cells.

Further antigen-binding moieties that bind to antigens expressed on myeloma cells, in particular BCMA can be derived from other known or commercially available antibodies or generated de novo by methods well known in the art. For example, variable domains specific for BCMA can be obtained by selecting variable fragments (Fvs) that are specific for BCMA. This can be accomplished, for example, by screening single-chain Fv (scFv) phage display libraries or through hybridoma technology. For instance, IgM-based phage display libraries of human scFv sequences can be subjected to several rounds of in vitro selection to enrich for binders specific to the BCMA (Example 1). Affinities of selected scFvs may be further increased by affinity maturation.

In certain embodiments, the BCMA-targeting moiety comprises a $V_H$ CDR1 comprising the amino acid sequence set forth in SEQ ID NO: 67, a $V_H$ CDR2 comprising the amino acid sequence set forth in SEQ ID NO: 68, a $V_H$ CDR3 comprising the amino acid sequence set forth in SEQ ID NO: 69, a $V_L$ CDR1 comprising the amino acid sequence set forth in SEQ ID NO: 70, a $V_L$ CDR2 comprising the amino acid sequence set forth in SEQ ID NO: 71, and a $V_L$ CDR3 comprising the amino acid sequence set forth in SEQ ID NO: 72.

In certain embodiments, the $V_H$ of the BCMA-targeting moiety comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous or identical to the amino acid sequence set forth in SEQ ID NO: 65.

In certain embodiments, the $V_L$ of the BCMA-targeting moiety comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous or identical to the amino acid sequence set forth in SEQ ID NO: 66.

In certain embodiments, the $V_H$ of the BCMA-targeting moiety comprises or has the amino acid sequence set forth in SEQ ID NO: 65. In certain embodiments, the $V_L$ of the BCMA-targeting moiety comprises or has the amino acid sequence set forth in SEQ ID NO: 66.

In certain embodiments, the $V_H$ of the BCMA-targeting moiety comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous or identical to the amino acid sequence set forth in SEQ ID NO: 37.

In certain embodiments, the $V_L$ of the BCMA-targeting moiety comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous or identical to the amino acid sequence set forth in SEQ ID NO: 38.

In certain embodiments, the $V_H$ of the BCMA-targeting moiety comprises or has the amino acid sequence set forth in SEQ ID NO: 65. In certain embodiments, the $V_L$ of the BCMA-targeting moiety comprises or has the amino acid sequence set forth in SEQ ID NO: 66.

In certain embodiments, the CD16A/BCMA binding antibody is a scFv-IgAb antigen-binding protein having a structure shown in FIG. 13, which comprises (a) two CD16A antigen-binding moieties in the format of scFvs fused to the C-terminus of a homodimeric human IgG CH2-CH3 Fc portion in the order of $V_L$-$V_H$ and (b) two target antigen-binding moieties provided by each Fv in the Fab arms of the IgG, wherein the target antigen-binding moieties bind to BCMA.

In certain embodiments, each of the CD16A antigen-binding moieties comprises a $V_H$ CDR1 comprising the amino acid sequence set forth in SEQ ID NO: 73, a $V_H$ CDR2 comprising the amino acid sequence set forth in SEQ ID NO: 74, a $V_H$ CDR3 comprising the amino acid sequence set forth in SEQ ID NO: 75, a $V_L$ CDR1 comprising the amino acid sequence set forth in SEQ ID NO: 76, a $V_L$ CDR2 comprising the amino acid sequence set forth in SEQ ID NO: 77, and a $V_L$ CDR3 comprising the amino acid sequence set forth in SEQ ID NO: 78. In certain embodiments, the CDRs are identified according to the Kabat numbering system. Each of the CD16A antigen-binding moiety comprises a $V_H$ having the amino acid sequence set forth in SEQ ID NO: 3, and a $V_L$ having the amino acid sequence set forth in SEQ ID NO: 2.

In certain embodiments, the CD16A antigen-binding moiety is fused to the C-terminus of the Fc portion connected via a connector having the amino acid sequence set forth in SEQ ID NO: 22 in the following order: $V_L$ (CD16A)-Linker L3-$V_L$ (CD16A), where Linker L3 has the amino acid sequence set forth in SEQ ID NO: 18.

In certain embodiments, each of the BCMA-targeting moieties comprises a $V_H$ CDR1 comprising the amino acid sequence set forth in SEQ ID NO: 67, a $V_H$ CDR2 comprising the amino acid sequence set forth in SEQ ID NO: 68, a $V_H$ CDR3 comprising the amino acid sequence set forth in SEQ ID NO: 69, a $V_L$ CDR1 comprising the amino acid sequence set forth in SEQ ID NO: 70, a $V_L$ CDR2 comprising the amino acid sequence set forth in SEQ ID NO: 71, and a $V_L$ CDR3 comprising the amino acid sequence set forth in SEQ ID NO: 72. In certain embodiments, the CDRs are identified according to the Kabat numbering system. Each of the BCMA-targeting moieties comprises a $V_H$ having the amino acid sequence set forth in SEQ ID NO: 65, and a $V_L$ having the amino acid sequence set forth in SEQ ID NO: 66.

In certain embodiments, the Fc portion of the CD16A/BCMA antibody is a silenced Fc portion that comprises a human IgG1 CH2, and CH3 heavy chain constant domain, which comprises the amino acid sequence set forth in SED ID NO: 29. The CH2 heavy chain constant domain has two silencing mutations (also referred to as "effector-less mutations"): L234F and L235E. The CH2 heavy chain constant domain comprises the amino acid sequence set forth in SED ID NO: 79. The CH3 heavy chain constant domain comprises the amino acid sequence set forth in SED ID NO: 109. The CH1 heavy chain constant domain that is connected to the BCMA targeting moiety comprises the amino acid sequence set forth in SEQ ID NO: 33.

In certain embodiments, the CD16A/BCMA antibody I comprises a polypeptide chain 1 having the amino acid sequence set forth in SEQ ID NO: 61, and a polypeptide chain 2 having the amino acid sequence set forth in SEQ ID NO: 62.

In certain embodiments, the CD16A/BCMA antibody is a KiH-scDb-Fc having a structure shown in FIG. 5, which comprises (a) two CD16A antigen-binding moieties in the format of scDb fused to the C-terminus of a IgG CH2-CH3 Fc portion in the order of $V_L$-$V_H$-$V_L$-$V_H$, and (b) a single target antigen-binding moiety in the format of scFv fused to the N-terminus of the Fc portion, wherein the target antigen-binding moiety binds to BCMA.

In certain embodiments, each of the CD16A antigen-binding moieties comprises a $V_H$ CDR1 comprising the amino acid sequence set forth in SEQ ID NO: 73, a $V_H$ CDR2 comprising the amino acid sequence set forth in SEQ ID NO: 74, a $V_H$ CDR3 comprising the amino acid sequence set forth in SEQ ID NO: 75, a $V_L$ CDR1 comprising the amino acid sequence set forth in SEQ ID NO: 76, a $V_L$ CDR2 comprising the amino acid sequence set forth in SEQ ID NO: 77, and a $V_L$ CDR3 comprising the amino acid sequence set forth in SEQ ID NO: 78. In certain embodiments, the CDRs are identified according to the Kabat numbering system. Each of the CD16A antigen-binding moieties comprises a $V_H$ having the amino acid sequence set forth in SEQ ID NO: 3, and a $V_L$ having the amino acid sequence set forth in SEQ ID NO: 2.

In certain embodiments, the CD16A antigen-binding moiety is fused to the heterodimeric Fc portion and connected via a connector having the amino acid sequence set forth in SEQ ID NO: 20 in the following order: $V_L$ (CD16A)-Linker L1-$V_H$ (CD16A)-Linker L2-$V_L$ (CD16A)-Linker L1-$V_H$ (CD16A), where Linker L1 has the amino acid sequence set forth in SEQ ID NO: 16, and Linker L2 has the amino acid sequence set forth in SEQ ID NO: 17.

In certain embodiments, each of the BCMA-targeting moieties comprises a $V_H$ CDR1 comprising the amino acid sequence set forth in SEQ ID NO: 67, a $V_H$ CDR2 comprising the amino acid sequence set forth in SEQ ID NO: 68, a $V_H$ CDR3 comprising the amino acid sequence set forth in SEQ ID NO: 69, a $V_L$ CDR1 comprising the amino acid sequence set forth in SEQ ID NO: 70, a $V_L$ CDR2 comprising the amino acid sequence set forth in SEQ ID NO: 71, and a $V_L$ CDR3 comprising the amino acid sequence set forth in SEQ ID NO: 72. In certain embodiments, the CDRs are identified according to the Kabat numbering system. Each of the BCMA-targeting moieties comprises a $V_H$ having the amino acid sequence set forth in SEQ ID NO: 65, and a $V_L$ having the amino acid sequence set forth in SEQ ID NO: 66.

In certain embodiments, the Fc portion of CD16A/BCMA antibody III is a silenced Fc portion that comprises a human IgG1 CH2 and CH3 heavy chain constant domain having the amino acid sequence set forth in SED ID NO: 31. The CH2 heavy chain constant domain has two silencing mutations or effector-less mutations: L234F and L235E. The CH2 heavy chain constant domain comprises the amino acid sequence set forth in SED ID NO: 79. The CH3 heavy chain constant domain has one silencing mutation or effector-less mutation D265A. The CH3 heavy chain constant domain comprises the amino acid sequence set forth in SED ID NO: 81.

In certain embodiments, the CD16A/BCMA antibody comprises a polypeptide chain 1 having the amino acid sequence set forth in SEQ ID NO: 63, and a polypeptide chain 2 having the amino acid sequence set forth in SEQ ID NO: 64.

In one embodiment of the multispecific antigen-binding protein of the invention the protein is a tetramer comprising polypeptides having the amino acid sequence as depicted in SEQ ID NOs: 61 and 62 or SEQ ID NOs: 63 and 64.

B. EGFR

Also provided are EGFR/CD16A antigen-binding proteins for a natural killer (NK) cell-based EGFR-targeting approach.

In some embodiment the antigen-binding moiety for EGFR described herein also binds to EGFRvIII. Thus, the EGFR/CD16A antigen-binding protein can be used for the treatment of both, EGFR-expressing and EGFRvIII-expressing cancers. EGFRvIII in contrast to EGFR is expressed exclusively on cancer cells but not on healthy tissue. Hence, a broader variety of EGFR- and/or EGFRvIII-positive tumors and, thus, a broader patient population can be targeted with the EGFR/CD16A antigen binding protein described herein. An example of an EGFR binding domain suitable for the antigen-binding proteins described herein comprises as VH the amino acid sequence depicted in SEQ ID NO:40 and as VL the amino acid sequence as depicted in SEQ ID NO:41.

IV. Polynucleotides

The antigen-binding protein according to any one of the embodiments described herein may be produced by expressing polynucleotides encoding the individual polypeptide chains which form the antigen-binding molecule. Therefore, further embodiments of the invention are polynucleotides, e.g., DNA or RNA, encoding the polypeptides of the antibody molecule as described herein above.

The polynucleotides may be constructed by methods known to the skilled person, e.g., by combining the genes encoding the variable domains either separated by peptide linkers or directly linked by a peptide bond of the polypeptide chains, into a genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotides in the respective host cell.

The polynucleotides may be inserted into vectors, preferably expression vectors, which represent a further embodiment of the invention.

A variety of expression vector/host systems may be utilized to contain and express the polynucleotides encoding the polypeptide chains of the present invention. Examples for expression vectors for expression in *E. coli* are pSKK (LeGall et al., J Immunol Methods. (2004); 285(1):111-27) or pcDNA5 (Invitrogen) for the expression in mammal cells.

V. Methods of Treatment

The invention further provides the multispecific antigen-binding protein, in particular, a composition comprising a multispecific antigen-binding protein as described herein above and at least one further component.

The invention further provides the multispecific antigen-binding protein or a composition comprising the multispecific antigen-binding protein as described herein above for use in a NK cell based immunotherapy. NK cell based immunotherapy includes active NK cell based therapies in which either endogenous or adoptively transferred NK cells are activated through engagement by the antigen-binding molecule of the invention. In particular, the ability of NK cells for attacking and killing abnormal cells, such as cancer cells is enhanced.

Furthermore, the current immuno-oncology (IO) landscape includes marketed checkpoint modulators such as anti-CTLA4 and anti-PD-1 antibodies. Even though, these agents have demonstrated clinical efficacy (typically 20-30% ORR across a range of indications), medical need and opportunity remains. Therefore, novel therapies are needed to achieve increased patient response rates and long-lasting remissions in a greater number of patients, despite such recent advances in the treatment. For example, NK cells play a key role in the immune response to MM and have been implicated in the clinical efficacy of current standard of care interventions, including IMiDs, proteasome inhibitors, recently approved immunotherapies and autologous stem cell transplantation (ASCT). Numerous strategies are being developed to enhance the natural NK cell cytotoxicity against myeloma cells, which is frequently dysregulated in MM. Approaches include modulation of activity, through cytokine stimulation or immune checkpoint targeting, and adoptive transfer of culture expanded NK cells in ASCT-eligible MM. While highly attractive, these approaches are non-targeted, as they rely on the natural cytotoxicity of NK cells, and may benefit from antigen-specific retargeting and effector activation.

Furthermore, rational combinations in IO should be based on agents that are able to unleash maximal immune efficacy, while keeping safety under control. Promising approaches go beyond adaptive immunity (most checkpoint antibodies are only active on T cells) and include activation of innate immunity, thus generating an integrated immune response. Based on the extended serum half-life, the antibody formats described herein are ideally suited for these purposes and allow for convenient dosing similar to current marketed monoclonal antibodies and could be ideally be combined with checkpoint modulators such as anti-LAG3 or anti-PD1 antibodies.

In certain embodiments, the invention provides a multispecific antigen-binding protein specifically binding to CD16A and an antigen expressed on a myeloma cell or plasma cell selected from the group consisting of BCMA, CS-1, CD19, CD20, CD22, CD38 and CD138 as described above for the use in the treatment of multiple myeloma, comprising the step of administering the multispecific antigen-binding protein. In a certain embodiment the invention provides a multispecific antigen-binding molecule specifically binding to a target cell antigen, e.g., a tumor antigen, and CD16A for the use in NK cell immunotherapy, wherein the multispecific antigen-binding protein is mixed with NK cells ex vivo and the composition of NK cells and the multispecific antigen-binding molecule is administered to a patient.

In a particular embodiment, the tumor antigen is BCMA and the composition is used for the treatment of a plasma cell disorder or autoimmune disease, in particular multiple myeloma.

Plasma cell disorders include multiple myeloma, plasmacytoma, plasma cell leukemia, macroglobulinemia, amyloidosis, Waldenstrom's macroglobulinemia, solitary bone plasmacytoma, extramedullary plasmacytoma, osteosclerotic myeloma, heavy chain disease, monoclonal gammopathy of undetermined significance (MGUS) and smoldering myeloma.

Autoimmune disease is for example systemic lupus erythematosus (SLE) or rheumatoid arthritis (RA).

Therefore, provided herein are in certain embodiments medical uses and methods wherein the antigen-binding protein specific for BCMA and CD16A, e.g., scDb-mFc, KiH-scDb-Fc, scDb-Trib(-scFv), scFv-IgAb, Bi-scFv-IgAb, KiH-scFv-Fc, Db-Fc, or Bi-scFv-Fc, as described herein above is administered in an effective dose to a subject for the treatment of a BCMA$^+$ cancer or autoimmune disease, for example multiple myeloma.

Administration is effected by different ways, e.g., by intravenous, intraperitoneal, subcutaneous, intramuscular, topical or intradermal administration. The dosage will be determined by the attending physician and other clinical factors. Dosages for any one subject depends on many factors, including the patient's body weight, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology. An "effective dose" useful for treating and/or preventing a BCMA$^+$ disease can be determined using known methods.

Moreover, the invention provides method for the treatment or amelioration of a disease, the method comprising the step of administering the multispecific antigen-binding protein of the invention to a subject in the need thereof.

In a preferred embodiment of the method for the treatment or amelioration of a disease said disease is multiple myeloma.

The present disclosure provides uses of the presently disclosed antigen binding molecules, e.g., CD16A/BCMA antigen binding molecules, for treating and/or preventing cancer, e.g., multiple myeloma. In certain embodiments, the method comprises administering a presently disclosed antigen binding molecule, e.g., a CD16A/BCMA antigen binding molecule, or a pharmaceutical composition comprising thereof to a subject suffering from multiple myeloma ("MM").

In certain embodiments, the subject receiving a treatment with an antigen binding molecules, e.g., a CD16A/BCMA antigen binding molecule, or a pharmaceutical composition comprising thereof is a relapsed/refractory ("R/R") multiple myeloma patient. In certain embodiments, the subject has received daratumumab. In certain embodiments, the subject is daratumumab naïve. In certain embodiments, the subject is daratumumab resistant. In certain embodiments, the subject is daratumumab refractory. In certain embodiments, the subject is daratumumab relapsed.

In certain embodiments, the subject receiving a treatment with an antigen binding molecule, e.g., a CD16A/BCMA antigen binding molecule, or a pharmaceutical composition comprising thereof, expresses a CD16A polymorph. For example, but not by way of limitation, the CD16A polymorphism is a CD16A-158V/F polymorphism. See Example 8 (e.g., FIGS. 31A and 31B).

In certain embodiments, the methods of treatment described herein further comprise administering a second therapy, e.g., a T-Cell-based therapy or a check-point inhibitor-based therapy. Such second therapies include, but are not limited to, therapies comprising administration of an anti-TIGIT antibody, therapies comprising administration of an anti-PD-1 antibody (e.g., nivolumab, pembrolizumab), therapies comprising administration of an anti-PD-L1 antibody (e.g., atezolizumab), therapies comprising administration of an anti-VEGF antibody (e.g., bevacizumab), and therapies comprising administration of a CD3 bispecific antibody (e.g., an anti-FcRH5/CD3 antibody (including, but not limited to, those such antibodies disclosed in PCT/US2016/037879, which is incorporated in its entirety by reference)).

In certain embodiments, the methods of treatment described herein further comprise the administration of a cytokine therapy. As used herein "cytokine therapy" refers to any therapy comprising a cytokine any derivative or modification thereof, including but not limited to pegylated cytokines and Fc fusion cytokines. Non-limiting examples of cytokines that can be used in connection with such embodiments include IL-15, IL-2, IL-12, IL-21, IL-17, IL-18, IL-23, IL-27, and IL-6. In certain embodiments, the method further comprises administering IL-15. In certain embodiments, the method further comprises administering IL-2. As shown in Example 8, IL-15 and IL-2 can increase the activity of a presently disclosed CD16A/BCMA antigen binding molecule.

In certain embodiments, the administration of an antigen binding molecule disclosed herein, e.g., a CD16A/BCMA antigen binding molecule, or a pharmaceutical composition comprising thereof will be as a first line (1L) therapeutic. For example, but not by way of limitation, such first line administration will occur in subjects exhibiting CD16A polymorphism that would indicate reduced effectiveness of a therapeutic functioning via an Fc-based MOA, e.g., daratumumab therapy. In certain embodiments, first line administration of the antigen binding molecules of the present disclosure will occur in subjects where NK cell fratricide is contraindicated. See Example 8 (e.g., FIGS. 40A-40E). In certain embodiments, first line administration of the antigen binding molecules of the present disclosure will occur in subjects where avoidance of CRS is desired.

In certain embodiments, the administration of an antigen binding molecule disclosed herein, e.g., a CD16A/BCMA antigen binding molecule, or a pharmaceutical composition comprising thereof will be as a second line (2L) or third line (3L) therapeutic. For example, but not by way of limitation, such second line or third line administrations will occur in subjects having already received a therapeutic functioning via an Fc-based MOA, e.g., daratumumab treatment. In certain embodiments, such second line or third line treatment will occur with subjects that are refractory or resistant to daratumumab treatment.

In certain embodiments, one or more of the following criteria is used for selecting a NK cell engager for use in treating multiple myeloma:

the NK cell engager is capable of binding to two targets: CD16A on NK cells, and BCMA on multiple myeloma cells, the NK cell engager is at least bivalent for CD16A, e.g., comprises at least two CD16A antigen-binding moieties, the NK cell engager is a NK cell bispecific antibody that is not cross-reactive with CD16B, and preferably is cross-reactive with non-human primates, the NK cell engager is potent and prevalent, and possesses target-dependent in vitro killing of BCMA$^+$ tumor cells (e.g., ≥ about 60% cells killed with an EC50≤5 nM) and primary myeloma, the NK cell engager does not significantly kill NK cells, e.g., reduces or avoids NK cell fratricide, the NK cell engager has an acceptable safety profile, e.g., has an in vitro cytokine release profile better than other T-cell engagers (e.g., the NK cell engager lacks CRS), adverse events are monitorable, manageable, and reversible, the NK cell engager can be administered to a multiple myeloma subject intravenously, and the NK cell engager requires an administrated frequency of once-weekly (QW) or less.

In certain embodiments, the following Pharmacodynamics (PD) biomarkers can be used in connection with the administration of the antigen binding proteins of the instant disclosure: concentration of serum M protein and free light chain (FLC), decrease of monoclonal plasma cells, NK cell activation and recruitment in post-treatment bone marrow samples, and peripheral NK cell activation. In certain embodiments, the methods of treatment can include a BMCA-dependent diagnostic, although such diagnostics are not necessarily needed based on the high prevalence of BMCA in multiple myeloma.

VI. Exemplary Embodiments

In certain embodiments, the present disclosure is directed to a multispecific antigen-binding protein comprising (a) at least a first target antigen-binding moiety, and (b) at least two CD16A antigen-binding moieties, wherein the at least two CD16A antigen-binding moieties are fused to a Fab fragment comprising at least one constant domain or a Fc portion. In certain embodiments, at least one of the two CD16A antigen-binding moieties is an antigen-binding molecule selected from the group consisting of a single-chain Fv (scFv), single-chain diabody (scDb) and a diabody Db. In certain embodiments, each of the at least the two CD16A antigen-binding moieties is a scFv. In certain embodiments, the at least two CD16A antigen-binding moieties are in the format of a scDb. I certain embodiments, each of the at least two CD16A antigen-binding moieties comprises a light chain variable region ($V_L$) and a heavy chain variable region ($V_H$) linked one after another in a polypeptide chain, and the variable region at the N-terminus of the polypeptide chain is the $V_L$. In certain embodiments, the variable regions of the at least two CD16A antigen-binding moieties in the polypeptide chain are positioned from the N-terminus to the C-terminus in the order of $V_L$-$V_H$, $V_L$-$V_L$-$V_H$-$V_H$ or $V_L$-$V_H$-$V_L$-$V_H$. In certain embodiments, the variable regions of the at least two CD16A antigen-binding moieties in the polypeptide chain are positioned from the N-terminus to the C-terminus in the order of $V_L$-$V_H$. In certain embodiments, the variable regions of the at least two CD16A antigen-binding moieties in the polypeptide chain are positioned from the N-terminus to the C-terminus in the order of $V_L$-$V_H$-$V_L$-$V_H$. In certain embodiments, (i) the C-terminus of the polypeptide chain is fused to the N-terminus of a CH2 domain of the Fc portion; or (ii) the C-terminus of the polypeptide chain is fused to the N-terminus of a Hinge of the Fc portion; (iii) the N-terminus of the polypeptide chain is fused to the C-terminus of a CH3 domain of the Fc portion, or (iv) the N-terminus of the polypeptide chain is fused to the C-terminus of a Fab fragment. In certain embodiments, the N-terminus of the polypeptide chain is fused to the C-terminus of a CH3 domain of the Fc portion. In certain embodiments, the Fc portion is selected from the group consisting of a monomeric CH2-CH3 fragment, a heterodimeric Fc region, and a homodimeric Fc region. In certain embodiments, the Fc portion does not bind to a Fc-gamma receptor, but retains binding to a neonatal Fc receptor. In certain embodiments, a scDb or Db comprising two CD16 antigen-binding moieties is fused to the C-terminus of one chain of the Fab fragment and the first target antigen-binding moiety is fused to the C-terminus of the other chain of the Fab fragment. In certain embodiments, the Fab fragment comprises N-terminally an HSA antigen-binding Fv.

In certain embodiments, the antigen-binding proteins described herein are tetravalent.

In certain embodiments, the multispecific antigen-binding proteins described herein comprise at least two target antigen-binding moieties.

In certain embodiments, the multispecific antigen-binding proteins described herein comprise a first target antigen-binding moiety, a second target antigen-binding moiety and at least two CD16A antigen-binding moieties fused to a dimeric Fc portion.

In certain embodiments, the multispecific antigen-binding proteins described herein comprise a CD16A antigen-binding moiety fused to the C-terminus of each heavy chain of an IgG, and where the IgG comprises N-terminally a first target antigen-binding Fv moiety in each of the two Fabs and a second target antigen-binding moiety is fused C-terminally to each of the CL domains.

In certain embodiments, the CD16A antigen-binding moieties described herein comprise: (i) a heavy chain variable region comprising a CDR1 having the amino acid sequence set forth in SEQ ID NO:50; a CDR2 having the amino acid sequence set forth in SEQ ID NO:51; and a CDR3 having the amino acid sequence set forth in SEQ ID NO:52, and/or (ii) a light chain variable region comprising a CDR1 having the amino acid sequence set forth in SEQ ID NO:53; a CDR2 having the amino acid sequence set forth in SEQ ID NO:54; and a CDR3 having the amino acid sequence set forth in SEQ ID NO:55.

In certain embodiments, the multispecific antigen-binding proteins described herein comprise a CD16A antigen-binding moiety comprising: (i) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and/or (ii) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78.

In certain embodiments, the multispecific antigen-binding proteins described herein comprise a CD16A antigen-binding moiety, which comprises (i) a heavy chain variable region comprising an amino acid sequence that is at least about 80% homologous or identical to the amino acid sequence set forth in SEQ ID NO: 3, and/or (ii) a light chain variable region comprising an amino acid sequence that is at least about 80% homologous or identical to the amino acid sequence set forth in SEQ ID NO: 2.

In certain embodiments, the multispecific antigen-binding proteins described herein comprise a CD16A antigen-binding moiety comprises (i) a heavy chain variable region comprising the amino acid sequence set forth in SEQ ID NO: 3, and/or (ii) a light chain variable region comprising the amino acid sequence set forth in SEQ ID NO: 2.

In certain embodiments, the multispecific antigen-binding proteins described herein bind a first target antigen that is selected from BCMA and EGFR. In certain embodiments, the multispecific antigen-binding proteins described herein bind a first target antigen that is BCMA.

In certain embodiments, the multispecific antigen-binding proteins described herein comprise a tetramer comprising a first polypeptide chain having the amino acid sequence set forth in SEQ ID NO: 61 or 63, and a second polypeptide chain having the amino acid sequence set forth in SEQ ID NO: 62 or 64. In certain embodiments, the multispecific antigen-binding proteins described herein comprise a tetramer comprising a first and a second polypeptide selected from: (i) a first polypeptide having the amino acid sequence set forth in SEQ ID NO: 61 and second polypeptide having the amino acid sequence set forth in SEQ ID NO: 62; (ii) a first polypeptide having the amino acid sequence set forth in SEQ ID NO: 61 and second polypeptide having the amino acid sequence set forth in SEQ ID NO: 64; (iii) a first polypeptide having the amino acid sequence set forth in SEQ ID NO: 63 and second polypeptide having the amino acid sequence set forth in SEQ ID NO: 62; and (iv) a first polypeptide having the amino acid sequence set forth in SEQ ID NO: 63 and second polypeptide having the amino acid sequence set forth in SEQ ID NO: 64.

In certain embodiments, the multispecific antigen-binding proteins described herein comprise a BCMA antigen-binding moiety comprising: (i) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and/or (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72.

In certain embodiments, the multispecific antigen-binding proteins described herein comprise a BCMA antigen-binding moiety comprising: (i) a heavy chain variable region comprising an amino acid sequence that is at least about 80% homologous or identical to the amino acid sequence set forth in SEQ ID NO: 65, and/or (ii) a light chain variable region comprising an amino acid sequence that is at least about 80% homologous or identical to the amino acid sequence set forth in SEQ ID NO: 66.

In certain embodiments, the multispecific antigen-binding proteins described herein comprise a BCMA antigen-binding moiety comprising: (i) a heavy chain variable region comprising the amino acid sequence set forth in SEQ ID NO: 65, and/or (ii) a light chain variable region comprising the amino acid sequence set forth in SEQ ID NO: 66.

In certain embodiments, the multispecific antigen-binding proteins described herein comprise a antigen-binding protein comprising: (i) a CD16A antigen-binding moiety comprising: (a) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and (b) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78; and (ii) a BCMA antigen-binding moiety comprising: (a) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72.

In certain embodiments, the present disclosure is directed to pharmaceutical compositions comprising a multispecific antigen-binding protein as described herein and a pharmaceutically acceptable carrier.

In certain embodiments, the multispecific antigen-binding proteins described herein is described for a use as a medicament.

In certain embodiments, the present disclosure is directed to a method for the treatment or amelioration of a disease, the method comprising administering a multispecific antigen-binding protein as described herein or a pharmaceutical composition as described herein to a subject in the need thereof. In certain embodiments, the disease is cancer. In certain embodiments, the disease is a hematologic cancer. In certain embodiments, the disease is multiple myeloma.

In certain embodiments, the present disclosure is directed to methods of treating and/or preventing a disease in a subject, the method comprising administering the bispecific antigen-binding protein as described herein or the pharmaceutical compositions described herein to a subject in the need thereof. In certain embodiments, the multispecific antigen-binding protein is administered intravenously. In certain embodiments, the multispecific antigen-binding protein is administered subcutaneously. In certain embodiments, the methods disclosed herein comprise administering a second therapy. In certain embodiments, the second therapy is selected from the group consisting of therapies comprising an anti-PD-1 antibody, therapies comprising an anti-PD-L1 antibodies, therapies comprising a CD3 bispecific antibody, therapies comprising an anti-TIGIT antibody, therapies comprising an anti-VEGF antibody, and therapies comprising an anti-FcRH5 antibody . In certain embodiments, the second therapy is a cytokine therapy. In certain embodiments, the cytokine therapy comprises the administration of a cytokine selected from the group consisting of IL-15, IL-2, IL-12, IL-21, and IL6. In certain embodiments, the cytokine therapy comprises the administration of IL-2. In certain embodiments, the cytokine therapy comprises the administration of IL-15.

In certain embodiments, the subject treated as described herein is a cancer patient. In certain embodiments, the subject is a hematological cancer patient. In certain embodiments, the subject is a multiple myeloma patient. In certain embodiments, the subject is a relapsed/refractory multiple myeloma patient. In certain embodiments, the subject has received an anti-CD38 therapy. In certain embodiments, the subject has received daratumumab. In certain embodiments, the subject is daratumumab naïve, daratumumab resistant, daratumumab refractory, or daratumumab relapsed. In certain embodiments, the subject is daratumumab resistant, daratumumab refractory, or daratumumab relapsed. In certain embodiments, the subject expresses a CD16A polymorphism. In certain embodiments, the CD16A polymorphism is a CD16A-158V/F polymorphism.

In certain embodiments, the present disclosure is directed to a bispecific antigen-binding protein comprising (a) at least a BCMA-binding moiety, and (b) at least two CD16A antigen-binding moieties, wherein the at least two CD16A antigen-binding moieties are fused to a Fab fragment comprising at least one constant domain or a Fc portion. In certain embodiments, at least one of the two CD16A antigen-binding moieties is an antigen-binding molecule selected from the group consisting of a single-chain Fv (scFv), single-chain diabody (scDb) and a diabody Db. In certain embodiments, each of the at least two CD16A antigen-binding moieties is a scFv. In certain embodiments, the at least two CD16A antigen-binding moieties are in the format of a scDb. In certain embodiments, each of the at least two CD16A antigen-binding moieties comprises a light chain variable region ($V_L$) and a heavy chain variable region ($V_H$) linked one after another in a polypeptide chain, and the variable region at the N-terminus of the polypeptide chain is the $V_L$. In certain embodiments, the variable regions of the at least two CD16A antigen-binding moieties in the polypeptide chain are positioned from the N-terminus to the C-terminus in the order of $V_L$-$V_H$, $V_L$-$V_L$-$V_H$-$V_H$ or $V_L$-$V_H$-$V_L$-$V_H$.

In certain embodiments, the variable regions of the at least two CD16A antigen-binding moieties in the polypeptide chain are positioned from the N-terminus to the C-terminus in the order of $V_L$-$V_H$. In certain embodiments, the variable regions of the at least two CD16A antigen-binding moieties in the polypeptide chain are positioned from the N-terminus to the C-terminus in the order of $V_L$-$V_H$-$V_L$-$V_H$.

In certain embodiments, the present disclosure is directed to a bispecific antigen-binding protein wherein: (i) the C-terminus of the polypeptide chain is fused to the N-terminus of a CH2 domain of the Fc portion; or (ii) the C-terminus of the polypeptide chain is fused to the N-terminus of a Hinge of the Fc portion; (iii) the N-terminus of the polypeptide chain is fused to the C-terminus of a CH3 domain of the Fc portion, or (iv) the N-terminus of the polypeptide chain is fused to the C-terminus of a Fab fragment. In certain embodiments, the N-terminus of the polypeptide chain is fused to the C-terminus of a CH3 domain of the Fc portion. In certain embodiments, the Fc portion is selected from the group consisting of a monomeric CH2-CH3 fragment, a heterodimeric Fc region, and a homodimeric Fc region. In certain embodiments, the Fc portion does not bind to a Fc-gamma receptor, but retains binding to a neonatal Fc receptor. In certain embodiments, the Fc portion comprises at least one effector-less mutation. In certain embodiments, the at least one effector-less mutation is selected from the group consisting of C220S, C229S, E233P, L234A, L234V, L234F, L235A, L235E, P238S, D265A, N297A, N297Q, and P331S. In certain embodiments, the at least one effector-less mutation is selected from the group consisting of L234A, L234V, L234F, L235A, L235E, P238S, and D265A. In certain embodiments, the at least one effector-less mutation is selected from the group consisting of L234F, L235E, and D265A. In certain embodiments, the Fc portion has two effector-less mutations. In certain embodiments, the two effector-less mutations are L234F and L235E. In certain embodiments, the Fc portion has three effector-less mutations. In certain embodiments, the three effector-less mutations are L234F, L235E, and D265A.

In certain embodiments, the bispecific antigen-binding proteins of the present disclosure comprise at least two CD16A antigen-binding moieties are fused to a Fc portion. In certain embodiments, the bispecific antigen-binding proteins of the present disclosure comprise two BCMA-targeting moieties. In certain embodiments, the bispecific antigen-binding proteins of the present disclosure comprise two CD16A antigen-binding moieties and two BCMA-targeting moieties. In certain embodiments, each of two CD16A antigen-binding moieties is fused to the C-terminus of each heavy chain of an IgG, and each of two BCMA-targeting moieties is fused to the N-terminus of the IgG.

In certain embodiments, the bispecific antigen-binding proteins of the present disclosure comprise bispecific antigen-binding proteins having the structure shown in FIG. 13. In certain of such embodiments, the bispecific antigen-binding proteins comprise one BCMA-targeting moiety. In certain of such embodiments, the BCMA-targeting moiety is fused to the N-terminus of the Fc portion to which the at least two CD16A antigen-binding moieties are fused.

In certain embodiments, the bispecific antigen-binding has the structure shown in FIG. 5.

In certain embodiments, the bispecific antigen-binding protein of the present disclosure comprise a CD16A antigen-binding moiety comprising: (i) a heavy chain variable region comprising a CDR1 having the amino acid sequence set forth in SEQ ID NO:50; a CDR2 having the amino acid sequence set forth in SEQ ID NO:51 or 56; and a CDR3 having the amino acid sequence set forth in SEQ ID NO:52, and/or (ii) a light chain variable region comprising a CDR1 having the amino acid sequence set forth in SEQ ID NO:53; a CDR2 having the amino acid sequence set forth in SEQ ID NO:54; and a CDR3 having the amino acid sequence set forth in SEQ ID NO:55. In certain embodiments, the heavy chain variable region CDR2 has the amino acid sequence set forth in SEQ ID NO:51. In certain embodiments, the heavy chain variable region CDR2 has the amino acid sequence set forth in SEQ ID NO:56.

In certain embodiments, the bispecific antigen-binding proteins of the present disclosure comprise a CD16A antigen-binding moiety comprising: (i) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and/or (ii) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78. In certain embodiments, the CD16A antigen-binding moiety comprises (i) a heavy chain variable region comprising an amino acid sequence that is at least about 80% homologous or identical to the amino acid sequence set forth in SEQ ID NO: 3, and/or (ii) a light chain variable region comprising an amino acid sequence that is at least about 80% homologous or identical to the amino acid sequence set forth in SEQ ID NO: 2. In certain embodiments, the CD16A antigen-binding moiety comprises (i) a heavy chain variable region comprising the amino acid sequence set forth in SEQ ID NO: 3, and/or (ii) a light chain variable region comprising the amino acid sequence set forth in SEQ ID NO: 2.

In certain embodiments, the bispecific antigen-binding proteins of the present disclosure comprise a BCMA antigen-binding moiety comprising: (i) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and/or (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72. In certain embodiments, the BCMA antigen-binding moiety comprises (i) a heavy chain variable region comprising an amino acid sequence that is at least about 80% homologous or identical to the amino acid sequence set forth in SEQ ID NO: 65, and/or (ii) a light chain variable region comprising an amino acid sequence that is at least about 80% homologous or identical to the amino acid sequence set forth in SEQ ID NO: 66. In certain embodiments, the BCMA antigen-binding moiety comprises (i) a heavy chain variable region comprising the amino acid sequence set forth in SEQ ID NO: 65, and/or (ii) a light chain variable region comprising the amino acid sequence set forth in SEQ ID NO: 66.

In certain embodiments, the bispecific antigen-binding proteins of the present disclosure comprise two CD16A antigen-binding moieties and two BCMA-targeting moieties, wherein: (a) each of the CD16A antigen-binding moieties comprises a $V_H$ CDR1 having the amino acid sequence set forth in SEQ ID NO:73, a $V_H$ CDR2 having the amino acid sequence set forth in SEQ ID NO:74, a $V_H$ CDR3 having the amino acid sequence set forth in SEQ ID NO:75, a $V_L$ CDR1 having the amino acid sequence set forth in SEQ ID NO:76, a $V_L$ CDR2 having the amino acid sequence set forth in SEQ ID NO:77, and a $V_L$ CDR3 having the amino acid sequence set forth in SEQ ID NO:78; and (b) each of the BCMA-targeting moieties comprises a $V_H$ CDR1 having the amino acid sequence set forth in SEQ ID NO:67, a $V_H$ CDR2 having the amino acid sequence set forth in SEQ ID NO:68, a CDR3 having the amino acid sequence set forth in SEQ ID NO:69, a $V_L$ CDR1 having the amino acid sequence set forth in SEQ ID NO:70, a $V_L$ CDR2 having the amino acid sequence set forth in SEQ ID NO:71, and a $V_L$ CDR3 having the amino acid sequence set forth in SEQ ID NO:72. In certain embodiments, (a) each of the CD16A antigen-binding moieties comprises a heavy chain variable region comprising the amino acid sequence set forth in SEQ ID NO: 3, and a light chain variable region comprising the amino acid sequence set forth in SEQ ID NO: 2; and (b) each of the BCMA-targeting moieties comprises a heavy chain variable region comprising the amino acid sequence set forth in SEQ ID NO: 65, and (ii) a light chain variable region comprising the amino acid sequence set forth in SEQ ID NO: 66.

In certain embodiments, the bispecific antigen-binding protein of the present disclosure is a tetramer comprising a first polypeptide having the amino acid sequence set forth in SEQ ID NO: 61 and a second polypeptide having the amino acid sequence set forth in SEQ ID NO: 62. In certain embodiments, the bispecific antigen-binding protein of the present disclosure is a tetramer comprising a first polypeptide having the amino acid sequence set forth in SEQ ID NO: 63 and a second polypeptide having the amino acid sequence set forth in SEQ ID NO: 64.

In certain embodiments, the bispecific antigen-binding protein of the present disclosure comprises two CD16A antigen-binding moieties and two BCMA antigen-binding moieties where: (i) the CD16A antigen-binding moieties each comprise: (a) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and (b) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78; and (ii) the BCMA antigen-binding moieties each comprises: (a) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72.

In certain embodiments, the present disclosure is directed to pharmaceutical compositions comprising a bispecific antigen-binding protein as described herein and a pharmaceutically acceptable carrier. In certain embodiments, the pharmaceutical composition is for use as a medicament.

In certain embodiments, the present disclosure is directed to a method of treating and/or preventing a disease, the method comprising administering the bispecific antigen-binding protein of or the pharmaceutical composition as described herein. In certain embodiments, said disease is cancer. In certain embodiments, said disease is a hematologic cancer. In certain embodiments, said disease is multiple myeloma. In certain embodiments, the bispecific antigen-binding protein is administered intravenously. In certain embodiments, the bispecific antigen-binding protein is administered subcutaneously. In certain embodiments, the bispecific antigen-binding protein is administered with a second therapy. In certain embodiments, the second therapy is selected from the group consisting of therapies comprising an anti-PD-1 antibody, therapies comprising an anti-PD-L$_1$ antibodies, therapies comprising a CD3 bispecific antibody, therapies comprising an anti-TIGIT antibody, therapies comprising an anti-VEGF antibody, and therapies comprising an anti-FcRH5 antibody. In certain embodiments, the second therapy is a cytokine therapy. In certain embodiments, the cytokine therapy is the administration of a cytokine selected from the group consisting of IL-15, IL-2, IL-12, IL-21, IL-17, IL-18, IL-23, IL-27, and IL-6. In certain embodiments, the cytokine is IL-15. In certain embodiments, the cytokine is IL-2. In certain embodiments, the subject is a cancer patient. In certain embodiments, the subject is a hematological cancer patient. In certain embodiments, the subject is a multiple myeloma patient. In certain embodiments, the subject is a relapsed/refractory multiple myeloma patient. In certain embodiments, the subject has received an anti-CD38 therapy. In certain embodiments, the subject has received daratumumab. In certain embodiments, the subject is daratumumab naïve, daratumumab resistant, daratumumab refractory, or daratumumab relapsed. In certain embodiments, the subject is daratumumab resistant, daratumumab refractory, or daratumumab relapsed. In certain embodiments, the subject expresses a CD16A polymorphism. In certain embodiments, the CD16A polymorphism is a CD16A-158V/F polymorphism.

In certain embodiments, the present disclosure is directed to a multispecific antigen-binding protein as described herein or a bispecific antigen binding protein as described herein, wherein the multispecific antigen binding protein or bispecific antigen binding protein does not substantially deplete or reduce a subject's Natural Killer (NK) cell population when administered to said subject.

In certain embodiments, the preset disclosure is directed to a method of treating a subject having a depleted or reduced NK cell population, comprising administering a multispecific antigen-binding protein as described herein or a bispecific antigen binding protein as described herein. In certain embodiments, the subject has been previously treated with an anti-cd38 therapy. In certain embodiments, the anti-cd38 therapy is daratumumab therapy.

In certain embodiments, the present disclosure is directed to a bispecific antigen-binding protein comprising two CD16A antigen-binding moieties and two BCMA-targeting moieties, wherein each of the two CD16A antigen-binding moieties is fused to the C-terminus of each heavy chain of an IgG, and each of the two BCMA-targeting moieties is fused to the N-terminus of each of the heavy chain of the IgG, and wherein: (i) the CD16A antigen-binding moieties each comprise: (a) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and (b) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78; and (ii) the BCMA antigen-binding moieties each comprises: (a) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72.

In certain embodiments, the present disclosure is directed to methods of treating cancer in a subject, comprising: administering to the subject a bispecific antigen-binding protein comprising two CD16A antigen-binding moieties and two BCMA-targeting moieties, wherein each of the two CD16A antigen-binding moieties is fused to the C-terminus of each heavy chain of an IgG, and each of the two BCMA-targeting moieties is fused to the N-terminus of each of the heavy chain of the IgG, and wherein: (i) the CD16A antigen-binding moieties each comprise: (a) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and (b) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78; and (ii) the BCMA antigen-binding moieties each comprises: (a) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72. In certain embodiments, the cancer is multiple myeloma.

In certain embodiments, the present disclosure is directed to an antibody or an antigen-binding protein that binds to or is capable of binding to CD16A and BCMA, comprising: (i) a first heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, (ii) a first light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78; (iii) a second heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (iv) a second light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72. For example, in certain embodiments, the antibody or antigen-binding protein that binds to or is capable of binding to CD16A and BCMA, comprises: (i) a first heavy chain variable region that comprises the amino acid sequence set forth in SEQ ID NO: 3; (ii) a first light chain variable region that comprises the amino acid sequence set forth in SEQ ID NO: 2; (iii) a second heavy chain variable region that comprises the amino acid sequence set forth in SEQ ID NO: 65; (iv) a second light chain variable region that comprises the amino acid sequence set forth in SEQ ID NO: 66; (v) a first heavy chain variable region that comprises the amino acid sequence set forth in SEQ ID NO: 3 and a first light chain variable region that comprises the amino acid sequence set forth in SEQ ID NO: 2; (vi) a second heavy chain variable region that comprises the amino acid sequence set forth in SEQ ID NO: 65 and a second light chain variable region that comprises the amino acid sequence set forth in SEQ ID NO: 66; or (vii) a first heavy chain variable region that comprises the amino acid sequence set forth in SEQ ID NO: 3; and a first light chain variable region that comprises the amino acid sequence set forth in SEQ ID NO: 2; and a second heavy chain variable region that comprises the amino acid sequence set forth in SEQ ID NO: 65 and a second light chain variable region that comprises the amino acid sequence set forth in SEQ ID NO: 66. In certain embodiments the antibody or an antigen-binding protein that binds to or is capable of binding to CD16A and BCMA as described herein does not bind to CD16B. In certain embodiments the antibody or an antigen-binding protein that binds to or is capable of binding to CD16A and BCMA as described herein does not substantially deplete or reduce a subject's Natural Killer (NK) cell population when administered to the subject. In certain embodiments the antibody or an antigen-binding protein that binds to or is capable of binding to CD16A and BCMA as described herein binds human CD16A. In certain embodiments the antibody or an antigen-binding protein that binds to or is capable of binding to CD16A and BCMA as described herein binds human BCMA.

In certain embodiments, the present disclosure is directed to a pharmaceutical composition comprising an antibody or an antigen-binding protein that binds to or is capable of binding to CD16A and BCMA as described herein and a pharmaceutically acceptable carrier.

In certain embodiments, the antibody or an antigen-binding protein that binds to or is capable of binding to CD16A and BCMA as described herein is for use as a medicament.

In certain embodiments the present disclosure is directed to a method of treating and/or preventing a disease, where the method comprises administering the antibody or an antigen-binding protein that binds to or is capable of binding to CD16A and BCMA as described herein or the pharmaceutical composition comprising the antibody or an antigen-binding protein that binds to or is capable of binding to CD16A and BCMA as described herein to a subject in the need thereof. In certain embodiments, the disease is cancer. In certain embodiments, the disease is a hematologic cancer. In certain embodiments, the disease is multiple myeloma. In certain embodiments, the antibody or antigen-binding protein is administered intravenously. In certain embodiments, the antibody or antigen-binding protein is administered subcutaneously. In certain embodiments, treating and/or preventing a disease, where the method comprises administering the antibody or an antigen-binding protein that binds to or is capable of binding to CD16A and BCMA as described herein or the pharmaceutical composition comprising the antibody or an antigen-binding protein that binds to or is capable of binding to CD16A and BCMA as described herein comprises administering a second therapy. In certain embodiments, the second therapy is selected from the group consisting of therapies comprising an anti-PD-1 antibody, therapies comprising an anti-PD-L1 antibodies, therapies comprising a CD3 bispecific antibody, therapies comprising an anti-TIGIT antibody, therapies comprising an anti-VEGF antibody, and therapies comprising an anti-FcRH5 antibody. In certain embodiments, the second therapy is a cytokine therapy. In certain embodiments, the cytokine therapy is the administration of a cytokine selected from the group consisting of IL-15, IL-2, IL-12, IL-21, IL-17, IL-18, IL-23, IL-27, and IL-6. In certain embodiments, the cytokine is IL-15. In certain embodiments, the cytokine is IL-2. In certain embodiments, the subject is a cancer patient. In certain embodiments, the subject is a hematological cancer patient. In certain embodiments, the subject is a multiple myeloma patient. In certain embodiments, the subject is a relapsed/refractory multiple myeloma patient. In certain embodiments, the subject has received an anti-CD38 therapy. In certain embodiments, the subject has received daratumumab. In certain embodiments, the subject is daratumumab naïve, daratumumab resistant, daratumumab refractory, or daratumumab relapsed. In certain embodiments, the subject is daratumumab resistant, daratumumab refractory, or daratumumab relapsed. In certain embodiments, the subject expresses a CD16A polymorphism. In certain embodiments, the CD16A polymorphism is a CD16A-158V/F polymorphism.

In certain embodiments, the present disclosure is directed to a method of treating a subject having a depleted or reduced NK cell population, comprising administering an antibody or an antigen-binding protein that binds to or is capable of binding to CD16A and BCMA as described herein or a pharmaceutical composition comprising the antibody or an antigen-binding protein that binds to or is capable of binding to CD16A and BCMA as described herein. In certain embodiments, the subject has been previously treated with an anti-CD38 therapy. In certain embodiments, the anti-CD38 therapy is daratumumab therapy.

In certain embodiments, the present disclosure is directed to an antibody or an antigen-binding protein, comprising at least one arm that binds to or is capable of binding to CD16A, and at least one arm that binds to or is capable of binding to BCMA, wherein: (i) the at least one arm that binds to or is capable of binding to CD16A comprises: (a) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and (b) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78; and (ii) the at least one arm that binds to or is capable of binding to BCMA comprises: (a) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72. In certain of such embodiments, the at least one arm that binds to or is capable of binding to CD16A is distinct from the at least one arm that binds to or is capable of binding to BCMA. In certain of such embodiments: (i) the at least one arm that binds to or is capable of binding to CD16A comprises a heavy chain variable region comprising the amino acid sequence set forth in SEQ ID NO: 3; (ii) the at least one arm that binds to or is capable of binding to CD16A comprises a light chain variable region comprising the amino acid sequence set forth in SEQ ID NO: 2; (iii) the at least one arm that binds to or is capable of binding to BCMA comprises a heavy chain variable region comprising the amino acid sequence set forth in SEQ ID NO: 65; (iv) the at least one arm that binds to or is capable of binding to BCMA comprises a light chain variable region comprising the amino acid sequence set forth in SEQ ID NO: 66; (v) the at least one arm that binds to or is capable of binding to CD16A comprises a heavy chain variable region comprising the amino acid sequence set forth in SEQ ID NO: 3 and a light chain variable region comprising the amino acid sequence set forth in SEQ ID NO: 2; (vi) the at least one arm that binds to or is capable of binding to BCMA comprises a heavy chain variable region comprising the amino acid sequence set forth in SEQ ID NO: 65 and a light chain variable region comprising the amino acid sequence set forth in SEQ ID NO: 66; or (vii) the at least one arm that binds to or is capable of binding to CD16A comprises a heavy chain variable region comprising the amino acid sequence set forth in SEQ ID NO: 3 and a light chain variable region comprising the amino acid sequence set forth in SEQ ID NO: 2; and the at least one arm that binds to or is capable of binding to BCMA comprises a heavy chain variable region comprising the amino acid sequence set forth in SEQ ID NO: 65 and a light chain variable region comprising the amino acid sequence set forth in SEQ ID NO: 66. In certain of such embodiments, the antibody or antigen-binding protein does not bind to CD16B. In certain of such embodiments, the antibody or antigen-binding protein does not substantially deplete or reduce a subject's Natural Killer (NK) cell population when administered to said subject. In certain of such embodiments, the antibody or antigen-binding protein binds human CD16A. In certain of such embodiments, the antibody or antigen-binding protein binds human BCMA.

In certain embodiments, the present disclosure is directed to a pharmaceutical composition comprising antibody or antigen-binding protein comprising at least one arm that binds to or is capable of binding to CD16A, and at least one arm that binds to or is capable of binding to BCMA as disclosed herein and a pharmaceutically acceptable carrier.

In certain embodiments, the present disclosure is directed to an antibody or an antigen-binding protein, comprising at least one arm that binds to or is capable of binding to CD16A, and at least one arm that binds to or is capable of binding to BCMA for use as a medicament.

In certain embodiments, the present disclosure is directed to a method of treating and/or preventing a disease, the method comprising: administering an antibody or an antigen-binding protein, comprising at least one arm that binds to or is capable of binding to CD16A, and at least one arm that binds to or is capable of binding to BCMA as described herein or a pharmaceutical composition comprising such an antibody or antigen-binding protein to a subject in the need thereof. In certain embodiments, the disease is cancer. In certain embodiments, the disease is a hematologic cancer. In certain embodiments, the disease is multiple myeloma. In certain embodiments, the antibody or antigen-binding protein is administered intravenously. In certain embodiments, the antibody or antigen-binding protein is administered subcutaneously. In certain embodiments, the method of treating and/or preventing a disease, the method comprising: administering an antibody or an antigen-binding protein, comprising at least one arm that binds to or is capable of binding to CD16A, and at least one arm that binds to or is capable of binding to BCMA as described herein or a pharmaceutical composition comprising such an antibody or antigen-binding protein to a subject in the need thereof comprises administering a second therapy. In certain embodiments, the second therapy is selected from the group consisting of therapies comprising an anti-PD-1 antibody, therapies comprising an anti-PD-L1 antibodies, therapies comprising a CD3 bispecific antibody, therapies comprising an anti-TIGIT antibody, therapies comprising an anti-VEGF antibody, and therapies comprising an anti-FcRH5 antibody. In certain embodiments, the second therapy is a cytokine therapy. In certain embodiments, the cytokine therapy is the administration of a cytokine selected from the group consisting of IL-15, IL-2, IL-12, IL-21, IL-17, IL-18, IL-23, IL-27, and IL-6. In certain embodiments, the cytokine is IL-15. In certain embodiments, the cytokine is IL-2. In certain embodiments, the subject is a cancer patient. In certain embodiments, the subject is a hematological cancer patient. In certain embodiments, the subject is a multiple myeloma patient. In certain embodiments, the subject is a relapsed/refractory multiple myeloma patient. In certain embodiments, the subject has received an anti-CD38 therapy. In certain embodiments, the subject has received daratumumab. In certain embodiments, the subject is daratumumab naïve, daratumumab resistant, daratumumab refractory, or daratumumab relapsed. In certain embodiments, the subject is daratumumab resistant, daratumumab refractory, or daratumumab relapsed. In certain embodiments, the subject expresses a CD16A polymorphism. In certain embodiments, the CD16A polymorphism is a CD16A-158V/F polymorphism. In certain embodiments, the method comprises treating a subject having a depleted or reduced NK cell population. In certain embodiments, the subject has been previously treated with an anti-CD38 therapy. In certain embodiments, the anti-CD38 therapy is daratumumab therapy.

In certain embodiments, the present disclosure is directed to an antibody or an antigen-binding protein that binds to or is capable of binding to BCMA, comprising: (i) a heavy chain variable region comprising a CDR1 having the amino acid sequence set forth in SEQ ID NO:67; a CDR2 having the amino acid sequence set forth in SEQ ID NO:68; and a CDR3 having the amino acid sequence set forth in SEQ ID NO:69, and (ii) a light chain variable region comprising a CDR1 having the amino acid sequence set forth in SEQ ID NO:70; a CDR2 having the amino acid sequence set forth in SEQ ID NO:71; and a CDR3 having the amino acid sequence set forth in SEQ ID NO:72. In certain embodiments, the BCMA is human BCMA. In certain embodiments, the antibody or antigen-binding protein comprises at least one arm that binds to or is capable of binding to CD16A. In certain embodiments, the CD16A is human CD16A. In certain of such embodiments, the at least one arm that binds to or is capable of binding to CD16A comprises: (i) a heavy chain variable region comprising a CDR1 having the amino acid sequence set forth in SEQ ID NO:73; a CDR2 having the amino acid sequence set forth in SEQ ID NO:74; and a CDR3 having the amino acid sequence set forth in SEQ ID NO:75, and (ii) a light chain variable region comprising a CDR1 having the amino acid sequence set forth in SEQ ID NO:76; a CDR2 having the amino acid sequence set forth in SEQ ID NO:77; and a CDR3 having the amino acid sequence set forth in SEQ ID NO:78. In certain of such embodiments, the antibody or antigen-binding protein that binds to or is capable of binding to BCMA, comprises: (i) a heavy chain variable region comprising the amino acid sequence set forth in SEQ ID NO: 3; (ii) a light chain variable region comprising the amino acid sequence set forth in SEQ ID NO: 2; (iii) a heavy chain variable region comprising the amino acid sequence set forth in SEQ ID NO: 65; (iv) a light chain variable region comprising the amino acid sequence set forth in SEQ ID NO: 66; (v) a heavy chain variable region comprising the amino acid sequence set forth in SEQ ID NO: 3 and a light chain variable region comprising the amino acid sequence set forth in SEQ ID NO: 2; (vi) a heavy chain variable region comprising the amino acid sequence set forth in SEQ ID NO: 65 and a light chain variable region comprising the amino acid sequence set forth in SEQ ID NO: 66; or (vii) a first heavy chain variable region comprising the amino acid sequence set forth in SEQ ID NO: 3, a first light chain variable region comprising the amino acid sequence set forth in SEQ ID NO: 2; and a second heavy chain variable region comprising the amino acid sequence set forth in SEQ ID NO: 65 and a second chain variable region comprising the amino acid sequence set forth in SEQ ID NO: 66.

In certain embodiments, the present disclosure is directed to a pharmaceutical composition comprising an antibody or an antigen-binding protein that binds to or is capable of binding to BCMA as disclosed herein, and a pharmaceutically acceptable carrier.

In certain embodiments, the present disclosure is directed to an antibody or an antigen-binding protein that binds to or is capable of binding to BCMA as disclosed herein for use as a medicament.

In certain embodiments, the present disclosure is directed to methods of treating and/or preventing a disease, the methods comprising administering an antibody or an antigen-binding protein that binds to or is capable of binding to BCMA or a pharmaceutical composition comprising the same to a subject in the need thereof. In certain embodiments, the disease is cancer. In certain embodiments, the disease is a hematologic cancer. In certain embodiments, the disease is multiple myeloma. In certain embodiments, the antibody or antigen-binding protein is administered intravenously. In certain embodiments, the antibody or antigen binding protein is administered subcutaneously. In certain embodiments, the methods of treating and/or preventing a disease, the methods comprising administering an antibody or an antigen-binding protein that binds to or is capable of binding to BCMA or a pharmaceutical composition comprising the same to a subject in the need thereof comprise administering a second therapy. In certain embodiments, the second therapy is selected from the group consisting of therapies comprising an anti-PD-1 antibody, therapies comprising an anti-PD-L1 antibodies, therapies comprising a CD3 bispecific antibody, therapies comprising an anti-TIGIT antibody, therapies comprising an anti-VEGF antibody, and therapies comprising an anti-FcRH5 antibody. In certain embodiments, the second therapy is a cytokine therapy. In certain embodiments, the cytokine therapy is the administration of a cytokine selected from the group consisting of IL-15, IL-2, IL-12, IL-21, IL-17, IL-18, IL-23, IL-27, and IL-6. In certain embodiments, the cytokine is IL-15. In certain embodiments, the cytokine is IL-2. In certain embodiments, the subject is a cancer patient. In certain embodiments, the subject is a hematological cancer patient. In certain embodiments, the subject is a multiple myeloma patient. In certain embodiments, the subject is a relapsed/refractory multiple myeloma patient. In certain embodiments, the subject has received an anti-CD38 therapy. In certain embodiments, the subject has received daratumumab. In certain embodiments, the subject is daratumumab naïve, daratumumab resistant, daratumumab refractory, or daratumumab relapsed. In certain embodiments, the subject is daratumumab resistant, daratumumab refractory, or daratumumab relapsed. In certain embodiments, the subject expresses a CD16A polymorphism. In certain embodiments, the CD16A polymorphism is a CD16A-158V/F polymorphism. In certain embodiments, the antibody or antigen-binding protein is administered to a subject having a depleted or reduced NK cell population. In certain embodiments, the subject has been previously treated with an anti-CD38 therapy. In certain embodiments, the anti-CD38 therapy is daratumumab therapy.

EXAMPLES

Example 1: Construction of a BCMA Antigen-Binding Moiety

For constructing the antigen-binding moieties antibody fragments with selective binding to a chosen target antigen can be isolated from a human antibody library by expression and display of single chain Fv domains (scFv) on filamentous fusion phage and enrichment of phage particles encoding scFv exhibiting target binding by panning on recombinant target antigen or target antigen-positive cells, as described, for example, in Smith GP (Science, 1985, 228: 1315-7) and Clackson et al. (Nature, 1991, 352: 624-8). To isolate BCMA-binding antibody fragments, recombinant human BCMA(1-54)-Fc, cynomolgus BCMA(1-53)-Fc and CHO cells stably expressing cell surface anchored human BCMA(1-54) or cynomolgus BCMA(1-53) fused to the transmembrane region and cytoplasmic domain of human CD3zeta can be used in subsequent panning rounds to enrich binding phage particles. For this, phage particles are incubated with recombinant Fc-fusion antigen in solution, e.g., for 2 h at room temperature, followed by capture with Protein G-coated beads and washing in PBS-Tween and PBS to remove unbound phage. Bound phage is eluted with glycine. For enrichment of binding phage on target antigen-expressing cells, phage is incubated with stably transfected CHO cells, e.g., for 1 h at room temperature, followed by washing with cell culture medium and elution of bound phage with glycine. To reduce enrichment of phage particles encoding antibody fragments with selective binding to Fc or non-transfected CHO cells, phage pools are incubated with irrelevant Fc-fusion antigen or target antigen-negative CHO cells. Subsequent to each round of panning and elution of bound phage, eluted phage particles are used to infect E. coli (XL1 Blue) and propagate phage and scFv-encoding DNA. Following repeated phage panning and propagation of enriched phage clones, DNA is isolated from E. coli and recloned into bacterial expression vectors, e.g., pSKK2, using standard molecular biology techniques for subsequent production of His-tagged (SEQ ID NO:59) scFv antibody fragments in E. coli and preparation of bacterial periplasmic extracts. Periplasmic extracts containing scFv antibody fragments are subjected to screening methods, such as ELISA or flow cytometry, to assess target antigen binding. For example, recombinant human BCMA(1-54)-Fc or cynomolgus BCMA(1-53)-Fc is bound by anti-human Fc antibody coated in standard ELISA microwell plates followed by incubation with bacterial periplasmic extracts and extensive washing. scFv binding is detected using anti-His-HRP conjugate. To assess scFv binding to cell-expressed BCMA, bacterial periplasmic extracts are incubated with recombinant CHO cells expressing cell surface anchored human or cynomolgus BCMA followed by washing and detection of bound scFv using anti-His-R-PE by flow cytometry. Plasmids encoding scFv antibody fragments with selective binding to human and/or cynomolgus BCMA antigen are isolated from the respective bacterial clones and analyzed by DNA sequencing to obtain scFv encoding DNA sequences. For example BCMA antigen-binding moiety having an amino acid sequence as depicted in SEQ ID NO:39, wherein VH is depicted in SEQ ID NO:37 and VL is depicted in SEQ ID NO:38 has been obtained.

Example 2: Generation of Different Antigen-Binding Protein Scaffolds 2.1 scDb-mFc (FIG. 1 and FIG. 2):

A scDb-mFc refers to an antigen-binding protein which is monomeric and comprises a bivalent CD16A antigen-binding moiety in the format of a scDb fused to a monomeric Fc portion. Either the scDb consisting of two CD16A antigen-binding moieties is fused to the N-terminus of the Fc portion which consists of a variant CH2-CH3 polypeptide and a scFv consisting of a single target antigen-binding moiety fused to the C-terminus of the Fc portion (FIG. 1) or the scDb consisting of two CD16A antigen-binding moieties is fused to the C-terminus of the Fc portion which consists of a variant CH2-CH3 polypeptide and a scFv consisting of a single target antigen-binding moiety fused to the N-terminus of the Fc portion (FIG. 2).

For expression of the scDb-mFc antigen binding protein in CHO cells, coding sequence of the molecule was cloned into the mammalian expression vector system. In brief, gene sequences encoding the anti-TAA (Tumor associated Antigen) Fv domains and the anti-CD16A Fv domains (SEQ ID NOs:1-13) in a scFv format connected by gene sequences encoding short peptide linkers (SEQ ID NOs:16-18) in a scFv were synthesized by Thermo Fisher Scientific/Invitrogen GeneArt (Regensburg, Germany). PCR-amplicons of the different variable domains and of the monomeric Fc portion containing the silencing point-mutations (SEQ ID NO:30) were generated with corresponding primers. Afterwards the different overlapping DNA-fragments and the linearized backbone vector are combined together in one isothermal reaction. The scDb-mFc expression construct was designed to contain coding sequences for an N-terminal signal peptide to facilitate antibody secretion and an Fc portion to facilitate antibody secretion and purification, respectively. Sequences of all constructs were confirmed by DNA sequencing at GATC (Köln, Germany) using custom made primers. The expression cassette for the scDb-mFc is cloned such that the anti-CD16A domains are positioned N- or C-terminal of the monomeric Fc portion and connected via a connector sequence (SEQ ID NOs:19-22) in the following possible orders:

1.) $V_L$(CD16A)-L1-$V_H$(CD16A)-L2-$V_L$(CD16A)-L1-$V_H$(CD16A)
2.) $V_H$(CD16A)-L1-$V_L$(CD16A)-L3-$V_H$(CD16A)-L1-$V_L$(CD16A)
3.) $V_L$(CD16A)-L4-$V_L$(CD16A)-L3-$V_H$(CD16A)-L4-$V_H$(CD16A)
4.) $V_H$(CD16A)-L4-$V_H$(CD16A)-L2-$V_L$(CD16A)-L4-$V_L$(CD16A)

In the structures of antigen-binding proteins scDb-mFc_01, scDb-mFc_02, scDb-mFc_05 and scDb-mFc_06 specific for SEQ ID NO:16 is used for linker L1, SEQ ID NO:17 is used for linker L2 and SEQ ID NO:18 is used for L3. In the structures of antigen-binding proteins scDb-mFc_03, scDb-mFc_04, scDb-mFc_07 and scDb-mFc_08 SEQ ID NO: 60 is used for linker L4, SEQ ID NO:17 is used for linker L2 and SEQ ID NO:18 is used for L3.

2.2 KiH-scDb-Fc (FIG. 3-6):

A KiH-scDb-Fc antigen-binding protein is heterodimeric and comprises a bivalent CD16A antigen-binding moiety in the format of a scDb fused to a heterodimeric (KiH) Fc portion. A single target antigen-binding moiety is provided by a scFv.

The DNA expression construct encoding the KiH-scDb-Fc is generated by cloning the encoding sequences of the anti-CD16A Fv domains (SEQ ID NOs: 1-13) into a modified mammalian expression vector containing CMV-controlled expression cassettes including IgG1 constant domains CH2 and CH3 with Fc silencing and "Knobs-into-Holes" point-mutations (SEQ ID NOs:31,32) for co-expression of two gene cassettes from the same vector. The "Knobs-into-Holes" mutations allowing the generation of heterodimeric trivalent bispecific (FIGS. 3-5) or tetravalent trispecific (FIG. 6) Fc fusion constructs. Afterwards PCR amplicons are generated from gene sequences encoding the anti-TAA (Tumor associated Antigen) Fv domains with corresponding primers. The resulting overlapping DNA-fragments are inserted into the co-expression vector at the relevant position. All needed gene sequences encoding variable domains and constant domains containing Fc-silencing and "Knobs-into-Holes" point-mutations were synthesized by Thermo Fisher Scientific/Invitrogen GeneArt (Regensburg, Germany). The KiH-scDb-Fc expression construct was designed to contain coding sequences for N-terminal signal peptides, a C-tag and/or a His-tag (6×His) to facilitate antibody secretion and purification, respectively. Sequences of all constructs were confirmed by DNA sequencing at GATC (Köln, Germany) using custom made primers. The expression cassettes for the KiH-scDb-Fc constructs are cloned such that the CD16A antigen-binding moieties are positioned N-terminal of the heterodimeric Fc portion and connected via a connector (SEQ ID NOs:19-22) and hinge (SEQ ID NO:23) or middle.hinge (SEQ ID NO:24) or C-terminal of the heterodimeric Fc portion and connected via connector (SEQ ID NOs:19-22) only in the following possible orders:

1.) $V_L$(CD16A)-L1-$V_H$(CD16A)-L2-$V_L$(CD16A)-L1-$V_H$(CD16A)
2.) $V_H$(CD16A)-L1-$V_L$(CD16A)-L3-$V_H$(CD16A)-L1-$V_L$(CD16A)
3.) $V_L$(CD16A)-L4-$V_L$(CD16A)-L3-$V_H$(CD16A)-L4-$V_H$(CD16A)
4.) $V_H$(CD16A)-L4-$V_H$(CD16A)-L2-$V_L$(CD16A)-L4-$V_L$(CD16A)

SEQ ID NO: 16 is used for linker L1, SEQ ID NO:17 is used for linker L2, SEQ ID NO:18 is used for linker L3 and SEQ ID NO:60 is used for linker L4.

Examples of such antigen binding proteins are KiH-scDb-Fc_08 and KiH-scDb-Fc_12 which comprise the following structure from the N- to the C-terminus:

First polypeptide chain $V_L$(CD16A)-$V_H$(CD16A)-$V_L$(CD16A)-$V_H$(CD16A)-middle.Hinge-CH2-CH3 and second polypeptide chain Hinge-CH2-CH3-$V_H$(target)-$V_L$(target) (FIG. 3); or first polypeptide chain middle.Hinge-CH2-CH3-$V_L$(CD16A)-$V_H$(CD16A)-$V_L$(CD16A)-$V_H$(CD16A) and second polypeptide $V_H$(target)-$V_L$(target)-Hinge-CH2-CH3 (FIG. 5).

2.3 scDb-TriBs or scDb-TriBs-scFv

A scDb-TriBs is a trispecific antigen-binding protein which is a heterodimeric Fab fragment comprising CD16A-, target and HSA antigen-binding moieties, wherein the antigen-binding moieties are either provided by two scDb fused to the C-terminus of the Fab fragment (FIG. 7) or a scDb comprising the two CD16A antigen-binding proteins and a scFv comprising the target antigen-binding moiety are fused to the C-terminus of the Fab fragment (FIG. 8).

The DNA expression construct encoding the scDb-TriBs (-scFv) is generated by cloning the encoding sequences of the anti-HSA Fv domains (SEQ ID NOs:14,15) into a modified mammalian expression vector containing CMV-controlled expression cassettes including Fab portion only heavy and light chain constant domains (SEQ ID NOs:33-

35) with fusions and for co-expression of two gene cassettes from the same vector. Afterwards PCR amplicons are generated from gene sequences encoding the anti-TAA (Tumor associated Antigen) Fv domains and the anti CD16A Fv domains (SEQ ID NOs:1-13) with corresponding primers. The resulting overlapping DNA-fragments are inserted into the co-expression vector at the relevant position. All needed gene sequences encoding variable domains and Fab portion only constant domains were synthesized by Thermo Fisher Scientific/Invitrogen GeneArt (Regensburg, Germany). The scDb-TriBs(-scFv) expression construct was designed to contain coding sequences for N-terminal signal peptides, a C-tag and/or a His-tag (6×His) to facilitate antibody secretion and purification, respectively. Sequences of all constructs were confirmed by DNA sequencing at GATC (Köln, Germany) using custom made primers. The expression cassettes for the scDb-TriBs(-scFv)constructs are cloned such that the anti-CD16A domains are positioned C-terminal of the CL or CH1 pf the Fab connected via a connector (SEQ ID NOs:19-22) to the heavy or light chain of the Fab in the following possible order:

1.) VL(CD16A)-L1-VH(CD16A)-L2-VL(CD16A)-L1-VH(CD16A)
2.) VL(CD16A)-L1-VL(CD16A)-L2-VH(CD16A)-L1-VH(CD16A)

Example of such an antigen binding protein is scDb-TriB-scFv_01 which comprises the following structure from the N- to the C-terminus: First polypeptide chain $V_H$(HSA)-CH1-$V_L$(CD16A)-$V_H$(CD16A)-$V_L$(CD16A)-$V_H$(CD16A) and second polypeptide chain $V_L$(HSA)-CL-$V_H$(target)-$V_L$(target) (FIG. 8). SEQ ID NO:16 is used for linker L1 and SEQ ID NO:17 or SEQ ID NO:18 is used for linker L2.

2.4 Db-Fc (FIG. 9-10):

A Db-Fc is an antigen-binding protein which is homodimeric and comprises a bivalent CD16A antigen-binding moiety in the format of a Db fused to the Hinge at the N-terminus of a homodimeric Fc portion (CH2-CH3) and two target antigen-binding moieties in the format of scFvs fused to the other terminus of the Fc portion. For expression of the Db-Fc antigen binding protein in CHO cells, coding sequence of the molecule was cloned into the mammalian expression vector system. In brief, gene sequences encoding the anti-TAA (Tumor associated Antigen) Fv domains and the anti-CD16A Fv domains (SEQ ID NOs:1-13) connected by a short peptide linker (SEQ ID NO:16) were synthesized by Thermo Fisher Scientific/Invitrogen GeneArt (Regensburg, Germany). PCR-amplicons of the different variable domains and of the Fc portion containing the silencing point-mutations (SEQ ID NO:29) were generated with corresponding primers. Afterwards the different overlapping DNA-fragments and the linearized backbone vector are combined in one isothermal reaction. The Db-Fc expression construct was designed to contain sequence for a N-terminal signal peptide to facilitate antibody secretion. Sequences of all constructs were confirmed by DNA sequencing at GATC (Köln, Germany) using custom made primers. The expression cassette for the Db-Fc is cloned such that the anti-CD16A domains are positioned N-terminal or C-terminal of the homodimeric Fc portion (CH2-CH3) connected via a connector (SEQ ID NOs: 19-22) to the middle.hinge (SEQ ID NO:24) or C-terminus of CH3 via a connector (SEQ ID NOs: 19-22) only in the following possible orders:

1.) VL(CD16A)-L1-VH(CD16A)
2.) VH(CD16A)-L1-VL(CD16A)

Example of such antigen binding proteins are Db-Fc_02 and Db-Fc_04 which comprise the following structure from the N- to the C-terminus:$V_L$(CD16A)-$V_H$(CD16A)-middle.Hinge-CH2-CH3-$V_H$(target)-VL(target) (FIG. 9); or $V_H$(target)-$V_L$(target)-middle.Hinge-CH2-CH3-$V_L$(CD16A)-$V_H$(CD16A)(FIG. 10).SEQ ID NO:16 is used for linker L1.

2.5 Bi-scFv-Fc (FIG. 11-12):

A Bi-scFv-Fc is a homodimeric and tetravalent antigen-binding protein comprising two CD16A antigen-binding moieties and two target antigen-binding moieties, each in the format of a scFv, fused to a Fc homodimer.

For expression of the Bi-scFv-Fc antigen binding protein in CHO cells, coding sequence of the molecule was cloned into the mammalian expression vector system. In brief, gene sequences encoding the anti-TAA (Tumor associated Antigen) Fv domains and the anti-CD16A Fv domains (SEQ ID NOs:1-13) which are connected by a short peptide linkers (SEQ ID NOs:17-18) were synthesized by Thermo Fisher Scientific GeneArt (Regensburg, Germany). PCR-amplicons of the different variable domains and either of the Fc portion containing the silencing point-mutations (SEQ ID NO:29) or the wild-type Fc portion (SEQ ID NO:36) were generated with corresponding primers. Afterwards the different overlapping DNA-fragments and the linearized backbone vector are combined together in one isothermal reaction. The Bi-scFv-Fc expression construct was designed to contain coding sequences for an N-terminal signal peptide and an Fc portion to facilitate antibody secretion and purification, respectively. Sequences of all constructs were confirmed by DNA sequencing at GATC (Köln, Germany) using custom made primers. The expression cassette for the Bi-scFv-Fc is cloned such that the anti-CD16A domains are positioned N-terminal of the Fc portion connected via a connector (SEQ ID NOs:19-22) or hinge (SEQ ID NO:23) or C-terminal of the Fc portion connected to CH3 via a connector (SEQ ID NOs:19-22) only in the following possible orders:

1.) VL(CD16A)-L3-VH(CD16A)
2.) VH(CD16A)-L2-VL(CD16A)

Example of such antigen binding proteins are Bi-scFv-Fc_27 and Bi-scFv-Fc_26 which comprise the following structure from the N- to the C-terminus: $V_L$(CD16A)-$V_H$(CD16A)-Hinge-CH2-CH3-$V_H$(target)-$V_L$(target) (FIG. 11); or $V_H$(target)-$V_L$(target)-Hinge-CH2-CH3-$V_L$(CD16A)-$V_H$(CD16A)(FIG. 12). SEQ ID NO:17 is used for linker L2 and SEQ ID NO:18 is used for linker L3.

2.6 scFv-IgAb (FIG. 13):

A scFv-IgAb antigen-binding protein comprises an IgG antibody and two CD16A antigen-binding moieties in the format of scFvs, wherein each of the scFv CD16A antigen-binding moiety is fused to the C-terminus of one of the H chains and two target antigen-binding moieties are provided by each Fv in the Fab arms of the IgG.

The DNA expression construct encoding the scFv-IgAb is generated by cloning the encoding sequences of the anti-TAA Fv domains into a modified mammalian expression vector containing CMV-controlled expression cassettes including heavy and light chain constant domains with Fc silencing point-mutations (SEQ ID NOs: 25, 27-28) or with the wild-type Fc portion (SEQ ID NO:26-28) for co-expression of both gene cassettes from the same vector. Afterwards PCR amplicons are generated from the gene sequences encoding the anti-CD16A Fv domains (SEQ ID NOs:1-13) separated by short peptide linkers (SEQ ID NOs:17-18) with corresponding primers. The resulting overlapping DNA-fragment is inserted into the co-expression vector at the relevant position. All needed gene sequences encoding variable domains and constant domains containing the Fc silencing point-mutations were synthesized by Thermo Fisher Scientific/Invitrogen GeneArt (Regensburg, Germany). The scFv-IgAb expression construct was designed to contain coding sequences for N-terminal signal peptides and an Fc portion to facilitate antibody secretion and purification, respectively. Sequences of all constructs were confirmed by DNA sequencing at GATC (Köln, Germany) using custom made primers. The expression cassette for the scFv-IgAb is cloned such that the anti-CD16A domains are positioned C-terminal of the Fc portion connected via a connector (SEQ ID NOs:19-22) in the following possible orders:

1.) VL(CD16A)-L3-VH(CD16A)
2.) VH(CD16A)-L2-VL(CD16A)

Example of such an antigen binding protein is scFv-IgAb_30 which comprises the following structure from the N- to the C-terminus:

First polypeptide chain $V_H$(target)-CH1-Hinge-CH2-CH3-$V_L$(CD16A)-$V_H$(CD16A) and second polypeptide chain $V_L$(target)-CL (FIG. 13). SEQ ID NO:17 is used for linker L2 and SEQ ID NO:18 is used for linker L3.

2.7 Bi-scFv-IgAb (FIG. 14):

A Bi-scFv-IgAb antigen-binding protein comprises an IgG antibody and four scFv antigen-binding moieties fused thereto, wherein each of the two CD16A antigen-binding moieties in the format of a scFv is fused to a C-terminus of one of the two H chains and each of two target antigen-binding moieties is fused to the C-terminus of one of the two CL regions.

The DNA expression construct encoding the Bi-scFv-IgAb is generated by cloning the encoding sequences of the anti-TAA Fv domains into a modified mammalian expression vector containing CMV-controlled expression cassettes including heavy and light chain constant domains with Fc silencing point-mutations (SEQ ID NOs: 25, 27-28) for co-expression of two gene cassettes from the same vector. Afterwards a PCR amplicons are generated from the gene sequences encoding the anti-CD16A or target antigen-binding Fv domains (SEQ ID NOs:1-13) separated by a short peptide linkers with corresponding primers. The resulting overlapping DNA-fragments are inserted into the co-expression vector at the relevant position. All needed gene sequences encoding variable domains and constant domains containing the Fc silencing point-mutations were synthesized by Thermo Fisher Scientific/Invitrogen GeneArt (Regensburg, Germany). The Bi-scFv-IgAb expression construct was designed to contain coding sequences for N-terminal signal peptides and an Fc portion to facilitate antibody secretion and purification, respectively. Sequences of all constructs were confirmed by DNA sequencing at GATC (Köln, Germany) using custom made primers. The expression cassette for the Bi-scFv-IgAb is cloned such that the anti-CD16A domains are positioned C-terminal of the Fc portion connected via a connector (SEQ ID NOs:19-22) in the following possible orders:

1.) VL(CD16A)-L3-VH(CD16A)
2.) VH(CD16A)-L2-VL(CD16A)

Example of such an antigen binding protein is Bi-scFv-IgAb_03 which comprises the following structure from the N- to the C-terminus:

First polypeptide chain $V_H$(target1)-CH1-Hinge-CH2-CH3-$V_L$(CD16A)-$V_H$(CD16A) and second polypeptide chain $V_L$(target1)-CL-$V_L$(target2)-$V_H$(target2) (FIG. 14). SEQ ID NO:17 is used for linker L2 and SEQ ID NO:18 is used for linker L3.

2.8 KiH-scFv-Fc (FIGS. 15a and 15b):

A KiH-scFv-Fc antigen-binding protein comprises four scFv antigen-binding moieties fused to a heterodimeric (KiH) Fc portion, wherein two CD16A antigen-binding moieties are fused either N- or C-terminally to the Fc portion.

The DNA expression construct encoding the KiH-scFv-Fc is generated by cloning the encoding sequences of the anti-CD16A Fv domains (SEQ ID NOs:1-13) into a modified mammalian expression vector containing CMV-controlled expression cassettes including IgG1 constant domains CH2 and CH3 with Fc silencing and "Knobs-into-Holes" point-mutations (SEQ ID NOs:31-32) for co-expression of two gene cassettes from the same vector. The "Knobs-into-Holes" mutations allowing the generation of bispecific Fc fusion constructs. Afterwards PCR amplicons are generated from gene sequences encoding the anti-TAA (Tumor associated Antigen) Fv domains with corresponding primers. The resulting overlapping DNA-fragments are inserted into the co-expression vector at the relevant position. All needed gene sequences encoding variable domains and constant domains containing Fc-silencing and "Knobs-into-Holes" point-mutations were synthesized by Thermo Fisher Scientific/Invitrogen GeneArt (Regensburg, Germany). The KiH-scFv-Fc expression construct was designed to contain coding sequences for N-terminal signal peptides, an Fc portion, a C-tag and a His-tag (6×His) to facilitate antibody secretion and purification, respectively. Sequences of all constructs were confirmed by DNA sequencing at GATC (Köln, Germany) using custom made primers. The expression cassettes for the KiH-scFv-Fc constructs are cloned such that the anti-CD16A domains are positioned N-terminal of the heterodimeric Fc portion connected via a connector (SEQ ID NOs:19-22) and hinge (SEQ ID NO:23) or C-terminal of the Fc portion via connector (SEQ ID NOs:19-22) only in the following possible orders:

1.) VL(CD16A)-L3-VH(CD16A)
2.) VH(CD16A)-L2-VL(CD16A)

Examples of such antigen-binding proteins are KiH-scFv-Fc_09 and KiH-scFv-Fc_11 which comprise the following structure from the N- to the C-terminus:

First polypeptide chain $V_L$(CD16A)-$V_H$(CD16A)-Hinge-CH2-CH3-$V_H$(target1)-$V_L$(target1) and second polypeptide chain $V_L$(CD16A)-$V_H$(CD16A)-Hinge-CH2-CH3-$V_H$(target2)-$V_L$(target2) (FIG. 15a); or first polypeptide chain $V_H$(target1)-$V_L$(target1)-Hinge-CH2-CH3-$V_L$(CD16A)-$V_H$(CD16A) and second polypeptide chain $V_H$(target2)-$V_L$(target2)-Hinge-CH2-CH3-$V_L$(CD16A)-$V_H$(CD16A) (FIG. 15b). SEQ ID NO:17 is used for linker L2 and SEQ ID NO:18 is used for linker L3.

Example 3: Production of NK Cell Engager Antibody Formats Using Stable CHO Cell Pools Host Cell Culture Flp-In CHO cells (Life Technologies), a derivative of CHO-K1 Chinese Hamster ovary cells (ATCC, CCL-61) (Kao and Puck, 1968), were cultured in Ham's F-12 Nutrient Mix supplemented with L-Glutamine, 10% FCS and 100 µg/ml Zeocin. Adherent cells were detached with 0.25 Trypsin-EDTA and subcultured according to standard cell culture protocols provided by Life Technologies.

For adaptation to growth in suspension, cells were detached from tissue culture flasks and placed in serum-free HyClone CDM4 CHO medium for subsequent incubation in shake flasks at 37° C., 5% $CO_2$ and 120 rpm. The standard medium for the culture of suspension-adapted Flp-In CHO Host cells was HyClone CDM4 CHO supplemented with L-Glutamine, HT Supplement, Penicillin/Streptomycin and 100 µg/ml Zeocin. Suspension-adapted cells were cryopreserved in medium with 10% DMSO and tested negative for Mycoplasma using MycoAlert Mycoplasma detection Kit (Lonza).

Generation of Stably Transfected Cell Pools

Recombinant Flp-In CHO cell lines stably expressing secreted recombinant antibodies, Fc fusion constructs or comparator antibodies were generated by transfection of suspension-adapted host cells. For this, cells were placed in standard medium without Zeocin one day prior to co-transfection with expression plasmids (2.5 µg) encoding the protein of interest (pcDNA5-FRT) and the Flp recombinase (pOG44, Life Technologies) using Polyethylenimine (PEI). In brief, vector DNA and transfection reagent were mixed at a DNA:PEI ratio of 1:3 (µg/µg) in a total of 100 µL OptiMEM I medium and incubated for 10 minutes before addition to 2E+6 Flp-In CHO cells suspended in 1 ml of CHO-S-SFMII medium (Life Technologies). Following 24-48 h incubation, selection for stably transfected cells was started by addition of 6-7 µg/mL Puromycin Dihydrochloride subsequent to diluting cultures to a density of 0.2E+6 viable cells/mL in CHO-S-SFMII medium. Flp recombinase mediates the insertion of the Flp-In expression construct into the genome at the integrated FRT site through site-specific DNA recombination (O'Gorman et al 1991). During selection viable cell densities were measured twice a week, and cells were centrifuged and resuspended in fresh selection medium at a maximal density of 0.2E+6 viable cells/mL. Cell pools stably expressing recombinant protein products were recovered after 2-3 weeks of selection at which point cells were transferred to standard culture medium in shake flasks. Expression of recombinant secreted proteins was confirmed by protein gel electrophoresis of cell culture supernatants using Criterion Stain-Free (Bio-Rad) technology (see below). Stable cell pools were cryopreserved in medium containing 7.5% DMSO.

Production of Recombinant Protein in Fed-Batch CHO Cell Suspension Cultures

Recombinant proteins were produced in 10- or 11-day fed-batch cultures of stably transfected CHO cells by secretion into the cell culture supernatant. For this, cells stably expressing recombinant antibodies, Fc fusion antigens or comparator antibodies were seeded at starting densities of 6E+5 cells/mL in standard culture medium in polycarbonate Erlenmeyer flasks with gas permeable caps (Corning) and incubated at 37° C. and 5% $CO_2$ with agitation at 140 rpm. During fed-batch culture, media were supplemented with 40 mL/L ActiCHO Feed A (GE Healthcare) and 4 mL/L ActiCHO Feed B (GE Healthcare) on day 0 (starting day), and with double amounts on day 3, 5, and 7. Cell culture supernatants were harvested after 10 or 11 days at culture viabilities of typically >75%. Samples were collected from the production cultures every other day prior to feeding and cell density and viability was assessed. On the day of harvest, cell culture supernatants were cleared by centrifugation and vacuum filtration (0.22 µm) using Millipore Express PLUS Membrane Filters (Millipore) before further use.

Expression Titer Quantification:

Protein expression titers and product integrity in cell culture supernatants (CSS) are analysed by SDS-PAGE on days 5, 7 and 10 or 11 of production cultures. Samples are mixed with SDS PAGE sample buffer prior to loading on 4-20% Criterion TGX Precast SDS PAGE Gels (Biorad). Total protein is visualized in the gel using the Criterion Stain-free Molecular Imaging System (Biorad). Product titers are determined semi-quantitatively by comparison with reference antibodies of known concentration.

Purification of Antigen-Binding Proteins

1. Antigen-Binding Proteins Comprising a Fc Portion (scDb-mFc, Db-Fc, Bi-scFv-Fc, Bi-scFv-IgAb, scFv-Fc, scFv-IgAb as Described in Example 2)

Target proteins were purified from clarified CHO cell culture supernatants in a two-step procedure comprising Protein A and preparative SEC. For Protein A the clarified supernatant was loaded on a HiTrap MabSelectSuRe column (GE-Healthcare). After washing with phosphate-buffered saline pH 7.4 and 10 mM sodium phosphate pH 7.0 protein was eluted in a two-step gradient with 50 mM sodium acetate pH 3.5 and 10 mM glycine/HCL pH 2.0. The purity of fractions was analyzed using SE-HPLC and SDS-PAGE. Fractions exhibiting acceptable purity were pooled and subjected to preparative gel filtration using a Superdex 200 prep grade column (GE-Healthcare). Eluate fractions containing purified target molecules were pooled and subjected to buffer exchange using Sephadex G-25 column with 10 mM sodium acetate, 4.5% sorbitol pH 5.0, and concentrated by ultrafiltration to a typical concentration of approx. 1 mg/ml. Typical purity of these constructs (measured by SE-HPLC) was in the range of 87.6% to 99.8% and homogeneity (in non-reducing SDS-PAGE) between 58.4% and 100%.

2. Antigen-Binding Proteins KiH-scDb-Fc and scDb-Tribody-scFv According to Example 2 Containing η-Light Chain and His-Tag Target proteins were purified from clarified CHO cell culture supernatants in a three-step procedure comprising Protein L, IMAC and preparative SEC. For Protein L the clarified supernatant was loaded on a HiTrap Protein L column (GE Healthcare). After washing with phosphate-buffered saline pH 7.4 and 10 mM sodium phosphate pH 7.0 protein was eluted in a two-step gradient with 10 mM glycine/HCL pH 3.0 and 10 mM glycine/HCL pH 2.0. The purity of fractions was analyzed using SE-HPLC and SDS-PAGE. Fractions exhibiting acceptable purity were pooled and subjected to a further IMAC purification. Thus, sample was diluted (1:4) with Equilibration buffer (50 mM Tris/HCL, 150 mM Sodium Chloride pH7.5 and loaded on a HisTrap FF column (GE Healthcare). After washing with Equilibration buffer (50 mM Tris/HCL, 150 mM Sodium Chloride pH 7.5) protein was eluted in a three-step gradient with 7%/30%/100% Elution buffer (50 mM Tris/HCL, 0.4 M Arginine, 500 mM Imidazole pH7.5). The purity of fractions was analyzed using SE-HPLC and SDS-PAGE. Fractions exhibiting acceptable purity were pooled and subjected to a preparative gel filtration using a Superdex 200 prep grade column (GE-Healthcare). Eluate fractions containing purified target molecules were pooled and subjected to buffer exchange using Sephadex G-25 column with 10 mM sodium acetate, 4.5% sorbitol pH 5.0, and concentrated by ultrafiltration to a typical concentration of approx. 1 mg/ml. Typical purity of these constructs (measured by SE-HPLC) was in the range of 95.9% to 99.8% and homogeneity (in non-reducing SDS-PAGE) between 72.2% and 99.0%.

3) Antigen-Binding Proteins Molecules KiH-scFv-Fc and KiH-scDb-Fc Containing a C-Tag on the First Polypeptide and a His-tag on the Second Polypeptide Target proteins were purified from clarified CHO cell culture supernatants in a three-step procedure comprising C-Tag Affinity Chromatography, IMAC and preparative SEC. For C-Tag Affinity Chromatography the clarified supernatant was loaded on a CaptureSelect C-tag XL column (Thermo Scientific). After washing with phosphate-buffered saline pH 7.4 protein was eluted with 20 mM Sodium Citrate pH 3.0. The purity of fractions was analyzed using SE- HPLC and SDS-PAGE. Fractions exhibiting acceptable purity were pooled and subjected to a further IMAC purification. Thus, sample was diluted (1:4) with Equilibration buffer (50 mM Tris/HCL, 150 mM Sodium Chloride pH7.5 and loaded on a HisTrap FF column (GE Healthcare). After washing with Equilibration buffer (50 mM Tris/HCL, 150 mM Sodium Chloride pH 7.5) protein was eluted in a three-step gradient with 7%/30%/100% Elution buffer (50 mM Tris/HCL,0.4 M Arginine, 500 mM Imidazole pH7.5). The purity of fractions was analyzed using SE-HPLC and SDS-PAGE. Fractions exhibiting acceptable purity were pooled and subjected to a preparative gel filtration using a Superdex 200 prep grade column (GE-Healthcare). Eluate fractions containing purified target molecules were pooled and subjected to buffer exchange using Sephadex G-25 column with 10 mM sodium acetate, 4.5% sorbitol pH 5.0, and concentrated by ultrafiltration to a typical concentration of approx. 1 mg/ml. Typical purity of these constructs (measured by SE-HPLC) was in the range of 94.8% to 99.0% and homogeneity (in non-reducing SDS-PAGE) between 86.8% and 100%.

4) scDb-Tribody

Proteins were purified from clarified CHO cell culture supernatants in a two-step procedure comprising IMAC and preparative SEC. For IMAC the clarified supernatant and 5 mM Imidazole pH7.0 was loaded on a HisTrap FF column (GE Healthcare). After washing with Equilibration buffer (50 mM Tris/HCL, 150 mM Sodium Chloride pH 7.5) protein was eluted in a three-step gradient with 7%/30%/ 100% Elution buffer (50 mM Tris/HCL, 0.4 M Arginine, 500 mM Imidazole pH7.5). The purity of fractions was analyzed using SE-HPLC and SDS-PAGE. Fractions exhibiting acceptable purity were pooled and subjected to a preparative gel filtration using a Superdex 200 prep grade column (GE-Healthcare). Eluate fractions containing purified target molecules were pooled and subjected to buffer exchange using Sephadex G-25 column with 10 mM sodium acetate, 4.5% sorbitol pH 5.0, and concentrated by ultrafiltration to a typical concentration of approx. 1 mg/ml. Typical purity of these constructs (measured by SE-HPLC) was in the range of 95.1% to 100% and homogeneity (in non-reducing SDS-PAGE) higher than 85.8%.

a) scDb-Tribody_09-10

Proteins were purified from clarified CHO cell culture supernatants in a two-step procedure comprising Fab/lambda Affinity Chromatography and preparative SEC. For Fab/lambda Affinity Chromatography the clarified supernatant was loaded on a Fab Select Lambda column (GE Healthcare). After washing with phosphate-buffered saline pH 7.4 protein was eluted with 100 mM Sodium Acetate pH 3.5. The purity of fractions was analyzed using SE-HPLC and SDS-PAGE. Fractions exhibiting acceptable purity were pooled and subjected to a preparative gel filtration using a Superdex 200 prep grade column (Ge-Healthcare). Eluate fractions containing purified target molecules were pooled and subjected to buffer exchange using Sephadex G-25 column with 10 mM sodium acetate, 4.5% sorbitol pH 5.0, and concentrated by ultrafiltration to a typical concentration of approx. 1 mg/ml. Typical purity of these constructs (measured by SE-HPLC) higher than 94.8% and homogeneity (in non-reducing SDS-PAGE) higher than 92.7%.

Protein Analytics

Homogeneity of the final samples were assessed by SDS-PAGE under reducing and non-reducing conditions. The samples were mixed with non-reducing 2×SDS PAGE sample buffer or reducing 2×SDS-Page sample buffer containing dithiothreitol (DTT) as reducing agent. All samples were heated at 95° C. for 5 min prior to loading on 4-20% Criterion TGX Precast SDS Page Gel. 2 µg of purified protein sample were loaded. To separate the proteins in the gel, SDS-PAGE were run in 1× Tris/Glycine/SDS buffer at 300 V for approx. 22 min. Total protein were visualized in the gel using the Criterion Stain-free Molecular Imaging System (Biorad). Page Ruler Unstained Protein ladder was used as molecular weight marker. Relative signal intensity of product band in non-reducing SDS-PAGE was compared to possible high or low molecular weight species.

Purity of protein preparations was evaluated by analytical SE-HPLC using Superdex 200 Increase 10/300GL column (GE-Healthcare).

Purified proteins were stored as aliquots at −80° C. until further use.

Example 4: Binding of CD16A Antigen-Binding Proteins to Primary Human NK Cells at 37° C. or to Recombinant Human CD16A Soluble Antigen in ELISA Methods Isolation of PBMC from Buffy Coats and Enrichment of Human NK Cells PBMCs were isolated from buffy coats (German Red Cross, Mannheim, Germany) by density gradient centrifugation. The buffy coat samples were diluted with a two-to-threefold volume of PBS (Invitrogen, cat.: 14190-169), layered on a cushion of Lymphoprep (Stem Cell Technologies, cat.: 07861) and centrifuged at 800×g for 25 min at room temperature w/o brake. PBMC located in the interface were collected and washed 3 times with PBS before they were cultured in complete RPMI 1640 medium supplemented with 10% FCS overnight without stimulation. For the enrichment of NK cells, PBMCs were harvested from overnight cultures and used for one round of negative selection using the EasySep™ Human NK Cell Enrichment Kit (Stem Cell Technologies, cat.: 19955) for the immunomagnetic isolation of untouched human NK cells and the Big Easy EasySep™ Magnet (Stem Cell Technologies, cat.: 18001) according to the manufacturer's instructions.

Cell Binding Assays and Flow Cytometric Analyses

Aliquots of enriched human NK cells were incubated with 100 µL of serial dilutions of the indicated CD16A AAF constructs in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) for 45 min at 37° C. After repeated washing with FACS buffer, cell-bound antibodies were detected with 15 µg/mL FITC-conjugated goat anti-human IgG (Dianova, cat.: 109-095-098). After the last staining step, the cells were washed again and resuspended in 0.2 mL of FACS buffer containing 2 µg/mL propidium iodide (PI) (Sigma, cat.: P4170) in order to exclude dead cells. The fluorescence of $2-5 \times 10^3$ living cells was measured using a Millipore Guava EasyCyte flow cytometer (Merck Millipore, Schwalbach, Germany). Mean fluorescence intensities of the cell samples were calculated using Incyte software (Merck Millipore, Schwalbach, Germany). After subtracting the fluorescence intensity values of the cells stained with the secondary and tertiary reagents alone, the values were used for non-linear regression analysis using the GraphPad Prism software (GraphPad Prism version 6.00 for Windows, GraphPad Software, La Jolla Calif. USA). For the calculation of $K_D$, the equation for one-site-binding (hyperbola) was used.

Analysis of CD16A Soluble Antigen Binding in ELISA 96-well ELISA plates (Immuno MaxiSorp; Nunc) were coated overnight at 4° C. with recombinant NK cell engager antibody formats or control antibodies in 100 mM Carbonate-bicarbonate buffer. Depending on the molecular weight, antibodies were coated at a concentrations of 2.0-5.0 μg/mL, corresponding to molar concentration of approximately 20 nM. After a blocking step with 3% (w/v) skim milk powder (Merck) dissolved in PBS, serial dilutions of biotinylated, recombinant human CD16A(48R-158V) fused to human IgG1 Fc portion in PBS containing 0.3% (w/v) skim milk powder were incubated on the plates for 1.5 h at room temperature. After washing three times with 300 μL per well of PBS containing 0.1% (v/v) Tween 20, plates were incubated with the detection conjugate, Streptavidin-HRP (Roche) at 1:10000 dilution for 1 hour at room temperature. After washing three times with 300 μL per well of PBS containing 0.1% (v/v) Tween 20, plates were incubated with Tetramethylbenzidine (TMB) substrate (Seramun) until colour development was clearly visible. The reaction was stopped through the addition of 100 μL per well of 0.5 M $H_2SO_4$. The absorbance was measured at 450 nm using a multilabel plate reader (Victor, Perkin Elmer). Absorbance values were plotted and analyzed using nonlinear regression, sigmoidal dose-response (variable slope), least squares (ordinary) fit with GraphPad Prism version 6.07 (GraphPad Software, La Jolla Calif. USA).

Results

The apparent binding affinities of the indicated CD16A antigen-binding proteins were determined on primary human NK cells at 37° C. in at least two independent experiments. Furthermore, CD16A antigen-binding proteins ability to bind soluble CD16A was analyzed in ELISA. Both methods demonstrate that the CD16A antigen-binding proteins show specific binding to CD16A. Due to bivalent CD16 binding high affinities are obtained. Differences in the absolute values of KD values measured in NK cell binding and EC50 values measured in ELISA are due to different methodologies, reagents and assay setups. The results are shown in Table 2.

TABLE 2

Apparent affinities of CD16A antibody constructs on primary human NK cells at 37° C. (mean $K_D$ and of independent experiments are presented) or apparent binding of CD16A antigen to coated antibody constructs analyzed by ELISA (EC50 values are presented).

| Product | NK cell engager format | CD16A binding domain | CD16A binding domain order | target binding domain1 | target binding domain2 | Connector1 SEQ ID | Hinge SEQ ID | Fc portion | Connector2 SEQ ID | NK cell binding mean $K_D$ [nM] | CD16A binding (ELISA) EC50 [nM] |
|---|---|---|---|---|---|---|---|---|---|---|---|
| scDb-mFc__01 | FIG. 1 | P2C47 | VL-VH-VL-VH | BCMA | | NO: 20 | no | Sil.mFc | NO: 20 | 1.2 | 0.32 |
| scDb-mFc__02 | FIG. 1 | P2C47 | VH-VL-VH-VL | BCMA | | NO: 20 | no | Sil.mFc | NO: 20 | 4.9 | 0.42 |
| scDb-mFc__03 | FIG. 1 | P2C47 | VL-VL-VH-VH | BCMA | | NO: 20 | no | Sil.mFc | NO: 20 | n.t. | 0.23 |
| scDb-mFc__04 | FIG. 1 | P2C47 | VH-VH-VL-VL | BCMA | | NO: 20 | no | Sil.mFc | NO: 20 | n.t. | 0.22 |
| scDb-mFc__06 | FIG. 2 | P2C47 | VL-VH-VL-VH | BCMA | | NO: 20 | no | Sil.mFc | NO: 20 | 3.8 | 0.64 |
| scDb-mFc__07 | FIG. 2 | P2C47 | VL-VL-VH-VH | BCMA | | NO: 20 | no | Sil.mFc | NO: 20 | n.t. | 0.29 |
| scDb-mFc__08 | FIG. 2 | P2C47 | VH-VH-VL-VL | BCMA | | NO: 20 | no | Sil.mFc | NO: 20 | n.t. | 0.33 |
| KiH-scDb-Fc__08 | FIG. 3 | P2C47 | VL-VH-VL-VH | BCMA | | NO: 19 | NO: 24 | Sil. | 0 | 0.9 | 0.27 |
| KiH-scDb-Fc__09 | FIG. 3 | P2C47 | VH-VL-VH-VL | BCMA | | NO: 19 | NO: 24 | Sil. | 0 | 6.2 | 0.40 |
| KiH-scDb-Fc__10 | FIG. 3 | P2C47 | VL-VL-VH-VH | BCMA | | NO: 19 | NO: 24 | Sil. | 0 | n.t. | 0.21 |
| KiH-scDb-Fc__11 | FIG. 3 | P2C47 | VH-VH-VL-VL | BCMA | | NO: 19 | NO: 24 | Sil. | 0 | n.t. | 0.19 |
| KiH-scDb-Fc__04 | FIG. 4 | P2C47 | VL-VH-VL-VH | BCMA | | NO: 19 | NO: 24 | Sil. | 0 | 1.0 | 0.19 |
| KiH-scDb-Fc__05 | FIG. 4 | P2C47 | VH-VL-VH-VL | BCMA | | NO: 19 | NO: 24 | Sil. | 0 | 28.0 | 0.23 |
| KiH-scDb-Fc__06 | FIG. 4 | P2C47 | VL-VL-VH-VH | BCMA | | NO: 19 | NO: 24 | Sil. | 0 | 2.3 | 0.22 |
| KiH-scDb-Fc__07 | FIG. 4 | P2C47 | VH-VH-VL-VL | BCMA | | NO: 19 | NO: 24 | Sil. | 0 | n.t. | 0.21 |
| KiH-scDb-Fc__12 | FIG. 5 | P2C47 | VL-VH-VL-VH | BCMA | | 0 | NO: 24 | Sil. | NO: 20 | 1.8 | 0.29 |
| KiH-scDb-Fc__13 | FIG. 5 | P2C47 | VH-VL-VH-VL | BCMA | | 0 | NO: 24 | Sil. | NO: 20 | 4.0 | 0.41 |
| KiH-scDb-Fc__14 | FIG. 5 | P2C47 | VL-VL-VH-VH | BCMA | | 0 | NO: 24 | Sil. | NO: 20 | n.t. | 0.39 |
| KiH-scDb-Fc__15 | FIG. 5 | P2C47 | VH-VH-VL-VL | BCMA | | 0 | NO: 24 | Sil. | NO: 20 | n.t. | 0.21 |
| KiH-scDb-Fc__01 | FIG. 6 | P2C47 | VL-VH-VL-VH | CD19 | BCMA | 0 | NO: 23 | Sil. | NO: 20 | n.t. | 0.17 |
| KiH-scDb-Fc__02 | FIG. 6 | P2C47 | VL-VH-VL-VH | CD20 | BCMA | 0 | NO: 23 | Sil. | NO: 20 | n.t. | 0.16 |
| KiH-scDb-Fc__03 | FIG. 6 | P2C47 | VL-VH-VL-VH | CD20 | BCMA | 0 | NO: 23 | Sil. | NO: 20 | n.t. | 0.11 |
| scDb-Tribody__01 | FIG. 7 | LSIV21 | VL-VL-VH-VH | HSA(N1) | EGFR | NO: 20 | no | no | NO: 20 | n.t. | 0.65 |
| scDb-Tribody__09 | FIG. 7 | P2C47 | VL-VH-VL-VH | HSA(N1) | BCMA | NO: 20 | no | no | NO: 20 | n.t. | 0.25 |
| scDb-Tribody__10 | FIG. 7 | P2C47 | VL-VH-VL-VH | HSA(N1) | BCMA | NO: 20 | no | no | NO: 20 | n.t. | 0.25 |
| scDb-TriB-scFv__01 | FIG. 8 | P2C47 | VL-VH-VL-VH | HSA(CA) | BCMA | NO: 20 | no | no | NO: 20 | n.t. | 0.30 |
| Db-Fc__01 | FIG. 9 | P2C47 | VH-VL | BCMA | | NO: 20 | NO: 24 | Sil. | NO: 20 | 87.7 | 0.27 |
| Db-Fc__02 | FIG. 9 | P2C47 | VL-VH | BCMA | | NO: 20 | NO: 24 | Sil. | NO: 20 | 1.5 | 0.15 |
| Db-Fc__03 | FIG. 10 | P2C47 | VH-VL | BCMA | | 0 | NO: 24 | Sil. | NO: 21 | 17.6 | 0.50 |
| Db-Fc__17 | FIG. 10 | P2C47 | VL-VH | BCMA | | 0 | NO: 24 | Sil. | NO: 22 | n.t. | 0.31 |
| Bi-scFv-Fc__02 | FIG. 11 | LSIV21 | VL-VH | EGFR | | 0 | NO: 23 | Sil. | NO: 20 | n.t. | 0.38 |
| Bi-scFv-Fc__04 | FIG. 11 | LSIV21 | VL-VH | EGFR | | 0 | no | WT | 0 | n.t. | 0.37 |
| Bi-scFv-Fc__17 | FIG. 11 | P2C47 | VH-VL | BCMA | | NO: 21 | NO: 23 | Sil. | NO: 20 | 5.1 | 0.29 |
| Bi-scFv-Fc__22 | FIG. 11 | LSIV21 | VL-VH | EGFR | | 0 | NO: 23 | Sil. | NO: 20 | n.t. | 0.39 |
| Bi-scFv-Fc__24 | FIG. 11 | LSIV21 | VL-VH | EGFR | | 0 | NO: 23 | WT | NO: 20 | n.t. | 0.34 |
| Bi-scFv-Fc__27 | FIG. 11 | P2C47 | VH-VL | BCMA | | 0 | NO: 23 | Sil. | NO: 20 | 1.7 | 0.33 |
| Bi-scFv-Fc__28 | FIG. 11 | P2C47 | VH-VL | BCMA | | 0 | NO: 23 | Sil. | NO: 20 | n.t. | 0.27 |
| Bi-scFv-Fc__31 | FIG. 11 | P2C47 | VL-VH | BCMA | | 0 | NO: 23 | WT | NO: 20 | 0.9 | 0.24 |
| Bi-scFv-Fc__32 | FIG. 11 | P2C47 | VL-VH | BCMA | | 0 | NO: 23 | WT | NO: 20 | n.t. | 0.27 |
| Bi-scFv-Fc__39 | FIG. 11 | LSIV21 | VL-VH | BCMA | | 0 | NO: 23 | Sil. | NO: 20 | n.t. | 0.38 |
| Bi-scFv-Fc__03 | FIG. 12 | LSIV21 | VH-VL | EGFR | | 0 | no | WT | 0 | n.t. | 0.47 |
| Bi-scFv-Fc__19 | FIG. 12 | P2C47 | VH-VL | BCMA | | 0 | NO: 23 | Sil. | NO: 22 | 4.2 | 0.23 |
| Bi-scFv-Fc__21 | FIG. 12 | LSIV21 | VL-VH | EGFR | | 0 | NO: 23 | Sil. | NO: 20 | 51.1 | 0.50 |
| Bi-scFv-Fc__23 | FIG. 12 | LSIV21 | VL-VH | EGFR | | 0 | NO: 23 | WT | NO: 20 | 6.4 | 0.33 |
| Bi-scFv-Fc__25 | FIG. 12 | P2C47 | VH-VL | BCMA | | 0 | NO: 23 | Sil. | NO: 20 | n.t. | 0.47 |

TABLE 2-continued

Apparent affinities of CD16A antibody constructs on primary human NK cells at 37° C. (mean $K_D$ and of independent experiments are presented) or apparent binding of CD16A antigen to coated antibody constructs analyzed by ELISA (EC50 values are presented).

Figure 16:
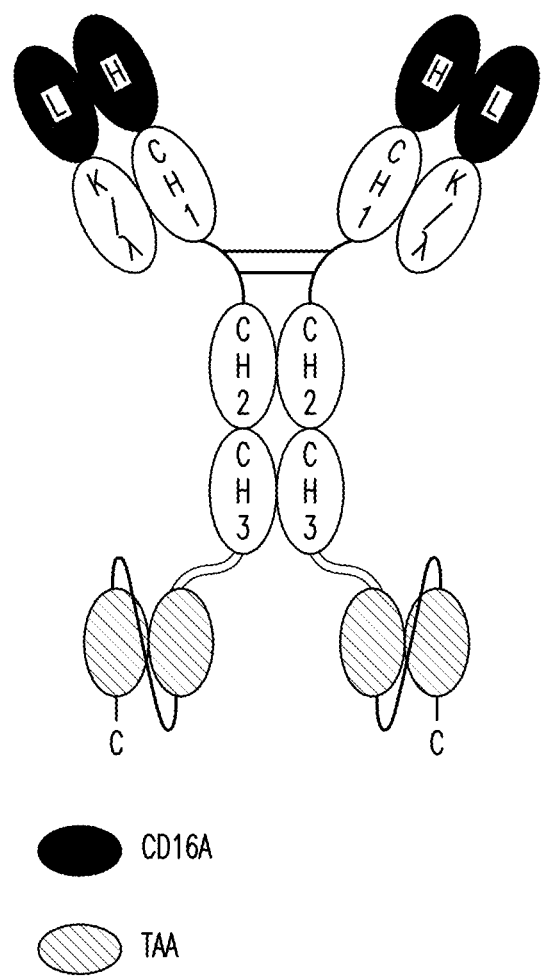
FIG. 16 shows a scFv-IgAb antigen-binding protein which comprises an IgG antibody-fusion with two target antigen-binding moieties in the format of scFvs fused to the C-terminus of the H chain, whereas two CD16A antigen-binding moieties are provided by each Fv in the Fab arms of the IgG. The target is a tumor associated target.

| Product | NK cell engager format | CD16A binding domain | CD16A binding domain order | target binding domain1 | target binding domain2 | Connector1 SEQ ID | Hinge SEQ ID | Fc portion | Connector2 SEQ ID | NK cell binding mean $K_D$ [nM] | CD16A binding (ELISA) EC50 [nM] |
|---|---|---|---|---|---|---|---|---|---|---|---|
| Bi-scFv-Fc_26 | FIG. 12 | P2C47 | VL-VH | BCMA | | 0 | NO: 23 | Sil. | NO: 20 | 15.7 | 0.47 |
| Bi-scFv-Fc_29 | FIG. 12 | P2C47 | VH-VL | BCMA | | 0 | NO: 23 | WT | NO: 20 | n.t. | 0.32 |
| Bi-scFv-Fc_30 | FIG. 12 | P2C47 | VL-VH | BCMA | | 0 | NO: 23 | WT | NO: 20 | n.t. | 0.29 |
| scFv-IgAb_03 | FIG. 13 | LSIV21 | VH-VL | EGFR | | 0 | no | WT | 0 | n.t. | 0.78 |
| scFv-IgAb_17 | FIG. 13 | P2C47 | VH-VL | BCMA | | 0 | NO: 23 | Sil. | NO: 22 | 8.0 | 0.44 |
| scFv-IgAb_18 | FIG. 13 | P2C47 | VL-VH | BCMA | | 0 | NO: 23 | Sil. | NO: 22 | 6.7 | 0.51 |
| scFv-IgAb_25 | FIG. 13 | LSIV21 | VL-VH | EGFR | | 0 | NO: 23 | Sil. | NO: 20 | n.t. | 0.85 |
| scFv-IgAb_27 | FIG. 13 | LSIV21 | VL-VH | EGFR | | 0 | no | WT | 0 | n.t. | 0.53 |
| scFv-IgAb_29 | FIG. 13 | P2C47 | VH-VL | BCMA | | 0 | NO: 23 | Sil. | NO: 20 | 20.9 | 0.82 |
| scFv-IgAb_30 | FIG. 13 | P2C47 | VL-VH | BCMA | | 0 | NO: 23 | Sil. | NO: 20 | 22.2 | 0.67 |
| scFv-IgAb_32 | FIG. 13 | P2C47 | VH-VL | BCMA | | 0 | no | WT | 0 | n.t. | 0.71 |
| scFv-IgAb_36 | FIG. 13 | P2C47 | VL-VH | CD20 | | 0 | NO: 23 | WT | NO: 20 | n.t. | 0.16 |
| scFv-IgAb_37 | FIG. 13 | P2C47 | VL-VH | CD20 | | 0 | NO: 23 | Sil. | NO: 20 | n.t. | 0.18 |
| scFv-IgAb_43 | FIG. 13 | P2C47 | VL-VH | EGFR | | 0 | NO: 23 | Sil. | NO: 22 | n.t. | 0.26 |
| Bi-scFv-IgAb_02 | FIG. 14 | P2C47 | VL-VH | CD20 | BCMA | 0 | NO: 23 | Sil. | NO: 20 | 22.0 | 0.21 |
| Bi-scFv-IgAb_03 | FIG. 14 | P2C47 | VL-VH | CD19 | BCMA | 0 | NO: 23 | Sil. | NO: 22 | n.t. | 0.25 |
| Bi-scFv-IgAb_04 | FIG. 14 | P2C47 | VL-VH | CD19 | His | 0 | NO: 23 | Sil. | NO: 22 | n.t. | 0.22 |
| Bi-scFv-IgAb_05 | FIG. 14 | P2C47 | VL-VH | BCMA | His | 0 | NO: 23 | Sil. | NO: 22 | n.t. | 0.16 |
| Bi-scFv-IgAb_06 | FIG. 14 | P2C47 | VL-VH | CD19 | RSV | 0 | NO: 23 | Sil. | NO: 22 | 11.3 | 0.21 |
| Bi-scFv-IgAb_07 | FIG. 14 | P2C47 | VL-VH | BCMA | RSV | 0 | NO: 23 | Sil. | NO: 22 | n.t. | 0.15 |
| KiH-scFv-Fc_09 | FIG. 15a | P2C47 | VL-VH | CD19 | BCMA | 0 | NO: 23 | Sil. | NO: 20 | 3.2 | 0.20 |
| KiH-scFv-Fc_10 | FIG. 15a | P2C47 | VL-VH | CD20 | BCMA | 0 | NO: 23 | Sil. | NO: 20 | n.t. | 0.22 |
| KiH-scFv-Fc_17 | FIG. 15a | P2C47 | VL-VH | CD20 | BCMA | 0 | NO: 23 | Sil. | NO: 20 | 3.2 | 0.20 |
| KiH-scFv-Fc_19 | FIG. 15a | P2C47 | VL-VH | CD19 | BCMA | 0 | NO: 23 | Sil. | NO: 20 | n.t. | 0.25 |
| KiH-scFv-Fc_20 | FIG. 15a | P2C47 | VL-VH | CD20 | BCMA | 0 | NO: 23 | Sil. | NO: 20 | n.t. | 0.22 |
| KiH-scFv-Fc_11 | FIG. 15b | P2C47 | VL-VH | CD19 | BCMA | 0 | NO: 23 | Sil. | NO: 20 | 22.6 | 0.41 |
| KiH-scFv-Fc_12 | FIG. 15b | P2C47 | VL-VH | CD20 | BCMA | 0 | NO: 23 | Sil. | NO: 20 | n.t. | 0.47 |
| KiH-scFv-Fc_18 | FIG. 15b | P2C47 | VL-VH | CD20 | BCMA | 0 | NO: 23 | Sil. | NO: 20 | 41.0 | 0.30 |
| KiH-scFv-Fc_21 | FIG. 15b | P2C47 | VL-VH | CD19 | BCMA | 0 | NO: 23 | Sil. | NO: 20 | n.t. | 0.50 |
| KiH-scFv-Fc_22 | FIG. 15b | P2C47 | VL-VH | CD20 | BCMA | 0 | NO: 23 | Sil. | NO: 20 | n.t. | 0.41 |
| scFv-IgAb_02 | FIG. 16 | LSIV21 | Fab | EGFR | n.a. | n.a. | NO: 23 | Sil. | NO: 20 | 7.7 | 0.24 |
| scFv-IgAb_22 | FIG. 16 | P2C47 | Fab | BCMA | n.a. | n.a. | NO: 23 | Sil. | NO: 20 | n.t. | 0.13 |
| scFv-IgAb_26 | FIG. 16 | LSIV21 | Fab | EGFR | n.a. | n.a. | NO: 23 | Sil. | NO: 20 | 5.3 | 0.19 |
| scFv-IgAb_31 | FIG. 16 | P2C47 | Fab | BCMA | n.a. | n.a. | NO: 23 | Sil. | NO: 20 | nt. | 0.16 |
| scFv-IgAb_34 | FIG. 16 | P2C47 | Fab | BCMA | n.a. | n.a. | NO: 23 | WT | NO: 20 | nt. | 0.13 |
| scFv-IgAb_35 | FIG. 16 | P2C47 | Fab | BCMA | n.a. | n.a. | NO: 23 | WT | NO: 20 | nt. | 0.17 |
| scFv-IgAb_42 | FIG. 16 | LSIV21 | Fab | BCMA | n.a. | n.a. | NO: 23 | Sil. | NO: 20 | 8.7 | 0.19 |
| scFv-IgAb_44 | FIG. 16 | LSIV21 | Fab | RSV | n.a. | n.a. | NO: 23 | Sil. | NO: 20 | nt. | 0.14 | n.t., not tested

Example 5: Cytotoxic Activity of CD16A Antigen-Binding Protein on Tumor Target Cells Methods:
Culture of Cell Lines A-431 (ATCC, cat.: CRL-1555) were cultured under standard conditions in DMEM medium supplemented with 10% heat-inactivated FCS, 2 mM L-glutamine and 100 IU/mL penicillin G sodium and 100 µg/mL streptomycin sulfate (all components from Invitrogen). RPMI-8226 (DSMZ, cat.: ACC402) and MM.1S (ATCC, cat.: CRL2974) were cultured in RPMI 1640 medium supplemented with 10% heat-inactivated FCS, 2 mM L-glutamine and 100 IU/mL penicillin G sodium and 100 ηg/mL streptomycin sulfate. SU-DHL-6 (DSMZ, cat.: ACC572) were cultured in RPMI 1640 medium supplemented with 20% heat-inactivated FCS, 2 mM L-glutamine and 100 IU/mL penicillin G sodium and 100 µg/mL streptomycin sulfate. NCI-H929 (DSMZ, cat.: ACC163) were cultured in RPMI 1640 medium supplemented with 20% heat-inactivated FCS, 2 mM L-glutamine and 100 IU/mL penicillin G sodium, 100 µg/mL streptomycin sulfate, 1 mM sodium pyruvate, and 50 µM mercaptoethanol (all components from Invitrogen).

All cell lines were cultured at 37° C. in a humidified atmosphere with 5% $CO_2$.

Isolation of PBMC from Buffy Coats and Enrichment of Human NK Cells

PBMCs were isolated from buffy coats (German Red Cross, Mannheim, Germany) by density gradient centrifugation. The buffy coat samples were diluted with a two-to-threefold volume of PBS (Invitrogen, cat.: 14190-169), layered on a cushion of Lymphoprep (Stem Cell Technologies, cat.: 07861) and centrifuged at 800×g for 25 min at room temperature w/o brake. PBMC located in the interface were collected and washed 3 times with PBS before they were cultured in RPMI 1640 medium supplemented with 10% heat-inactivated FCS, 2 mM L-glutamine and 100 IU/mL penicillin G sodium and 100 µg/mL streptomycin sulfate overnight without stimulation. For the enrichment of NK cells PBMC were harvested from overnight cultures and used for one round of negative selection using the EasySep™ Human NK Cell Enrichment Kit (Stem Cell Technologies, cat.: 19055) for the immunomagnetic isolation of untouched human NK cells and the Big Easy EasySep™ Magnet (Stem Cell Technologies, cat.: 18001) according to the manufacturer's instructions.

4 h Calcein-Release Cytotoxicity Assays

For calcein-release cytotoxicity assays the indicated target cells were harvested from cultures, washed with RPMI 1640 medium without FCS, and labeled with 10 µM calcein AM (Invitrogen/Molecular Probes, cat.: C3100MP) for 30 min in RPMI medium without FCS at 37° C. After gently washing the labeled cells were resuspended in complete RPMI medium (RPMI 1640 medium supplemented with 10% heat-inactivated FCS, 4 mM L-glutamine, 100 U/mL penicillin G sodium, 100 µg/mL streptomycin sulfate) to a density of $1\times10^5$/mL. $1\times10^4$ target cells were then seeded together with enriched primary human NK cells at the indicated (effector-to-target) E:T ratio (usually 5:1 or 2:1) and the indicated antibodies in individual wells of a round-bottom 96-well micro plate in a total volume of 200 µL/well in duplicates. Spontaneous release, maximal release and killing of targets by effectors in the absence of antibodies were determined in quadruplicate on each plate.

After centrifugation for 2 min at 200 g the assay was usually incubated for 4 h (in some assays 3 h, as indicated) at 37° C. in a humidified atmosphere with 5% $CO_2$. 15 min prior to the end of incubation 20 µL of 10% Triton X-100 in RPMI medium were added to wells containing target cells. 20 µL RPMI medium was added to all other wells. 100 µL cell culture supernatant were harvested from each well after an additional centrifugation for 5 min at 500 g, and the fluorescence of the released calcein was measured at 520 nm using a fluorescence plate reader (Victor 3, Perkin Elmer). On the basis of the measured counts, the specific cell lysis was calculated according to the following formula: [fluorescence (sample)−fluorescence (spontaneous)]/[fluorescence (maximum)−fluorescence (spontaneous)]×100%. Fluorescence (spontaneous) represents the fluorescent counts from target cells in the absence of effector cells and antibodies and fluorescence (maximum) represents the total cell lysis induced by the addition of Triton X-100. Sigmoidal dose response curves and $EC_{50}$ values were calculated by non-linear regression/4-parameter logistic fit using the GraphPad Prism software (GraphPad Prism version 6.00 for Windows, GraphPad Software, La Jolla Calif. USA).

The results of the cytotoxic activity of antigen-binding proteins against tumor target cells are shown in Table 3.

TABLE 3

Antibody-mediated lysis of the indicated tumor cell lines was assessed in calcein-release assays with enriched human NK cells as effector cells at the indicated E:T ratios (5:1 or 2:1) in the presence of serial dilutions of the indicated antibody constructs and 3 h or 4 h assay incubation.

| Product | NK cell engager Format | CD16A binding domain | CD16A binding domain order | target binding domain1 | target binding domain2 | Fc portion | target cell line | E:T ratio | incubation time [h] | mean EC50 [pM] |
|---|---|---|---|---|---|---|---|---|---|---|
|  |  | P2C47 | VH-VL-VH-VL | BCMA |  | Sil. mFc | MM.IS | 5 | 4 | 6.8 |
| scDb-mFc_06 | FIG. 2 | P2C47 | VH-VL-VH-VL | BCMA |  | Sil. mFc | MM.1S | 5 | 4 | 3.3 |
| KiH-scDb-Fc_08 | FIG. 3 | P2C47 | VL-VH-VL-VH | BCMA |  | Sil. | MM.1S | 5 | 4 | 1.6 |
| KiH-scDb-Fc_09 | FIG. 3 | P2C47 | VH-VL-VH-VL | BCMA |  | Sil. | MM.1S | 5 | 4 | 9.4 |
| KiH-scDb-Fc_06 | FIG. 4 | P2C47 | VL-VL-VH-VH | BCMA |  | Sil. | MM.1S | 5 | 4 | 5.0 |
| KiH-scDb-Fc_12 | FIG. 5 | P2C47 | VL-VH-VL-VH | BCMA |  | Sil. | RPMI-8226 | 5 | 4 | 54.2 |
| scDb-Tribody_01 | FIG. 7 | LSIV21 | VL-VL-VH-VH | HSA(N1) | EGFR | no | A-431 | 2 | 4 | 10.1 |
| scDb-Tribody_02 | FIG. 7 | LSIV21 | VL-VH-VL-VH | HSA(N1) | EGFR | no | A-431 | 2 | 4 | 6.3 |
| scDb-Tribody_03 | FIG. 7 | LSIV21 | VL-VL-VH-VH | HSA(CA) | EGFR | no | A-431 | 2 | 4 | 40.1 |
| scDb-Tribody_04 | FIG. 7 | LSIV21 | VL-VH-VL-VH | HSA(CA) | EGFR | no | A-431 | 2 | 4 | 16.7 |
| scDb-TriB-scFv_01 | FIG. 8 | P2C47 | VL-VH-VL-VH | HSA(CA) | BCMA | no | MM.IS | 5 | 4 | 6.4 |
| Db-Fc_01 | FIG. 9 | P2C47 | VH-VL | BCMA |  | Sil. | NCI-H929 | 5 | 4 | 53.0 |
| Db-Fc_02 | FIG. 9 | P2C47 | VL-VH | BCMA |  | Sil. | NCI-H929 | 5 | 4 | 4.9 |
| Db-Fc_03 | FIG. 10 | P2C47 | VH-VL | BCMA |  | Sil. | NCI-H929 | 5 | 4 | 17.0 |
| Bi-scFv-Fc_02 | FIG. 11 | LSIV21 | VL-VH | EGFR |  | Sil. | A-431 | 2 | 4 | 6.6 |
| Bi-scFv-Fc_04 | FIG. 11 | LSIV21 | VL-VH | EGFR |  | WT | A-431 | 2 | 4 | 5.4 |
| Bi-scFv-Fc_17 | FIG. 11 | P2C47 | VH-VL | BCMA |  | Sil. | RPMI-8226 | 2 | 4 | 160.7 |
| Bi-scFv-Fc_22 | FIG. 11 | CD16LSIV21 | VL-VH | EGFR |  | Sil. | A-431 | 2 | 4 | 7.5 |
| Bi-scFv-Fc_24 | FIG. 11 | CD16LSIV2I | VL-VH | EGFR |  | WT | A-431 | 2 | 4 | 8.3 |
| Bi-scFv-Fc_27 | FIG. 11 | P2C47 | VL-VH | BCMA |  | Sil. | RPMI-8226 | 2 | 4 | 100.0 |
| Bi-scFv-Fc_31 | FIG. 11 | P2C47 | VL-VH | BCMA |  | WT | RPMI-8226 | 2 | 4 | 64.1 |
| Bi-scFv-Fc_03 | FIG. 12 | LSIV21 | VH-VL | EGFR |  | WT | A-431 | 2 | 4 | 2.7 |
| Bi-scFv-Fc_19 | FIG. 12 | P2C47 | VH-VL | BCMA |  | Sil. | RPMI-8226 | 2 | 3 | 432.7 |
| Bi-scFv-Fc_21 | FIG. 12 | LSIV21 | VL-VH | EGFR |  | Sil. | A-431 | 2 | 4 | 5.1 |
| Bi-scFv-Fc_23 | FIG. 12 | LSIV21 | VL-VH | EGFR |  | WT | A-431 | 2 | 4 | 3.6 |
| Bi-scFv-Fc_26 | FIG. 12 | P2C47 | VL-VH | BCMA |  | Sil. | RPMI-8226 | 2 | 4 | 1361.5 |
| scFv-IgAb_03 | FIG. 13 | LSIV21 | VH-VL | EGFR |  | WT | A-431 | 2 | 4 | 2.5 |
| scFv-IgAb_17 | FIG. 13 | P2C47 | VH-VL | BCMA |  | Sil. | RPMI-8226 | 2 | 3 | 190.2 |
| scFv-IgAb_18 | FIG. 13 | P2C47 | VL-VH | BCMA |  | Sil. | NCI-H929 | 5 | 4 | 48.7 |
| scFv-IgAb_29 | FIG. 13 | P2C47 | VH-VL | BCMA |  | Sil. | RPMI-8226 | 2 | 3 | 2029.5 |
| scFv-IgAb_30 | FIG. 13 | P2C47 | VL-VH | BCMA |  | Sil. | RPMI-8226 | 2 | 3 | 892.0 |
| Bi-scFv-IgAb_02 | FIG. 14 | P2C47 | VL-VH | CD20 | BCMA | Sil. | SU-DHL-6 | 5 | 4 | 1.2 |
| Bi-scFv-IgAb_03 | FIG. 14 | P2C47 | VL-VH | CD19 | BCMA | Sil. | SU-DHL-6 | 5 | 4 | 13.5 |
| Bi-scFv-IgAb_04 | FIG. 14 | P2C47 | VL-VH | CD19 | His | Sil. | SU-DHL-6 | 5 | 4 | 23.1 |
| Bi-scFv-IgAb_05 | FIG. 14 | P2C47 | VL-VH | BCMA | His | Sil. | SU-DHL-6 | 5 | 4 | 16.8 |
| KiH-scFv-Fc_09 | FIG. 15a | P2C47 | VL-VH | CD19 | BCMA | Sil. | SU-DHL-6 | 5 | 4 | 11.8 |
| KiH-scFv-Fc_17 | FIG. 15a | P2C47 | VL-VH | CD20 | BCMA | Sil. | SU-DHL-6 | 5 | 4 | 4.3 |
| scFv-IgAb_02 | FIG. 16 | LSIV21 | Fab | EGFR | n.a. | Sil. | A-431 | 2 | 4 | 4.3 |
| scFv-IgAb_22 | FIG. 16 | P2C47 | Fab | BCMA | n.a. | Sil. | RPMI-8226 | 2 | 3 | 170.3 |
| scFv-IgAb_26 | FIG. 16 | LSIV21 | Fab | EGFR | n.a. | Sil. | A-431 | 2 | 4 | 5.8 |
| scFv-IgAb_31 | FIG. 16 | P2C47 | Fab | BCMA | n.a. | Sil. | RPMI-8226 | 2 | 3 | 325.1 |
| scFv-IgAb_34 | FIG. 16 | P2C47 | Fab | BCMA | n.a. | WT | RPMI-8226 | 2 | 3 | 74.6 |
| scFv-IgAb_35 | FIG. 16 | P2C47 | Fab | BCMA | n.a. | WT | RPMI-8226 | 2 | 3 | 244.4 |

Sigmoidal dose-response analysis was used to calculate $EC_{50}$ [pM] values. Mean values of at least two independent experiments are presented.

Example 6: Assessment of NK-NK Lysis by CD16A Antigen-Binding Protein

Methods:

Isolation of PBMC from Buffy Coats and Enrichment of Human NK Cells

PBMCs were isolated from buffy coats (German Red Cross, Mannheim, Germany) by density gradient centrifugation. The buffy coat samples were diluted with a two-to-threefold volume of PBS (Invitrogen, cat.: 14190-169), layered on a cushion of Lymphoprep (Stem Cell Technologies, cat.: 07861) and centrifuged at 800×g for 25 min at room temperature w/o brake. PBMC located in the interface were collected and washed 3 times with PBS before they were cultured in complete RPMI 1640 medium supplemented with 10% FCS overnight without stimulation. For the enrichment of NK cells PBMC were harvested from overnight cultures and used for one round of negative selection using the EasySep™ Human NK Cell Enrichment Kit (Stem Cell Technologies, cat.: 19055) for the immunomagnetic isolation of untouched human NK cells and the Big Easy EasySep™ Magnet (Stem Cell Technologies, cat.: 18001) according to the manufacturer's instructions.

4 h Calcein-Release Cytotoxicity Assays

For calcein-release cytotoxicity assays to assess NK-NK cell lysis half of the enriched, non-activated NK cells were washed with RPMI 1640 medium without FCS and labeled with 10 μM calcein AM (Invitrogen/Molecular Probes, cat.: C3100MP) for 30 min in RPMI medium without FCS at 37° C. After gently washing the labeled cells were resuspended in complete RPMI medium (RPMI 1640 medium supplemented with 10% heat-inactivated FCS, 4 mM L-glutamine, 100 U/mL penicillin G sodium, 100 μg/mL streptomycin sulfate). $5×10^4$ target cells were then seeded together with NK cells from the same donor at an E:T ratio of 1:1 and the indicated antibodies in individual wells of a round-bottom 96-well micro plate in a total volume of 200 μL/well in duplicates. Spontaneous release, maximal release and killing of targets by effectors in the absence of antibodies were determined in quadruplicate on each plate.

After centrifugation for 2 min at 200×g the assay was incubated for 4 h at 37° C. in a humidified atmosphere with 5% $CO_2$. 15 min prior to the end of incubation 20 μL of 10% Triton X-100 in RPMI medium were added to wells containing target cells. 20 μL RPMI medium was added to all other wells. 100 μL cell culture supernatant were harvested from each well after an additional centrifugation for 5 min at 500 g, and the fluorescence of the released calcein was measured at 520 nm using a fluorescence plate reader (Victor 3, Perkin Elmer). On the basis of the measured counts, the specific cell lysis was calculated according to the following formula: [fluorescence (sample)−fluorescence (spontaneous)]/[fluorescence (maximum)−fluorescence (spontaneous)]×100%. Fluorescence (spontaneous) represents the fluorescent counts from target cells in the absence of effector cells and antibodies and fluorescence (maximum) represents the total cell lysis induced by the addition of Triton X-100. Sigmoidal dose response curves were calculated by non-linear regression/4-parameter logistic fit using the GraphPad Prism software (GraphPad Prism version 6.00 for Windows, GraphPad Software, La Jolla Calif. USA), and used to determine $EC_{50}$ [pM] and $E_{max}$ [%] values.

The CD16A antigen-binding protein is considered as negative for inducing NK-NK lysis, when there is no or only minimal lysis below 10% measurable at antibody concentrations up to 30 μg/mL in assays in which daratumumab induced more than 50% NK lysis.

Results:

Each of the antigen-binding proteins was tested in at least two independent 4 h calcein-release cytotoxicity assays for NK cell-mediated NK lysis.

Figure 17A:
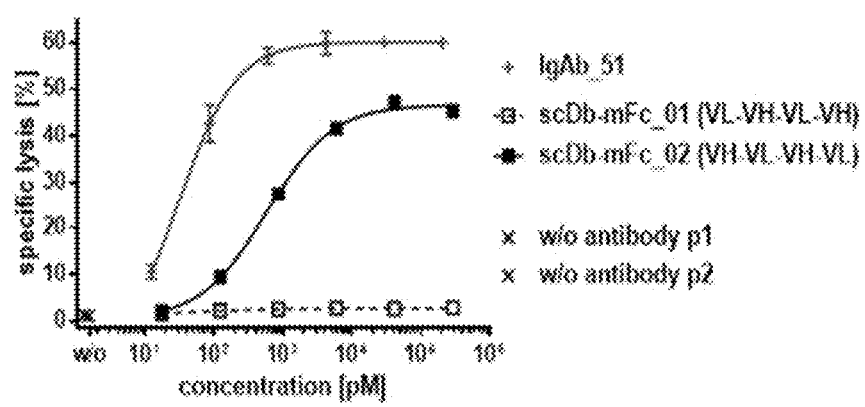
Figure 17C:
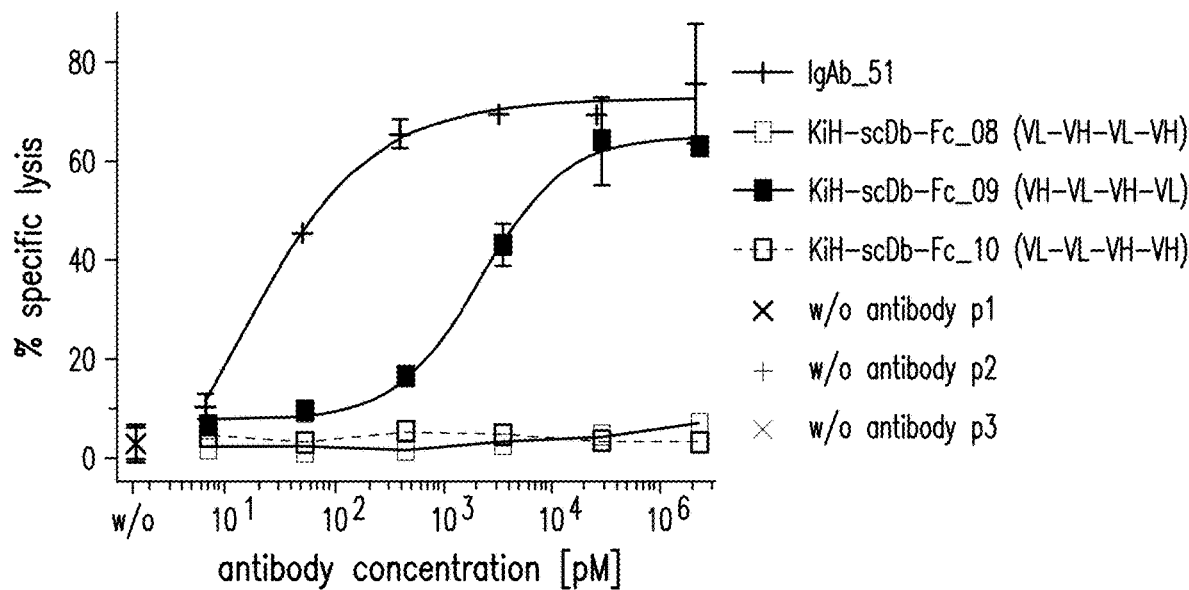
FIG. 17C shows two anti-CD16A moieties in Diabody format (scDb) fused to asymmetric Fc at N-terminus (and scFv targeting TAA to C-terminus), as shown in FIG. 3.
Figure 17D:
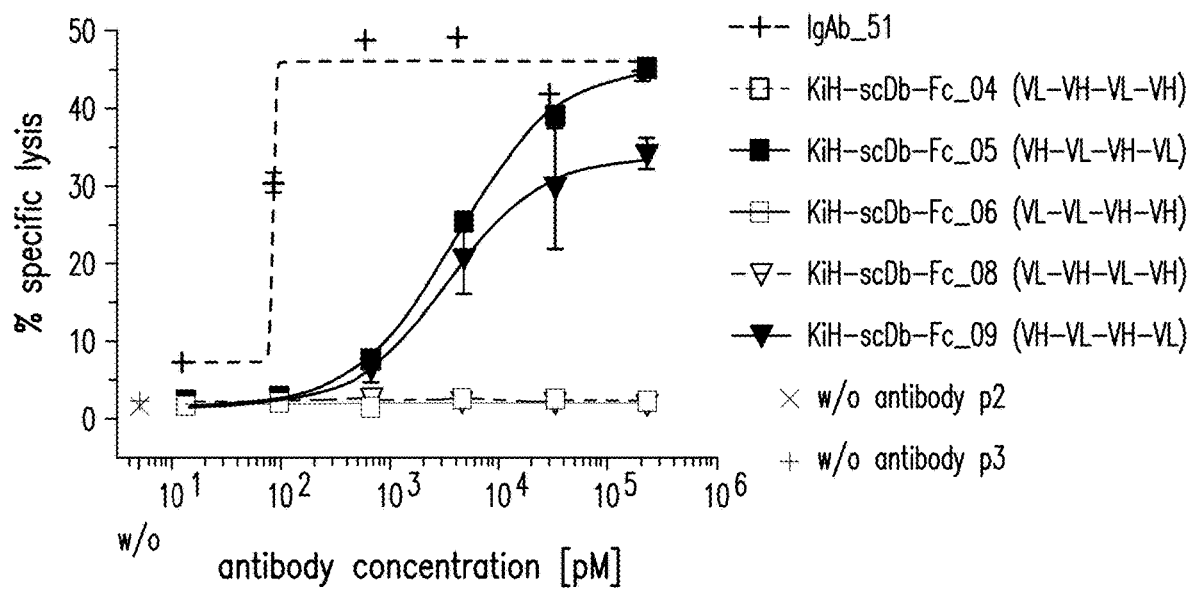
FIG. 17D shows two anti-CD16A moieties in Diabody format (scDb) fused to asymmetric Fc at N-terminus (and scFv targeting TAA to N-terminus), as shown in FIG. 4.
Figure 17E:
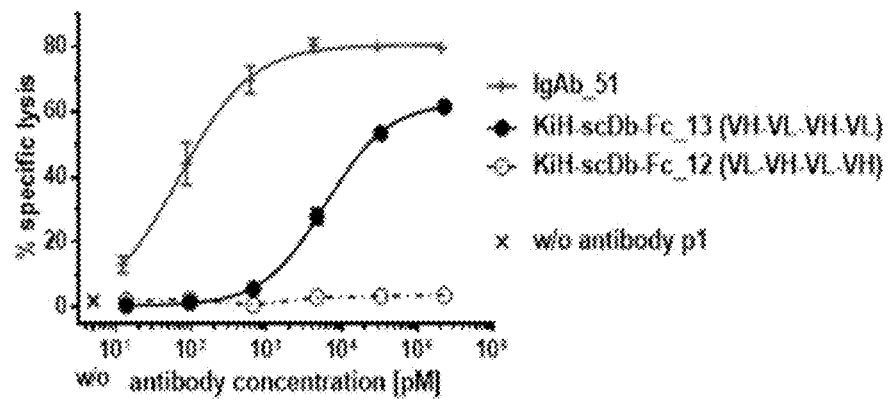
FIG. 17E shows two anti-CD16A moieties in Diabody format (scDb) fused to asymmetric Fc at C-terminus (and scFv targeting TAA to N-terminus), as shown in FIG. 5.
Figure 17F:
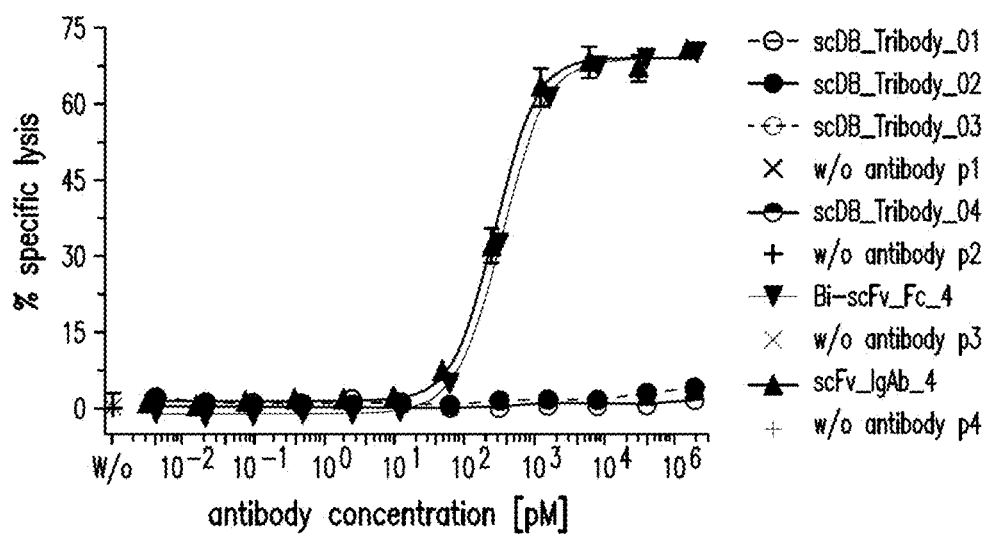
FIG. 17F shows two anti-CD16A moieties in Diabody format (scDb) fused to Fab at C-terminus of CL (and scDb targeting TAA to C-terminus of CH1), as shown in FIG. 7.
Figure 17G:
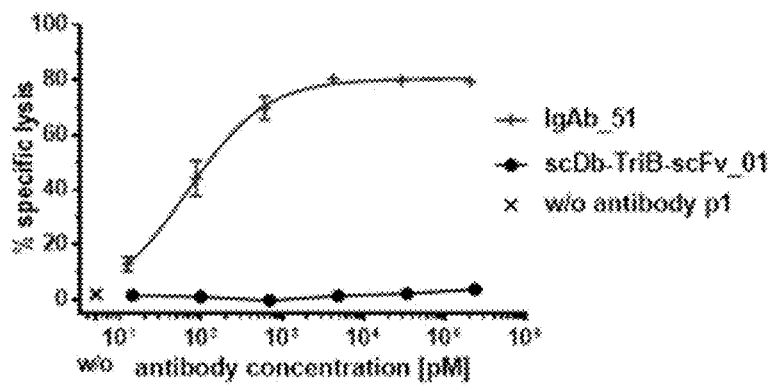
FIG. 17G shows two anti-CD16A moieties in Diabody format (scDb) fused to Fab at C-terminus of CH1 (and scDb targeting TAA to C-terminus of CL), as shown in FIG. 8.
Figure 17H:
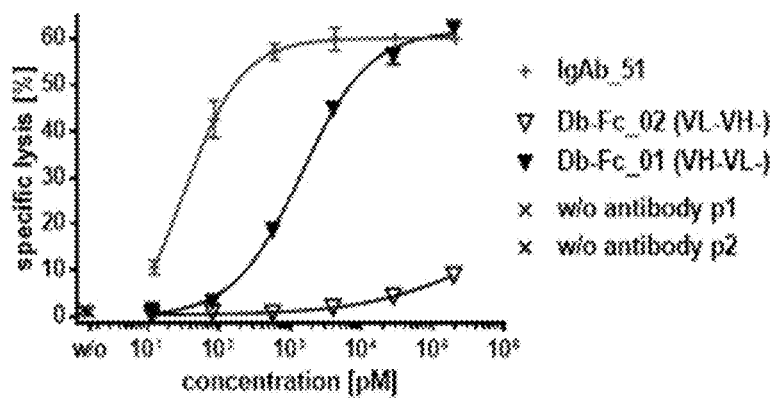
FIG. 17H shows two anti-CD16A moieties in Diabody (Db) format fused to Fc at N-terminus (and scFvs targeting TAA to C-terminus), as shown in FIG. 9.
Figure 17I:
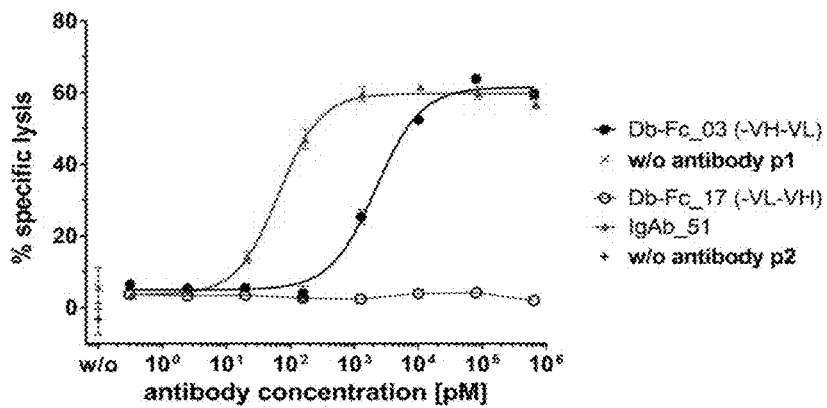
FIG. 17I shows two anti-CD16A moieties in Diabody (Db) format fused to Fc at C-terminus (and scFvs targeting TAA to N-terminus), as shown in FIG. 10.
Figure 17J:
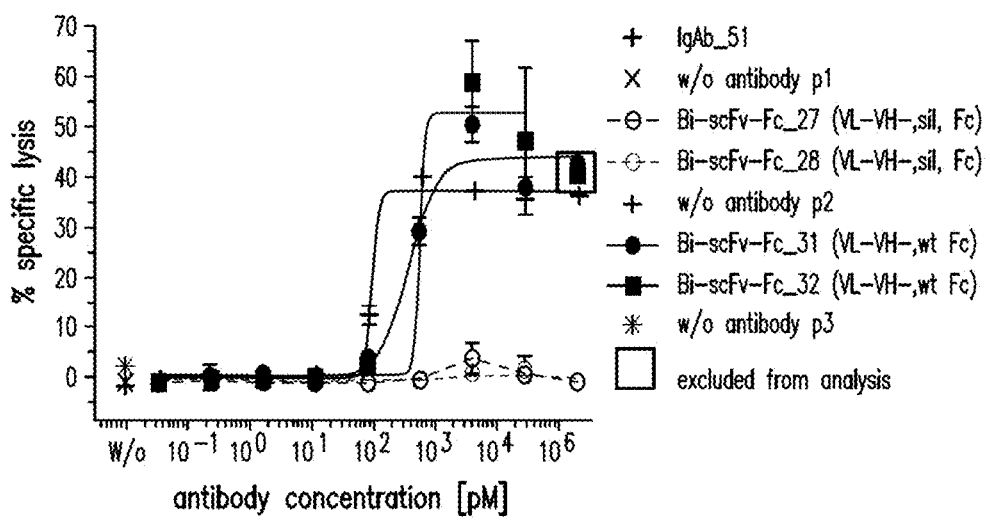
FIG. 17J shows two anti-CD16A moieties in scFv format fused to Fc at N-terminus (and scFvs targeting TAA to C-terminus), as shown in FIG. 11.

The results summarized in Table 4 and FIGS. 17A-17N clearly demonstrate that the potency ($EC_{50}$) and efficacy ($E_{max}$) for NK-NK lysis induced by CD16A antigen-binding proteins does not correlate with the apparent binding affinity of these proteins to recombinant CD16A antigen or CD16A on NK cells (summarized in Table 2). In addition, the potency ($EC_{50}$) of CD16A antigen-binding proteins for the lysis of antigen-positive tumor target cells does also not correlate with the potency in mediating NK-NK lysis. From these findings it can be concluded that the propensity for mediating NK-NK lysis is not a property of the anti-CD16A Fv domain per se and not a function of their apparent affinity, but a characteristic property of the format, in particular of the domain order of variable heavy and light chain segments of a given CD16A antigen-binding protein.

TABLE 4

Antibody-mediated NK-NK cell lysis was assessed in a 4 h calcein-release assay with calcein-labeled NK cells as target cells and non-labeled NK cells from the same donor as effector cells at an E:T ratio of 1:1 in the presence of serial dilutions of the indicated antibody constructs.

| Product | NK cell engager format | CD16A binding domain | CD16A binding domain order | target binding domain1 | target binding domain2 | Connector 1 SEQ ID | Hinge SEQ ID | Fc portion | Connector 2 SEQ ID | mean $EC_{50}$ [pM] for NK-NK lysis | mean $E_{max}$ [%] |
|---|---|---|---|---|---|---|---|---|---|---|---|
| scDb-mFc__01 | FIG. 1 | P2C47 | VL-VH-VL-VH | BCMA | | NO: 20 | no | Sil. mFc | NO: 20 | no | no |
| scDb-mFc__02 | FIG. 1 | P2C47 | VH-VL-VH-VL | BCMA | | NO: 20 | no | Sil. mFc | NO: 20 | 1418.4 | 46.6 |
| scDb-mFc__04 | FIG. 1 | P2C47 | VH-VH-VL-VL | BCMA | | NO: 20 | no | Sil. mFc | NO: 20 | no | no |
| scDb-mFc__06 | FIG. 2 | P2C47 | VH-VL-VH-VL | BCMA | | NO: 20 | no | Sil. mFc | NO: 20 | 2810.1 | 44.0 |
| scDb-mFc__07 | FIG. 2 | P2C47 | VL-VH-VL-VH | BCMA | | NO: 20 | no | Sil. mFc | NO: 20 | no | no |
| scDb-mFc__08 | FIG. 2 | P2C47 | VH-VH-VL-VL | BCMA | | NO: 20 | no | Sil. mFc | NO: 20 | no | no |
| KiH-scDb-Fc__08 | FIG. 3 | P2C47 | VL-VH-VL-VH | BCMA | | NO: 19 | NO: 24 | Sil. | 0 | no | no |
| KiH-scDb-Fc__09 | FIG. 3 | P2C47 | VH-VL-VH-VL | BCMA | | NO: 19 | NO: 24 | Sil. | 0 | 3302.0 | 45.8 |
| KiH-scDb-Fc__10 | FIG. 3 | P2C47 | VL-VL-VH-VH | BCMA | | NO: 19 | NO: 24 | Sil. | 0 | no | no |
| KiH-scDb-Fc__04 | FIG. 4 | P2C47 | VL-VH-VL-VH | BCMA | | NO: 19 | NO: 24 | Sil. | 0 | no | no |
| KiH-scDb-Fc__05 | FIG. 4 | P2C47 | VH-VL-VH-VL | BCMA | | NO: 19 | NO: 24 | Sil. | 0 | 2506.9 | 52.2 |

TABLE 4-continued

Antibody-mediated NK-NK cell lysis was assessed in a 4 h calcein-release assay with calcein-labeled NK cells as target cells and non-labeled NK cells from the same donor as effector cells at an E:T ratio of 1:1 in the presence of serial dilutions of the indicated antibody constructs.

| Product | NK cell engager format | CD16A binding domain | CD16A binding domain order | target binding domain1 | target binding domain2 | Connector 1 SEQ ID | Hinge SEQ ID | Fc portion | Connector 2 SEQ ID | mean EC$_{50}$ [pM] for NK-NK lysis | mean E$_{max}$ [%] |
|---|---|---|---|---|---|---|---|---|---|---|---|
| KiH-scDb-Fc__06 | FIG. 4 | P2C47 | VL-VL-VH-VH | BCMA | | NO: 19 | NO: 24 | Sil. | 0 | no | no |
| KiH-scDb-Fc__12 | FIG. 5 | P2C47 | VL-VH-VL-VH | BCMA | | 0 | NO: 24 | Sil. | NO: 20 | no | no |
| KiH-scDb-Fc__13 | FIG. 5 | P2C47 | VH-VL-VH-VL | BCMA | | 0 | NO: 24 | Sil. | NO: 20 | 4235.5 | 58.0 |
| KiH-scDb-Fc__14 | FIG. 5 | P2C47 | VL-VL-VH-VH | BCMA | | 0 | NO: 24 | Sil. | NO: 20 | no | no |
| KiH-scDb-Fc__15 | FIG. 5 | P2C47 | VH-VH-VL-VL | BCMA | | 0 | NO: 24 | Sil. | NO: 20 | no | no |
| scDb-Tribody__01 | FIG. 7 | LSIV21 | VL-VL-VH-VH | HSA(N1) | EGFR | NO: 20 | no | no | 0 | no | no |
| scDb-Tribody__02 | FIG. 7 | LSIV21 | VL-VH-VL-VH | HSA(N1) | EGFR | NO: 20 | no | no | 0 | no | no |
| scDb-Tribody__03 | FIG. 7 | LSIV21 | VL-VL-VH-VH | HSA(CA) | EGFR | NO: 20 | no | no | 0 | no | no |
| scDb-Tribody__04 | FIG. 7 | LSIV21 | VL-VH-VL-VH | HSA(CA) | EGFR | NO: 20 | no | no | 0 | no | no |
| scDb-Tribody__09 | FIG. 7 | P2C47 | VL-VH-VL-VH | HSA(N1) | BCMA | NO: 20 | no | no | 0 | no | no |
| scDb-Tribody__10 | FIG. 7 | P2C47 | VL-VH-VL-VH | HSA(N1) | BCMA | NO: 20 | no | no | 0 | no | no |
| scDb-TriB-scFv__01 | FIG. 8 | P2C47 | VL-VH-VL-VH | HSA(CA) | BCMA | NO: 20 | no | no | 0 | no | no |
| Db-Fc__01 | FIG. 9 | P2C47 | VH-VL | BCMA | | NO: 20 | NO: 24 | Sil. | NO: 20 | 2511.3 | 52.8 |
| Db-Fc__02 | FIG. 9 | P2C47 | VL-VH | BCMA | | NO: 20 | NO: 24 | Sil. | NO: 20 | no | no |
| Db-Fc__03 | FIG. 10 | P2C47 | VH-VL | BCMA | | 0 | NO: 24 | Sil. | NO: 21 | 1191.5 | 57.8 |
| Db-Fc__17 | FIG. 10 | P2C47 | VL-VH | BCMA | | 0 | NO: 24 | Sil. | NO: 22 | no | no |
| Bi-scFv-Fc__02 | FIG. 11 | LSIV21 | VL-VH | EGFR | | 0 | NO: 23 | Sil. | NO: 20 | no | no |
| Bi-scFv-Fc__04 | FIG. 11 | LSIV21 | VL-VH | EGFR | | 0 | no | WT | 0 | 394.0 | 75.8 |
| Bi-scFv-Fc__17 | FIG. 11 | P2C47 | VH-VL | BCMA | | NO: 21 | NO: 23 | Sil. | NO: 20 | 648.4 | 11.1 |
| Bi-scFv-Fc__27 | FIG. 11 | P2C47 | VL-VH | BCMA | | 0 | NO: 23 | Sil. | NO: 20 | no | no |
| Bi-scFv-Fc__28 | FIG. 11 | P2C47 | VL-VH | BCMA | | 0 | NO: 23 | Sil. | NO: 20 | no | no |
| Bi-scFv-Fc__31 | FIG. 11 | P2C47 | VL-VH | BCMA | | 0 | NO: 23 | WT | NO: 20 | 273.4 | 56.9 |
| Bi-scFv-Fc__32 | FIG. 11 | P2C47 | VL-VH | BCMA | | 0 | NO: 23 | WT | NO: 20 | 416.5 | 64.2 |
| Bi-scFv-Fc__39 | FIG. 11 | LSIV21 | VL-VH | BCMA | | 0 | NO: 23 | Sil. | NO: 20 | no | no |
| Bi-scFv-Fc__03 | FIG. 12 | LSIV21 | VH-VL | EGFR | | 0 | no | WT | 0 | 1215.1 | 38.6 |
| Bi-scFv-Fc__19 | FIG. 12 | P2C47 | VH-VL | BCMA | | 0 | NO: 23 | Sil. | NO: 22 | 2510.7 | 27.3 |
| Bi-scFv-Fc__21 | FIG. 12 | LSIV21 | VH-VL | EGFR | | 0 | NO: 23 | Sil. | NO: 20 | no | no |
| Bi-scFv-Fc__25 | FIG. 12 | P2C47 | VH-VL | BCMA | | 0 | NO: 23 | Sil. | NO: 20 | 4935.5 | 28.1 |
| Bi-scFv-Fc__26 | FIG. 12 | P2C47 | VH-VL | BCMA | | 0 | NO: 23 | Sil. | NO: 20 | no | no |
| Bi-scFv-Fc__29 | FIG. 12 | P2C47 | VH-VL | BCMA | | 0 | NO: 23 | WT | NO: 20 | 300.8 | 40.8 |
| Bi-scFv-Fc__30 | FIG. 12 | P2C47 | VH-VL | BCMA | | 0 | NO: 23 | WT | NO: 20 | 555.6 | 12.7 |
| scFv-IgAb__03 | FIG. 13 | LSIV21 | VH-VL | EGFR | | 0 | no | WT | 0 | 1482.5 | 31.8 |
| scFv-IgAb__17 | FIG. 13 | P2C47 | VH-VL | BCMA | | 0 | NO: 23 | Sil. | NO: 22 | 4419.9 | 17.1 |
| scFv-IgAb__18 | FIG. 13 | P2C47 | VL-VH | BCMA | | 0 | NO: 23 | Sil. | NO: 22 | no | no |
| scFv-IgAb__25 | FIG. 13 | LSIV21 | VL-VH | EGFR | | 0 | NO: 23 | Sil. | NO: 20 | no | no |
| scFv-IgAb__29 | FIG. 13 | P2C47 | VH-VL | BCMA | | 0 | NO: 23 | Sil. | NO: 20 | 15622.0 | 15.2 |
| scFv-IgAb__30 | FIG. 13 | P2C47 | VL-VH | BCMA | | 0 | NO: 23 | Sil. | NO: 20 | no | no |
| scFv-IgAb__32 | FIG. 13 | P2C47 | VH-VL | BCMA | | 0 | no | WT | 0 | 495.3 | 39.9 |
| scFv-IgAb__37 | FIG. 13 | P2C47 | VL-VH | CD20 | | 0 | NO: 23 | Sil. | NO: 20 | no | no |
| scFv-IgAb__43 | FIG. 13 | P2C47 | VL-VH | EGFR | | 0 | NO: 23 | Sil. | NO: 22 | no | no |
| Bi-scFv-IgAb__02 | FIG. 14 | P2C47 | VL-VH | CD20 | BCMA | 0 | NO: 23 | Sil. | NO: 20 | no | no |
| Bi-scFv-IgAb__03 | FIG. 14 | P2C47 | VL-VH | CD19 | BCMA | 0 | NO: 23 | Sil. | NO: 22 | no | no |
| Bi-scFv-IgAb__04 | FIG. 14 | P2C47 | VL-VH | CD19 | His | 0 | NO: 23 | Sil. | NO: 22 | no | no |
| Bi-scFv-IgAb__05 | FIG. 14 | P2C47 | VL-VH | BCMA | His | 0 | NO: 23 | Sil. | NO: 22 | no | no |
| Bi-scFv-IgAb__06 | FIG. 14 | P2C47 | VL-VH | CD19 | RSV | 0 | NO: 23 | Sil. | NO: 22 | no | no |
| KiH-scFv-Fc__09 | FIG. 15a | P2C47 | VL-VH | CD19 | BCMA | 0 | NO: 23 | Sil. | NO: 20 | no | no |
| KiH-scFv-Fc__17 | FIG. 15a | P2C47 | VL-VH | CD20 | BCMA | 0 | NO: 23 | Sil. | NO: 20 | no | no |
| KiH-scFv-Fc__11 | FIG. 15b | P2C47 | VL-VH | CD19 | BCMA | 0 | NO: 23 | Sil. | NO: 20 | no | no |
| KiH-scFv-Fc__18 | FIG. 15b | P2C47 | VL-VH | CD20 | BCMA | 0 | NO: 23 | Sil. | NO: 20 | no | no |
| scFv-IgAb__02 | FIG. 16 | LSIV21 | Fab | EGFR | n.a. | n.a. | NO: 23 | Sil. | NO: 20 | 10989.3 | 32.2 |
| scFv-IgAb__22 | FIG. 16 | P2C47 | Fab | BCMA | n.a. | n.a. | NO: 23 | Sil. | NO: 20 | 2389.0 | 16.1 |

TABLE 4-continued

Antibody-mediated NK-NK cell lysis was assessed in a 4 h calcein-release assay with calcein-labeled NK cells as target cells and non-labeled NK cells from the same donor as effector cells at an E:T ratio of 1:1 in the presence of serial dilutions of the indicated antibody constructs.

| Product | NK cell engager format | CD16A binding domain | CD16A binding domain order | target binding domain1 | target binding domain2 | Connector 1 SEQ ID | Hinge SEQ ID | Fc portion | Connector 2 SEQ ID | mean EC$_{50}$ [pM] for NK-NK lysis | mean E$_{max}$ [%] |
|---|---|---|---|---|---|---|---|---|---|---|---|
| scFv-IgAb_26 | FIG. 16 | LSIV21 | Fab | EGFR | n.a. | n.a. | NO: 23 | Sil. | NO: 20 | 8085.3 | 27.0 |
| scFv-IgAb_31 | FIG. 16 | P2C47 | Fab | BCMA | n.a. | n.a. | NO: 23 | Sil. | NO: 20 | 2221.5 | 7.2 |
| scFv-IgAb_34 | FIG. 16 | P2C47 | Fab | BCMA | n.a. | n.a. | NO: 23 | WT | NO: 20 | 522.8 | 61.5 |
| scFv-IgAb_35 | FIG. 16 | P2C47 | Fab | BCMA | n.a. | n.a. | NO: 23 | WT | NO: 20 | 602.1 | 63.1 |
| scFv-IgAb_42 | FIG. 16 | LSIV21 | Fab | BCMA | n.a. | n.a. | NO: 23 | Sil. | NO: 20 | 19538.0 | 16.8 |
| scFv-IgAb_44 | FIG. 16 | LSIV21 | Fab | RSV | n.a. | n.a. | NO: 23 | Sil. | NO: 20 | 4402.7 | 19.1 |
| IgAb_51 (daratumumab) | | | | | | | 0 | | 0 | 144.2 | >50 |

Sigmoidal dose-response analysis was used to calculate EC$_{50}$ [pM] and E$_{max}$ [%] values. Mean values of two independent experiments are presented.
N.t., not tested;
n.a., not applicable;
no, no target cell lysis.

Table 4 shows that antigen-binding proteins comprising two CD16A antigen-binding moieties in the format scDb, Db or scFv fused to a Fc portion or a Fab region do not induce NK-NK lyse, if the variable regions are arranged from the N- to the C-terminus in a scDb $V_L$-$V_H$-$V_L$-$V_H$ or a scDb $V_L$-$V_L$-$V_H$-$V_H$, in a Db VL-VH or scFv $V_L$-$V_H$. Thereby, the results demonstrate that NK-NK lysis is independent of the apparent binding affinity of these antigen-binding moieties to recombinant CD16A or CD16A on NK cells as defined by EC50 and Emax. Further, NK-NK lysis is also independent from the target antigen binding domain.

Example 7—Redirected Optimized CellKkilling (ROCK®): A Highly Versatile Mutlispecific Fit-for-Purpose Antibody Platform for Engaging Innate Immunity

SUMMARY

A portfolio of immune cell engagers with unique properties were developed based on the ROCK® (Redirected Optimized Cell Killing) platform. This novel and modular platform leads to advantages of NK cell engagement over classical monoclonal antibodies and other engager concepts. Molecular design, binding affinity, activation of immune effector cells and PK properties were considered. The ROCK® platform can be used for generating novel antibodies aimed at the activation of innate and adaptive immunity.

In this Example, a novel and fully modular platform, called "redirected optimized cell killing" (ROCK®) platform is presented that includes a wide spectrum of different formats equipped with such a unique anti-CD16A binding domain for generating a new class of NK cell recruiting antibodies aimed at the activation of innate and adaptive immunity.

Materials & Methods
Generation of ROCK® Recombinant Antibodies, Controls and Antigen Variants Gene sequences for different recombinant proteins (antigens, antibodies, controls) were synthesized by Thermo Fisher Scientific/Invitrogen GeneArt (Regensburg, Germany) or derived by PCR. Expression vectors, encoding these recombinant proteins, were generated by cloning of the respective sequence elements into the mammalian expression vector pcDNA5/FRT (Life Technologies) or a modified version thereof using standard molecular biology techniques. Soluble recombinant antigen variants were constructed as fusion proteins of the ECD sequences to monomeric Fc (Ying et al., J Biol Chem 2012; 287:19399-408). For the expression of cell surface anchored antigen variants, ECD sequences were either fused to the transmembrane domain of human EGFR (Wang et al., Blood 2011; 118: 1255-63) or anchored via GPI using the human CD16B endogenous sequence with the full length propeptide sequence for posttranslational processing and lipidation for GPI-anchorage. In some expression constructs, the original vector was modified to contain two CMV-promotor controlled expression cassettes for coexpression of two antibody chains. A further modification of the mammalian expression vector was the replacement of the Hygromycin resistance with a Puromycin resistance gene. Expression constructs were furthermore designed to contain coding sequences for N-terminal signal peptides to facilitate secretion. For recombinant fusion constructs (e.g., antigens with IgG1 Fc portion) sequences encoding the fusion partners were PCR amplified using elongated primers to construct corresponding linker or connector sequences for gene fusion or restriction enzyme digestion. The resulting overlapping DNA-fragments were inserted into the co-expression vector at the relevant position using the Gibson assembly method to yield the final construct (Gibson et al., Nat Methods 2010; 7:901-3; Gibson et al., Nat Methods 2009; 6:343-5). Sequences of all constructs were confirmed by Sanger sequencing performed at GATC (Köln, Germany) using custom made primers.

Soluble antibodies or antigens or cell surface anchored antigens were expressed in CHO as previously described (Reusch et al., Clin Cancer Res 2016; 22:5829-38). Target proteins were purified from cell culture supernatant using one or two standard affinity chromatographic methods (protein A, protein L, Capture Select C-tag or IMAC) depending on monomeric or multimeric (homodimeric-, heterodimeric or -tetrameric) product form and on fused affinity tags, presence of η-light chain or Fc part. All protein preparations were further polished via Size-exclusion chromatography and analyzed using SEC-MALS, SDS-PAGE and UV-Vis spectroscopy.

Dotblot, SDS-PAGE and Western Blot

Purified recombinant CD16 antigen variants were spotted on Nitrocellulose membranes, or mixed with sample buffer and separated on 4-20% Criterion TGX Precast Gels (Bio- Rad). Total protein was imaged using the Bio-Rad Molecular Imager Gel Documentation system. Protein was transferred by Western blotting to PVDF Midi Membranes using the Trans-Blot Turbo system (Bio-Rad). Membranes were blocked for 30 min with 3% (w/v) skimmed milk powder (Merck) dissolved in TBS and incubated with 2-4 µg/mL of anti-CD16 scFv antibodies for 1 hour at room temperature followed by washing with TBST (TBS containing 0.1% (v/v) Tween 20) and two times with TBS. Membranes were incubated with anti-Penta-His-HRP (QIAGEN) 1:3000 diluted as secondary detection conjugate for 1 hour at room temperature. After washing, colorimetric development was started by addition of a freshly prepared mixture of 0.66 mg/mL DAB, 0.02% $CoCl_2$, 0.015% $H_2O_2$ in TBS and stopped by washing membranes in water. Membranes were dried and photographed.

Analysis of CD16A Antigen Binding in ELISA 96-well ELISA plates (Immuno MaxiSorp; Nunc) were coated overnight at 4° C. with recombinant antigens or different NK cell engager antibody formats in 100 mM Carbonate-bicarbonate buffer. Depending on the molecular mass, 0.5-3 µg/mL of antigen or 2-5 µg/mL of antibody formats were coated, equalizing molarities to approximately 30 nM for coated antigens or 10-20 nM for coated antibodies. After blocking with 3% (w/v) skim milk powder (Merck) dissolved in PBS, serial dilutions of His-tagged scFv antibodies or of a biotinylated CD16A-158V ECD-monomeric Fc-fusion antigen in PBS containing 0.3% (w/v) skim milk powder were incubated on the plates coated with antigen or antibodies, respectively, for 1.5 hours at room temperature. To assess binding competition, scFvs were titrated and coincubated on the plates with 1 nM or 10 nM of 3G8 mAb. After washing three times with 300 µL per well of PBS containing 0.1% (v/v) Tween 20, plates were incubated with detection conjugates, Penta-His-HRP (Qiagen), at 1:3000 dilution, Streptavidin-HRP (Roche) or for the detection of competitor 3G8, Peroxidase AffiniPure Goat Anti-Mouse IgG (H+L) (Dianova) at 1:10000 dilution for 1 hour at room temperature. After washing, plates were incubated with Tetramethylbenzidine (TMB) substrate (Seramun) for 1-2 min or until color development was clearly visible. Reaction was stopped by addition of 0.5M $H_2SO_4$ (100 µL/well). Absorbance was measured at 450 nm (1 s) using a multi-well plate reader (Victor, Perkin Elmer). Absorbance values were plotted and EC50 values were determined by fitting a non-linear regression model to sigmoidal dose-response curves (four parameters logistic fit) using GraphPad Prism version 6.07 (GraphPad Software, La Jolla Calif. USA).

Cell Lines and Cell Culture

NCI-H929 (DSMZ, cat.: ACC-163), MC/CAR (ATCC, cat.: CRL-8083), MM.1S (ATCC, cat.: CRL-2974), RPMI-8226 (DSMZ, cat.: ACC 402), KARPAS-299 (DSMZ, cat.: ACC 31), and SW-982 (ATCC, cat.: HTB-93) were purchased, and A-431 were provided by Dr. G. Moldenhauer (DKFZ Heidelberg). All cells were cultured under standard conditions in DMEM (cat.: 41965-039), IMDM (cat.: 12440-053), or RPMI 1640 (cat.: 21875-034) medium supplemented with: 10% heat-inactivated fetal calf serum (FCS) (cat.: 10270-106), 100 U/mL penicillin G/100 mg/mL streptomycin (cat.: 1540-122), and 2 mM L-glutamine (cat.: 25030-024; all Life Technologies) at 37° C. in a humidified 5% $CO_2$ atmosphere.

Isolation of Human NK Cells

Peripheral blood mononuclear cells (PBMC) were isolated from healthy volunteers' buffy coats (German Red Cross, Mannheim, Germany) by density gradient centrifugation using Lymphoprep (StemCell Technologies, cat.: 07861), as described before (Fuss et al., Curr Protoc Immunol 2009; Chapter 7:Unit7 1). PBMC were cultured O/N in RPMI 1640 medium supplemented with 10% heat-inactivated FCS, 2 mM L-glutamine, and 100 U/mL penicillin G sodium/100 µg/mL streptomycin sulfate at 37° C. and 5% $CO_2$ in a humidified atmosphere before NK cells were enriched by negative bead selection using EasySEP™ Negative NK Cell Enrichment Kit (StemCell Technologies, cat.: 17955) according to manufacturer's instructions. The purity of NK cell isolation was determined by flow cytometry, and demonstrated usually >80% $CD56^+$ cells (data not shown).

Cell Binding Assays and Flow Cytometric Analysis

Aliquots of $0.2-1\times10^6$ enriched human NK cells were incubated with 100 µL of serial dilutions of the indicated constructs in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) in the absence or, if indicated in the presence of 10 mg/mL polyclonal human IgG (Gammanorm, Octapharma) for 45 min at 37° C. After repeated washing with FACS buffer, cell-bound His-tagged scFv, TandAb, or aTriFlex antibodies were detected with 10 µg/mL anti-His mAb 13/45/31-2 (Dianova, Hamburg, Germany, cat.: DIA910-1MG) followed by 15 µg/mL FITC-conjugated goat anti-mouse IgG (Dianova, cat.: 115-095-062). Bispecific BCMA/CD16A antibody constructs were detected with soluble His-tagged BCMA followed by 10 µg/mL anti-His mAb 13/45/31-2 followed by 15 µg/mL FITC-conjugated goat anti-mouse IgG, and bispecific Fc-containing EGFR/CD16A constructs with 15 µg/mL FITC-conjugated goat anti-human IgG (Dianova, cat.: 109-095-098). After the last staining step, the cells were washed again and resuspended in 0.2 mL of FACS buffer containing 2 µg/mL propidium iodide (PI) (Sigma, cat.: P4170) in order to exclude dead cells. The fluorescence of $2-5\times10^3$ living cells was measured using a Millipore Guava EasyCyte flow cytometer (Merck Millipore, Schwalbach, Germany) or CytoFlex cytometer (Beckman Coulter, Krefeld, Germany) and median fluorescence intensities of the cell samples were determined. After subtracting the fluorescence intensity values of the cells stained with the secondary and/or tertiary reagents alone, the values were used for non-linear regression analysis. Equilibrium dissociation constants ($K_D$) were calculated using the one-site-binding (hyperbolic) fit and GraphPad Prism software V6 or V7 (GraphPad Software, La Jolla Calif. USA).

Cytotoxicity Assays

For the calcein-release assay, target cells were labeled with 10 mM calcein AM (Life Technologies, cat.: C3100MP) for 30 min in RPMI medium at 37C, washed, and $1\times10^4$ tumor target cells were seeded, in individual wells of a 96-well micro plate, together with effector cells in a total volume of 200 µL at the indicated effector:target (E:T) ratios in the presence of increasing antibody concentrations. For the assessment of NK fratricide, $5\times10^4$ calcein-labeled primary human NK cells were co-incubated with autologous NK cells at an E:T ratio of 1:1 in the presence of increasing antibody concentrations. After incubation at 37° C. in a humidified 5% $CO_2$ atmosphere for 4 h if not otherwise indicated, the fluorescence (F) of calcein released into the supernatant was measured by a plate reader at 520 nm (Victor 3 or EnSight, Perkin Elmer, Turku, Finland). The specific cell lysis was calculated as: [F(sample)−F(spontaneous)]/[F(maximum)−F(spontaneous)]×100%. F(spontaneous) represents fluorescence released from target cells in the absence of effector cells and antibodies, and F(maximum) represents that released after total cell lysis induced by addition of Triton X-100 (Roth, cat.: 3051.2) to a final concentration of 1%. Mean values of specific target cell lysis (%) and standard deviations (SD) were plotted and in vitro potency ($EC_{50}$) was determined by fitting the non-linear regression model to sigmoidal dose-response curves (variable slope) using GraphPad Prism (v6 and v7; GraphPad Software, La Jolla Calif. USA).

Surface Plasmon Resonance

Kinetic binding analyses of monovalent interactions to CD16A and qualitative dissociation phase comparison of monovalent and bivalent anti-CD16A binding analytes were performed on a Biacore T200 Instrument (GE Healthcare) at 25° C. using HBS-P+(10 mM HEPES, 150 mM NaCl, 0.05% (w/v) polysorbate 20, pH 7.4) as running buffer and for dilutions. CAP sensor chips (Biotin Capture Kit, GE Healthcare) were pre-conditioned overnight using HBS-P+ buffer. In a pre-capturing step, chip surfaces were treated with Biotin CAPture reagent (GE Healthcare) at 5 µL/min for 100 s in flow cells 1-4.

For kinetic binding analyses of various anti-CD16A scFvs, biotinylated mono-Fc(silent)-Avi-tagged receptors were prepared in HBS-P+ and captured (human CD16A-158V, human CD16A-158F approx. 40 RU for measuring interaction with scFvs and approx. 10 RU for measuring interactions with IgG) in flow cells Fc 2 and Fc 4. IgGs and scFvs were prepared in HBS-P+ buffer at indicated concentration series and are injected to reference surfaces (Fc 1, Fc 3) and receptor captured surface (Fc 2, Fc 4) at a flow rate of 40 µL/min (association time 180 s, dissociation time 300 s). Interactions were measured using Multi Cycle Kinetic mode (all antibodies were prepared in a 4-fold dilution series: scFv-Ab16$^{mid}$ 150 nM-0.586 nM; scFv-Ab16$^{hi}$ 50 nM-0.195 nM, scFv-AB16$^{lo}$ 500 nM-1.953 nM, scFv-3G8 and human IgG1 Fc-enhanced 200 nM-0.781 nM, human IgG1 and human IgG1 Fc-silenced 2000 nM-7.813 nM) following a regeneration cycle with 6 M guanidine-HCl/250 mM NaOH at 10 mL/min for 120 s. Data were referenced by subtraction of signals from reference surfaces (Fc 2-1, Fc 4-3) and zero concentration (buffer control) signals. Kinetic evaluation was performed by fitting data to a 1:1 binding model (Rmax and RI locally fitted) using Biacore T200 Evaluation Software (v3.1). For qualitative comparison of sensograms, a single concentration (312.5 nM) of scFvs and IgGs was injected over reference and receptor captured surface at increased capture levels (human CD16A-158V 180 RU and human CD16A-158F 90 RU). Referenced curves were normalized to each curves maximum and overlaid. For investigation of receptor retention via qualitative dissociation phase comparison of monovalent and bivalent CD16A-binding antibodies or ligands, biotinylated mono-Fc(silent)-Avi-tagged receptors were prepared in HBS-P+ and captured (human CD16A-158V approx. 160 RU, cynomolgus CD16 approx. 320 RU) in flow cells Fc 2 and Fc 3. Antibodies of interest (scFv-IgAb, Db-Fc, KiH-scDb-Fc, TandAb) incorporating Ab16$^{hi}$ binding domain and comparators, enhanced human IgG1 Fc (S239D/I332E) and monovalent binding scFv-Ab16$^{hi}$ were diluted to a concentration of 50 nM in HBS-P+ buffer and are injected to reference surfaces (Fc 1) and receptor captured surface (Fc 2, Fc 3) at a flow rate of 30 µL/min (association time 180 s, dissociation time 3 h). Surface was regenerated with 6 M guanidine-HCl/250 mM NaOH at 10 mL/min for 120 s. Data were referenced by subtraction of signals from reference surfaces (Fc 2-1, Fc 4-3) and zero concentration (buffer control) signals. Referenced curves were normalized to each curves maximum and overlaid Pharmacokinetic Studies of ROCK Engagers Basic pharmacokinetic parameters of the different ROCK® platform formats were assessed in CD-1 SWISS mice. In life phases were conducted by Heidelberg Pharma GmbH. CD-1 SWISS female mice (e.g., n=24) received an intravenous single administration of 0.3 mg (~10 mg/kg bodyweight) of the Test Item. At different time points blood was collected for a period of 1 to 3 weeks. Serum from the blood was taken and analysed with established assays based on ELISA or MSD technology. A representative blood withdrawal schedule covered 13 timepoints, e.g., predose d-7, 5 minutes, 30 minutes, 30 minutes, 1 hour, 4 hours, 8 hours, and days 1, 2, 3, 4, 7, 14, and 21. Serum concentrations were determined by ELISA on a Tristar LB941 (Berthold instruments) using enhanced chemolumninescence (ECL) detection. For the establishing the Assay set-ups, different combinations of serum Antigens and/or monoclonal antibodies as capture and/or detector were tested. The Assays were characterized regarding further critical parameters, like inter-/intra-assay precision and accuracy, dilution linearity and selectivity, Hook effect and matrix effects.

NK Cell Activation Assay $5×10^5$ human PBMCs were seeded in individual wells of a flat-bottom 96-well micro plate in the presence or absence of $1×10^4$ RPMI-8226 cell in complete RPMI 1640 medium in the presence of the indicated antibody concentrations. Following 22 h incubation at 37° C. with 5% $CO_2$ in a humidified atmosphere, cells were harvested, washed and resuspended in FACS/hIgG buffer (FACS buffer supplemented with 1mg/mL polyclonal human IgG). Cells were then stained with CD56-PC7 and CD69-PC5 in FACS/hIgG buffer for 15 min on ice in the dark. After repeated washing with FACS buffer, $1×10^3$-$1×10^4$ cells were analyzed by flow cytometry and percentage of CD69$^+$ cells of CD56$^+$ NK cells were quantified.

Cytokine Release Assay

Flat-bottom 96-well microtiter plates were blocked with RPMI-1640/5% FCS for 2-4 h at RT before seeding of $5×10^5$ PBMC with or without $1×10^4$ NCI-H929 tumor cells with or without 10 µg/mL of the indicated antibodies in a total volume of 200 µL/well. Plates were incubated for 24 h at 37° C. and 5% $CO_2$ in a humidified incubator. Cell culture supernatants were harvested and stored at −80° C. until quantification of cytokines at Bioassay GmbH (Heidelberg, Germany) using BD™ Cytometric Bead Array (CBA) Human Th1/Th2 Cytokine Kit II (BD Bioscience).

Results

Rational for Generation of Anti-CD16A Antibody Domains

Most classical therapeutic antibodies containing an Fc portion show low intrinsic CD16A binding affinity (FcγRIIIA) binding affinity, and immuno-engagers which employ the recognition site on CD16A also bound by the Fc proportion of IgG antibodies (de Palazzo et al., Cancer Res. 1990; 50:7123-8; de Palazzo et al., Cancer Res. 1992; 52:5713-9) and have to compete with serum IgGs for CD16A binding, thereby limiting CD16A occupancy and increasing the required dose of therapeutic antibody to be efficacious. Competition with plasma IgGs might be even more pronounced in disease conditions which are characterized by high levels of plasma IgGs such as multiple myeloma (Michallet et al., Leukemia 2017). In addition, CD16A polymorphisms in humans (Mahaweni et al., Sci. Rep 2018; 8:15983), with the most prominent variants CD16A-158V and CD16A-158F differing in binding affinities to IgG and hence FcR functions like ADCC, result in different levels of efficacy of classical mAb therapy depending on the patient's individual CD16A genotype (Bowles et al., Blood 2006; 108:2648-54; Burchard et al., Cancer Genetics 2013; 206:130-4). Leveraging the ROCK® platform, the inventors created an anti-CD16A domain that recognizes a unique epitope on CD16A2 and that is virtually unaffected by plasma IgG competition and CD16A polymorphism. In addition, it was designed for high affinity binding to CD16A mediating highly potent ADCC and thus effective immuno-surveillance.

Figure 18A:
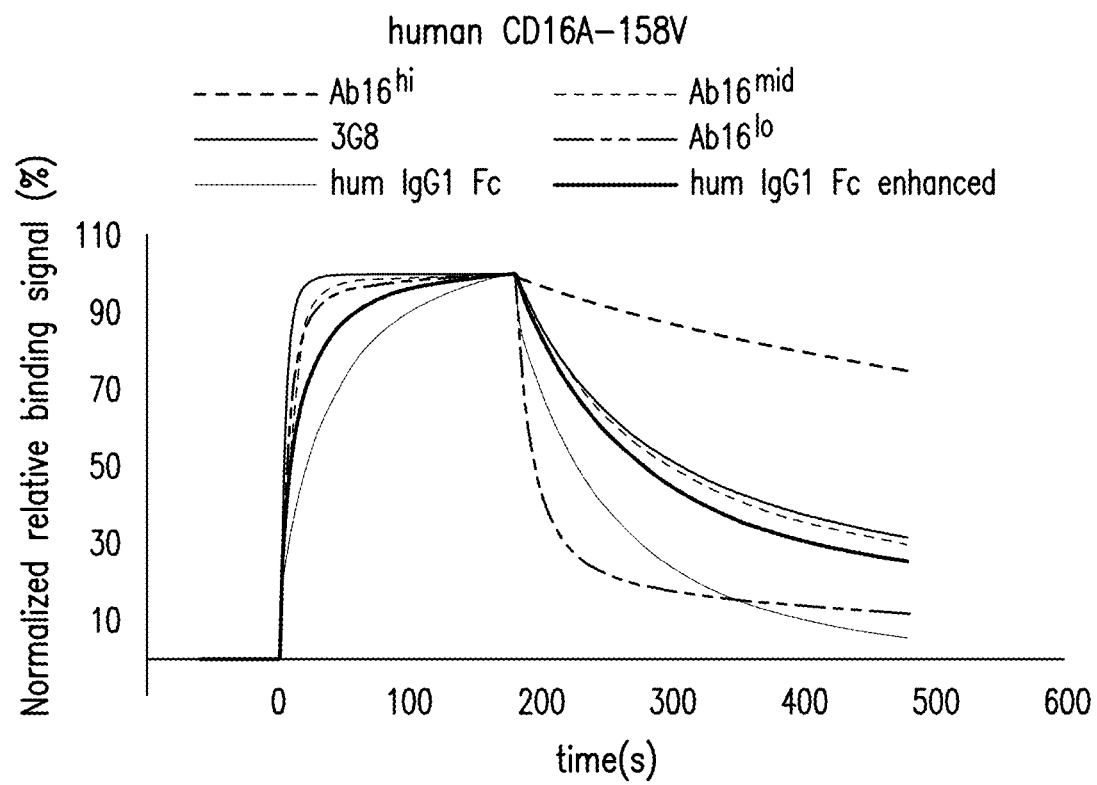
FIGS. 18A and 18B SPR analysis of different anti-CD16 scFv. SPR sensograms of normalized relative binding signals of anti-CD16 binding scFv antibodies (Ab16$^{hi}$, Ab16$^{mid}$, 3G8, Ab16$^{lo}$) compared to wildtype IgG1, and engineered human IgG1 Fc (S239D/I332E).
Figure 18B:
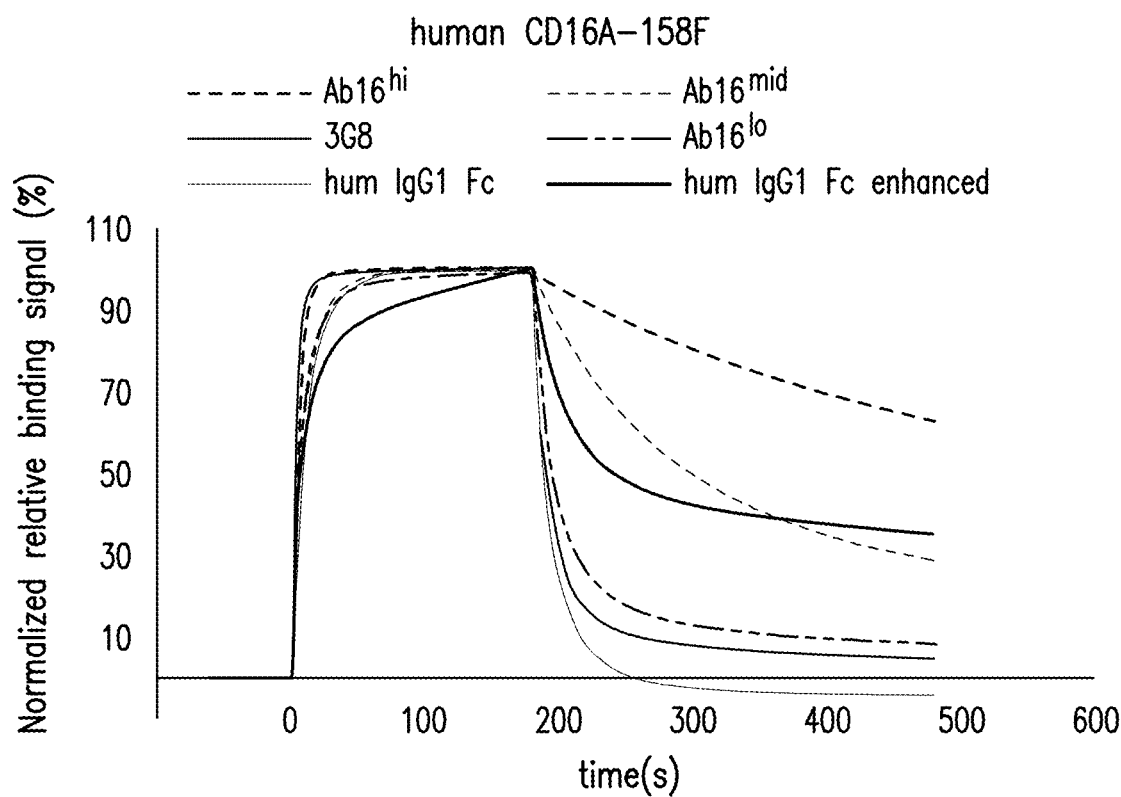
Figure 19A:
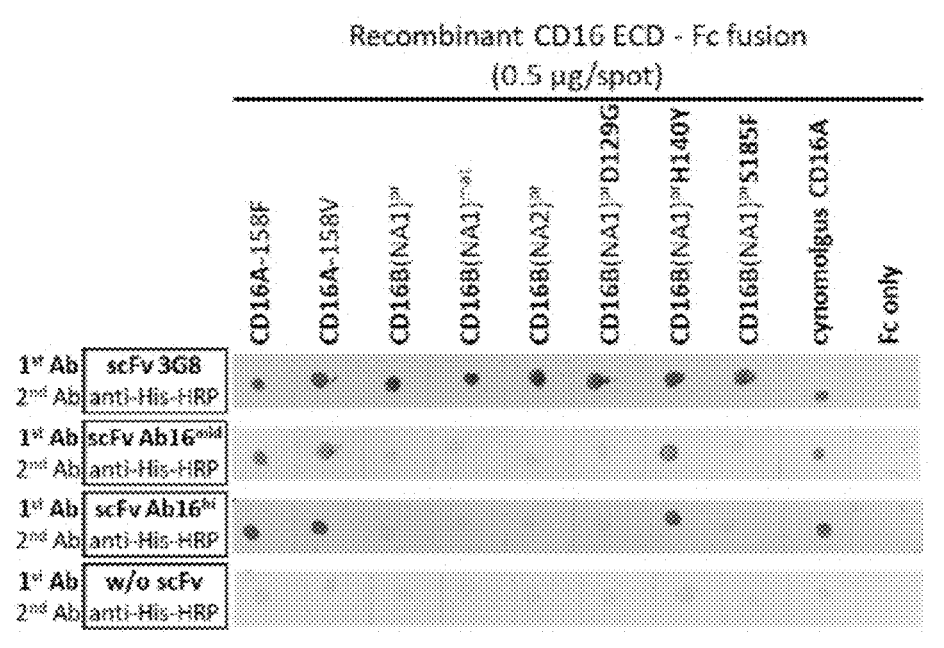

In order to fulfill the above described criteria of such antibody moieties with high affinity and selectivity for CD16A, a library of scFv derived from human PBMCs was screened. Using human CD16B variants for negative selection an antibody with initially low affinity, but high selectivity for CD16A could be identified. Using different approaches for affinity maturation (e.g., light chain shuffling, rationale mutations in CDRs of heavy chain) the affinity towards CD16A could be increased by at least factor 100 up to a Kd of 2 nM (AB16hi, Table 5). CD16A binding properties of low affinity) ($Ab16^{lo}$), medium affinity ($Ab16^{mid}$), and high affinity binding scFv ($Ab16^{hi}$) antibodies were characterized in SPR and compared with a previously described and well characterized CD16 pan-specific antibody 3G8 (Tamm et al., J Immunol 1996; 157:1576-81), as well as IgG1 Fc or a genetically modified Fc variant with CD16A-binding- and Fc-mediated effector function enhancing mutations S239D/I332E (Lazar et al., Proc Natl Acad Sci USA 2006; 103:4005-10) or silencing mutations L234F/L235E/D265A (Vidarsson et al., Front Immunol 2014; 5:520; Baudino et al., J Immunol 2008; 181:6664-9; Hezareh et al., Journal of virology 2001; 75:12161-8). Both, $Ab16^{mid}$ and $Ab16^{hi}$ confirmed superior binding properties for CD16A (FIGS. 18A and 18B). While CD16A binding kinetics of wildtype IgG1 Fc, enhanced IgG1 Fc and of the CD16 pan-specific antibody 3G8 depended on CD16A polymorphism, $Ab16^{hi}$ as well as $Ab16^{mid}$ and $Ab16^{lo}$ showed comparable kinetic binding properties regardless of the allelic forms, CD16A-158V and CD16A-158F (Table 5, FIGS. 18A, 18B and 20). Both antibodies furthermore showed good cross-reactivity with cynomolgus CD16A (FIG. 19A, Table 6). Furthermore, the characterization of the anti-CD16A binders identified from the different affinity maturation strategies confirmed another unique characteristic: Engagement of CD16A uniformly and regardless of CD16A genotypic variation (Table 5, FIGS. 18A, 18B and 20).

TABLE 5

SPR binding kinetics of different CD16A binding scFvs or Fc portions.

| CD16 binding moiety | human CD16A-158V | | | human CD16A-158F | | |
|---|---|---|---|---|---|---|
| | $k_a$ (M$^{-1}$s$^{-1}$) | $k_d$ (s$^{-1}$) | $K_D$ (nM) | $k_a$ (M$^{-1}$s$^{-1}$) | $k_d$ (s$^{-1}$) | $K_D$ (nM) |
| scFv $Ab16^{lo}$ | 1.73E+05 ± 1.21E+03 | 5.34E−02 ± 1.55E−04 | 308 | 1.66E+05 ± 1.09E+03 | 4.74E−02 ± 1.26E−04 | 286 |
| scFv $Ab16^{mid}$ | 6.05E+5 ± 3.12e+3 | 1.27E−02 ± 5.44E−05 | 21 | 5.14E+05 ± 2.81E+03 | 1.02E−02 ± 4.36E−05 | 19.80 |
| scFv $Ab16^{hi}$ | 7.07E+05 ± 4.52E+02 | 1.38E−03 ± 5.96E−07 | 1.96 | 6.42E+05 ± 3.53E+02 | 2.01E−03 ± 5.49E−07 | 3.13 |
| scFv 3G8 | 1.24E+06 ± 6.01E+03 | 1.06E−02 ± 4.15E−05 | 8.60 | Complex binding interaction, 1:1 Binding evaluation not possible | | |
| IgG1 Fc (wildtype) | 2.35E+04 ± 9.50E+01 | 9.95E−03 ± 1.23E−05 | 424 | 2.48E+04 ± 2.19E+02 | 6.75E−02 ± 1.78E−04 | 2720 |
| IgG1 Fc (enhanced, S239D/I332E) | 4.74E+05 ± 3.85E+03 | 6.39E−03 ± 3.46E−05 | 13.50 | Complex binding interaction, 1:1 Binding evaluation not possible | | |
| IgG1 Fc (silenced, L234F/L235E/ D265A) | No binding signal | | | 2.04E+04 ± 3.02E+02 | 7.10E−01 ± 6.34E−03 | 34700 |

Mean binding constants and standard errors SE are shown (association rate constant $k_a$ (M$^{-1}$s$^{-1}$), dissociation rate constant (s$^{-1}$), Equilibrium dissociation constant $K_D$ (nM)). Sensograms are given in FIG. 20.

TABLE 6

Summary of binding of different anti-CD16 scFv antibodies to CD16 antigen variants coated at concentrations of 1.5 μg/mL (32 nM) and analyzed in ELISA.

| | 3G8 scFv | | $Ab16^{mid}$ scFv | | $Ab16^{hi}$ scFv | |
|---|---|---|---|---|---|---|
| coated antigens | Mean EC$_{50}$ [nM] | SD | Mean EC$_{50}$ [nM] | SD | Mean EC$_{50}$ [nM] | SD |
| Human CD16A-158F | 0.58 | 0.33 | 8.90 | 0.42 | 1.55 | 0.36 |
| Human CD16A-158V | 0.33 | 0.15 | 8.33 | 0.88 | 1.13 | 0.26 |
| Human CD16B$^{mat}$ | 0.28 | 0.12 | no binding | n.a. | no binding | n.a. |
| Human CD16B$^{pr}$ | 0.25 | 0.09 | no binding | n.a. | no binding | n.a. |
| Human CD16B$^{pr-D129G}$ | 0.25 | 0.06 | no binding | n.a. | no binding | n.a. |
| Human CD16B$^{pr-H140Y}$ | 0.26 | 0.05 | 6.43 | 0.06 | 0.93 | 0.09 |
| Human CD16B$^{pr-S185F}$ | 0.34 | 0.07 | no binding | n.a. | no binding | n.a. |
| Cynomolgus CD16A | 0.87 | 0.24 | 13.69 | 1.58 | 1.55 | 0.10 |

Mean EC$_{50}$ [nM] of binding scFv with SD, measured in 2 independent assay are shown.

CD16A Specific Binding to a Distinct Epitope and in the Presence of Serum IgG

Besides CD16A that shows a high degree of polymorphism, allotypic variants of human CD16B (FcγRIIIB) differ in five amino acids of the extracellular domain (ECD) (FIG. 21), some enabling additional glycosylation, resulting in three different variants of the GPI-anchored CD16B granulocyte antigens named NA1, NA2 and SH. Notably, only two amino acid positions consistently differ in the mature ECD of CD16A and B (FIG. 21). Additional variation resides in the different modes of membrane anchorage of CD16A and CD16B. A caboxyterminal propeptide sequence of CD16B cleaved off in the mature GPI-anchored form has high homology to the sequence connecting CD16A ECD to its transmembrane domain (FIG. 21). To investigate which of the CD16A/CD16B sequence variations determines the binding site for our strictly CD16A-selective antibodies, a set of recombinant CD16 antigen variants were generated and characterized. CD16B(NA1) ECD was either expressed as the maturated form (lacking the propeptide) (CD16B$^{mat}$), or as the precursor containing the propeptide sequence (CD16B$^{pr}$). In addition, CD16B$^{pr}$ ECD mutants in which CD16B-specific amino acids were replaced with the homologous residues of CD16A were generated and tested in binding assays: CD16B$^{pr,D129G}$, CD16B$^{pr,H140Y}$, CD16B$^{pr,S185F}$.

Figure 19B:
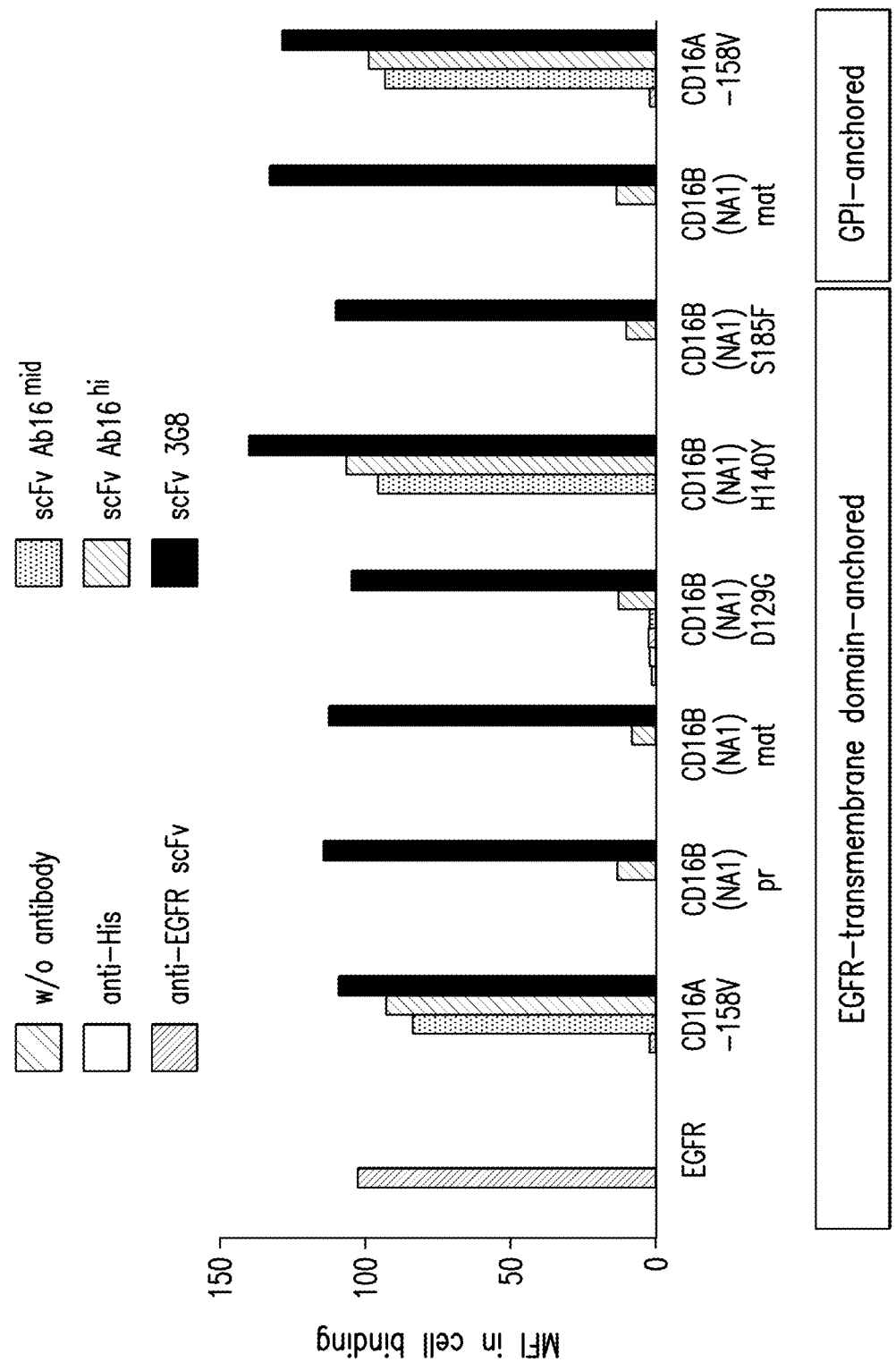
Figure 19C:
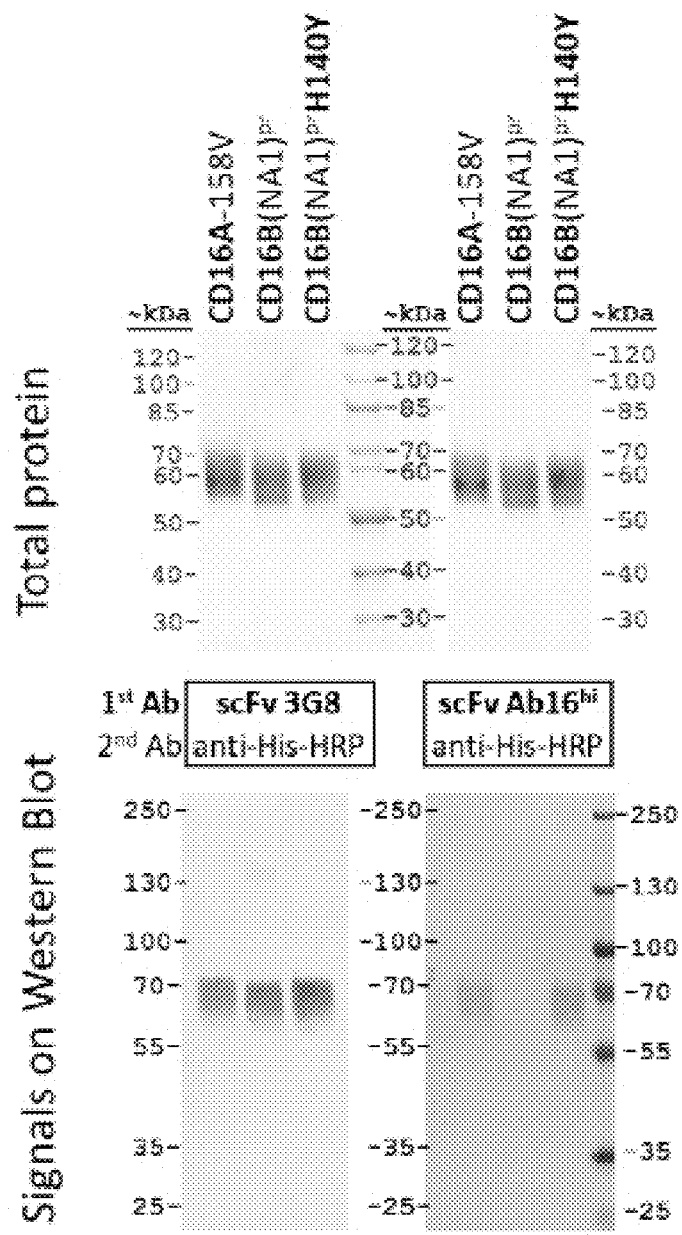
Figure 20:
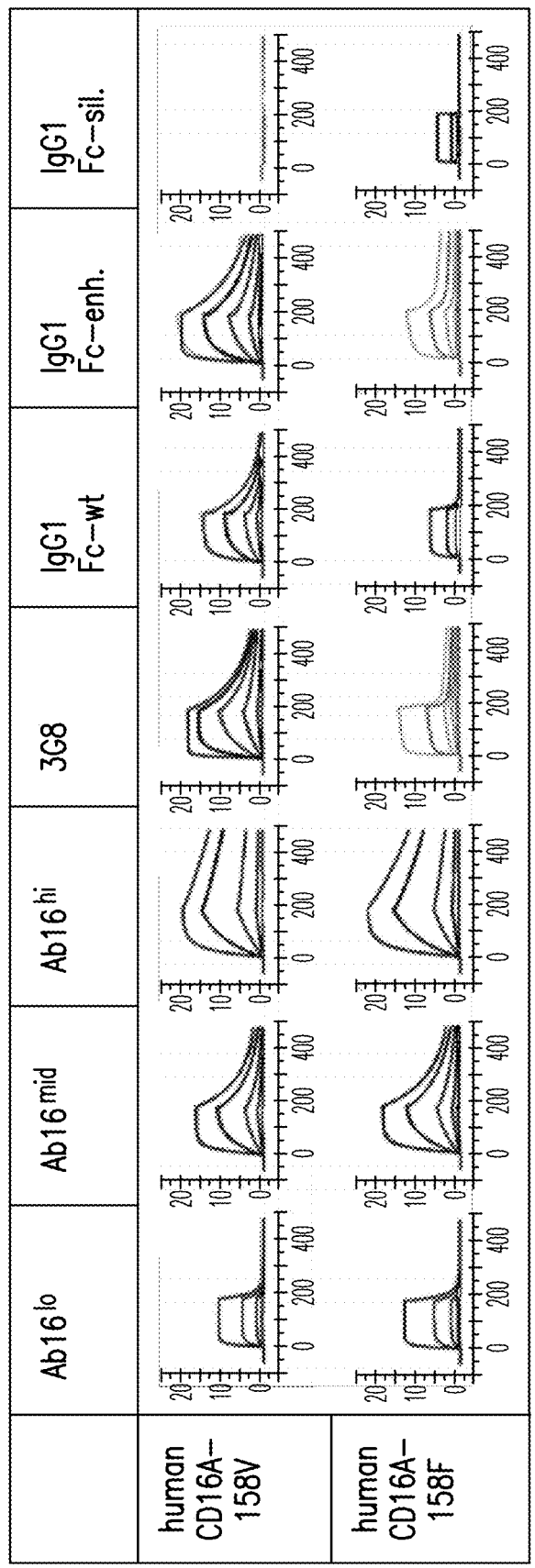
FIG. 20 shows SPR sensograms of anti-CD16 binding domains (Ab16lo, Ab16mid, Ab16hi, 3G8) in comparison to human IgG1 Fc-wildtype, human IgG1 Fc enhanced (S239D/I332E), human IgG1 Fc-silenced (L234F/L235E/D265A), binding to human CD16A-158V and human CD16A-158F. KD values were calculated using 1:1 Binding model and are shown in Table 5. Abscissa: Response (RU), ordinate: time [s].

All tested CD16A and CD16B antigen variants were recognized by the CD16 pan-specific antibody 3G8 confirming their molecular integrity (FIGS. 19A, 19B, 19C and Table 6). ScFv antibodies Ab16$^{mid}$ or the affinity-improved Ab16$^{hi}$ recognized the CD16A antigen, but not the mature or propeptide-containing ECD fusion antigens of CD16B. If, however CD16B ECD Histidine (H) at position 140 was mutated to Tyrosine (Y)—the amino acid present at the corresponding position in CD16A—this mutant form of CD16B (CD16B$^{pr,H140Y}$) was well recognized by the affinity optimized scFv antibodies Ab16$^{mid}$ and Ab16$^{hi}$ (FIGS. 19A-19C, Table 6). As shown in FIGS. 19A, 19B, and 19C, Tyrosine (Y) in position 140 is crucial for formation of a conformational epitope and CD16A-specific reactivity of scFv antibodies.

Both anti-CD16 scFv maintained good cross-reactivity with cynomolgus CD16 (FIGS. 19A, 19B, 19C, and Table 6), despite the fact that the cynomolgus CD16 ECD sequence differs in a total of 16 amino acids from human CD16A (see alignment in FIG. 21). Binding selectivity and importance of Tyrosine (Y) at position 140 in the CD16 ECD for CD16A-specific recognition by the tested antibodies Ab16$^{mid}$ and Ab16$^{hi}$ was confirmed using recombinant CHO cells with transgenic expression of different CD16 antigen variants (FIG. 19B). CD16A or CD16B$^{pr,H140Y}$, in contrast to CD16B$^{pr}$ or CD16B$^{mat}$ antigen variants were also recognized after SDS-PAGE on Western blot using these scFv antibodies (FIG. 19C and data not shown). No signals were obtained on Western blots of reduced samples (data not shown), suggesting a conformational epitope which in the case of recognition by Ab16$^{mid}$, and Ab16$^{hi}$, could be determined by Tyrosine in position 140 of CD16.

Figure 22:
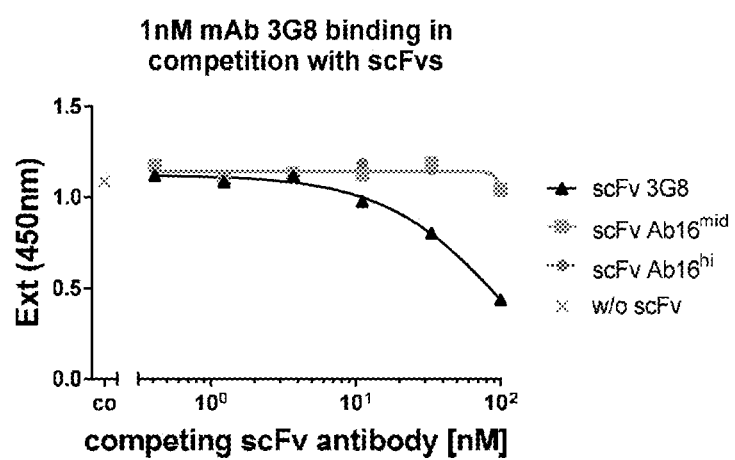
FIG. 22 shows binding competition of different anti-CD16 scFv antibodies with mAb 3G8 to CD16A in ELISA. Plates coated with CD16A-158V ECD-Fc fusion antigen were incubated with a mixture of 1 nM of mAb 3G8 and serial dilutions of different anti-CD16 scFvs in the indicated concentration range. CD16A-bound mAb 3G8 was detected with Peroxidase conjugated goat anti-mouse IgG(H+L). TMB substrate reactions were measured at 450 nm (Ext (450 nm)), plotted and analysed.

The IgG binding site on CD16A is a discontinuous binding area on the membrane proximal ECD of the receptor. Crucial amino acids for the low-affinity interaction of CD16A with the Fc part of IgG were previously identified and described (Ahmed et al., J Struct Biol 2016; 194:78-89). Antibody 3G8 was reported to bind CD16A and CD16B and block IgG binding (Tamm et al., J Immunol 1996; 157:1576-81). No blocking of binding of the tested antibodies to CD16A by IgGs was observed. While binding of 3G8 mAb to CD16A was outcompeted with increasing concentrations of a scFv antibody containing the corresponding variable domains of 3G8, the anti-CD16 scFv antibodies Ab16$^{mid}$ and Ab16$^{hi}$ did not block or displace 3G8 mAb on CD16A and bind independently (FIG. 22) and with similar affinity in the absence or presence of competing 3G8 mAb (Table 8). As shown in Table 8, 3G8 blocked the Fc binding site on CD16. Since occupation of the 3G8 binding site on CD16A is known to block IgG binding, it was concluded that the binding site of the tested anti-CD16 antibodies on CD16A is distinct from the IgG binding site. Accordingly, NK cell binding KD values of scFv antibodies Ab16$^{hi}$ and Ab16$^{mid}$ were only mildly affected by addition of 10 mg/mL human IgG, whereas binding affinity of CD16-binding moieties of the antibody 3G8 was more than 20-fold reduced in the presence of physiological IgG concentrations (Table 7). Therefore, these results suggest that the tested CD16A-binding antibodies Ab16$^{hi}$ and Ab16$^{mid}$ offer the advantage of high affinity binding to a CD16A-specific epitope which is not or only minimally impaired by competing IgG levels (e.g., in human blood) and next their power was exploited in multivalent anti-tumor NK cell-engaging ROCK® antibodies.

TABLE 7

Apparent affinities of anti-CD16 scFv to primary human NK cells.

| scFv clone | $K_D$ [nM] in the presence of buffer | | $K_D$ [nM] in the presence of 10 mg/mL IgG | | fold loss in affinity induced by 10 mg/mL IgG | |
|---|---|---|---|---|---|---|
| | mean | SD | mean | SD | mean | SD |
| 3G8 | 3.8 | 2.3 | 64.6 | 58.4 | 21.4 | 10.5 |
| Ab16$^{mid}$ | 52.3 | 18.8 | 138.3 | 22.1 | 2.7 | 0.5 |
| Ab16$^{hi}$ | 7.9 | 2.4 | 37.2 | 39.5 | 7.7 | 3.9 |

$K_D$ values for the indicated scFv were determined in 4 independent experiments on enriched primary human NK cells at 37° C. in the presence or absence of 10 mg/mL polyclonal human IgG.

TABLE 8

Summary of binding and competition of different anti-CD16 scFv antibodies to CD16 antigen coated at a concentration of 0.5 µg/mL (10 nM) and analyzed in ELISA in the absence or presence of an equimolar concentration of the CD16-pan specific antibody 3G8 (10 nM) as competitor.

| | 3G8 scFv | | Ab16$^{mid}$ scFv | | Ab16$^{hi}$ scFv | |
|---|---|---|---|---|---|---|
| | Mean EC$_{50}$ [nM] | SD | Mean EC$_{50}$ [nM] | SD | Mean EC$_{50}$ [nM] | SD |
| without competition | 0.9 | 0.9 | 13.3 | 7.0 | 2.1 | 1.1 |
| with 8-10 nM 3G8 IgG | 19.7 | 9.9 | 12.3 | 6.2 | 3.3 | 1.5 |
| | fold inhibition | | fold inhibition | | fold inhibition | |
| fold inhibition by 3G8 | 30.5 | | 0.9 | | 1.6 | |

Mean EC$_{50}$ [nM] with SD, measured in 2 independent assay are shown.

The ROCK® Platform
ROCK® Formats

In order to demonstrate the versatility of the anti-CD16A domain and to exploit its full potential, a wide spectrum of ROCK® architectures based on known antibody formats (Spiess et al., Mol Immunol 2015; 67:95-106) and newly designed variants thereof was created.

Figure 23:
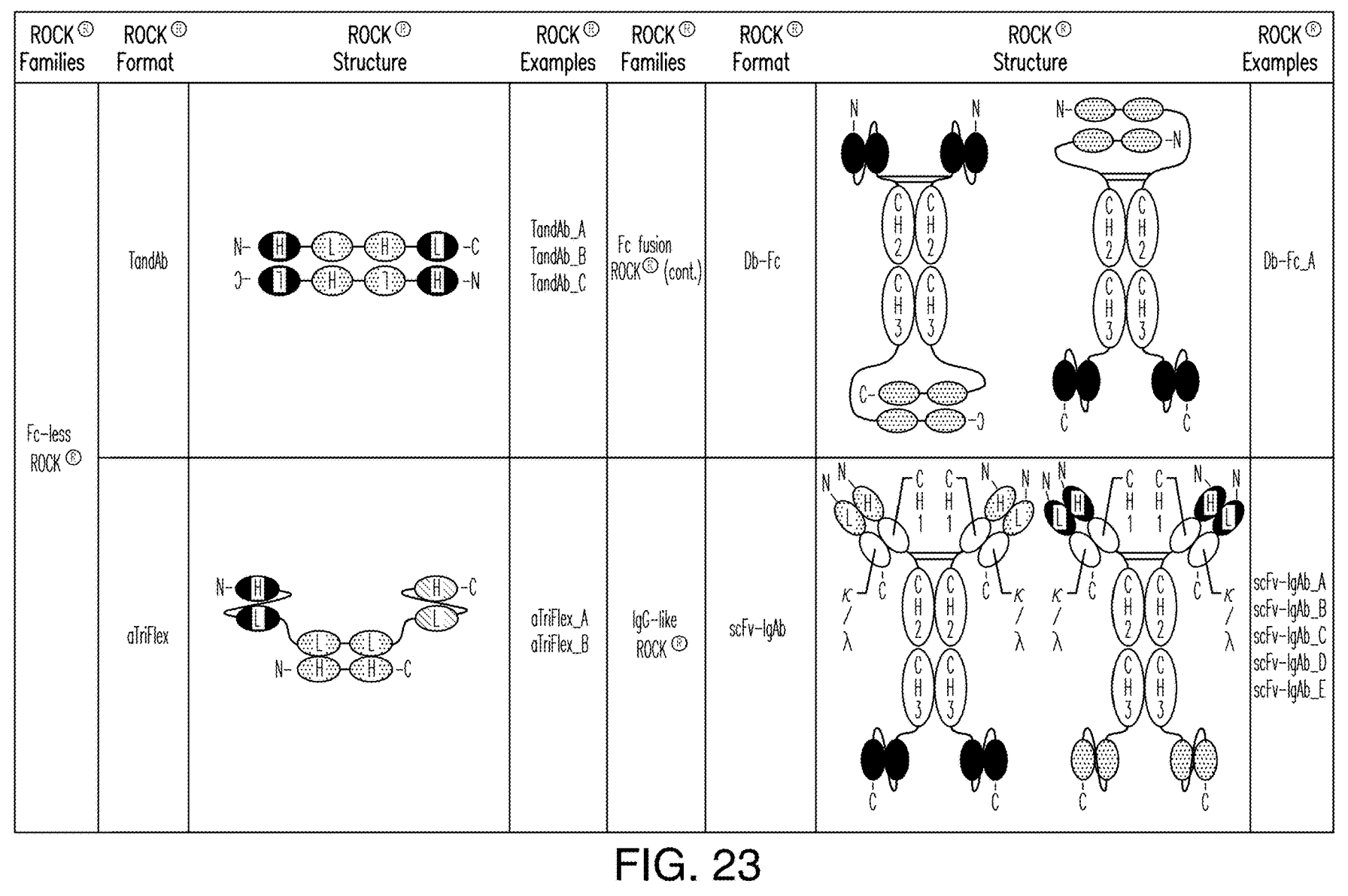
Figure 23:
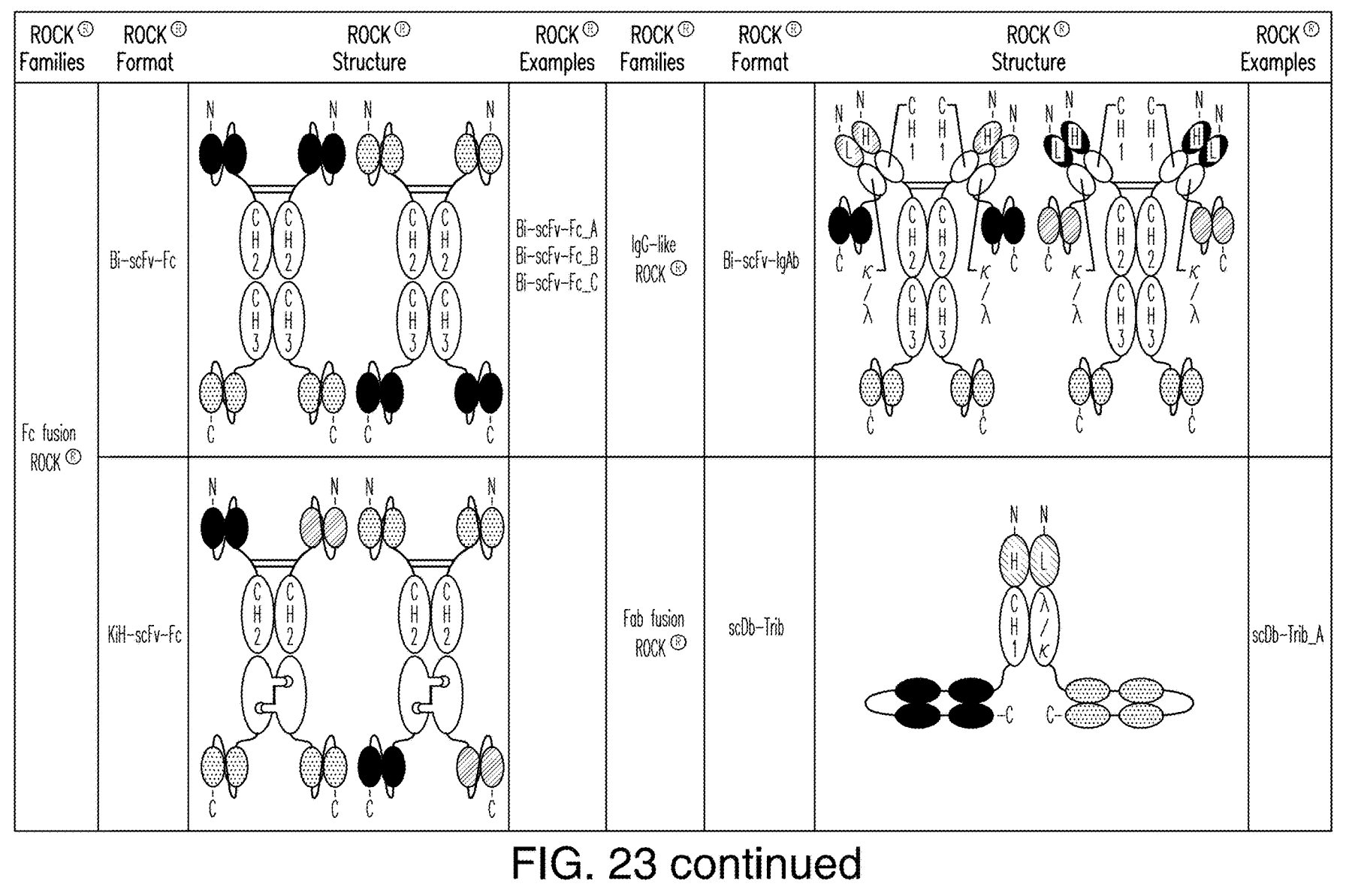
Figure 23:
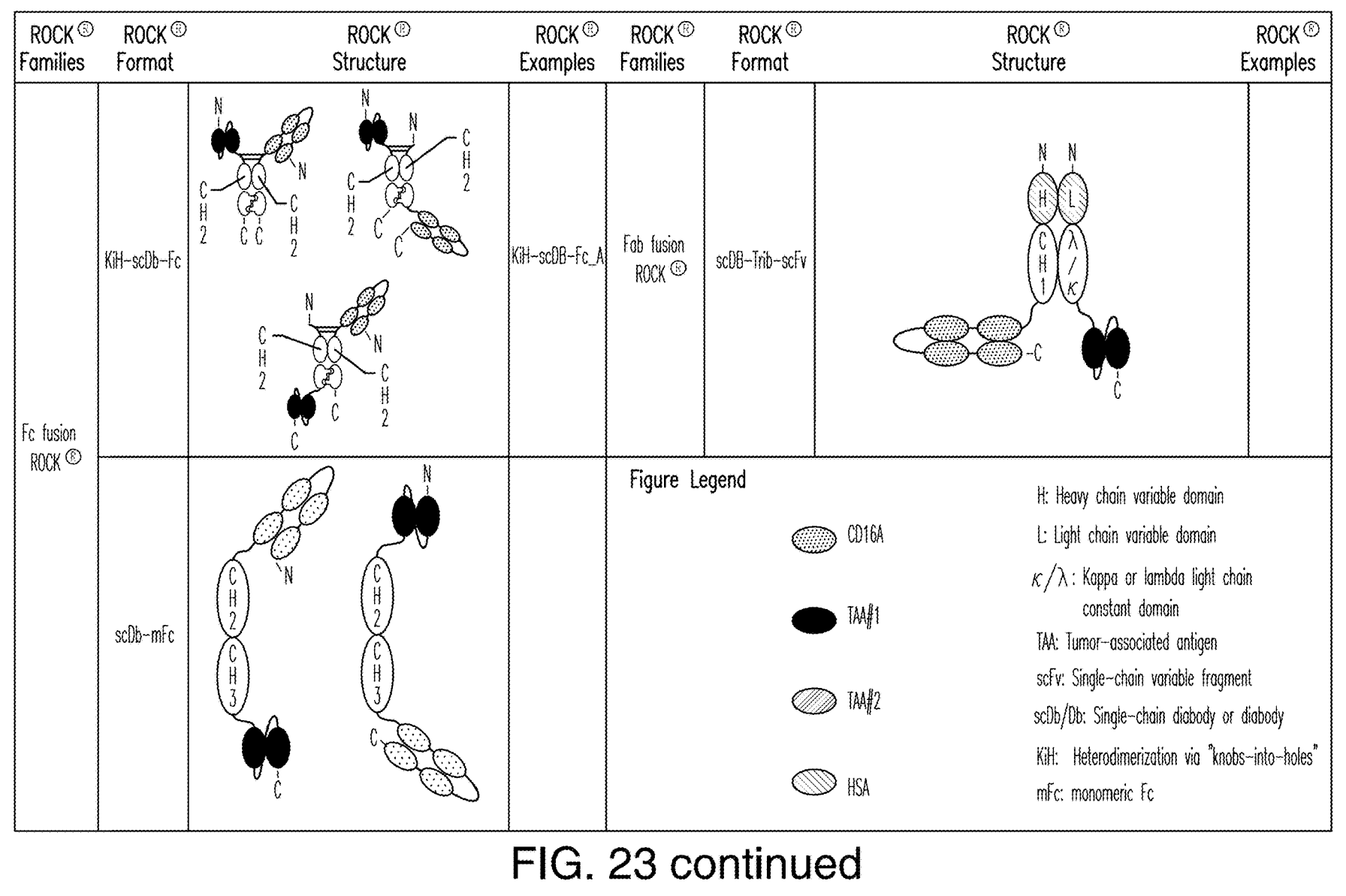

ROCK® platform antibodies are multivalent and multispecific with at least one target-binding site and two CD16A antigen-binding moieties enabling bivalent binding. Dependent on desired features, such as valency, multispecificity, pharmacokinetic and pharmacodynamic properties, the constructs are modularily assembled from binding domains with or without a constant region. The ROCK® antibody formats can be grouped into four different families comprising i) Fc-less ROCK®, ii) Fc fusion ROCK®, iii) IgG-like ROCK® and iv) fragment antibody binding domain (Fab) fusion ROCK®. The target and effector cell binding moieties of family members ii), iii) and iv) can be either formatted as single chain Fv (scFv), single-chain diabody (scDb), diabody (Db) or as Fab enabling a range of functionalities. The binding domains are either fused to the N- and C-terminus of CH2/CH3 constant domains via a flexible linker or, alternatively, to the N-terminus via a hinge or shorter middle hinge (Merchant et al., Proc. Natl. Acad. Sci. U.S.A. 2013; 110:E2987-96). For family i) the binding domains are connected by peptide linkers and assembled as TandAb (McAleese et al., Future Oncol 2012; 8:687-95) or aTriFlex molecules (Gantke et al., Protein Eng Des Sel 2017; 30:673-84). In order to ensure powerful engagement and activation of NK cells, the anti-CD16A moiety was designed for bivalent binding in all families. The tumor target binding domain in ROCK® engagers can be either monovalent or bivalent, depending on desired binding strength and/or target biology. Modularity of the platform furthermore facilitates construction of multivalent and multispecific engagers for the co-targeting of more than one tumor antigen. FIG. 23 shows all four ROCK® families (i-iv), their associated formats. In order to show the versatility of the ROCK® formats, different target binding moieties such as BCMA, CD19, CD20, EGFR, HSA or RSV were chosen.

Representative examples of ROCK® constructs that are characterized in more detail in functional assays described herein target the solid tumor target EGFR or B cell maturation antigen (BCMA), a target in multiple myeloma (Tables 9A, 9B, and 9C). The symbols shown in the structures in Tables 9A, 9B, and 9C are consistent with the symbols shown in FIG. 23. All ROCK® constructs were comprised of fully human antibody domains and have an approximate molecular weight of 102-250 kDa. In several cases, tags (C-tag and/or 6×His tag) were added at the C-terminus to enable selective purification of heterodimeric antibodies via affinity chromatography, analysis of the two different polypeptide chains in asymmetric products and, finally, high purity (>90%) of the desired product species.

Fc-less ROCK® family (i): This group of Fc-less constructs combines the well-known TandAb, of which several products are already in clinical development (Reusch et al., MAbs 2014; 6:728-39; Reusch et al., MAbs 2015; 7:584-604; Ellwanger et al., Frontiers in Oncology 2017; 7; Reusch et al., Clin. Cancer Res. 2016; 22:5829-38) and the aTriFlex (Gantke et al., Protein Eng Des Sel 2017; 30:673-84) molecules. The latter can be engineered as trispecific format, employing two different scFv specificities to address two different tumor-associated antigens or target epitopes or be used for PK-extension. For that purpose, an anti-human serum albumin (HSA) binding domain was used to extend the serum half-life of the otherwise short-lived Fc-less antibody format. Both formats within this family assemble as dimers by interaction of corresponding heavy and light chain variable domains on two separate polypeptide chains as head-to-tail homodimers (TandAb format) or as heterodimers in a head-to-tail or head-to-head fashion (aTriFlex). Members of this group are the smallest ROCK® bispecific constructs in size with an approximate mass of 105 kDa of the functional dimer and lack both, an Fc-part and glycosylation.

Fc fusion ROCK® family (ii): This family of Fc-containing antibody formats comprises several Fc variants (Vidarsson et al., Front Immunol 2014; 5:520; Baudino et al., J Immunol 2008; 181:6664-9; Hezareh et al., Journal of virology 2001; 75:12161-8) in order to avoid Fcγ receptor binding but still maintaining FcγRn binding for half-life extension. Thus, Fcγ receptor binding is exclusively mediated by the NK cell binding domain and restricted to CD16A. In addition, the Fc part of this family can be either a IgG1-based homodimeric (Bi-scFv-Fc, Db-Fc), a heterodimeric (KiH-scFv-Fc, KiH-scDb-Fc) or a monomeric Fc (scDb-mFc). To facilitate heterodimerization, the "Knobs-into-holes" (KiH) technology using classical Y407T ("hole") and T366Y ("knob") mutations have been used (Ridgway et al., Protein Eng 1996; 9:617-21). The monomeric Fc (mFc) part has been engineered as previously published (Ying et al., J. Biol. Chem. 2012; 287:19399-408) using flexible connectors for fusion with target and NK cell binding moieties. The anti-CD16A is either located opposite to the anti-target binding domain at the N- or C-terminus or juxtaposed to it at the N-terminus as it has been shown for one of the KiH-scDb-Fc constructs. A scDb format for the CD16A binding domain was applied in KiH-scDb-Fc and scDb-mFc constructs. The Db-Fc format is a homodimer which exhibits a diabody molecule at the C- or N-terminus. This Db-Fc format assembles from two VL/VH domains that were fused to the constant regions via a flexible linker at C- or via an extended hinge region at the N-terminus.

IgG-like ROCK® family (iii): This bispecific antibody group encompassed the scFv-IgAbs and Bi-scFv-IgAbs which are in principle "extended human IgG1" molecules (Coloma et al., Nat Biotechnol 1997; 15:159-63) with two CD16A antigen-binding moieties fused to the C-terminus or located at the N-terminus as variable fragments (Fv) within both Fab arms. The same holds true for the tumor target-binding domains which are located at the corresponding opposite ends. Bi-scFv-IgAb molecules exhibit a hexavalent trispecific IgG-like architecture with two additional pairs of antigen-binding scFv fused to C-terminus of a kappa or lambda constant region and CH3 via flexible linkers.

Fab fusion ROCK® family (iv): Members of this group are "extended Fab" molecules and can be subdivided in the scDb-TriB and the scDb-TriB-scFv formats. Both include anti-CD16A binding moieties as a bivalent scDb fused to C-terminus of a kappa or lambda constant region in scDb-TriB-scFv or, in the case of scDb-TriB, to the C-terminal end of CH 1. For PK-extension, the variable domain at the N-terminus of the Fab fragment provides HSA binding. Tumor-targeting is achieved either by monovalent (scDb-TriB-scFv) or bivalent (scDb-TriB) binding moieties (scFv vs. scDb) fused to the respective free C-terminus.

TABLE 9A

Overview of ROCK ® examples containing CD16 binding moieties (depicted in blue) in Fab or scFv-fusion arrangement used in functional assays.

| ROCK ® Examples | | scFv-IgAb_A | scFv-IgAb_B | scFv-IgAb_C |
|---|---|---|---|---|
| | | 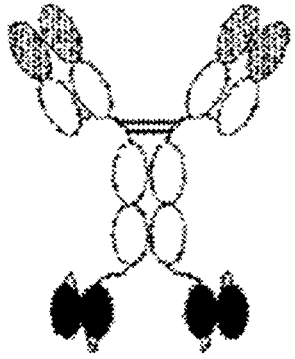 | 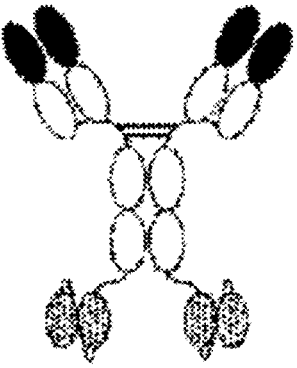 | 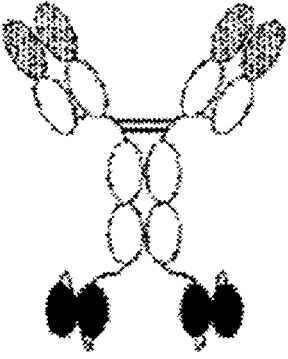 |
| ROCK ® | Family | IgG-like | IgG-like | IgG-like |
| | Format | scFv-IgAb | scFv-IgAb | scFv-IgAb |
| Anti-CD16 | Position | N | C | N |
| | Fv | Mid | mid | hi |
| | Format | Fab | scFv (HL) | Fab |
| Target | | EGFR | EGFR | EGFR |
| Constant region | | silenced[#] | silenced[#] | silenced[#] |

| ROCK ® Examples | | scFv-IgAb_D | scFv-IgAb_E | scFv-IgAb_F |
|---|---|---|---|---|
| | | 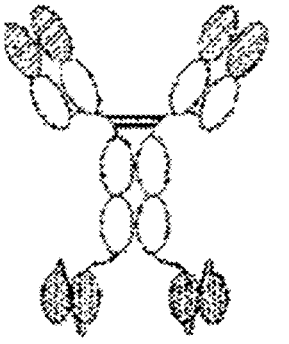 | 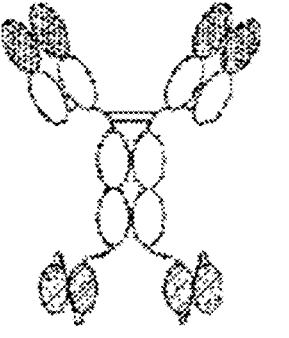 | 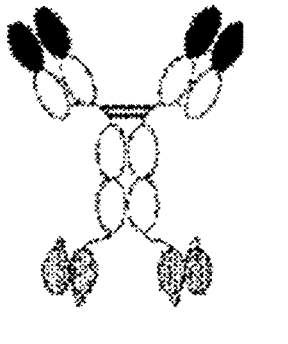 |
| ROCK ® | Family | IgG-like | IgG-like | IgG-like |
| | Format | scFv-IgAb | scFv-IgAb | scFv-IgAb |
| Anti-CD16 | Position | C | N | C |
| | Fv | hi | mid | hi |
| | Format | scFv (LH) | Fab | scFv (LH) |
| Target | | BCMA | BCMA | EGFR |
| Constant region | | silenced[#] | silenced[#] | silenced[#] |

| ROCK ® Examples | | scFv-IgAb_G | Bi-scFv-Fc_A | Bi-scFv-Fc_B |
|---|---|---|---|---|
| | | 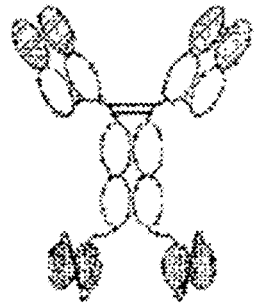 | 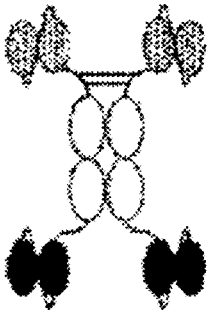 | 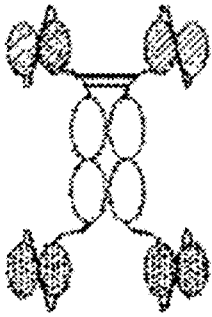 |

TABLE 9A-continued

Overview of ROCK ® examples containing CD16 binding moieties (depicted in blue) in Fab or scFv-fusion arrangement used in functional assays.

| ROCK ® | Family | IgG-like | Fc fusion | Fc fusion |
|---|---|---|---|---|
|  | Format | scFv-IgAb | Bi-scFv-Fc | Bi-scFv-Fc |
| Anti-CD16 | Position | C | N | C |
|  | Fv | Hi | mid | hi |
|  | Format | scFv (LH) | scFv (LH) | scFv (LH) |
| Target |  | CD19 | EGFR | BCMA |
| Constant region |  | silenced# | silenced# | silenced# |

| ROCK ® Examples | Bi-scFv-Fc_C | Bi-scFv-Fc_D |
|---|---|---|

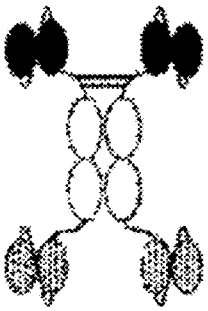
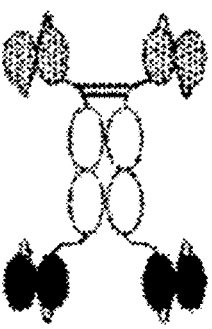

| ROCK ® | Family | Fc fusion | Fc fusion |
|---|---|---|---|
|  | Format | Bi-scFv-Fc | Bi-scFv-Fc |
| Anti-CD16 | Position | C | N |
|  | Fv | mid | hi |
|  | Format | scFv (HL) | scFv (LH) |
| Target |  | EGFR | EGFR |
| Constant region |  | silenced# | silenced# |

TABLE 9B

Overview of ROCK ® examples containing CD16 binding moieties (depicted in blue) in diabody (Db)-like arrangement used in functional assays.

| ROCK ® Examples | KiH-scDb-Fc_A | Db-Fc_A | TandAb_A |
|---|---|---|---|

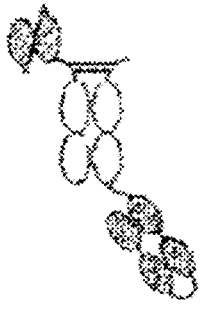
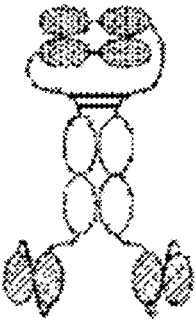
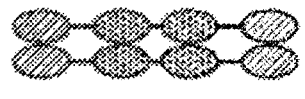

| ROCK ® | Family | Fc fusion | Fc fusion | Fc-less |
|---|---|---|---|---|
|  | Format | KiH-scDb-Fc | Db-Fc | TandAb |
| Anti-CD16 | Position | C | N | Core |
|  | Fv | Hi | hi | Hi |
|  | Format | scDb | Db (LH) | Db (-LH-) |
| Target(s) |  | BCMA | BCMA | BCMA |
| Constant region |  | silenced# | silenced# | — |

| ROCK ® Examples | TandAb_B | TandAb_C | aTriFlex_A |
|---|---|---|---|

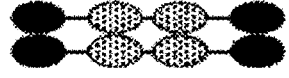
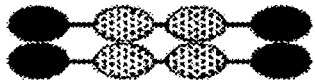
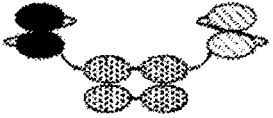

TABLE 9B-continued

Overview of ROCK ® examples containing CD16 binding moieties (depicted in blue) in diabody (Db)-like arrangement used in functional assays.

| ROCK ® Anti-CD16 | Family Format Position Fv Format | Fc-less TandAb core mid Db (-LH-) | Fc-less TandAb core hi Db (-LH-) | Fc-less aTriFlex core mid hetDb (-LL-/HH) |
|---|---|---|---|---|
| Target(s) | | EGFR | EGFR | EGFR/HSA[hi] |
| Constant region | | — | — | — |

| ROCK ® Examples | aTriFlex_B | scDb-Trib_A |
|---|---|---|
| |  | 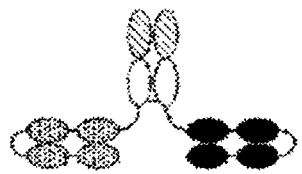 |

| ROCK ® Anti-CD16 | Family Format Position Fv Format | Fc-less aTriFlex Core Mid hetDb (-LL-/HH) | Fab fusion scDb-Trib C mid scDb |
|---|---|---|---|
| Target(s) | | EGFR/HSA[lo] | EGFR/HSA[lo] |
| Constant region | | — | — |

[#]Fc silenced by mutations L234F/L235E/D265A;
HSA[lo]: low affinity anti-HSA domain,
HSA[hi]: high affinity anti-HAS domain

TABLE 9C

Overview control antibodies used in functional assays.

| Name | | Isotype | Anti-CD16 Fv | Target | Constant Region |
|---|---|---|---|---|---|
| IgAb_A | 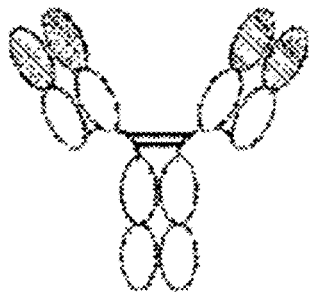 | huIgG1 | — | BCMA | wildtype |
| IgAb_B | 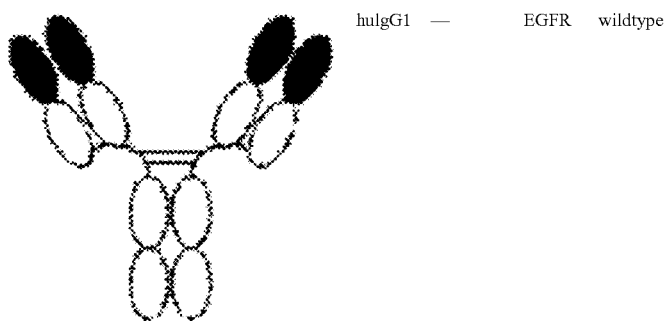 | huIgG1 | — | EGFR | wildtype |

TABLE 9C-continued

Overview control antibodies used in functional assays.

| Name | | Isotype | Anti-CD16 Fv | Target | Constant Region |
|---|---|---|---|---|---|
| IgAb_C | 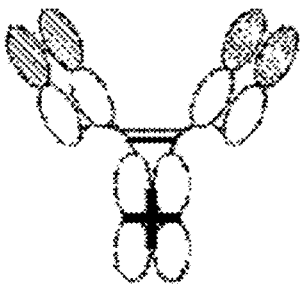 | huIgG1 | — | BCMA | enhanced* |
| IgAb_D | 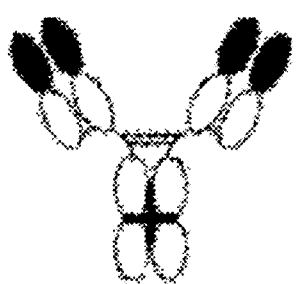 | huIgG1 | — | EGFR | enhanced* |
| IgAb_E | 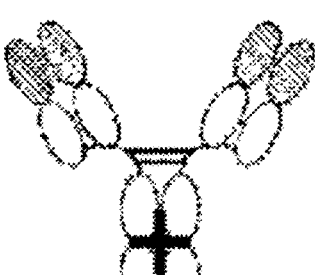 | huIgG1 | — | CD19 | enhanced* |
| scFv Ab16hi | 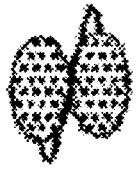 | — | hi | — | — |
| BIKE | 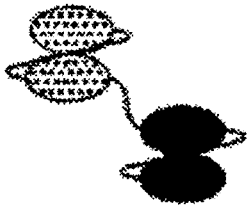 | — | hi | EGFR | — |

Figure 24A:
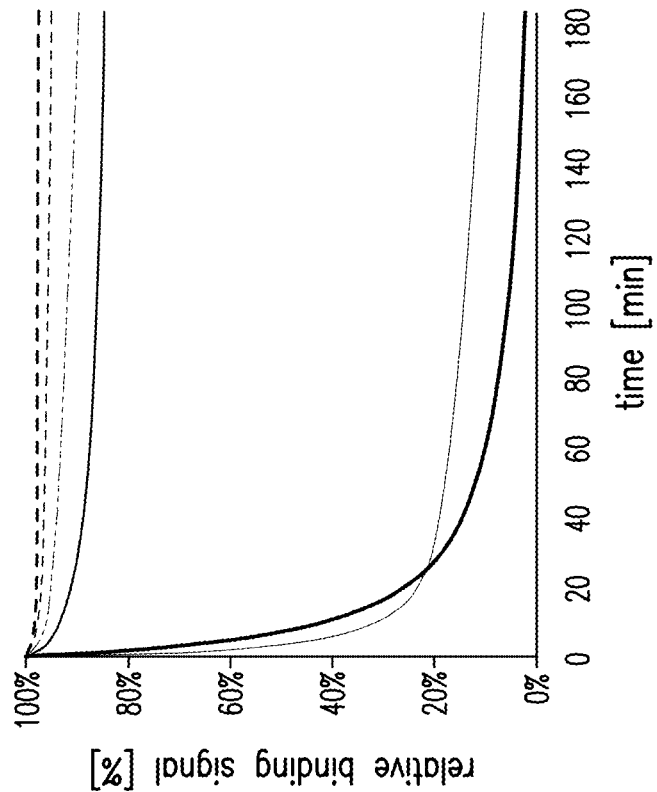
FIGS. 24A-24C show SPR sensograms of normalized relative binding dissociation phases of diverse CD16A bivalently binding ROCK® engagers. Bivalent anti-CD16A domain containing scFv-IgAb_C, Db-Fc_A, scFv-IgAb_D, KiH-scDb-Fc_A, TandAb_C were compared to IgAb_E (Fc-enhanced; S239D/I332E) and monovalent anti-CD16A fragment scFv Ab16$^{hi}$ on immobilized human CD16A-158V and cynomolgus CD16.
Figure 24B:
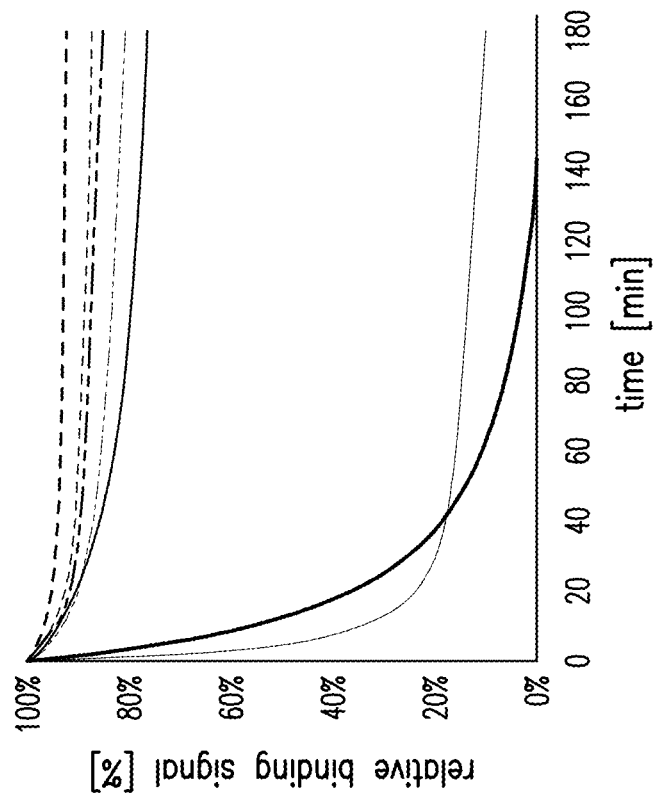
Figure 24C:
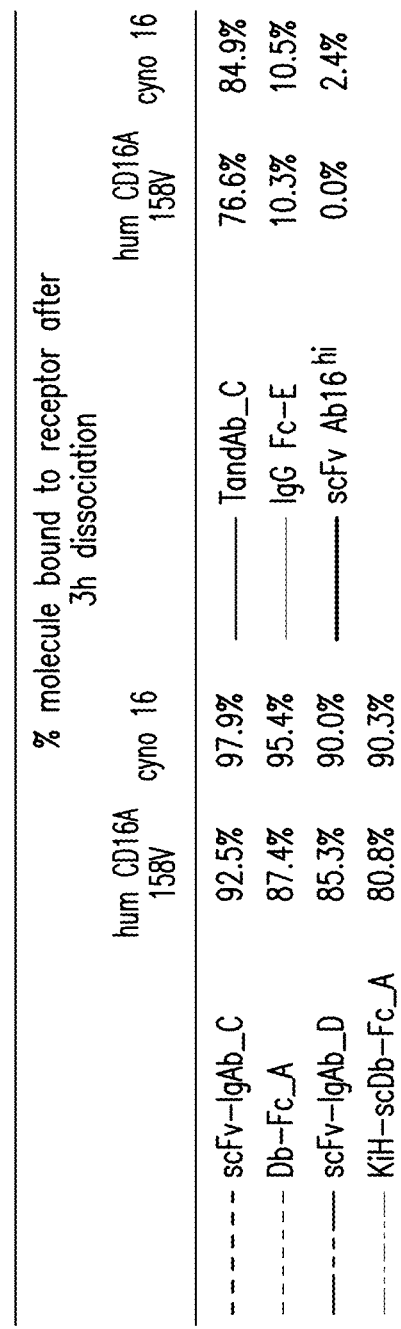
Figure 25:
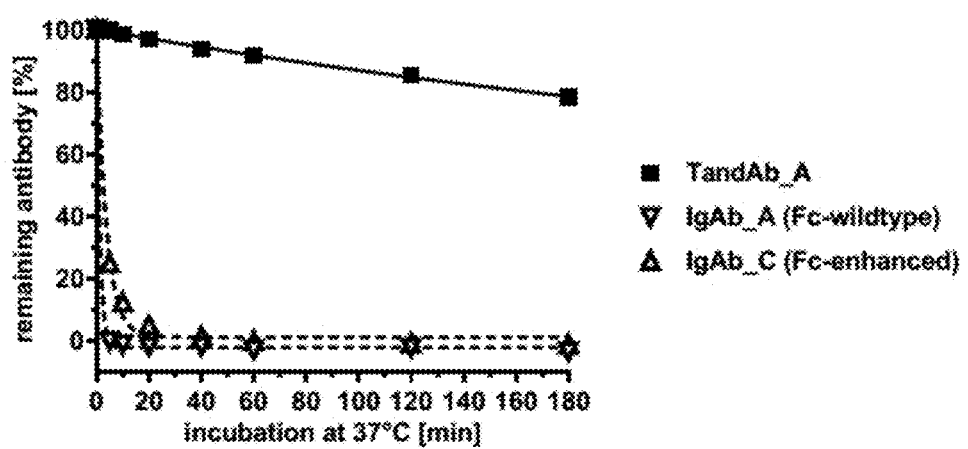
FIG. 25 shows cell surface retention of ROCK® antibodies in comparison to IgG on NK cells. Enriched primary human NK cells were preloaded with 100 µg/mL TandAb or 400 µg/mL IgG for 45 min on ice, washed and incubated for the indicated periods of time at 37° C. to allow dissociation. After washing, remaining antibodies were detected by His-tagged soluble BCMA followed by 10 µg/mL mAb anti-His and 15 µg/mL FITC-conj. goat anti-mouse IgG. The mean fluorescence intensities from time-point 0 were set to 100% and the percentage of remaining antibodies was plotted using non-linear regression.

*Fc enhanced by mutations S239D/I332E (depicted with + in bold)
ROCK® engagers exploit avidity to maximize NK cell engagement via CD16A CD16A binding retention of diverse ROCK® engager formats was investigated in SPR and compared to the monovalent binding of scFv Ab16$^{hi}$ and that of engineered human IgG1 Fc (S239D/I332E), enhancing binding to human CD16A, by comparing dissociation from human CD16A-158V or cynomolgus CD16. Relative binding signals of the tested antibodies during 3 h dissociation showed clear superiority in receptor retention of all tested ROCK® engagers on both, human CD16A-158V (76.6%-92.5%) and cynomolgus CD16 (84.9%-97.9%) compared to the much faster dissociating IgG Fc (S239D/I332E) (10%) or monovalently binding scFv Ab16$^{hi}$ (0%-2.4%) (FIGS. 24A-24C). Consistent with the results of the dissociation measurements by SPR, ROCK® engagers, such as the TandAb with the Ab16$^{hi}$ Fv domains, exhibited substantial longer retention on the surface of NK cells than classical IgG with a wildtype Fc domain or enhanced IgG with S239D/I332E mutations in the Fc (FIG. 25).

Figure 26A:
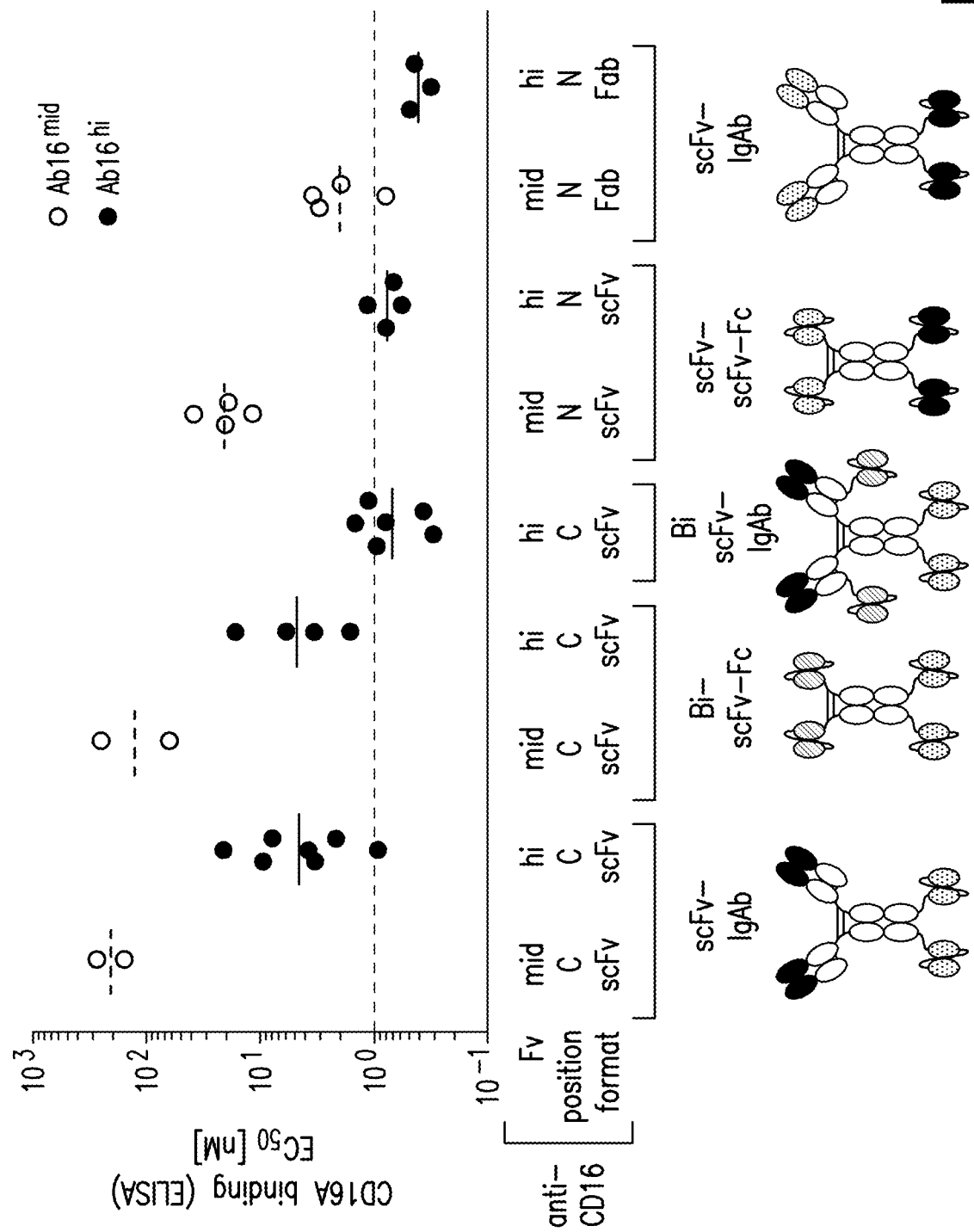
FIGS. 26A-26C show CD16A apparent affinity in ROCK® formats is tunable by variable domains, positioning and connector lengths. Binding of soluble CD16 antigen to ROCK® antibodies containing different CD16 binding Fvs (Ab16$^{mid}$, Ab16$^{hi}$) in different positions (N: anti-CD16 Fvs N-terminal of Fc, C: anti-CD16 Fvs C-terminal of Fc), antibody formats, and different domain orders was analyzed in ELISA. Representative pictograms with CD16-binding Fvs depicted in dotted symbols are shown below each group.
Figure 26B:
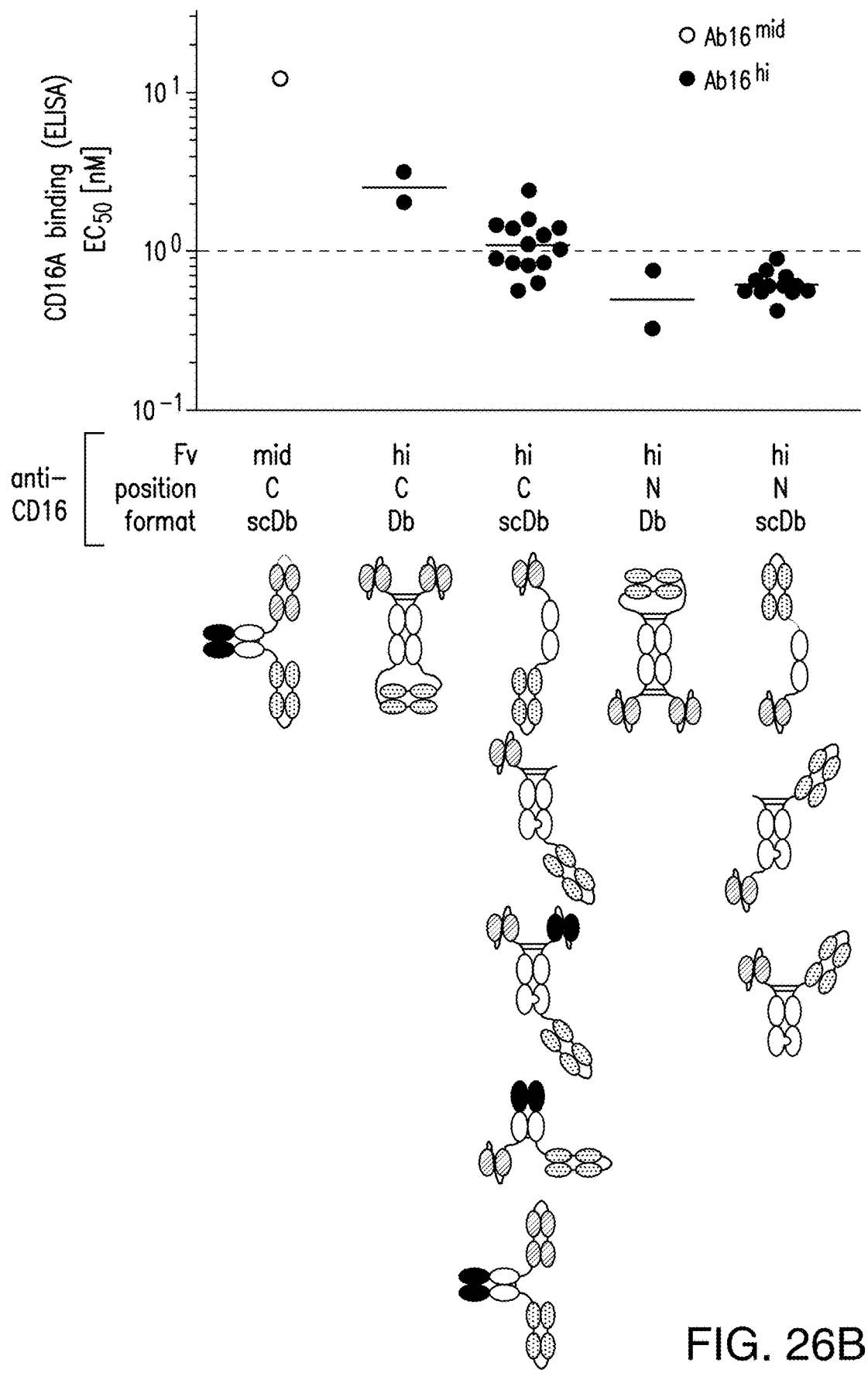
Figure 26C:
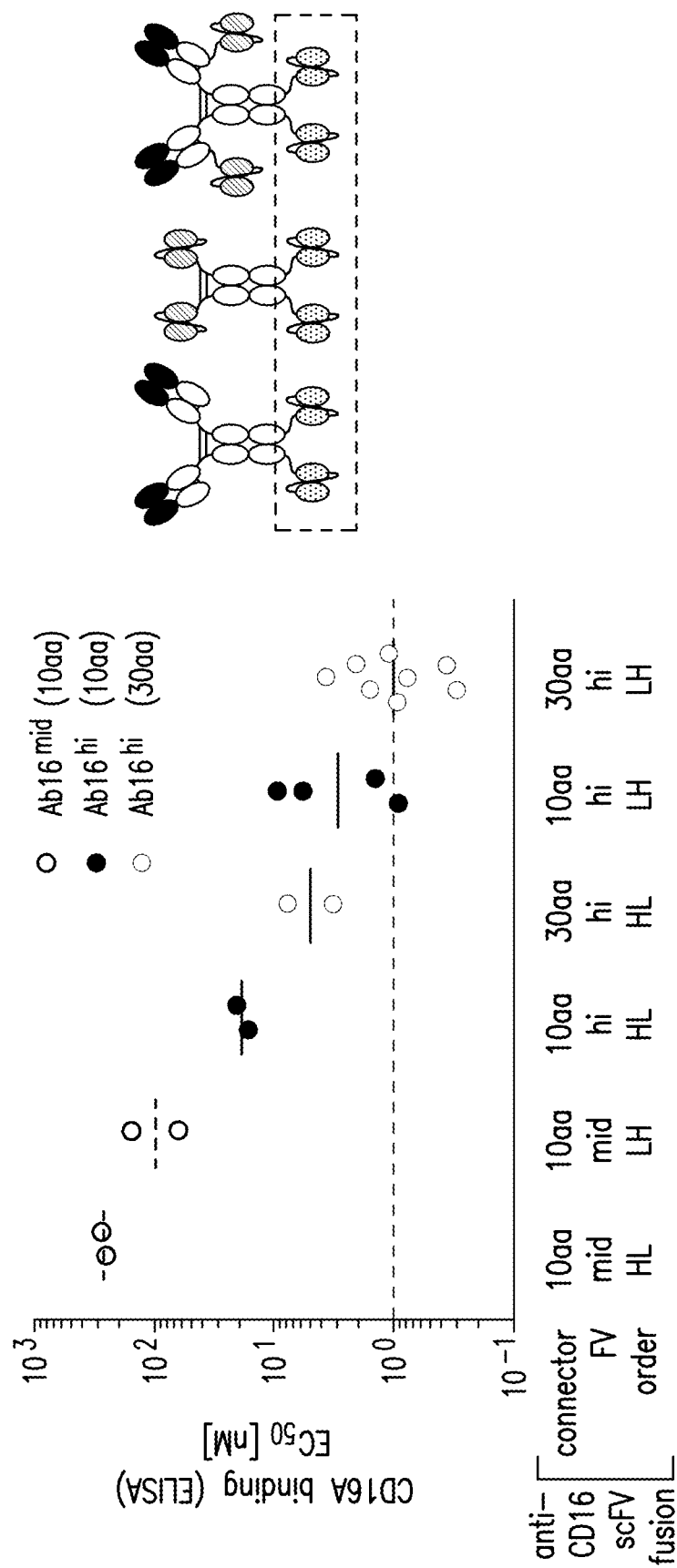

Apparent CD16-binding strengths of different ROCK® NK cell engagers, all containing two binding sites for CD16A furthermore depended on the anti-CD16 variable domain identity (high affinity Ab16$^{hi}$, or medium affinity Ab16$^{mid}$), antibody format and position of anti-CD16 moieties in the multispecific (including, but not limited to, bi- or trispecific) and multivalent (tetra or hexavalent) ROCK® NK cell engagers. Similar to the monovalent binding properties, bivalent CD16A-binding by Ab16$^{hi}$ containing ROCK® antibodies had higher apparent affinities in ELISA than corresponding ROCK® engagers containing Ab16$^{mid}$ domains. Additionally, different positioning of anti-CD16A domains in ROCK® engagers enabled gradual affinity tuning: ROCK® architectures containing CD16 binding moieties at the N-terminus of Fc domains mediated higher apparent binding affinity for CD16A than antibodies containing a fusion of anti-CD16 domains to the C-terminus of Fc (FIGS. 26A and 26B). Fine-tuning of binding affinities could be accomplished by using either Fab or Diabody-based binding modules at the N-terminus of Fc which enhanced binding strength as compared to the fusion of two CD16-binding scFvs (FIGS. 26A and 26B). Further adjustment of CD16-binding strength in ROCK® engagers containing scFvs at the C-terminus of Fc could be achieved by varying lengths of the connector whereby a longer connector facilitated higher apparent affinity CD16 binding than a shorter connector (FIG. 26C). Likely, avidity but also sterical aspects influence apparent binding affinities in these setups, whereas the impact of different target binding specificities engineered on CD16A binding was negligible.

Figure 27A:
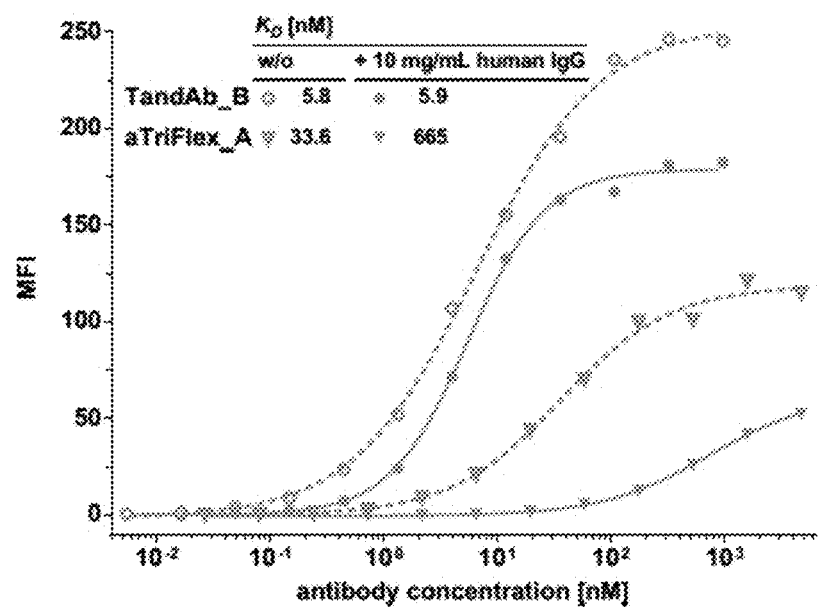
FIGS. 27A-27C shows Binding of ROCK® antibodies to primary human NK cells in the presence or absence of human IgG.
Figure 27B:
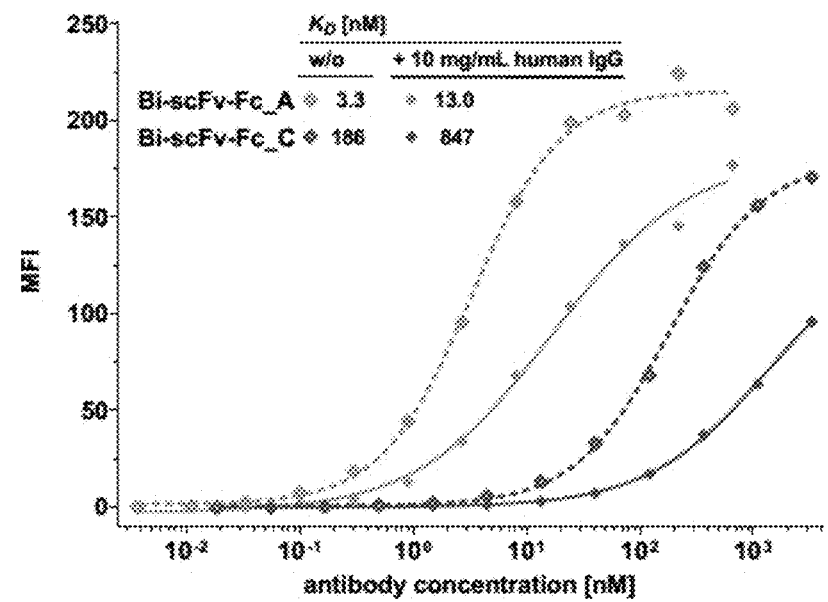
Figure 27C:
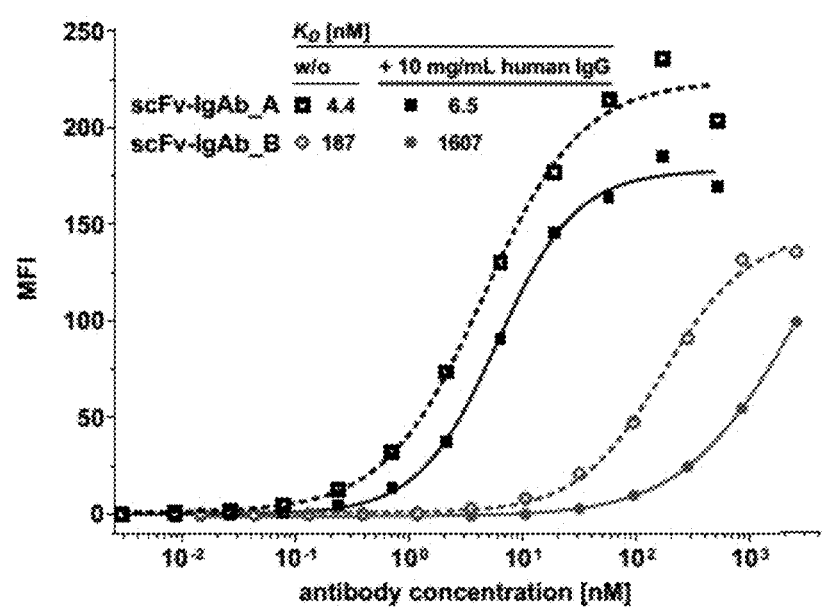

To assess whether the CD16A binding properties measured by ELISA correlate with binding to NK cells, a selected set of ROCK® engagers containing the Ab16$^{mid}$ Fv domains was titrated on primary human NK cells in the absence or presence of polyclonal human IgG mimicking the physiological situation in human serum, and the apparent affinities were determined by non-linear regression (FIGS. 27A, 27B, and 27C). Again, constructs with the anti-CD16A domains in a N-terminal Fab or scFv (scFv-IgAb_A & Bi-scFv-Fc_A) exhibited a substantial higher affinity to NK cells relative the corresponding constructs with the anti-CD16A domains in a C-terminal scFv (scFv-IgAb_B & Bi-scFv-Fc_C). Interestingly, the TandAb with a central anti-CD16A diabody (Table 9B) showed similar high affinity to NK cells as the constructs with N-terminal Fab or scFv whereas the aTriFlex displayed the lowest affinity to NK cells despite a similar anti-CD16A diabody motif in the core of the construct but also an asymmetric variable domain order. High IgG concentrations had no substantial impact on the apparent affinity of the TandAb and the scFv-IgAb constructs with anti-CD16A domains in the N-terminal Fab, moderate impact (factor 4-9) on the binding of constructs containing anti-CD16A scFv independent whether N- or C-terminally fused to the construct, and the strongest inhibitory effect was observed for the affinity of the aTriflex.

NK Cell Fratricide and Design of ROCK® Formats

Figure 28:
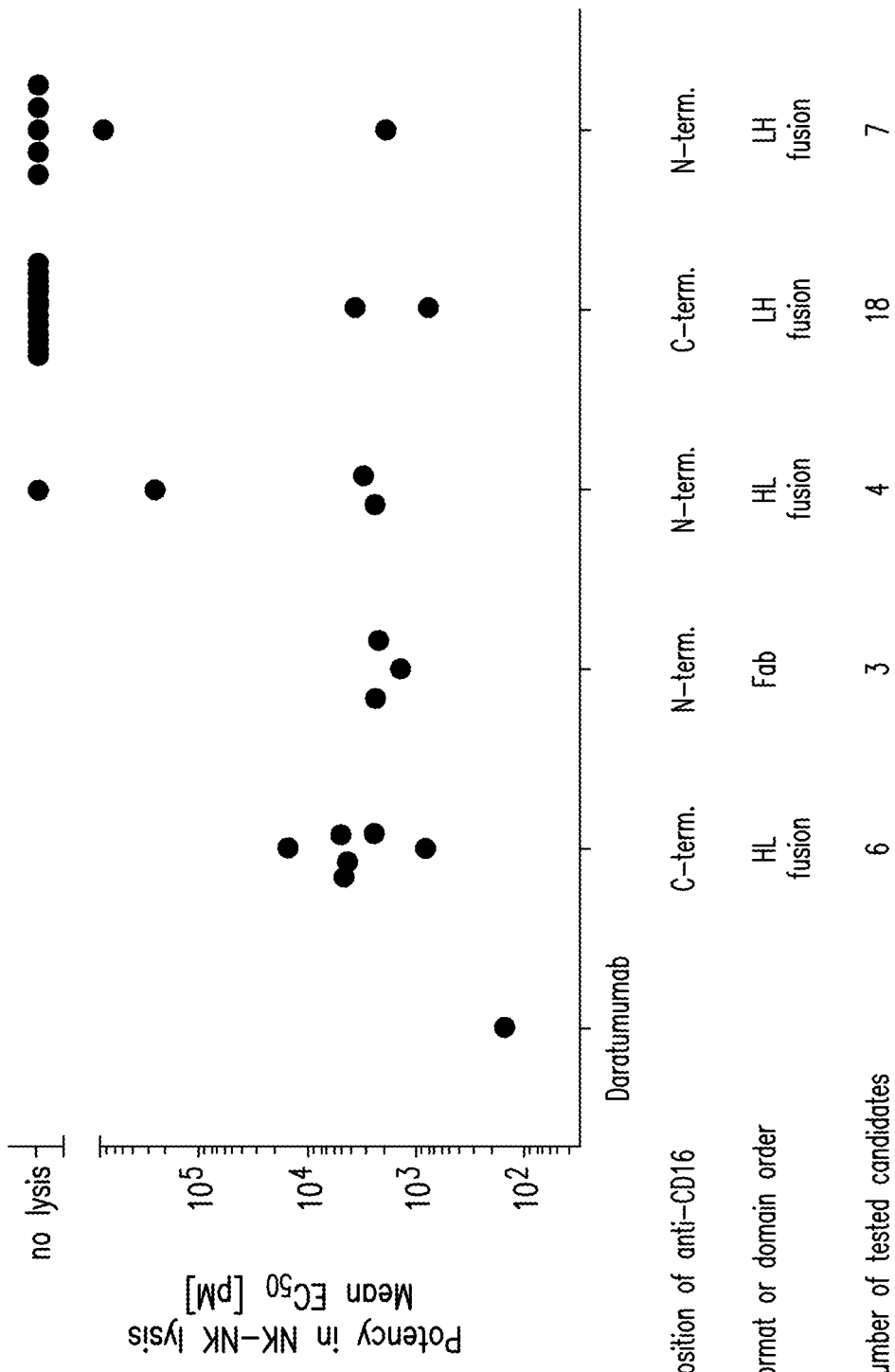
FIG. 28 shows comparative analysis of various ROCK® antibody formats regarding NK fratricide in vitro. In vitro calcein-release cytotoxicity assays of enriched primary human NK cells in presence of different ROCK® antibody formats towards autologous NK cells after 4 h co-incubation at an E:T of 1:1. Mean $EC_{50}$ values of several independent experiments are summarized and plotted as individual dots. The ROCK® antibody formats are categorized based on the position of the anti-CD16 domain and the format/domain order. Only constructs containing the high affinity anti-CD16 domain and silenced Fc are included in the graph. HL: scFv domain order VH-VL, LH: scFv domain order VL-VH. N-term.=N-terminal, C-term.=C-terminal.

Multivalent high affinity binding of antibodies to CD16 harbors the risk of cross-linking the receptor on multiple NK cells resulting in CD16A-mediated killing of cross-linked cells thus depleting the NK cell population (Choi et al., Immunology 2008; 124:215-22). This NK cell fratricide has already been shown for other monoclonal antibodies like daratumumab which targets CD38 on the plasma membrane of NK cells (Casneuf et al., Blood Adv. 2017 Oct. 24; 1(23):2105-2114). Diminishing the main effector cell population presumably hampers the efficacy of an antibody-mediated anti-tumoral response. For that reason, an in vitro assay to monitor the degree of NK cell fratricide induced by various ROCK® formats was established. Herein, primary human NK cells from the same donor were used as effector and target cells thus allowing to determine the potency of NK cell lysis as described above. As a positive control, daratumumab was included in the assay setup. The inventors have never observed NK-NK fratricide with antibodies containing only a single binding site for CD16A suggesting that bivalency of CD16A is a prerequisite for NK cell crosslinking and subsequent fratricide. Intriguingly, depending on the ROCK® antibody format or the domain order, not only the occurrence of NK cell fratricide but also the potency of NK cell killing could be modulated (FIG. 28).

In general, all analyzed ROCK® antibody formats showed an ameliorated NK cell fratricide profile compared to daratumumab which led to NK cell directed killing with a mean potency of 158 pM. All tested ROCK® antibody formats either induced a less pronounced or no NK cell killing at all.

CD16A engagement via N-terminally fused anti-CD16A moieties of the ROCK® antibody appeared to avoid NK cell fratricide more robustly compared to CD16A engagement at the C-terminus. However, focusing on N-terminal CD16 engagement in detail, revealed a more pronounced NK cell depletion using Fab based CD16A engagement with mean potency values between 1439 and 2389 pM.

Intriguingly, by analyzing the domain order of the CD16 Fv, a substantially lower number of constructs induced NK cell fratricide when the domain order was VL-VH in contrast to constructs containing the VH-VL domain order which all induced NK cell lysis. Among those ROCK® antibodies containing CD16 Fv VL-VH domains, either at the C or a the N-terminus, only few constructs induced NK cell fratricide at all.

In summary, the proportion of NK cell fratricide inducing antibodies as well as the potency of NK cell killing could be efficiently ameliorated by avoiding Fab-based CD16A engagement and focusing on the beneficial VL-VH order of the CD16 binding Fv domain.

Superior in Vitro Cytotoxicity of ROCK Engagers

Figure 29A:
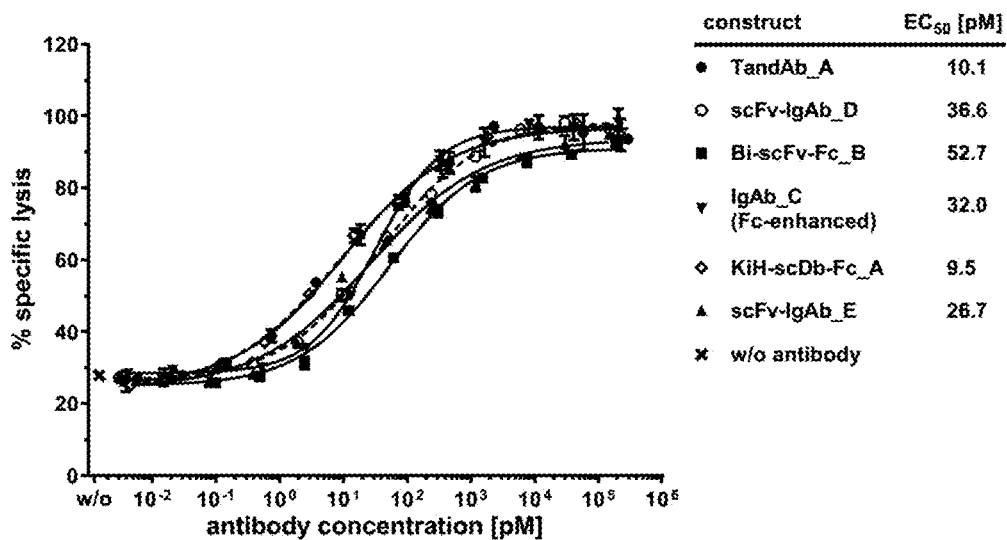
FIGS. 29A-29E show in vitro cytotoxicity of enriched primary human NK cells in the presence of several ROCK® antibodies towards cell lines expressing their corresponding tumor target.
Figure 29B:
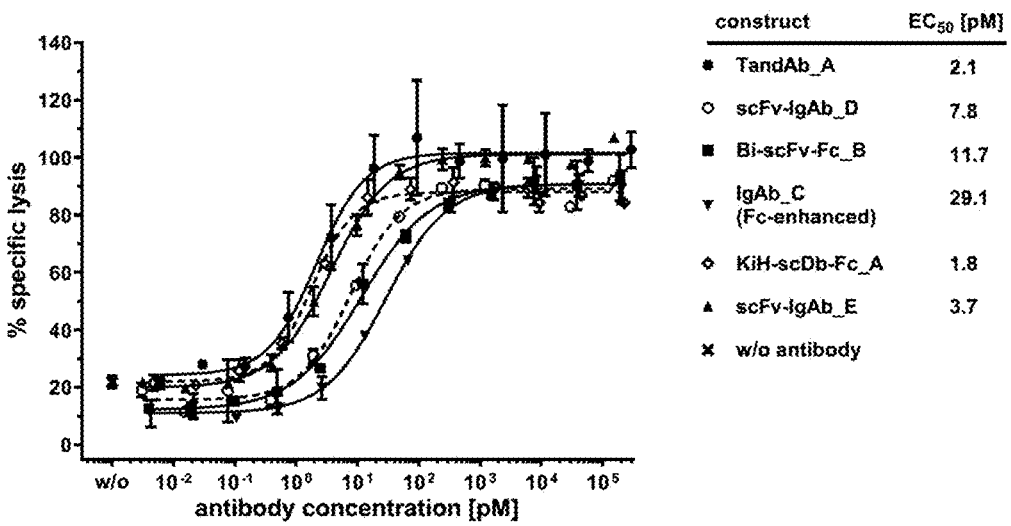
Figure 29C:
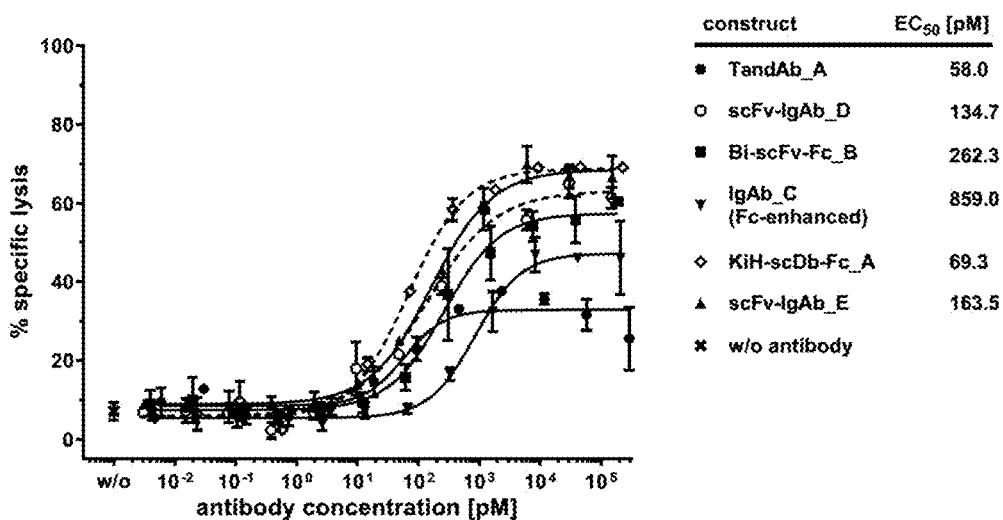
Figure 50:
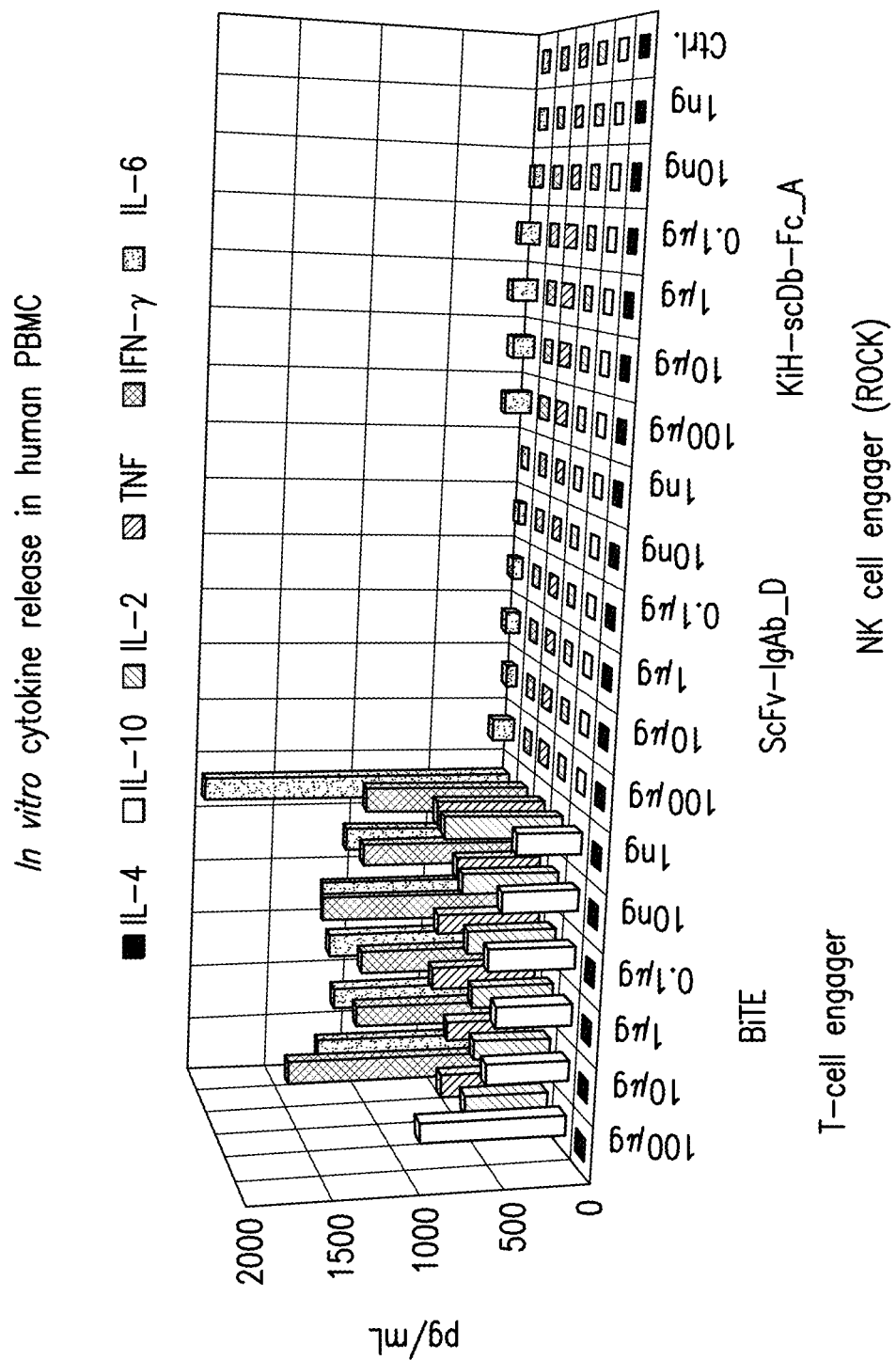
FIG. 50 shows comparison of inflammatory cytokine release in human PBMC cultures induced by BCMA-directed T cell engagers and ROCK engagers. Freshly isolated human PBMC were co-cultured with BCMA+ cell line NCI-H929 (E:T ratio 50:1) in presence or absence of increasing concentration of BCMA/CD3 BiTE, or NK-cell engaging ROCK engagers scFv-IgAb_D or KiH-scDb-Fc_A. Following 24 h incubation, the concentration of cytokines in supernatants was quantified. Ctrl.: No antibody added.

In vitro cytotoxicity of various ROCK® engagers targeting EGFR or BCMA was assessed in calcein-release assays (FIGS. 29A, 29B, 29C, 29D, and 29E). BCMA-targeting engagers with Ab16$^{hi}$ Fv domains (TandAb_A, scFv-IgAb_D, Bi-scFv-Fc_B, and KiH-scDb-Fc_A) were compared with the Ab16$^{mid}$ Fv-containing engager scFv-IgAb_E and Fc-enhanced anti-BCMA IgG1 with S239D/I332E mutations in the Fc (IgAb_C) on target cells expressing high (NCI-H929), mid (MM.1S), or low (MC/CAR) BCMA levels on the cell surface (FIGS. 29A-29C). The exemplary cytotoxicity results revealed only minor differences in potency and efficacy among the different ROCK® engager formats on BCMA$^{high}$ NCI-H929 target cells (EC$_{50}$ range: 9.5 pM-52.7 pM), similar efficacy but stronger differences in potency (EC$_{50}$ range: 1.8 pM-29.1 pM) on BCMA$^{mid}$ MM.1S target cells, and strong differences in efficacy and potency (EC$_{50}$ range: 59 pM-859 pM) on BCMA$^{low}$ MAC/CAR target cells. Lower EC$_{50}$ values were produced for the BCMA-targeting TandAb_A, the KiH-scDb-Fc_A and the scFv-IgAb_D. These results suggest that two valencies for CD16A and apparent affinities for NK cells are advantageous for triggering NK cell-mediated lysis of less susceptible target cells and/or target cells expressing lower numbers of cell surface target antigens. Of note, bivalency for CD16A alone was not sufficient to mediate NK cell activation as antibody-induced expression of NK cell activation marker CD69 and cytokine release in human PBMC cultures were strictly dependent on the presence of target cells (FIGS. 49A-49F). Furthermore, inflammatory cytokine levels released in human PBMC cultures by NK cell engaging ROCK® antibodies were several orders of magnitude lower than those released by a BCMA-directed T cell engager (FIG. 50).

52B), most likely due to serum IgG-induced degranulation by NK cells (Jacobi et al., Clin. Immunol. 2009; 133:393-401). However, competition with monoclonal IgG (FIG. 52C) or Fc-engineered IgG (FIG. 52D) completely blocked activity or clearly impaired potency and efficacy of the conventional antibodies. The ROCK CD30/CD16A TandAb antibody showed maximum cytotoxic potency and efficacy under all tested conditions even in the presence of physiological concentrations of competing IgG (FIGS. 52A-52D, Table 10).

TABLE 10

Summary of potency (EC50) and efficacy (Emax) of different anti-CD30 antibodies in in vitro cytotoxicity assays in the presence or absence of competing polyclonal, monoclonal, or Fc-enhanced IgG.

| | $EC_{50}$ [pM] | | | | $E_{max}$ [%] | | | |
|---|---|---|---|---|---|---|---|---|
| | | +IgG competition (10 mg/mL) | | | | +IgG competition (10 mg/mL) | | |
| competitor anti-CD30 antibody | medium w/o | polyclonal human IgG | anti-EGFR human IgG1 (IgAb_B) | anti-EGFR human IgG1$^{S239D/I332E}$ (IgAb_D (Fc-enhanced)) | medium w/o | polyclonal human IgG | anti-EGFR human IgG1 (IgAb_B) | anti-EGFR human IgG1$^{S239D/I332E}$ (IgAb_D (Fc-enhanced)) |
| ROCK anti-CD30/CD16A (TandAb) | 22.2 | 107.8 | 53.9 | 68.6 | 77.4 | 49.2 | 73.8 | 72.4 |
| anti-CD30 IgG1 (IgAb) | 517.9 | n/a | n/a | n/a | 44.1 | no | no | no |
| anti-CD30 IgG1$^{S239D/I332E}$ (IgAb (Fc-enhanced)) | 89.2 | 371.8 | 671.4 | 612.6 | 55.0 | 38.2 | 55.4 | 8.8 |

4 h calcein-release cytotoxicity assays with calcein-labeled CD30+ KARPAS-299 target cells with primary human NK cells as effector cells at an E:T ratio of 5:1 in the presence of serial dilutions of CD30/CD16A TandAb, anti-CD30 IgG1 (IgAb), or Fc-enhanced anti-CD30 IgG1 (IgAb (Fc-enhanced)). Assays were performed in RPMI 1640 medium alone, or supplemented with 10 mg/mL polyclonal human IgG, 10 mg/mL monoclonal anti-EGFR IgG1 (IgAb_B), or 10 mg/mL Fc-enhanced anti-EGFR IgG1 (IgAb_D (Fc-enhanced)).

Figure 29D:
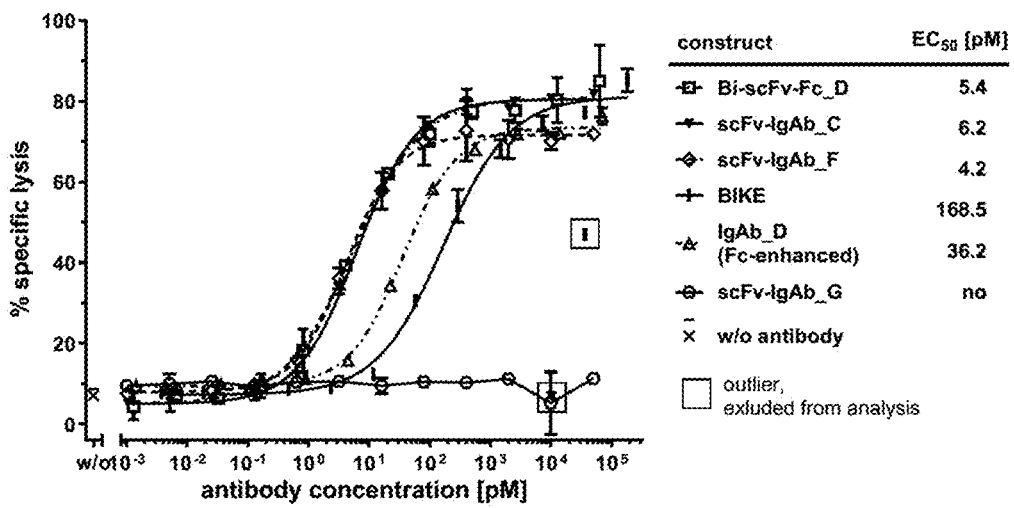
Figure 51:
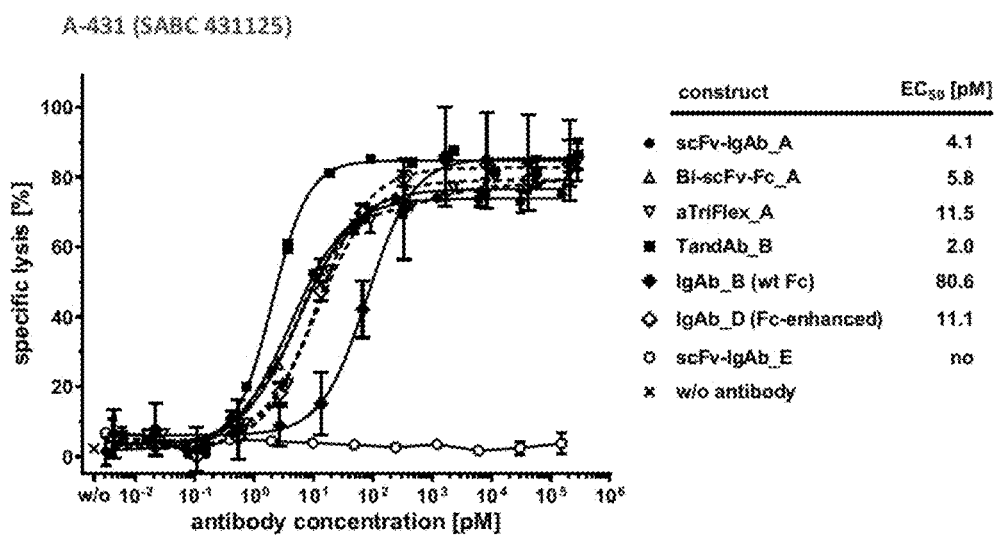
FIG. 51 shows in vitro cytotoxicity of enriched primary human NK cells towards A-431 cells in the presence of several ROCK® antibody formats. Representative sigmoidal dose-response curves of the indicated EGFR-targeting ROCK antibodies in a 4 h calcein-release cytotoxicity assay at an E:T ratio of 5:1. SABC, specific antibody-binding capacity (mean value of ≥3 assays).
Figure 52A:
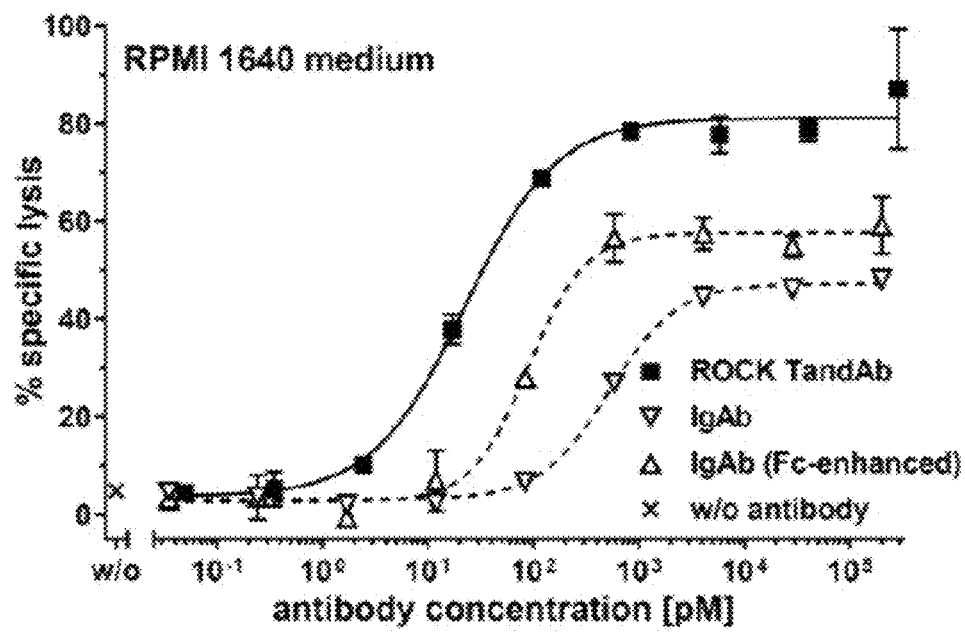
FIGS. 52A-52D show comparison of ROCK® and IgG antibodies in in vitro cytotoxicity assays in the presence or absence of competing polyclonal, monoclonal, or Fc-enhanced IgG. 4 h calcein-release cytotoxicity assays with calcein-labeled CD30+ KARPAS-299 target cells with primary human NK cells as effector cells at an E:T ratio of 5:1 in the presence of serial dilutions of CD30/CD16A TandAb, anti-CD30 IgG1 (IgAb), or anti-CD30 IgG1 with Fc-mediated effector function enhancing mutations S239D/I332E (IgAb (Fc-enhanced)). Assays were performed in RPMI 1640 medium, or medium supplemented with 10 mg/mL polyclonal human IgG, 10 mg/mL monoclonal human anti-EGFR IgG1 (IgAb), or 10 mg/mL Fc-enhanced monoclonal human anti-EGFR IgG1 (IgAb (Fc-enhanced)).
Figure 52B:
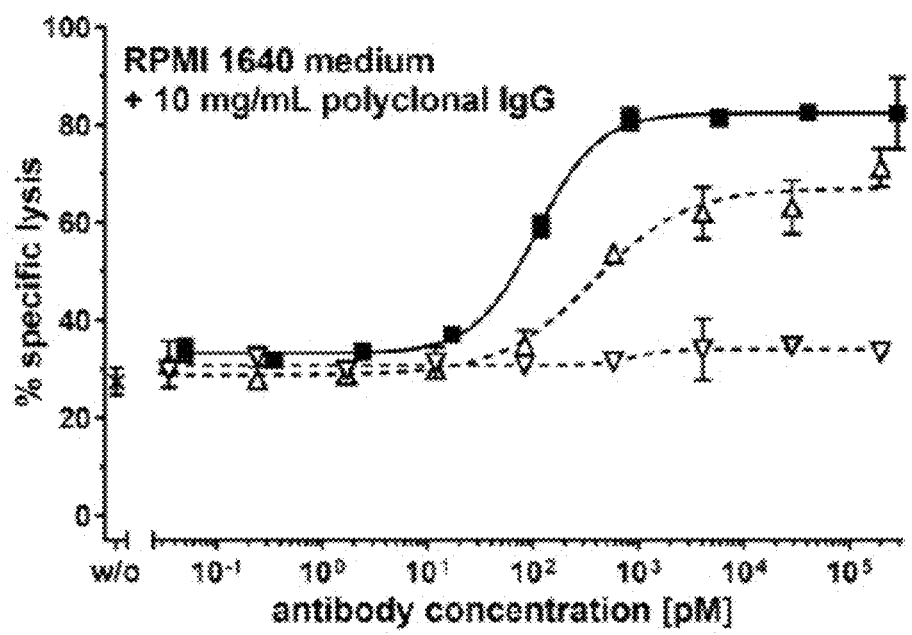
Figure 52C:
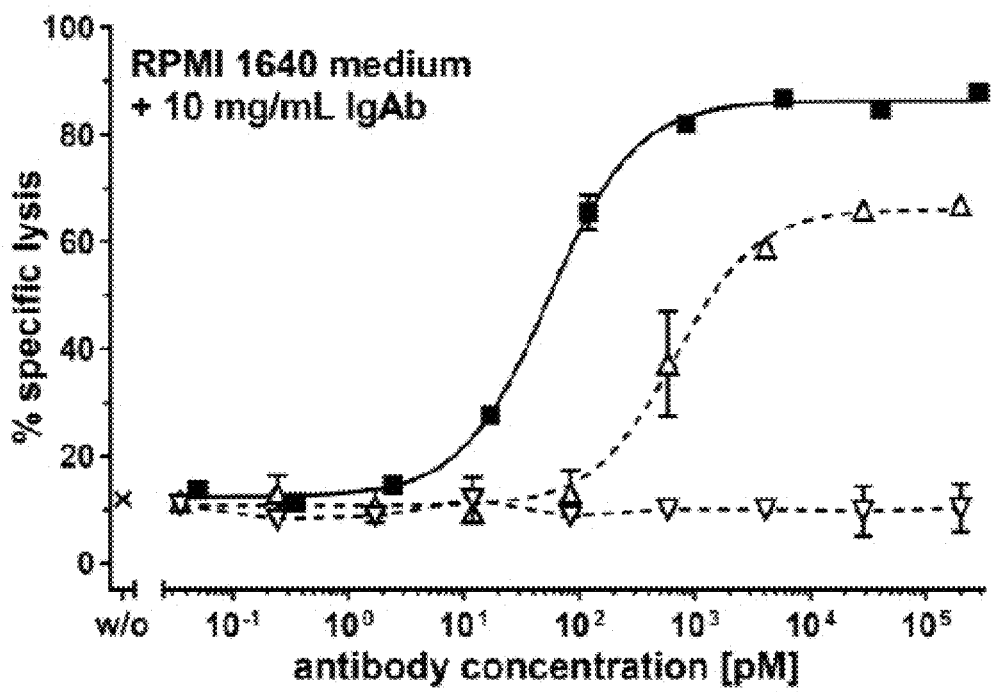
Figure 52D:
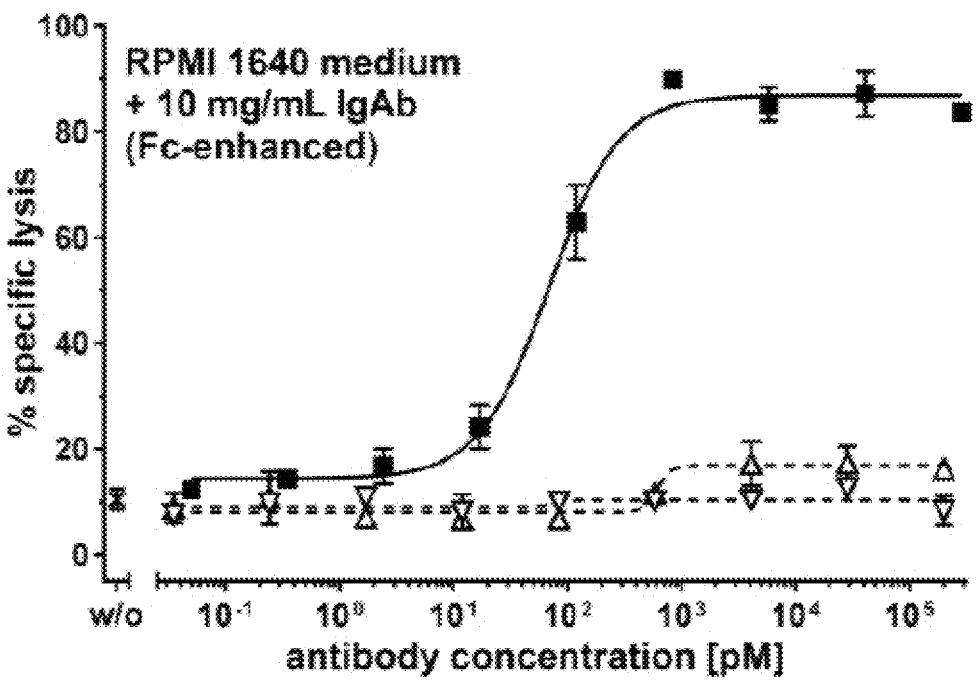

Similar to the results obtained with BCMA-targeting ROCK engagers, EGFR-targeting ROCK° engagers, EGFR-targeting ROCK® engagers showed superior potency in killing assays on SW-982 and A-431 target cells, reaching single digit pM $EC_{50}$ values, when compared to Fc-enhanced anti-EGFR IgG1 with S239D/I332E mutations in the Fc (IgAb_D), classical EGFR-targeting IgG1 (IgAb_B) or monovalently binding bispecific engager (BiKE) comprising the identical effector- and target-binding domains (FIG. 29D, and FIG. 51). The EGFR/CD16A aTriFlex_A, despite substantial lower apparent affinity to human NK cells than other ROCK® engagers (FIGS. 27A-27C) unveiled similar potency as the Fc-enhanced anti-EGFR IgG1 (IgAb_D) (FIG. 51). Nonspecific killing can be excluded since the BCMA-targeting scFv-IgAb_E showed no killing activity on the EGFR positive, BCMA negative target cell line A-431 (FIG. 51).

Figure 29E:
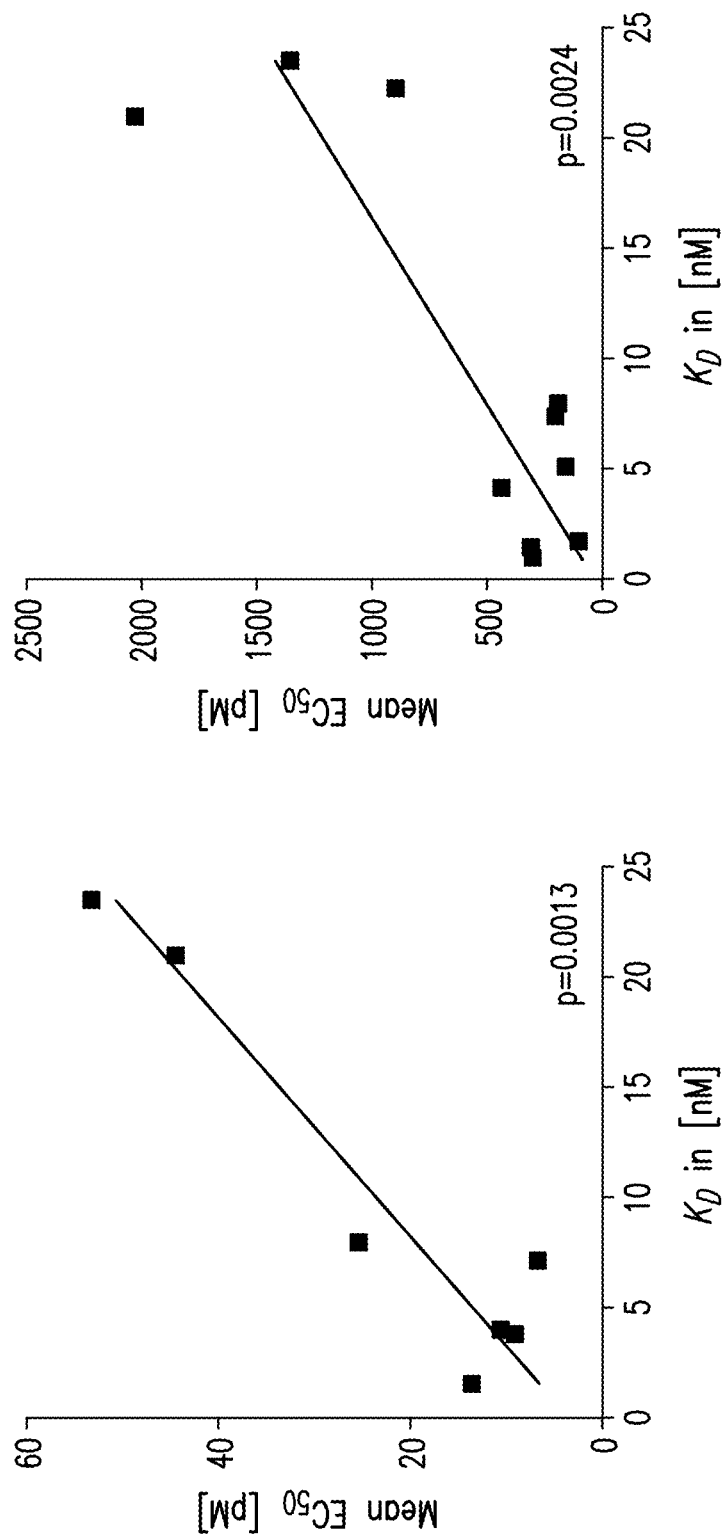

The analysis of the apparent affinities of various BCMA/CD16A engagers and the respective potency in in vitro cytotoxicity assays shown in FIG. 29E suggests a correlation of the apparent affinity for CD16A on the NK cells and potency. The correlation was not only observed in 3 h cytotoxicity assays on RPMI-8226 target cells at an E:T of 2:1 but also in 4 h assays on NCI-H929 target cells at an E:T ratio of 5:1 supporting that high affinity binding to CD16A on NK cells contributes to superior cytotoxic potency.

Superiority of a ROCK® CD30/CD16A targeting TandAb over conventional and Fc-engineered anti-CD30 antibodies was even more pronounced when in vitro cytotoxicity assays were performed in the presence of physiological levels of competing IgG. Supplementation with 10 mg/mL polyclonal IgG clearly increased background lysis in all cultures (FIG.

Modulation of PK

Another important parameter for therapeutic antibodies is their serum half-life. For highly cytotoxic antibodies, a short half-life might be preferred enabling rapid clearance. In contrast, for antibodies with good safety profiles, longer half-lives are likely to be favored to increase patient convenience by avoiding frequent dosing or the need for continuous infusion.

Figure 30:
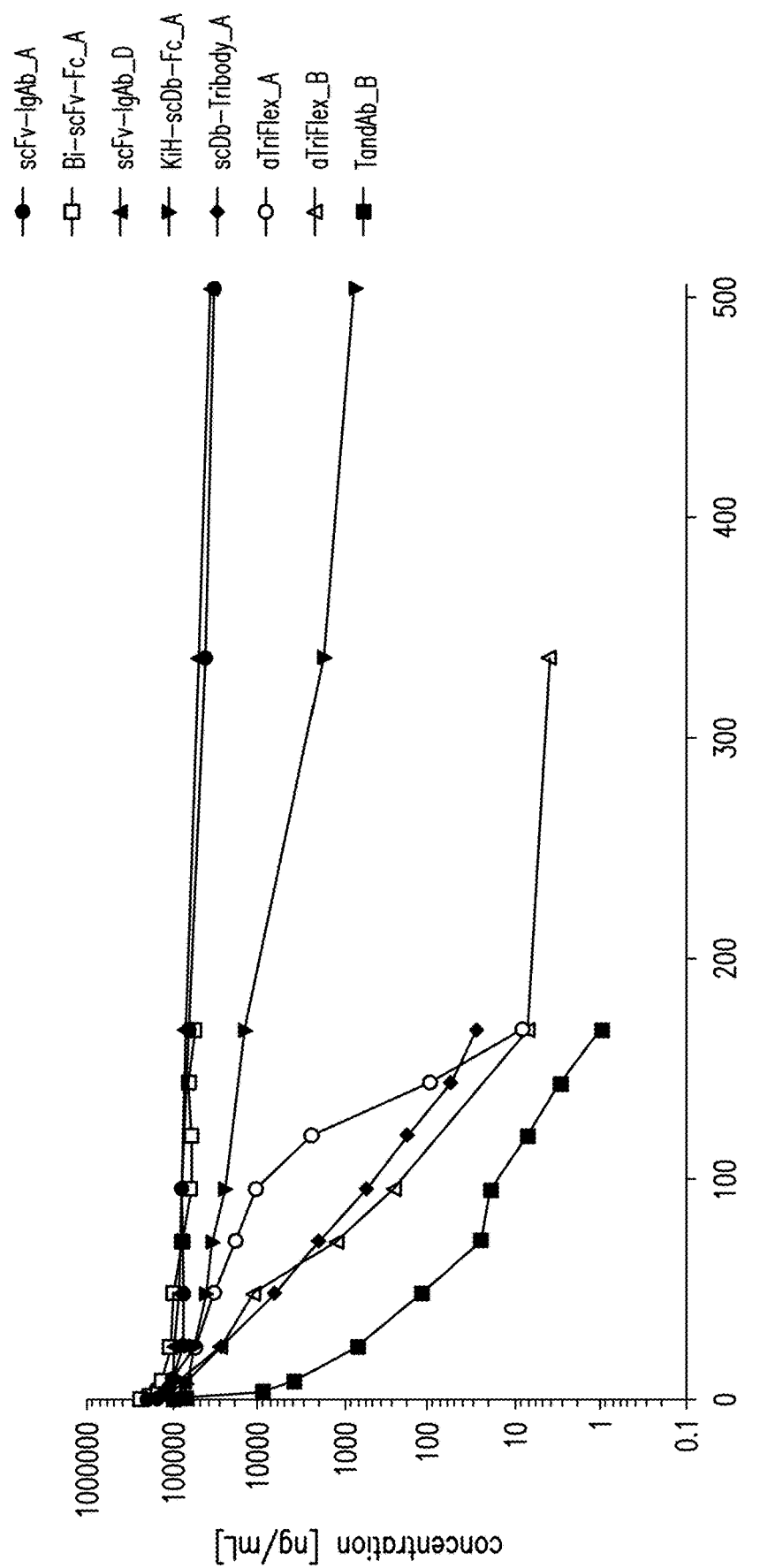
FIG. 30 shows the comparison of the pharmacokinetic of different ROCK® engager formats: concentration of antibodies over time (1 or 3 weeks observation period) after single i.v. administration of 300 µg test item.

Basic pharmacokinetic parameters of a selected set of ROCK® platform formats were analyzed in CD-1 SWISS mice. For the IgG-like family of ROCK® engagers two representative scFv-IgAb antibodies (scFv-IgAb_A and scFv-IgAb_D) either containing anti-CD16 moieties in N-terminal Fab or as scFvs fused to the C-terminus of CH3 were chosen. For Fc fusion family of ROCK® engagers a symmetric Bi-scFv-Fc_A and an asymmetric, scDb-containing KiH-scDb-Fc_A antibody were analyzed. Finally, for the Fab fusion and Fc-less families, the TandAb_B, aTriFlex_A, aTriFlex_B and scDb-Trib_A antibodies were selected for PK analysis. The latter two employ an HSA-binding moiety with low affinity compared with a high affinity HSA binding domain in aTriFlex_A for PK-extension. The tumor targeting domains in the selected ROCK® engagers were either specific to human EGFR or BCMA. As both target- and CD16A-binding moieties are not cross-reactive to the corresponding mouse analogues (data not shown), no target-related pharmacodynamic effects could be postulated. Blood serum samples from animals having received a single intravenous administration of 0.3 mg (~10 mg/kg body weight) of the different test items were collected at different time points for a period of 1 or 3 weeks and analyzed with established assays based on ELISA or MSD technology. Basic pharmacokinetic parameters were determined by noncompartmental pharmacokinetic analysis (Table 11). The symbols shown in the structures in Table 11 are consistent with the symbols shown in FIG. 23. Following intravenous administration of the different ROCK® formats, serum concentrations declined in a bi-exponential manner (FIG. 30). Half-lives of both IgG-like formats were shown to be in the same range of 329.2 and 364.3 hours, respectively, and are comparable to standard IgG molecules[63]. Shorter half-lives of 95.8 or 74.3 hours, respectively, were measured for the Fc fusion formats Bi-scFv-Fc_A and KiH-scDb-Fc_A. Serum half-lives of those were between the IgG-like and the Fc-less and Fab fusion ROCK® formats. However, the observation period for Bi-scFv-Fc_A was only 1 week compared to 3 weeks for both of the scFv-IgAb formats. Therefore, this value may be underestimated. The shortest half-lives were measured for the Fc-less and the Fab fusion ROCK® formats. Mean apparent terminal half-lives were 37.4 hours for aTriFlex_A containing a high affinity anti-HSA binding moiety, and 18.0 hours for the TandAb. The low affinity anti-HSA domain in scDb-Trib_A could not prolong half-life of this construct (14.0 hours). A similar ranking could be performed based on the mean residence times (MRT), which defines the unchanged drug in the circulation. The highest MRTs were shown for the IgG-like and Fc fusion test items with 528.5 to 110.6 hours followed by relatively short MRT values from 61.6 to 28.5 hours for the Fc-less and Fab fusion formats represented by the TandAb, aTriFlex and scDb-Trib, respectively. This ranking holds also true for the clearance (C) ranging between 0.006 to 1.228 mL/h with the highest value obtained for the TandAb construct containing neither Fc nor an anti-HSA domain. An important parameter is also determined by the area under der curve (AUC) that defines the maximal amount or exposure of a molecule in the organism over time. As expected highest AUC values were achieved with the Fc-containing formats. Nearly 10-fold lower values were measured for the smaller Fc-less formats. Again, the TandAb demonstrated the lowest exposure with a 100-fold difference in AUC compared to the long-lived test items. The steady-state distribution volume ($V_{ss}$) that defines the apparent volume needed to account for the total amount of drug in the body if the drug was evenly distributed throughout the body was highest for the TandAb (4.8 mL), followed by both IgG-like (3.3 mL and 3.1 mL, respectively), the Fc fusion (2.2 mL), the aTriFlex (2.2 mL) and the scDb Tribody (1.5 mL). The lower $V_{ss}$ value of the scDb Tribody implies that the majority of the molecule remains in the blood compartment (blood). In conclusion, different ROCK® formats showed distinct PK profiles in CD-1 mice with half-lives ranging from 14 to 364 hours.

TABLE 11

ROCK ® formats analyzed in mouse PK studies

| ROCK ® examples | | scFv-IgAb_A | scFv-IgAb_D | Bi-scFv-Fc_A |
|---|---|---|---|---|
| ROCK ® family | | IgG-like | IgG-like | Fc fusion |
| ROCK ® format | | scFv-IgAb | scFv-IgAb | Bi-scFv-Fc |
| anti-CD16 | Position | N | C | N |
| | Fv | mid | hi | mid |
| | Format | Fab | scFv (LH) | scFv (LH) |
| Fc | | silenced[#] | silenced[#] | silenced[#] |
| Target(s) | | EGFR | BCMA | EGFR |
| Analysis | Weeks | 3 | 3 | 1 |
| C max | [ng/mL] | 204933 | 183848 | 227758 |
| t max | [h] | 0.1 | 0.1 | 0.1 |
| AUC ∞ $_{(area)}$ | [(ng/mL) * h] | $4.36 * 10^7$ | $4.94 * 10^7$ | $2.17 * 10^7$ |
| AUC ∞ $_{(expo)}$ | [(ng/mL) * h] | $4.40 * 10^7$ | $4.91 * 10^7$ | $1.89 * 10^7$ |
| $t_{half\ (E\ phase)}$ | [h] | 329.2 | 364.3 | 95.8 |
| $t_{half\ (D/A\ phase)}$ | [h] | 14.7 | 1.9 | 1.17 |
| MRT $_{(expo)}$ | [h] | 496.3 | 528.5 | 139.9 |
| Clearance $_{(area)}$ | [mL/h] | 0.007 | 0.006 | 0.014 |
| $V_{ss\ (area)}$ | [mL] | 3.3 | 3.1 | 2.2 |
| $V_{ss\ (expo)}$ | [mL] | 3.2 | 3.2 | 2.2 |
| $R^2$ | | 0.987 | 0.975 | 0.977 |

TABLE 11-continued

ROCK® formats analyzed in mouse PK studies

| ROCK® examples | | KiH-scDb-Fc_A | TandAb_B | aTriFlex_A |
|---|---|---|---|---|
| | | 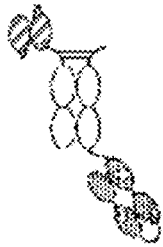 |  |  |
| ROCK® family | | Fc fusion | Fc-less | Fc-less |
| ROCK® format | | KiH-scDb-Fc | TandAb | aTriFlex |
| anti-CD16 | Position | C | core | core |
| | Fv | hi | mid | mid |
| | Format | scDb | Db (-LH-) | hetDb (LL/HH) |
| Fc | | silenced[#] | — | — |
| Target(s) | | BCMA | EGFR | EGFR/HSA[hi] |
| Analysis | Weeks | 3 | 1 | 3 |
| C max | [ng/mL] | 159789 | 144739 | 230447 |
| t max | [h] | 0.1 | 0.1 | 0.0 |
| AUC ∞ $_{(area)}$ | [(ng/mL) * h] | $7.55 *10^6$ | $2.44 *10^5$ | $5.37*10^6$ |
| AUC ∞ $_{(expo)}$ | [(ng/mL) * h] | $7.07 *10^6$ | $2.45 *10^5$ | $4.90*10^6$ |
| t $_{half\,(E\,phase)}$ | [h] | 74.3 | 18.0 | 37.4 |
| t $_{half\,(D/A\,phase)}$ | [h] | 2.3 | 5.4 | 4.9 |
| MRT $_{(expo)}$ | [h] | 110.6 | 33.8 | 61.1 |
| Clearance $_{(area)}$ | [mL/h] | 0.040 | 1.228 | 0.056 |
| V $_{ss\,(area)}$ | [mL] | 3.8 | 4.8 | 2.2 |
| V $_{ss\,(expo)}$ | [mL] | 4.4 | 10.7 | 2.6 |
| $R^2$ | | 0.980 | 0.947 | 0.994 |

| ROCK® examples | | aTriFlex_B | scDb-Trib_A |
|---|---|---|---|
| | |  | 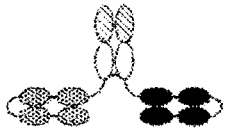 |
| ROCK® family | | Fc-less | Fab fusion |
| ROCK® format | | aTriFlex | scDb-Trib |
| anti-CD16 | Position | core | C |
| | Fv | mid | mid |
| | Format | hetDb (LL/HH) | scDb |
| Fc | | — | — |
| Target(s) | | EGFR/HSA[lo] | EGFR/HSA[lo] |
| Analysis | Weeks | 3 | 1 |
| C max | [ng/mL] | 235349 | 289826 |
| t max | [h] | 0.1 | 0.1 |
| AUC ∞ $_{(area)}$ | [(ng/mL * h] | $2.39*10^6$ | $2.71*10^6$ |
| AUC ∞ $_{(expo)}$ | [(ng/mL * h] | $2.15*10^6$ | $2.51*10^6$ |
| t $_{half\,(E\,phase)}$ | [h] | 11.8 | 14.4 |
| t $_{half\,(D/A\,phase)}$ | [h] | 1.1 | 5.3 |
| MRT $_{(expo)}$ | [h] | 18.1 | 28.5 |
| Clearance $_{(area)}$ | [mL/h] | 0.126 | 0.120 |
| V $_{ss\,(area)}$ | [mL] | 2.0 | 1.5 |
| V $_{ss\,(expo)}$ | [mL] | 2.2 | 1.7 |
| $R^2$ | | 0.986 | 0.989 |

C max: peak plasma concentration;
t max: time to reach C max;
AUC: Area under the curve;
t $_{half}$: half-life of a molecule.
MRT: Mean residence time;
V $_{ss}$: steady state distribution volume;
[#]Fc silenced by mutations L234F/L235E/D265A Example 8—Activities of CD16A/BCMA Binding Antibodies 8.1. CD16A/BCMA Binding Antibodies In this Example, studies of CD16A/BCMA binding antibodies: CD16A/BCMA antibody I, CD16A/BCMA antibody II, and CD16A/BCMA antibody III, are presented.

As demonstrated by the data shown in this Example, CD16A/BCMA antibody I is an NK cell engager for use in treating multiple myeloma with a similar mechanism as ADCC and has the potential to achieve significant activity with a favorable safety profile. In addition, CD16A/BCMA antibody I has been shown to have potential to treat daratumumab (anti-CD38 antibody) resistant and refectory multiple myeloma patients. Furthermore, CD16A/BCMA antibody I can be combined with another treatment for multiple myeloma, e.g., treatments comprising an antibody (including, but not limited to, an anti-TIGIT antibody, an anti-PD1 antibody, an anti-PD-L1 antibody, and an anti-VEGF antibody), and treatments including a cytokine (e.g., IL-12, IL-2, etc.).

8.1.1. CD16A/BCMA Antibody I

CD16A/BCMA antibody I is a scFv-IgAb antigen-binding protein having a structure shown in FIG. 13, which comprises (a) two CD16A antigen-binding moieties in the format of scFvs fused to the C-terminus of a homodimeric human IgG CH2-CH3 Fc portion in the order of $V_L$-$V_H$ and (b) two target antigen-binding moieties provided by each Fv in the Fab arms of the IgG, wherein the target antigen-binding moieties bind to BCMA.

Each of the CD16A antigen-binding moiety comprises a $V_H$ CDR1 comprising the amino acid sequence set forth in SEQ ID NO: 73, a $V_H$ CDR2 comprising the amino acid sequence set forth in SEQ ID NO: 74, a $V_H$ CDR3 comprising the amino acid sequence set forth in SEQ ID NO: 75, a $V_L$ CDR1 comprising the amino acid sequence set forth in SEQ ID NO: 76, a $V_L$ CDR2 comprising the amino acid sequence set forth in SEQ ID NO: 77, and a $V_L$ CDR3 comprising the amino acid sequence set forth in SEQ ID NO: 78. The CDRs are identified according to the Kabat numbering system. Each of the CD16A antigen-binding moiety comprises a $V_H$ having the amino acid sequence set forth in SEQ ID NO: 3, and a $V_L$ having the amino acid sequence set forth in SEQ ID NO: 2.

The CD16A antigen-binding moiety of CD16A/BCMA antibody I is fused to the C-terminus of the Fc portion of the molecule and is connected via a connector (having the amino acid sequence set forth in SEQ ID NO: 22) in the following order: $V_L$ (CD16A)-Linker L3-$V_L$ (CD16A). Linker L3 has the amino acid sequence set forth in SEQ ID NO: 18.

Each of the BCMA-targeting moieties comprises a $V_H$ CDR1 comprising the amino acid sequence set forth in SEQ ID NO: 67, a $V_H$ CDR2 comprising the amino acid sequence set forth in SEQ ID NO: 68, a $V_H$ CDR3 comprising the amino acid sequence set forth in SEQ ID NO: 69, a $V_L$ CDR1 comprising the amino acid sequence set forth in SEQ ID NO: 70, a $V_L$ CDR2 comprising the amino acid sequence set forth in SEQ ID NO: 71, and a $V_L$ CDR3 comprising the amino acid sequence set forth in SEQ ID NO: 72. The CDRs are identified according to the Kabat numbering system. Each of the BCMA-targeting moieties comprises a $V_H$ having the amino acid sequence set forth in SEQ ID NO: 65, and a $V_L$ having the amino acid sequence set forth in SEQ ID NO: 66.

CD16A/BCMA antibody I comprises two CD16A antigen-binding moieties and two BCMA-targeting moieties, wherein (a) each of the two CD16A antigen-binding moieties comprises a $V_H$ CDR1 comprising the amino acid sequence set forth in SEQ ID NO: 73, a $V_H$ CDR2 comprising the amino acid sequence set forth in SEQ ID NO: 74, a $V_H$ CDR3 comprising the amino acid sequence set forth in SEQ ID NO: 75, a $V_L$ CDR1 comprising the amino acid sequence set forth in SEQ ID NO: 76, a $V_L$ CDR2 comprising the amino acid sequence set forth in SEQ ID NO: 77, and a $V_L$ CDR3 comprising the amino acid sequence set forth in SEQ ID NO: 78; and (b) each of the two BCMA-targeting moieties comprises a $V_H$ CDR1 comprising the amino acid sequence set forth in SEQ ID NO: 67, a $V_H$ CDR2 comprising the amino acid sequence set forth in SEQ ID NO: 68, a $V_H$ CDR3 comprising the amino acid sequence set forth in SEQ ID NO: 69, a $V_L$ CDR1 comprising the amino acid sequence set forth in SEQ ID NO: 70, a $V_L$ CDR2 comprising the amino acid sequence set forth in SEQ ID NO: 71, and a $V_L$ CDR3 comprising the amino acid sequence set forth in SEQ ID NO: 72.

Figure 53A:
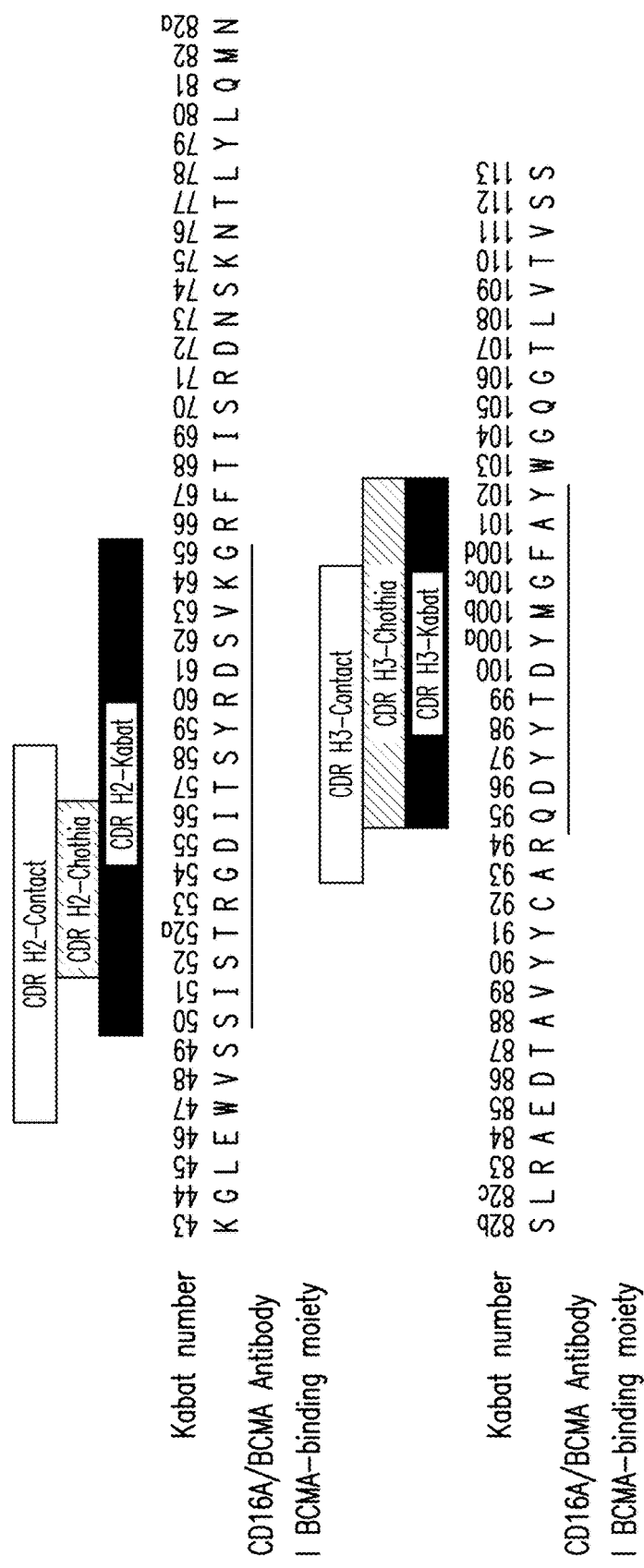

A summary of the CDR sequences of the CD16A antigen-binding moieties and BCMA-targeting moieties for CD16A/BCMA antibody I is shown in FIGS. 53A and 53C.

CD16A/BCMA antibody I comprises two CD16A antigen-binding moieties and two BCMA-targeting moieties, wherein (a) each of the two CD16A antigen-binding moieties comprises a $V_H$ comprising the amino acid sequence set forth in SEQ ID NO: 3, and a $V_L$ comprising the amino acid sequence set forth in SEQ ID NO: 2; and (b) each of the two BCMA-targeting moieties comprises a $V_H$ comprising the amino acid sequence set forth in SEQ ID NO: 65 and a $V_L$ comprising the amino acid sequence set forth in SEQ ID NO: 66.

A summary of the $V_H$ and $V_L$ sequences of the CD16A antigen-binding moieties and BCMA-targeting moieties for CD16A/BCMA antibody I is shown in FIGS. 53B and 53D. The Fc portion of CD16A/BCMA antibody I is a silenced Fc portion that comprises a human IgG1 CH2, and CH3 heavy chain constant domain, which comprises the amino acid sequence set forth in SED ID NO: 29. The CH2 heavy chain constant domain has two silencing mutations (also referred to as "effector-less mutations"): L234F and L235E. The CH2 heavy chain constant domain comprises the amino acid sequence set forth in SED ID NO: 79. The CH3 heavy chain constant domain comprises the amino acid sequence set forth in SED ID NO: 109. The CH1 heavy chain constant domain that is connected to the BCMA targeting moiety comprises the amino acid sequence set forth in SEQ ID NO: 33.

CD16A/BCMA antibody I comprises a polypeptide chain 1 comprising one CD16A antigen-binding moiety, a homodimeric human IgG CH2-CH3 Fc portion, the $V_H$ of the BCMA-targeting moiety, wherein the polypeptide chain 1 has the amino acid sequence set forth in SEQ ID NO: 61. CD16A/BCMA antibody I comprises a polypeptide chain 2 comprising the $V_L$ of the BCMA-targeting moiety, wherein the polypeptide chain 2 has the amino acid sequence set forth in SEQ ID NO: 62.

8.1.2. CD16A/BCMA Antibody II

CD16A/BCMA antibody II is a Fc-less TandAb having a structure shown in FIG. 23 (see the structure for "TandAb"), which comprises two CD16A antigen-binding moieties and two target antigen-binding moieties, wherein the CD16A antigen-binding moiety is provided in the format of scFv and positioned between the $V_H$ and the VL of the target antigen-binding moiety.

The CD16A antigen-binding moiety is fused to the target antigen-binding moiety in the following order:

V$_H$BCMA-Linker L5-V$_L$ CD16A-Linker L6-V$_H$CD16A-Linker L5-V$_L$ BCMA

Linker L5 has the amino acid sequence set forth in SEQ ID NO: 129. Linker L5 has the amino acid sequence set forth in SEQ ID NO: 130.

Each of the CD16A antigen-binding moiety comprises a V$_H$ CDR1 comprising the amino acid sequence set forth in SEQ ID NO: 73, a V$_H$ CDR2 comprising the amino acid sequence set forth in SEQ ID NO: 74, a V$_H$ CDR3 comprising the amino acid sequence set forth in SEQ ID NO: 75, a V$_L$ CDR1 comprising the amino acid sequence set forth in SEQ ID NO: 76, a V$_L$ CDR2 comprising the amino acid sequence set forth in SEQ ID NO: 77, and a V$_L$ CDR3 comprising the amino acid sequence set forth in SEQ ID NO: 78. The CDRs are identified according to the Kabat numbering system. Each of the CD16A antigen-binding moiety comprises a V$_H$ having the amino acid sequence set forth in SEQ ID NO: 3, and a V$_L$ having the amino acid sequence set forth in SEQ ID NO: 2.

Each of BCMA-targeting moieties comprises a V$_H$ CDR1 comprising the amino acid sequence set forth in SEQ ID NO: 67, a V$_H$ CDR2 comprising the amino acid sequence set forth in SEQ ID NO: 68, a V$_H$ CDR3 comprising the amino acid sequence set forth in SEQ ID NO: 69, a V$_L$ CDR1 comprising the amino acid sequence set forth in SEQ ID NO: 70, a V$_L$ CDR2 comprising the amino acid sequence set forth in SEQ ID NO: 71, and a V$_L$ CDR3 comprising the amino acid sequence set forth in SEQ ID NO: 72. The CDRs are identified according to the Kabat numbering system. Each of the BCMA-targeting moieties comprises a V$_H$ having the amino acid sequence set forth in SEQ ID NO: 65, and a V$_L$ having the amino acid sequence set forth in SEQ ID NO: 66.

CD16A/BCMA antibody II comprises two polypeptides, each of which has the amino acid sequence set forth in SEQ ID NO: 126.

8.1.3. CD16A/BCMA Antibody III

CD16A/BCMA antibody III is a KiH-scDb-Fc having a structure shown in FIG. 5, which comprises (a) two CD16A antigen-binding moieties in the format of scDb fused to the C-terminus of an IgG CH2-CH3 Fc portion in the order of V$_L$-V$_H$-V$_L$-V$_H$, and (b) a single target antigen-binding moiety in the format of scFv fused to the N-terminus of the Fc portion, wherein the target antigen-binding moiety binds to BCMA.

Each of the CD16A antigen-binding moiety comprises a V$_H$ CDR1 comprising the amino acid sequence set forth in SEQ ID NO: 73, a V$_H$ CDR2 comprising the amino acid sequence set forth in SEQ ID NO: 74, a V$_H$ CDR3 comprising the amino acid sequence set forth in SEQ ID NO: 75, a V$_L$ CDR1 comprising the amino acid sequence set forth in SEQ ID NO: 76, a V$_L$ CDR2 comprising the amino acid sequence set forth in SEQ ID NO: 77, and a V$_L$ CDR3 comprising the amino acid sequence set forth in SEQ ID NO: 78. The CDRs are identified according to the Kabat numbering system. Each of the CD16A antigen-binding moiety comprises a V$_H$ having the amino acid sequence set forth in SEQ ID NO: 3, and a V$_L$ having the amino acid sequence set forth in SEQ ID NO: 2.

The CD16A antigen-binding moiety is fused to the heterodimeric Fc portion and connected via a connector having the amino acid sequence set forth in SEQ ID NO: 20 in the following order: V$_L$(CD16A)-Linker L1-V$_H$(CD16A)-Linker L2-V$_L$(CD16A)-Linker L1-V$_H$ (CD16A). Linker L1 has the amino acid sequence set forth in SEQ ID NO: 16, and Linker L2 has the amino acid sequence set forth in SEQ ID NO: 17.

The BCMA-targeting moiety comprises a V$_H$ CDR1 comprising the amino acid sequence set forth in SEQ ID NO: 67, a V$_H$ CDR2 comprising the amino acid sequence set forth in SEQ ID NO: 68, a V$_H$ CDR3 comprising the amino acid sequence set forth in SEQ ID NO: 69, a V$_L$ CDR1 comprising the amino acid sequence set forth in SEQ ID NO: 70, a V$_L$ CDR2 comprising the amino acid sequence set forth in SEQ ID NO: 71, and a V$_L$ CDR3 comprising the amino acid sequence set forth in SEQ ID NO: 72. The CDRs are identified according to the Kabat numbering system. Each of the BCMA-targeting moieties comprises a V$_H$ having the amino acid sequence set forth in SEQ ID NO: 65, and a V$_L$ having the amino acid sequence set forth in SEQ ID NO: 66.

CD16A/BCMA antibody III comprises two CD16A antigen-binding moieties and one BCMA-targeting moiety, wherein (a) each of the two CD16A antigen-binding moieties comprises a V$_H$ CDR1 comprising the amino acid sequence set forth in SEQ ID NO: 73, a V$_H$ CDR2 comprising the amino acid sequence set forth in SEQ ID NO: 74, a V$_H$ CDR3 comprising the amino acid sequence set forth in SEQ ID NO: 75, a V$_L$ CDR1 comprising the amino acid sequence set forth in SEQ ID NO: 76, a V$_L$ CDR2 comprising the amino acid sequence set forth in SEQ ID NO: 77, and a V$_L$ CDR3 comprising the amino acid sequence set forth in SEQ ID NO: 78; and (b) the BCMA-targeting moiety comprises a V$_H$ CDR1 comprising the amino acid sequence set forth in SEQ ID NO: 67, a V$_H$ CDR2 comprising the amino acid sequence set forth in SEQ ID NO: 68, a V$_H$ CDR3 comprising the amino acid sequence set forth in SEQ ID NO: 69, a V$_L$ CDR1 comprising the amino acid sequence set forth in SEQ ID NO: 70, a V$_L$ CDR2 comprising the amino acid sequence set forth in SEQ ID NO: 71, and a V$_L$ CDR3 comprising the amino acid sequence set forth in SEQ ID NO: 72.

The Fc portion of CD16A/BCMA antibody III is a silenced Fc portion that comprises a human IgG1 CH2 and CH3 heavy chain constant domain having the amino acid sequence set forth in SED ID NO: 31. The CH2 heavy chain constant domain has two silencing mutations ("effector-less" mutations): L234F and L235E. The CH2 heavy chain constant domain comprises the amino acid sequence set forth in SED ID NO: 79. The CH3 heavy chain constant domain has one silencing mutation (effector-less mutation) D265A. The CH3 heavy chain constant domain comprises the amino acid sequence set forth in SED ID NO: 81.

CD16A/BCMA antibody III comprises a polypeptide chain 1 comprising two CD16A antigen-binding moieties and an IgG CH2-CH3 Fc portion, wherein the polypeptide chain 1 has the amino acid sequence set forth in SEQ ID NO: 63. CD16A/BCMA antibody III comprises a polypeptide chain 2 comprising one BCMA-targeting moiety, wherein the polypeptide chain 2 has the amino acid sequence set forth in SEQ ID NO: 64.

8.2. Binding Characteristics

Both CD16A/BCMA antibody I and CD16A/BCMA antibody III specifically bind to CD16A but not CD16B. CD16A/BCMA antibody I has a high binding affinity to CD16A and BCMA, e.g., the antibody binds to CD16A with a KD of about 16 nM, and binds to BCMA with a KD of about 2 nM.

Figure 31A:
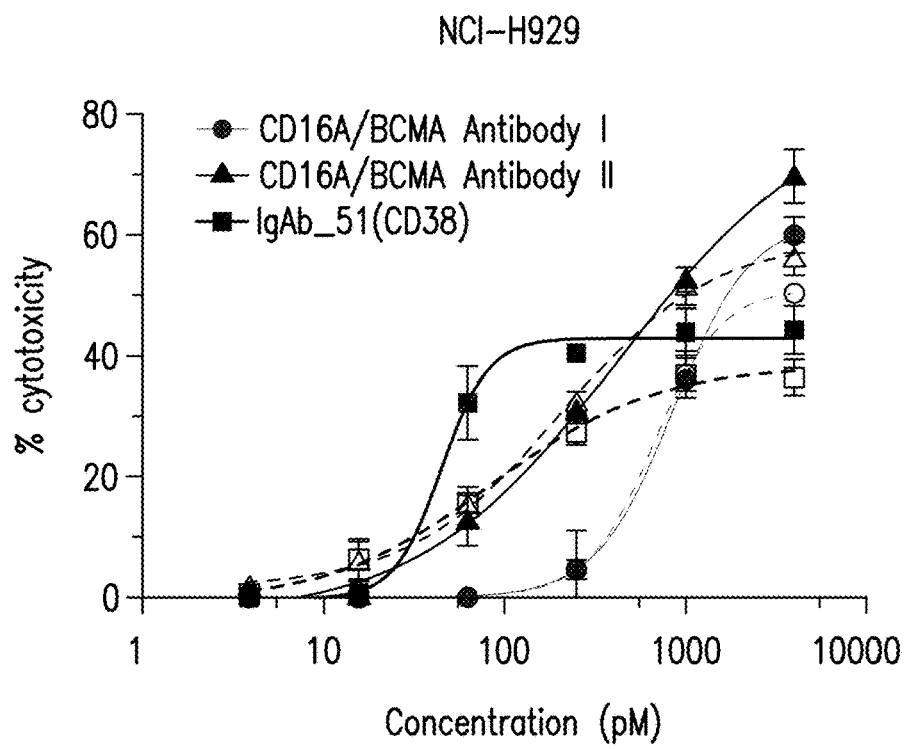
FIGS. 31A-31B show the cytotoxicity of CD16A/BCMA antibody I for CD16A-158V/V healthy donors (solid lines) and for CD16A-158F/F (dashed lines).
Figure 31B:
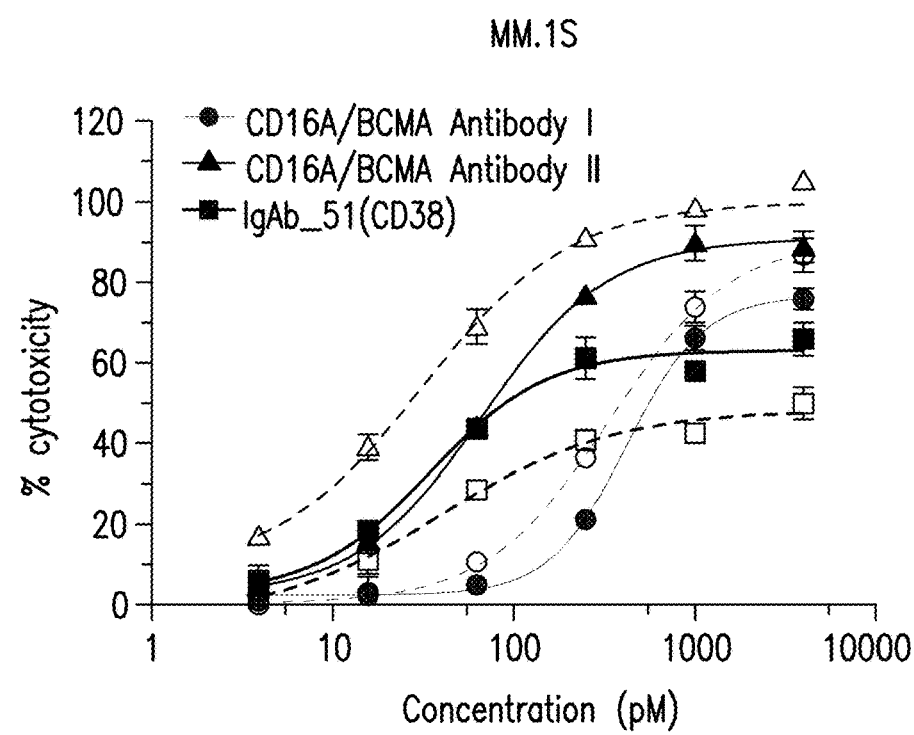

CD16A/BCMA antibody I lacks FcγR binding as confirmed by ELISA. Since CD16A/BCMA antibody I does not bind via its Fc region to CD16A, it binds to CD16A independent of CD16A polymorphisms. For example, the cytotoxicity of CD16A/BCMA antibody I for multiple myeloma cell lines was assessed with CD16A-158V/V healthy donors and with CD16A-158F/F healthy donors on the same day. The results are shown in FIGS. 31A and 31B. CD16A/BCMA antibody I exhibited either no change or even increased activity with CD16A-158F/F as compared to CD16A-158V/V. By contrast, daratumumab, which binds via its Fc region to CD16a, showed reduced activity with CD16A-158F/F as compared to CD16A-158V/V. The cytotoxicity of CD16A/BCMA antibody I for multiple myeloma cell lines was also assessed with CD16A-158V/F healthy donors, which was about between the cytotoxicity observed for CD16A-158F/F and CD16A-158V/V (data not shown).

8.3 In Vitro Cytotoxicity of Multiple Myeloma Target Cells 8.3.1. Assessment of Cytotoxicity Using Calcein AM Cytotoxicity Assays Calcein AM cytotoxicity assays were performed using human NK cells as effector cells and multiple myeloma cell line as target cells. Briefly, target cells were freshly labeled with 10 uM calcein AM (Thermo Fisher Scientific; Waltham, Mass.) for 30 minutes at 37° C. with serum-free medium. After two washes by centrifugation, cells were resuspended in assay medium (RPMI 1640 supplemented with 10% heat-inactivated fetal bovine serum) and dispensed into 96-well, U-bottom tissue culture plates at a density of $1 \times 10^4$ cells/well. Freshly prepared effector cells were then added to each well at a density of $5 \times 10^4$ cells/well. After 30 minutes of incubation, serial dilutions of test samples (0.64, 3.2, 16, 80, 400, and 2000 pm) were added to the plates and incubated for an additional 4 hours at 37C in a humidified incubator with 5% $CO_2$. Following incubation, the plates were centrifuged at 300×g for 10 minutes. The supernatants were transferred to a black, opaque, 96-well microplate (OptiPlate-96; PerkinElmer; Waltham, Mass.) and fluorescent signals were measured in relative fluorescence units (RFU) using an Infinite M1000 PRO plate reader (Tecan Trading AG; Männedorf, Switzerland) with excitation/emission at 495/515 nm. Signals from the wells containing only the target cells represented spontaneous release of the calcein from labeled cells while wells containing target cells lysed with 10% Triton X-100 (Sigma-Aldrich; St. Louis, Mo.) represented the maximal release. Nonspecific effector cell mediated cytotoxicity was measured in wells containing target and effector cells without the addition of test samples. The extent of specific cytotoxicity was calculated as follows:

% cytotoxicity=100*(experimental release−nonspecific release)/(maximum release−spontaneous release)

Data were analyzed and plotted by fitting to a four-parameter nonlinear regression model using GraphPad Prism 6 software (GraphPad Software; San Diego, Calif.).

The results are shown in Table 12.

TABLE 12 cytotoxic potency of CD16A/BCMA antibody I

| Cell Line | Anti-BCMA SABC | Mean $ED_{50}$ [pM] |
|---|---|---|
| NCI-H929 | 51,479 | 21.8 |
| RPMI-8226 | 14,707 | 55.1 |
| MM.1S | 13,182 | 12.1 |
| U266 | 10,614 | 19.8 |
| Daudi | 10,371 | 5.7 |
| SK-MM2 | 3,617 | 3.3 |
| HuNS1 | 1,438 | 59.3 |

TABLE 12-continued cytotoxic potency of CD16A/BCMA antibody I

| Cell Line | Anti-BCMA SABC | Mean $ED_{50}$ [pM] |
|---|---|---|
| ARH77 | 1,183 | 79.6 |
| MC/CAR | 449 | 96.5 |

* SABC stands for specific antibody binding capacity, in this case, determined by anti-BCMA mAb ANC3B1 and QIFIKIT(Agilent).

8.3.2. Assessment of Cytotoxicity Using FACS

Human PBMC and isolated NK cells were isolated from a healthy human blood donor A and frozen for later experimentation. PBMC upon thaw were ~85% viable by trypan blue staining and later confirmed by FACS with 7AAD. PBMC were co-cultured with BCMA+ multiple myeloma tumor cell lines with an E:T ratio about 0.4 or about 4-5, and exposed to 3-fold serial diluted test articles from 0.1-3000 pM for approximately 20 hours at 37C with 5% $CO_2$. Antibody staining and FACS were used to determine BCMA expression on MM tumor cells and monitor cytotoxicity of multiple myeloma target cells. Data were analyzed with the software programs FlowJo and GraphPad Prism 6. The results are shown in FIGS. 32A-32E, 33A-33C, and 34A-34C. FIGS. 32A-32E show that CD16A/BCMA antibody I was efficacious at an E:T ratio of about 0.4 (determined from a cohort of multiple myeloma patients). FIGS. 33A-33C and 34A-34C show that human NK cells exposed to CD16A/BCMA antibody I specifically targeted and depleted $BCMA^+$ target cells.

The assessments by both methods demonstrate that CD16A/BCMA antibody I was potent in vitro across a wide range of target expression levels. The observed efficacy was not correlated with E:T ratio, and was not correlated with the BCMA expression. In addition, CD16A/BCMA antibody I showed similar potency as daratumumab on multiple myeloma cell lines. See FIGS. 33A-33C.

8.4. In Vitro Cytotoxicity Against Low BCMA Expressing Tumor Cells

In vitro cytotoxicity against low BCMA expressing Raji tumor cell line of CD16A/BCMA antibody I was assessed by Calcein-release assay and FACS. The Calcein-release assays used for assessing the in vitro cytotoxicity of multiple myeloma target cells as described above were used in this study. The E:T ratio of the freshly prepared NK cells and the Raji Burkitt's Lymphoma tumor cell line was about 5. The results are shown in FIGS. 35A-35D. In vitro lysis of BCMA+ target cells was observed for CD16A/BCMA antibody I, CD16A/BCMA antibody II, and CD16A/BCMA antibody III, despite almost undetectable BCMA surface expression.

Figure 36A:
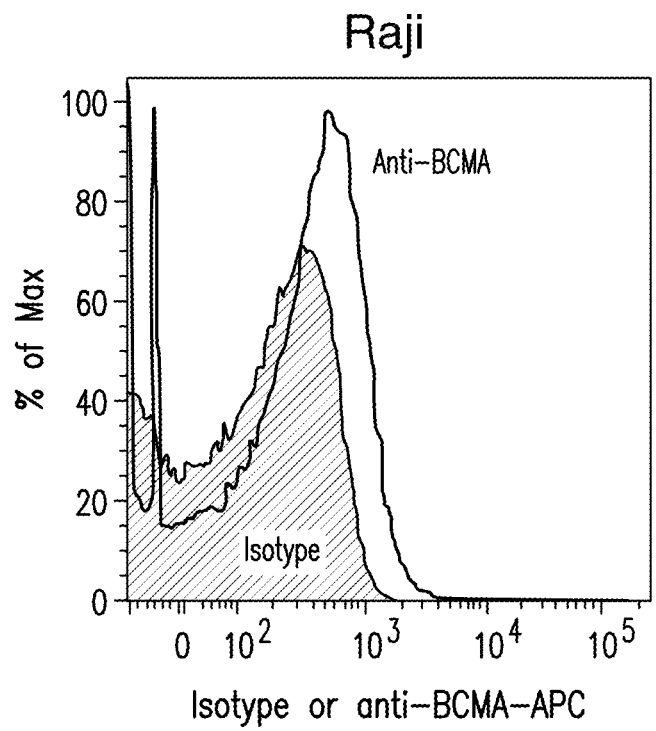
FIGS. 36A-36C show the in vitro cytotoxicity of CD16A/BCMA antibody I against low BCMA expressing Raji tumor cell lines.
Figure 36B:
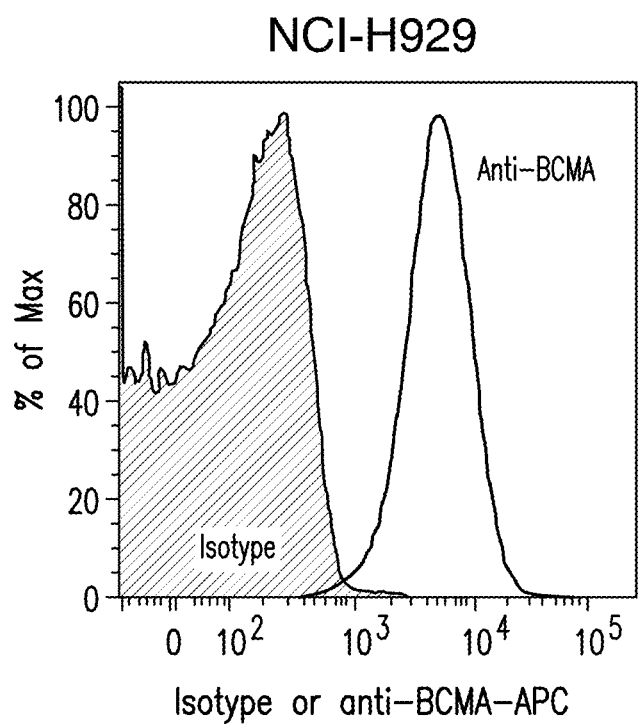
Figure 36C:
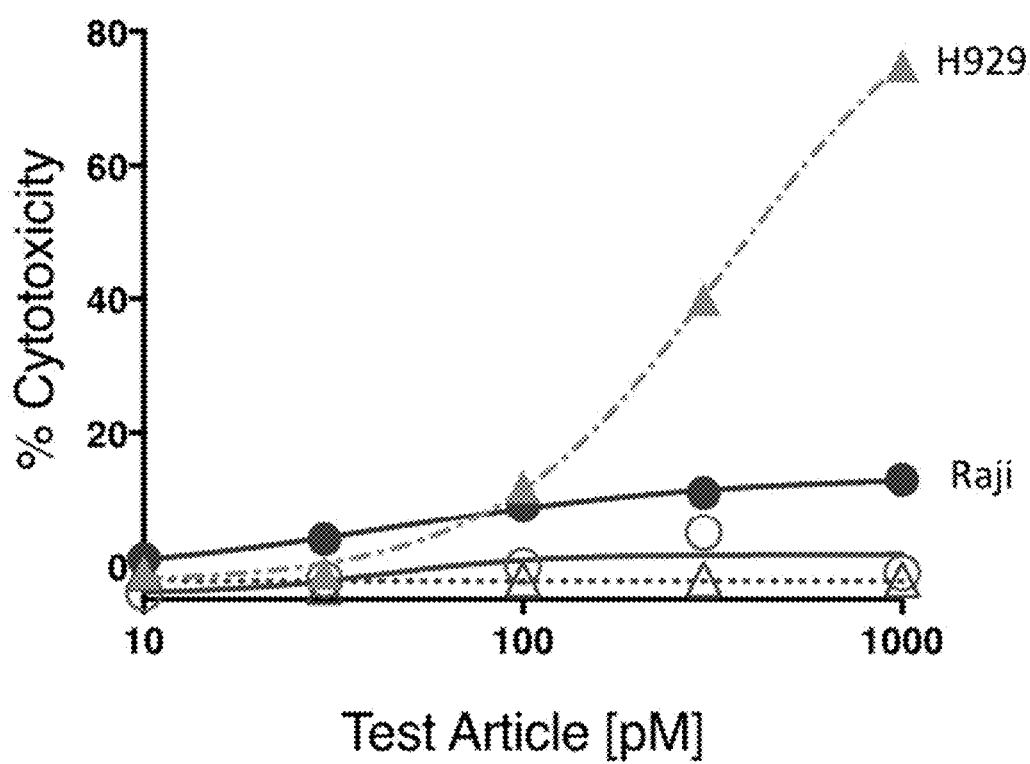

For the FACS assays, human NK cells were isolated from a healthy human blood donor. NK and Raji cells were preincubated separately with 0.5 mg/ml low endotoxin hIgG for at least 1 hour prior to assay setup. NK cells were co-cultured with Raji Burkitt's Lymphoma tumor cell line at an approximate E:T ration of 5, and exposed to 3-fold serial diluted test articles from 10-1000 pM for approximately 20 hours at 37° C. with 5% $CO_2$. Antibody staining and FACS were used to monitor cytotoxicity of RAJI target cells. Data were analyzed with the software programs FlowJo and GraphPad Prism 6. The results are shown in FIGS. 36A-36C. As shown in FIG. 36C, CD16A/BCMA antibody I exhibited in vitro cytotoxicity against low BCMA expressing Raji tumor cell line.

8.5. In Vitro Activity Against Autologous $BCMA^+$ Normal Human Plasma Cells

In vitro activity against autologous $BCMA^+$ normal human plasma cells of CD16A/BCMA antibody I was assessed by FACS. Human NK were isolated from peripheral blood of a healthy human blood donor. Bone marrow from the same human donor was used to isolate human plasma cells. NK, plasma cells and NCI-H929 cells were preincubated separately with 0.5 mg/ml low endotoxin hIgG for at least 1 hour prior to assay setup. Allogeneic: NK cells were co-cultured with NCI-H929 tumor cell line at an approximate E:T ratio of 3, and simultaneously exposed to 3-fold serial diluted test articles ranging from 3-3000 pM for approximately 20 hours at 37C with 5% CO2. Autologous: NK cells were co-cultured with human plasma cells at an approximate E:T ratio of 23 and incubated with test articles as described above. Antibody staining with anti-CD56 E-450 and CD138-APC followed by FACS were used to monitor cytotoxicity of H929 and plasma cells. Data were analyzed with the software programs FlowJo and GraphPad Prism 6.

Figure 37A:
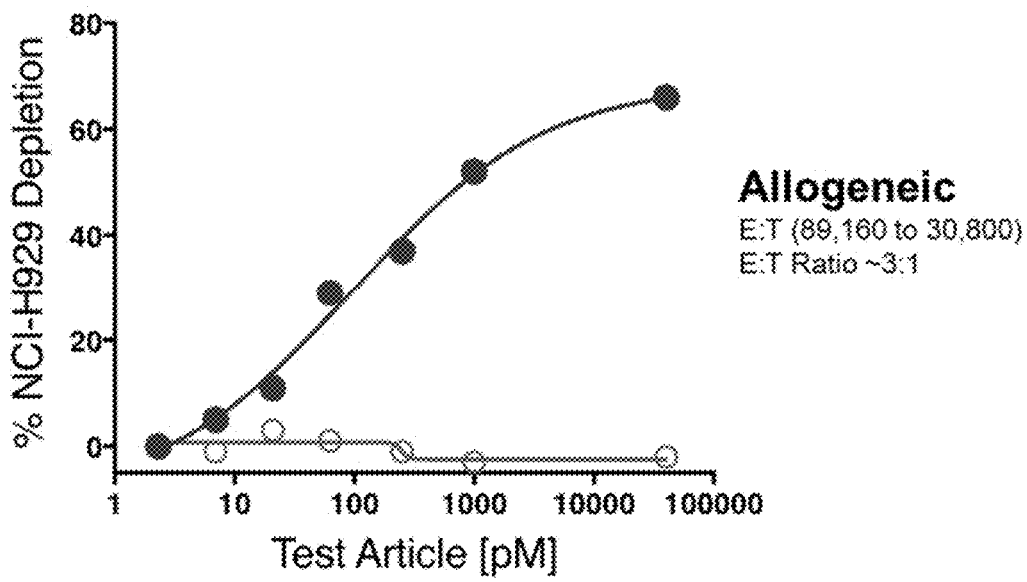
FIGS. 37A and 37B show the in vitro activity of CD16A/BCMA antibody I against autologous BCMA+ normal human plasma cells.
Figure 37B:
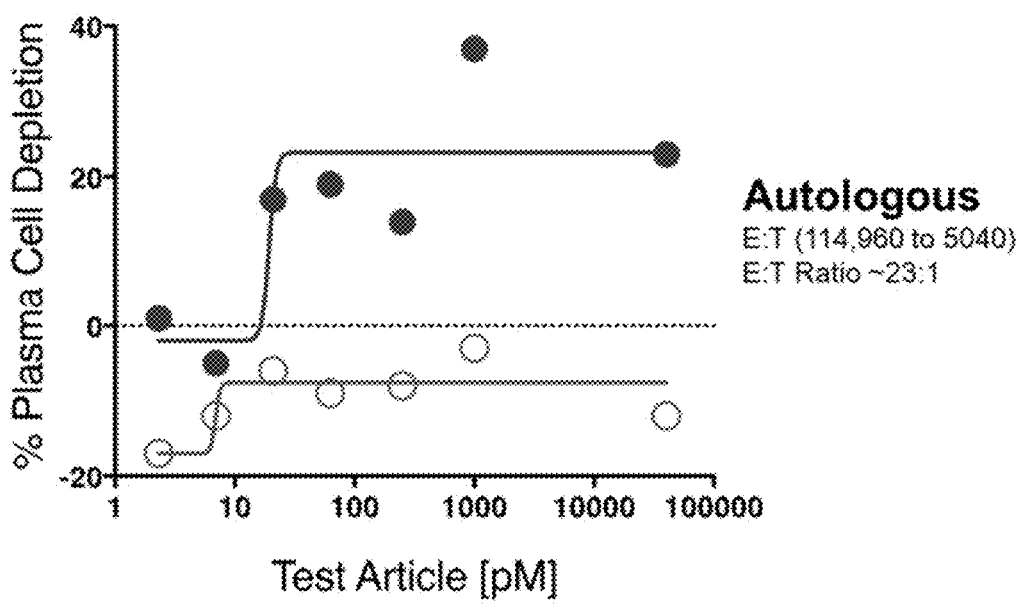

The results are shown in FIGS. 37A and 37B. CD16A/BCMA antibody I exhibited in vitro activity against autologous BCMA$^+$ normal human plasma cells.

8.6. Lack of Activation of CD16A in Absence Of BCMA$^+$ Target Cells

Figure 34A:
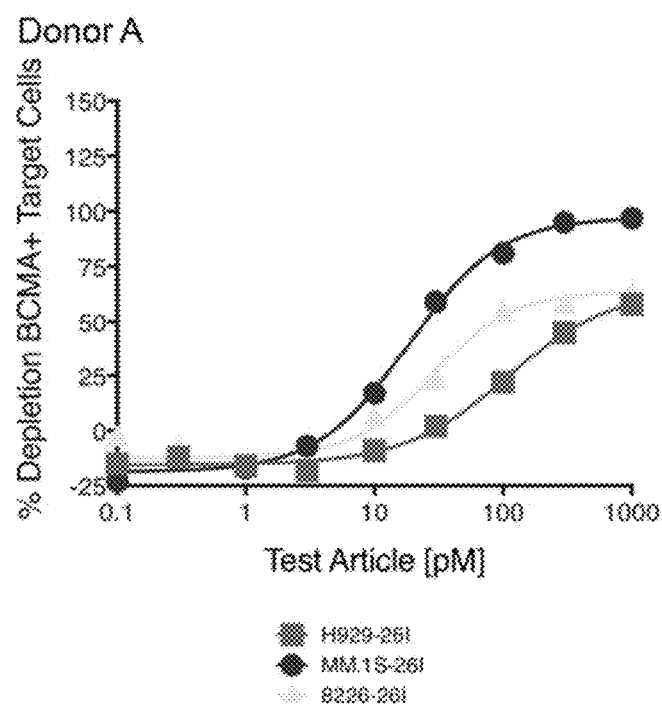
FIGS. 34A-34C show the in vitro cytotoxicity of CD16A/BCMA antibody I on multiple myeloma cell lines. NK cells were co-cultured with BCMA+ multiple myeloma tumor cell lines with an E:T ~4-5. Donor A—NK and tumor cells were preincubated with 0.5 mg/ml low endotoxin hIgG for at least 30 minutes prior to addition of NK cells and test articles. Donor B-no preincubation step.
Figure 34B:
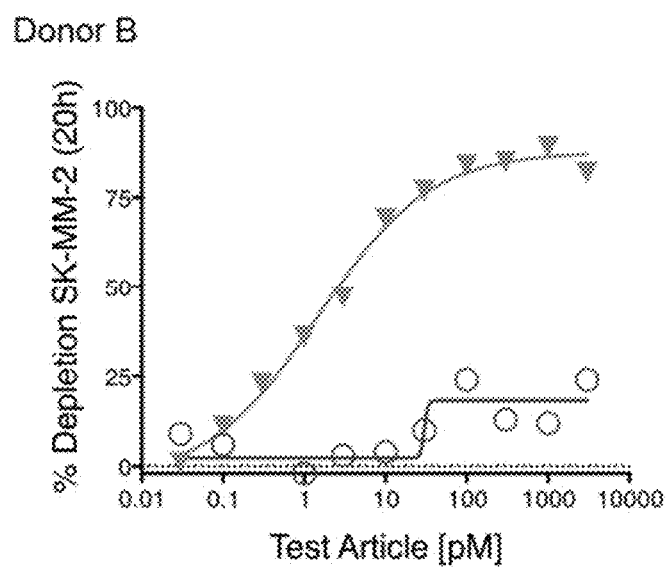
Figure 34C:
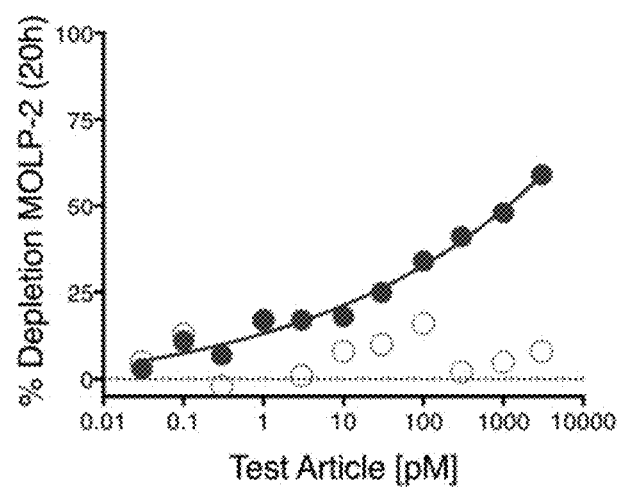
Figure 35A:
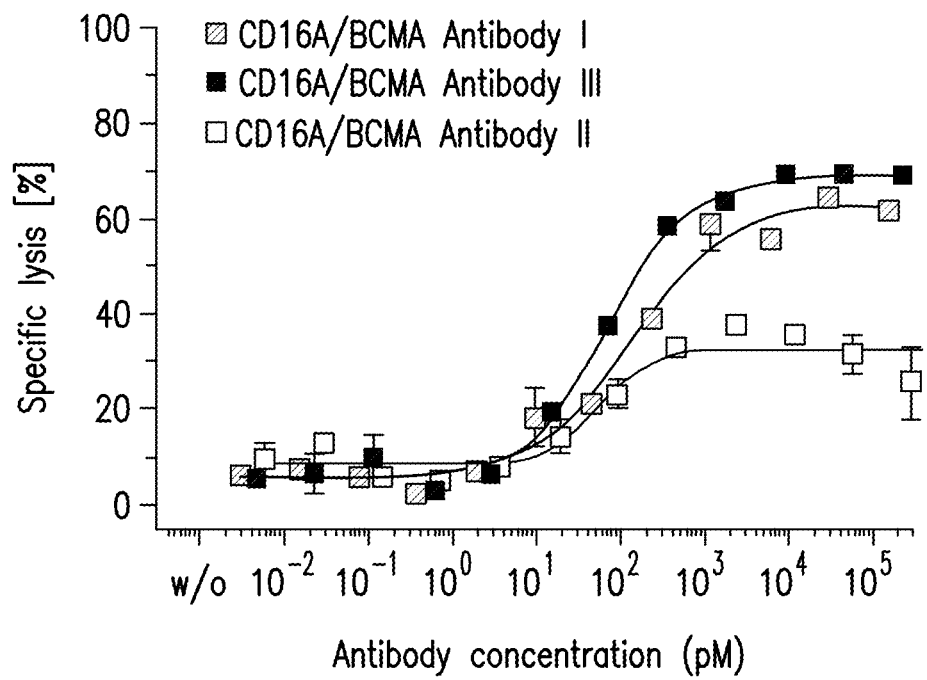
FIGS. 35A-35D show in vitro cytotoxicity of CD16A/BCMA antibody I, CD16A/BCMA antibody II, and CD16A/BCMA antibody III against low BCMA expressing Raji tumor cell lines. The in vitro lysis of BCMA+ target cells is observed despite almost undetectable BCMA surface expression. This in vitro cytotoxicity assay was performed using a 4 h calcein-release assay of enriched primary human NK cells, E:T 5:1.
Figure 35B:
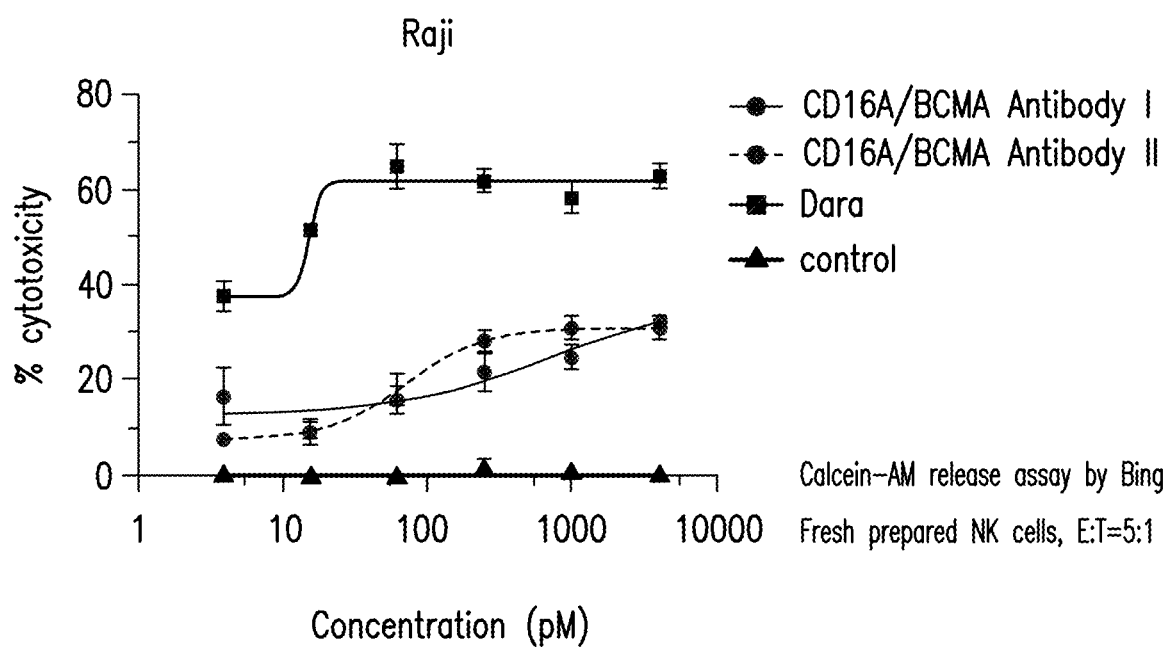
Figure 35C:
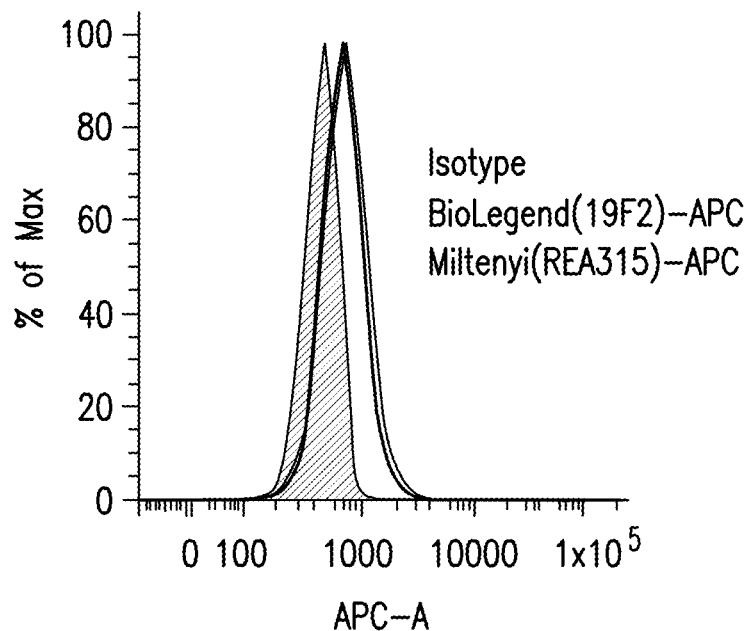
Figure 35D:
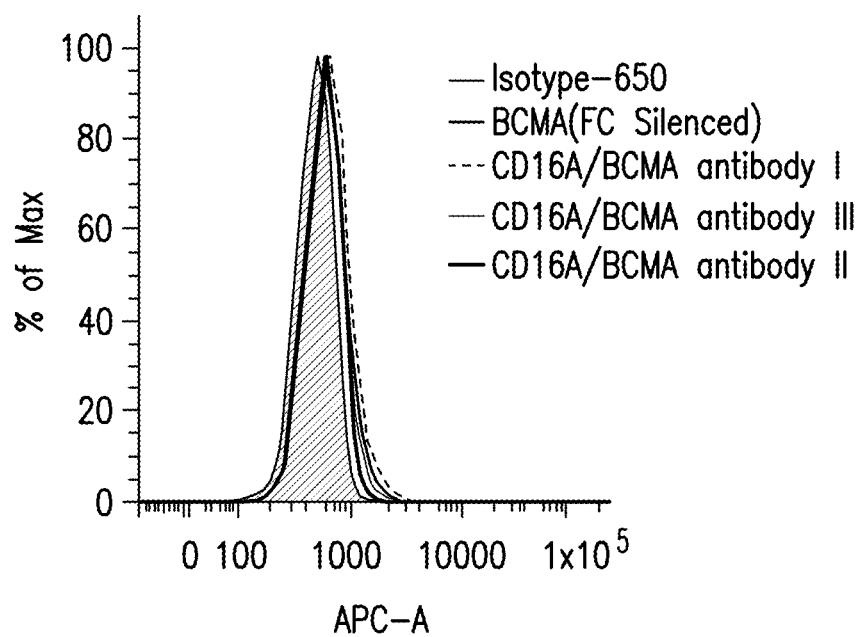
Figure 38A:
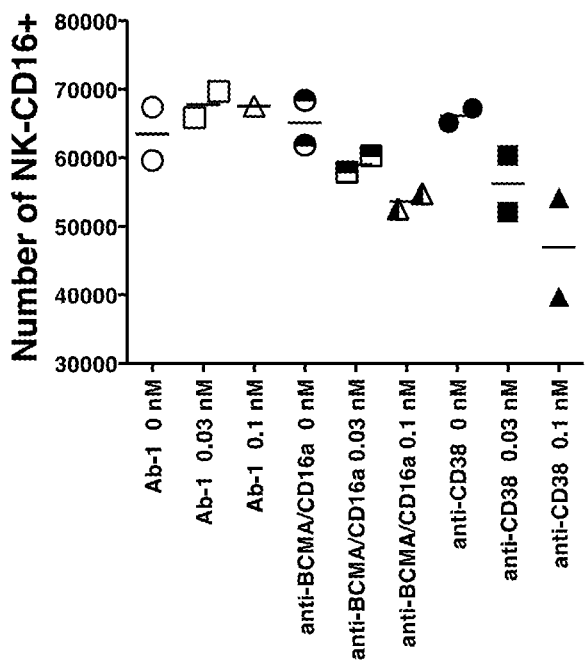
FIGS. 38A-38C show the activation of CD16 on NK cells by of CD16A/BCMA antibody I in the presence of $BCMA^+$ target cells.
Figure 38B:
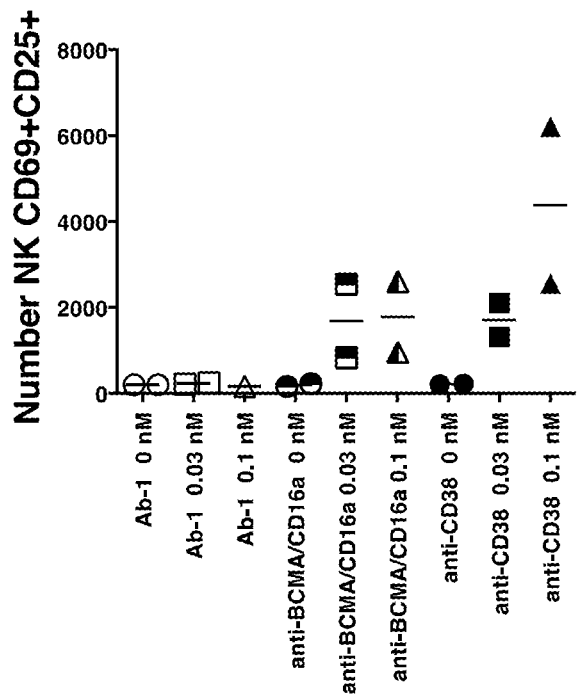
Figure 38C:
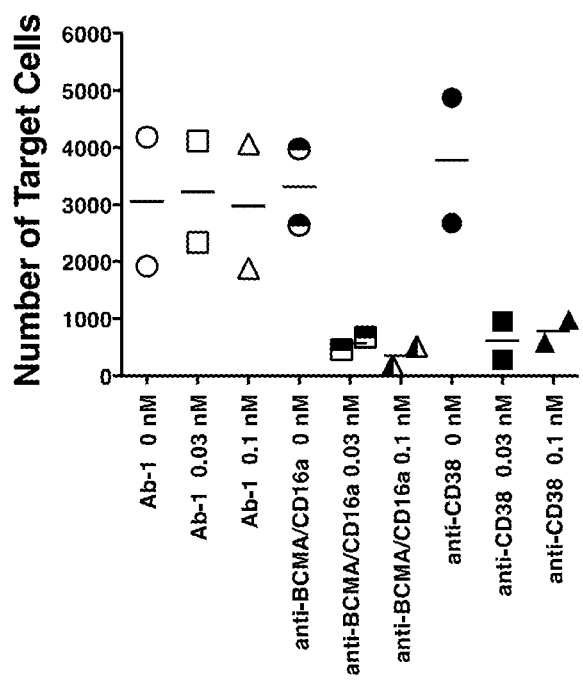

The inventors also investigated whether CD16A/BCMA antibody I can active NK cells in the absence of BCMA$^+$ target cells. First, the activation of CD16 and maintenance of CD16 levels on NK cells in the presence of BCMA$^+$ target cells were studied. NK cells were derived from two independent healthy human blood donors. NK cells were co-cultured with MM.1S BCMA$^+$ target cells and exposed to either 0, 0.03 or 0.1 nM of anti-BCMA/CD16A antibody I or Ab-1 (negative control/CD16a) or Anti-CD38 (DARA positive control) for 20 hours at 37° C. Antibody staining and FACS were used to determine the number of live CD56$^{dim}$/CD16$^+$ cells and CD56$^{dim}$/CD16$^+$/CD69$^+$/CD25$^+$ as illustrated in FIGS. 34A and 34B, respectively. Depletion of BCMA$^+$ target cells is presented in FIG. 34C. Data were analyzed with the software programs FlowJo and GraphPad Prism 6. The results are shown in FIGS. 38A-38C. CD16A/BCMA antibody I activated and maintained CD16 levels on NK cells in presence of BCMA$^+$ target cells.

Figure 32A:
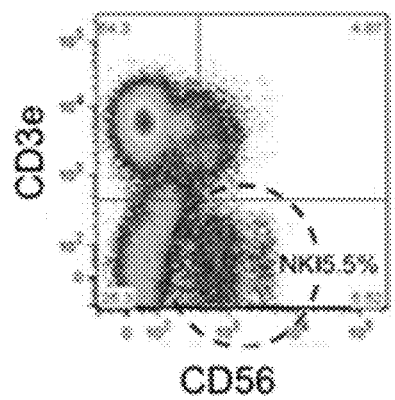
FIGS. 32A-32E show the in vitro cytotoxicity of CD16A/BCMA antibody I on multiple myeloma cell lines. The approximate number of CD56+CD3e− NK cells per 165K of PBMC was about ~8000 cells, thus the NK:Tumor ratio was ~0.4 (similar to clinical data estimating MM patient NK to tumor cell ratio; data not shown).
Figure 32B:
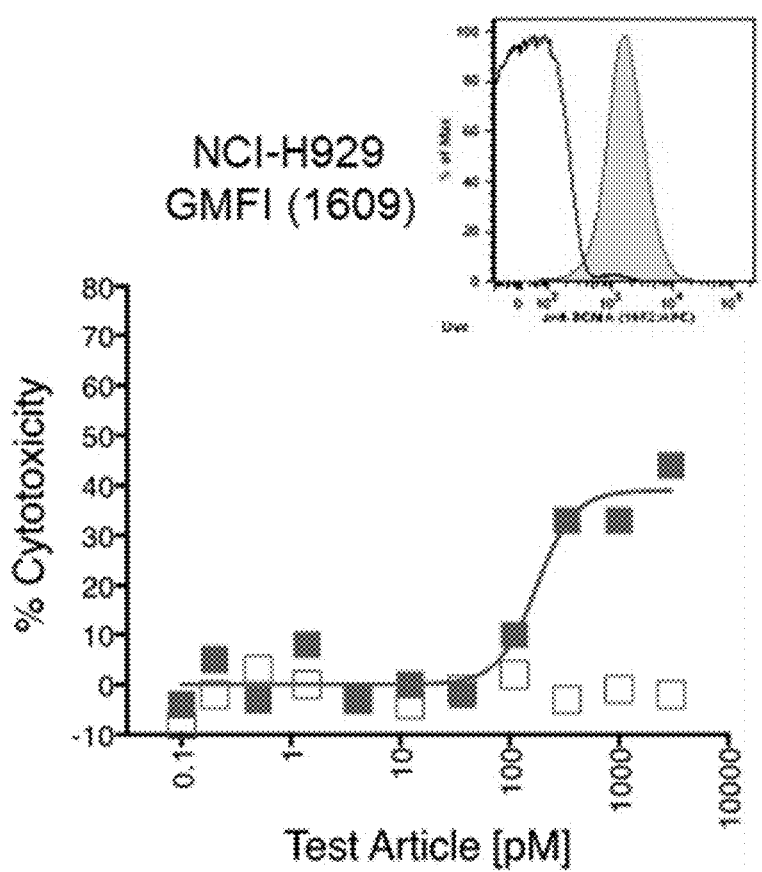
Figure 32C:
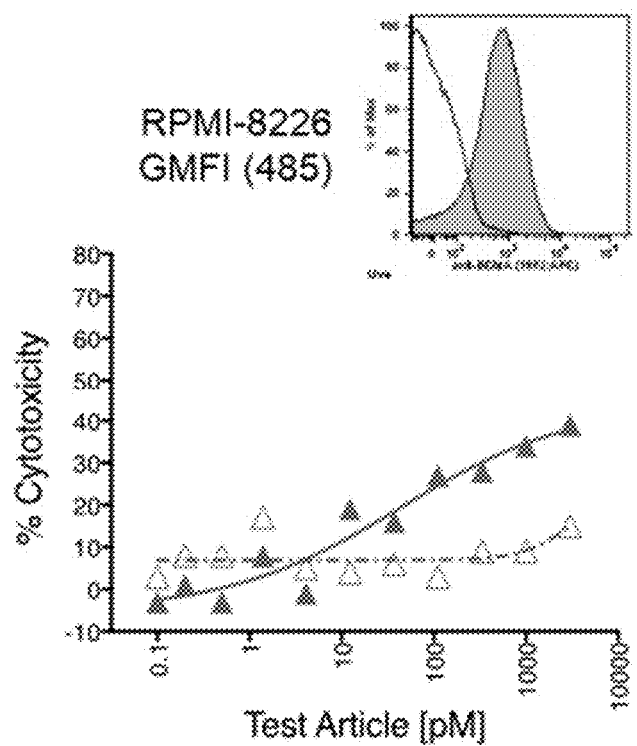
Figure 32D:
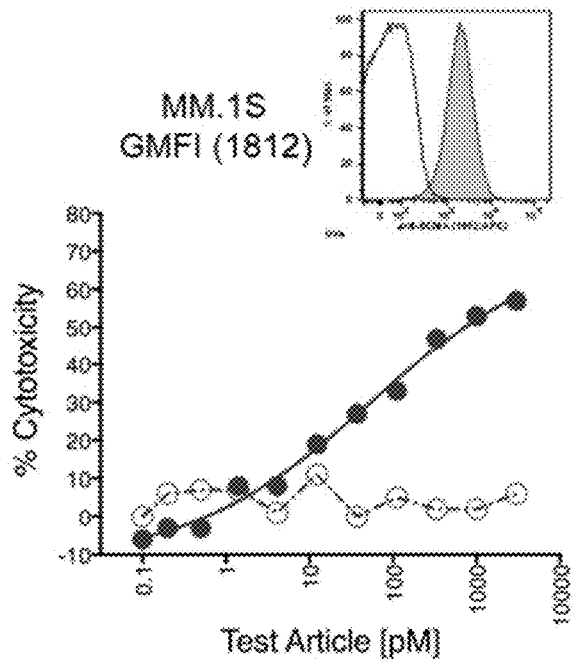
Figure 32E:
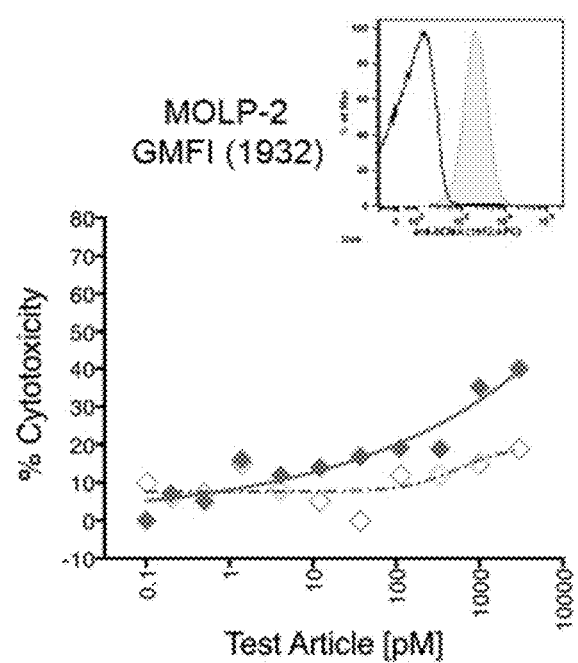
Figure 33A:
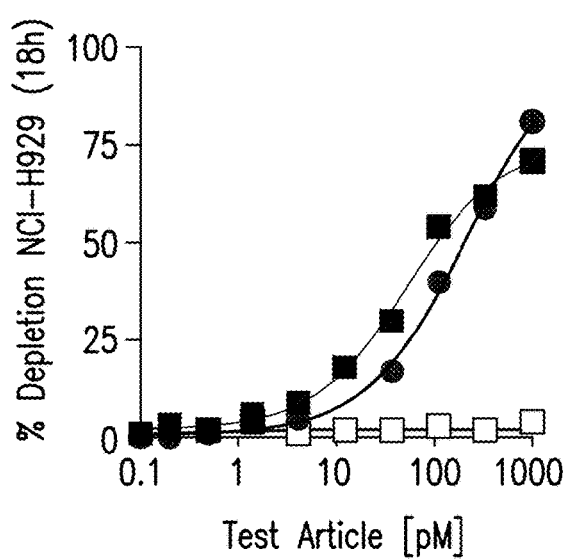
FIGS. 33A-33C show the in vitro cytotoxicity of CD16A/BCMA antibody I on multiple myeloma cell lines.
Figure 33B:
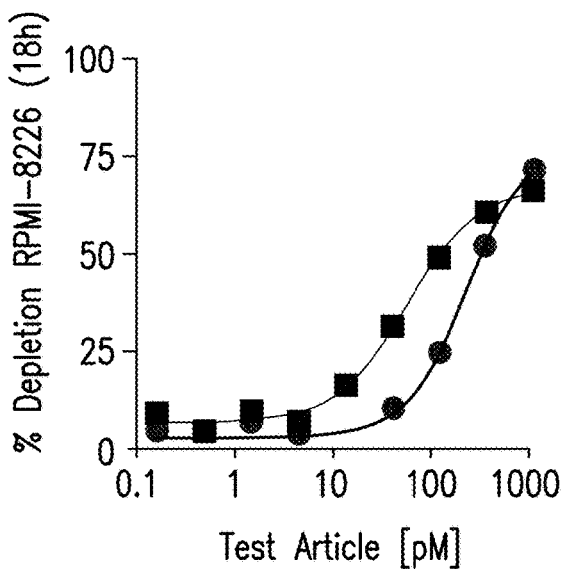
Figure 33C:
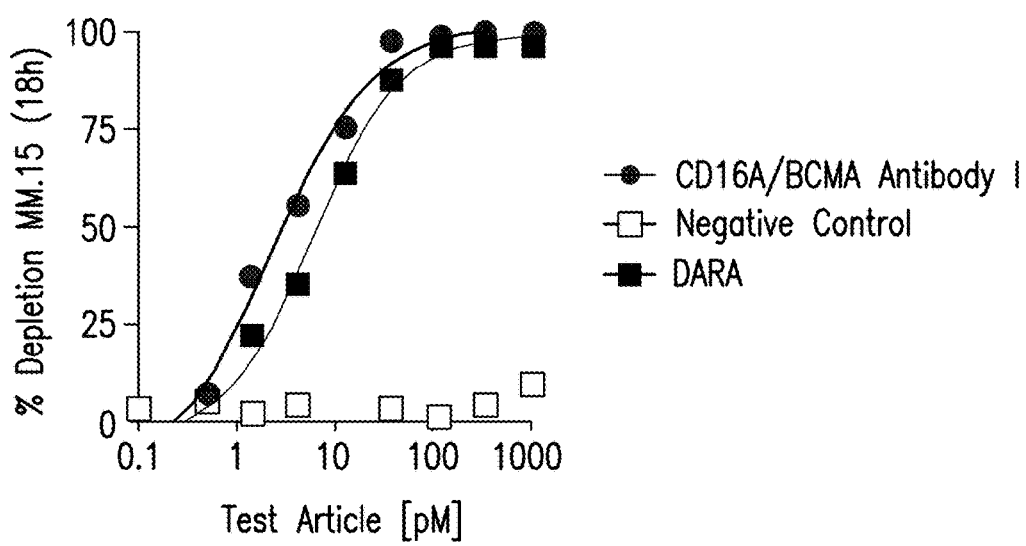
Figure 39A:
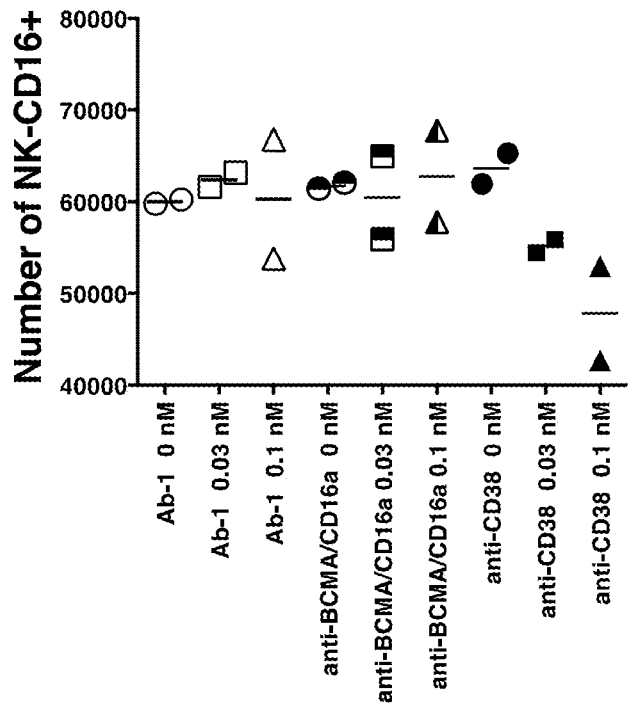
FIGS. 39A and 39B show the activation of CD16 on NK cells by of CD16A/BCMA antibody I in the absence of $BCMA^+$ target cells.
Figure 39B:
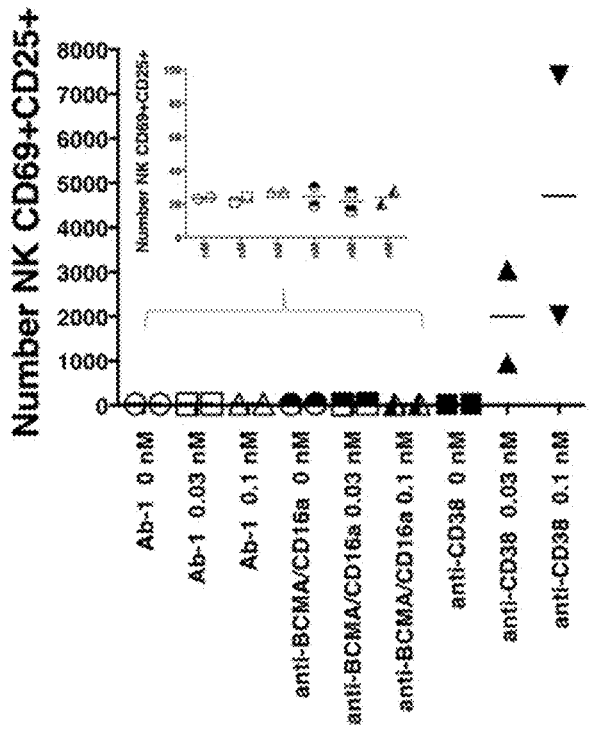

Next, the activation of CD16 and maintenance of CD16 levels on NK cells in the absence of BCMA$^+$ target cells were studied. NK cells were derived from two independent healthy human blood donors. NK cells were cultured alone and exposed to either 0, 0.03 or 0.1 nM of anti-BCMA/CD16a antibody I or Ab-1 (negative control/CD16a) or Anti-CD38 (DARA positive control) for 20 hours at 37° C. Antibody staining against CD markers (CD56, CD16, CD69 and CD25) and FACS were used to determine the number of live CD56$^{dim}$/CD16$^+$ cells and CD56$^{dim}$/CD16$^+$/CD69$^+$/CD25$^+$ as illustrated in FIGS. 32A and 32B, respectively. Data were analyzed with the software programs FlowJo and GraphPad Prism 6. The results are shown in FIGS. 39A-39C. As shown in FIGS. 39A-39C, CD16A/BCMA antibody I did not activate nor decrease CD16 levels on NK cells in the absence of BCMA$^+$ target cells. In comparison to daratumumab, CD16A/BCMA antibody I showed minimal decrease in number and expression of CD16$^+$ on NK cells and exhibited significantly lower number of CD69$^+$25$^+$ NK cells (e.g., ~100-fold (n=2 donors; single experiment)) in the absence of BCMA$^+$ target cells. In the presence of BCMA$^+$ target cells, CD16A/BCMA antibody I showed similar activity to daratumumab. See FIG. 38C.

8.7. Activity in the Presence of Serum Ig

Binding of CD16A/BCMA antibody I to NK cells and cytotoxicity and NK survival of CD16A/BCMA antibody I in the presence of serum or Ig were studied.

Human NK cells were isolated from a healthy human blood donor. NK cells and NCI-H929 cells or MM.1S cells were preincubated separately in 10 mg/mL serum Ig, 50% human autologous serum, or 100% human serum for 2 hours prior to assay setup. NK cells were co-cultured with NCI-H929 or MM.1S cells at an approximate E:T ration of 5, and exposed to 10-fold serial diluted test articles from 0.1-100 nM for approximately 20 hours at 37° C. with 5% CO$_2$. Antibody staining with CD138 and CD56 followed by FACS were used to monitor cytotoxicity of MM.1S or NCI-H929 target cells and NK survival. Data were analyzed with the software programs FlowJo and GraphPad Prism 6.

Figure 40A:
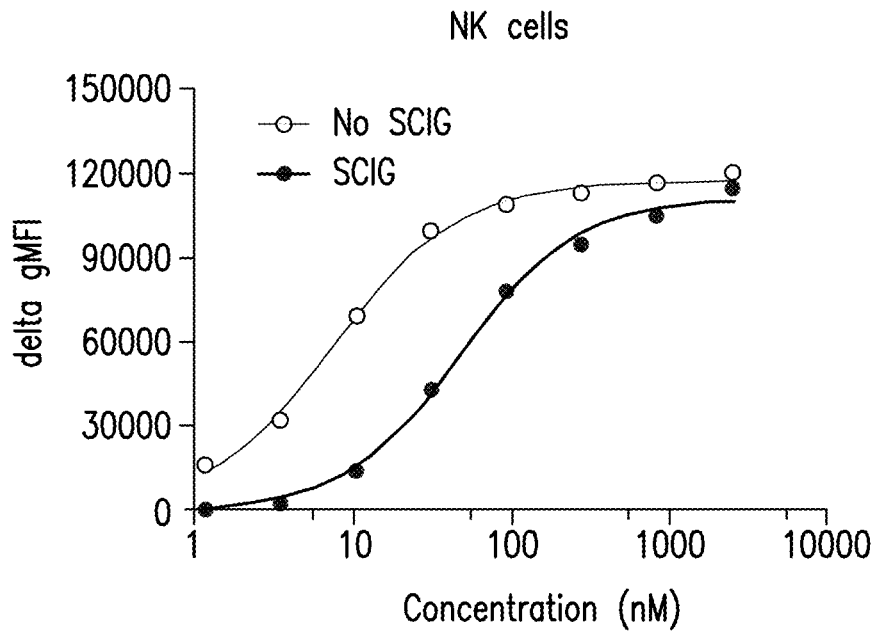
FIGS. 40A-40E show the binding of CD16A/BCMA antibody I to NK cells and cytotoxicity of CD16A/BCMA antibody I in the presence of serum.
Figure 40B:
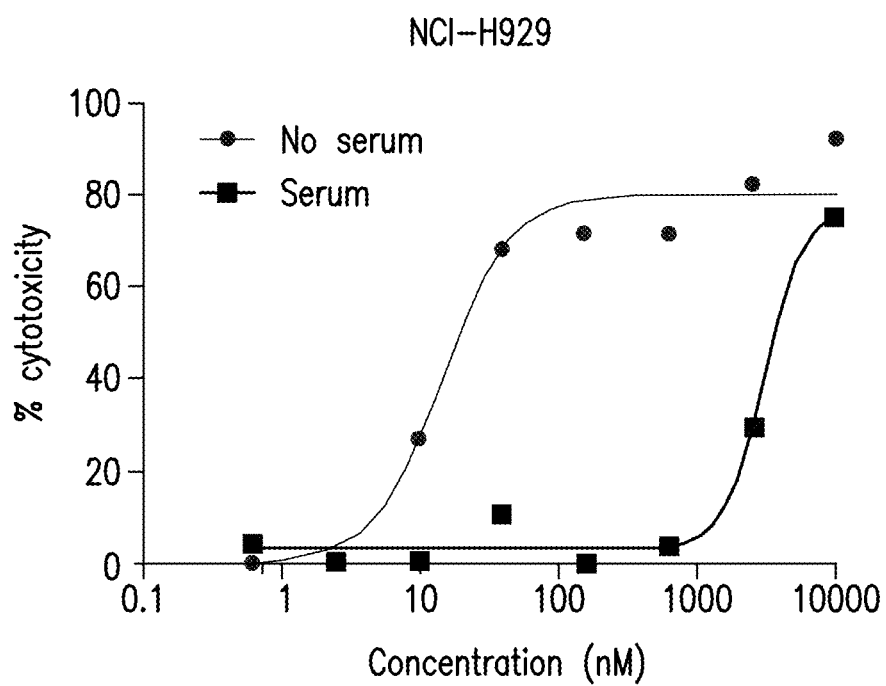
Figure 40C:
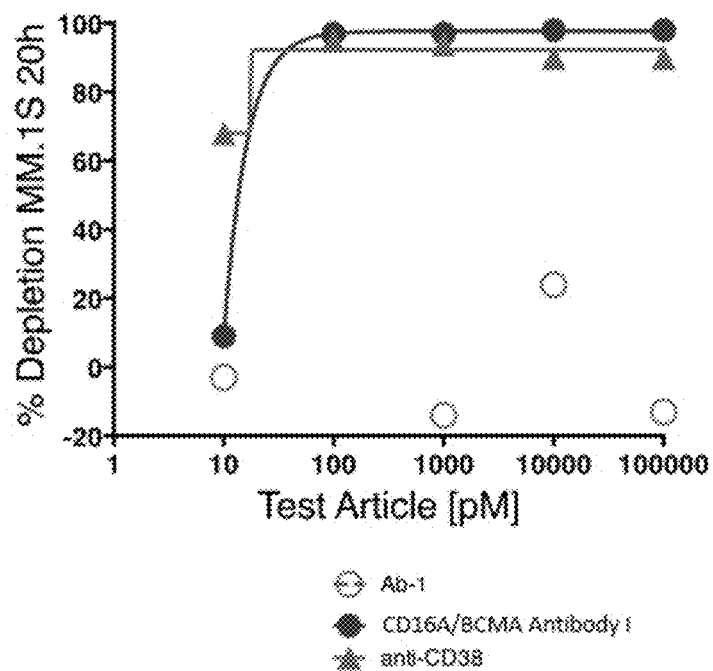
Figure 40D:
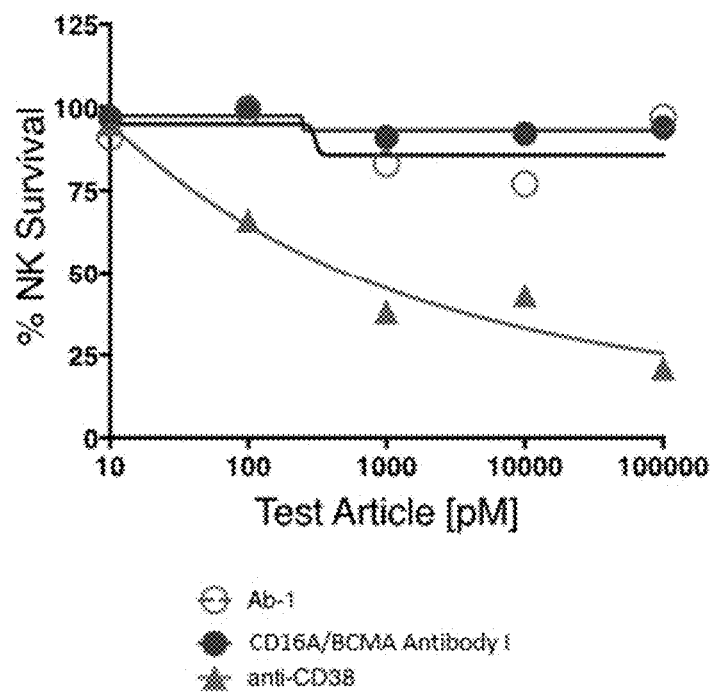
Figure 40E:
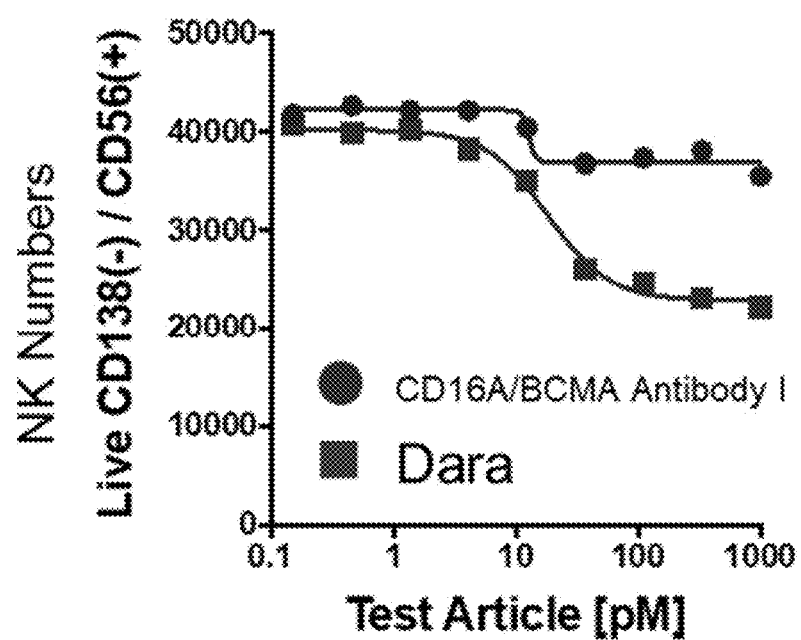

As shown in FIG. 40A, CD16A/BCMA antibody I was able to bind to NK cells in the presence of 10 mg/mL Ig or serum with reduced affinity as compared to in the absence of Ig or serum. As shown in FIG. 40B, CD16A/BCMA antibody I was able to kill BCMA$^+$ target cells in the presence of serum with reduced potency as compared to in the absence of Ig or serum. As shown in FIGS. 40C and 40D, CD16A/BCMA antibody I depleted BCMA$^+$ target cells in the presence of 50% autologous human serum without loss of NK cells. As shown in FIGS. 40D and 40E, CD16A/BCMA antibody I did not deplete NK cells while daratumumab did. Thus, human Ig will not interfere with NK activity of CD16A/BCMA antibody I.

In the absence of BCMA$^+$ target cells, serum influenced CD16A expression and activation of NK cells. See FIGS. 41A and 41B. As shown in FIG. 41A, serum lowered CD16A expression. As shown in FIG. 41B, serum increased non-targeted mediated activation of NK cells. Thus, low CD16 expression in the presence of serum suggests a non-CD16A mediated activation of NK cells.

8.8. Combination Therapy with Cytokines

Daratumumab and elotuzumab are effective in combination with Immunomodulatory Drugs (IMiDs) and proteasome inhibitors. The mechanism of combination activity is expected to apply to NK cell engagers. For example, IMiDs affect the production of TNF-α, IL-12, and IL-6 and stimulates T cells to secrete IL-2 and IFN-γ indirectly enhancing NK cell number and function (Liu et al., Jour. Of Leukocyte. (2018); 103(5):821-828). Protease inhibitors decrease expression of MH class I. Rationale for combining CD16A/BCMA antibody I with iMiDs include the followings: IL-15 increases NK cell number through proliferation, anti-TIGIT antibody is a checkpoint inhibitor for CD8+ T cells and NK cells, and an anti-FcRH5/CD3 antibody uses NK cells for their cytotoxic potential and to drive additional T cell infiltration into tumors.

Figure 42A:
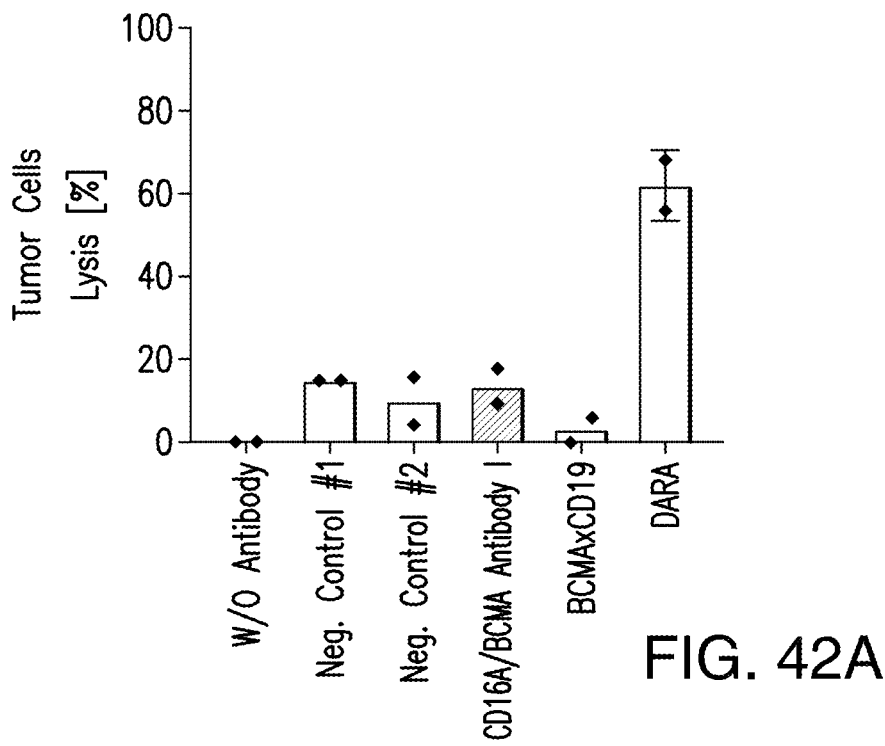
FIGS. 42A-42C show IL-15 treatment increased activity of anti-CD16A/BCMA antibodies on MM cells.
Figure 42B:
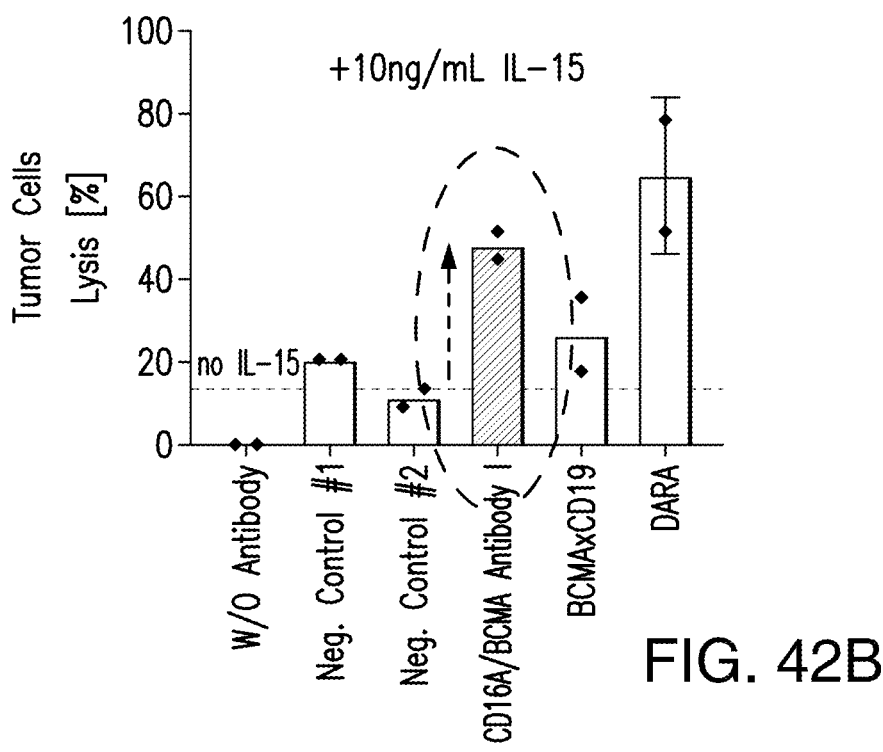
Figure 42C:
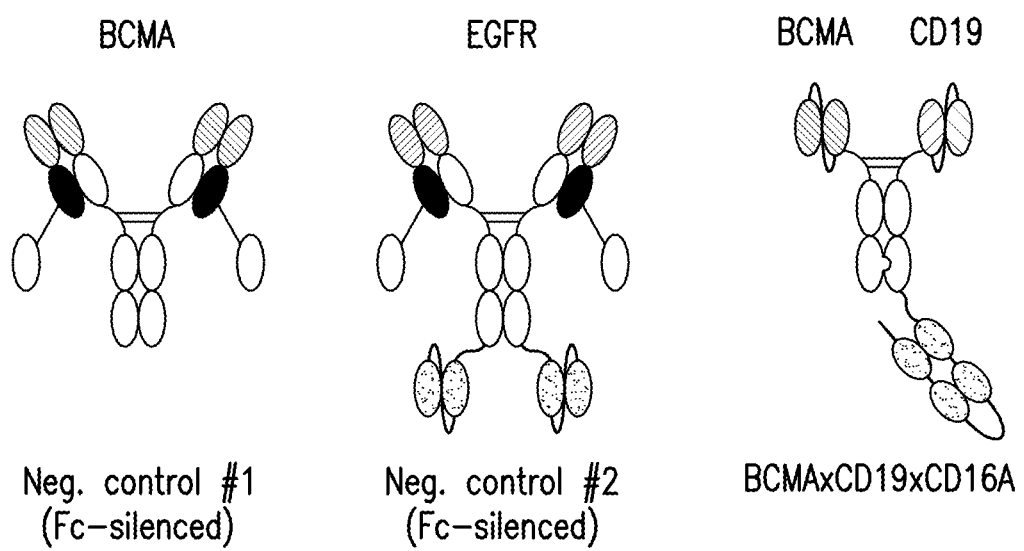

To investigate whether cytokine treatment can impact the activity of CD16A/BCMA antibodies, IL-15 was added to the treatment of CD16A/BCMA antibody I. As shown in FIGS. 42A and 42B, IL-15 increased the activity of CD16A/BCMA antibody I in MM cells. An increase in MM depletion was observed for CD16A/BCMA antibody I with the addition of IL-15, but not for daratumumab.

8.9. Use of CD16A/BCMA Antibody I for Treating Daratumumab R/R Multiple Myeloma Patients CD16A/BCMA antibodies are different from daratumumab (also referred to as "Dara"). For example, daratumumab has complement dependent cytotoxicity activity in multiple myeloma (also referred to as "MM") (de Weers, M. et al., *J. immun.* 2011, 186(3):1840-1848) and the ability to induce apoptosis by signaling through cross linking of CD38 (Overdijk, M. B. et al., *Journal of immunology* 2016; 197(3):807-813). However, CD16A/BCMA antibody I does not have these activities.

Unlike daratumumab, the activity of CD16A/BCMA antibody I is unaffected by CD16A polymorphisms that reduce activity of Fc-mediated drugs. See FIGS. 31A and 31B. Furthermore, unlike a CD38 therapy (e.g., daratumumab), CD16A/BCMA antibody I does not deplete NK cells. See FIGS. 40A, 40B, 40C, 40D, and 40E. In addition, IL-15 treatment increases the activity of CD16A/BCMA antibody I but not daratumumab. See FIGS. 42A and 42B.

Given the features of the anti-BCMA/CD16A antibodies disclosed herein, e.g., CD16A/BCMA antibody I, that distinguish them from daratumumab, these anti-BCMA/CD16A antibodies, e.g., CD16A/BCMA antibody I, are candidates for treating Relapsed/Refractory ("R/R") MM patients (e.g., daratumumab R/R multiple myeloma patient). The daratumumab-refractory phenotype appears to be mediated by CD38 downregulation and upregulation of complement inhibitory proteins (Nijhof et al., Leukemia (2015); 29(10); 2039-2049 Nijhof et al., Blood (2016); 128(7):959-970). Loss of such CD38 expression as well as NK-cell fratricide also contributes to daratumumab resistance. The mechanism of action of the anti-BCMA/CD16A antibodies disclosed herein indicates that such anti-BCMA/CD16A antibodies can be used to treat daratumumab R/R multiple myeloma patients.

Figure 43:
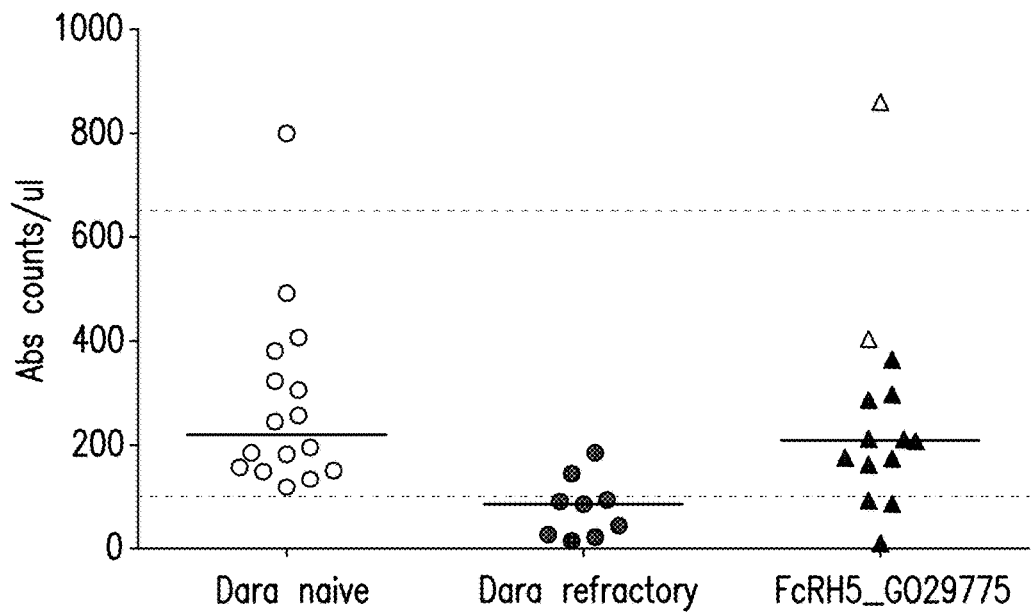
FIG. 43 shows the number of NK cells in peripheral blood of dara naïve patients, dara refractory patients.

Daratumumab refractory patients have lower NK levels in peripheral blood (Casneuf et al., Blood Adv. (2017); 24; 1(23):2105-2114). Steward et al., Blood Cancer J. (2019); 9(2):17 discloses a phase I study of DFRF4539A, an anti-FcRH5 antibody-drug conjugated to monomethyl auristatin E (MMAE) for treating R/R MM. The number of NK cells in peripheral blood of Dara naive MM patients, Dara refractory MM patients, and the R/R MM patients in the phase I study of DFRF4539A were compared and the results are shown in FIG. 43.

Figure 44:
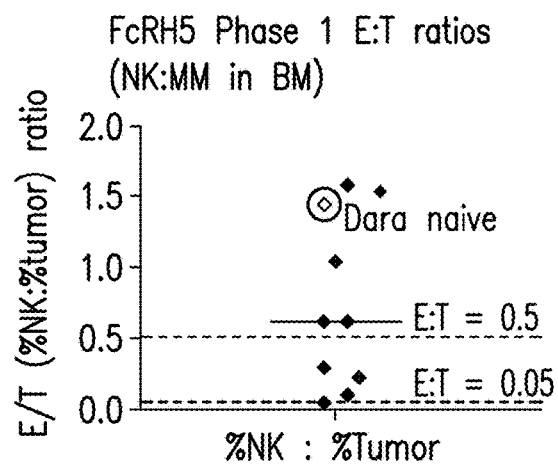
FIG. 44 shows the NK/tumor ratios in R/R MM patients bone marrow.
Figure 45A:
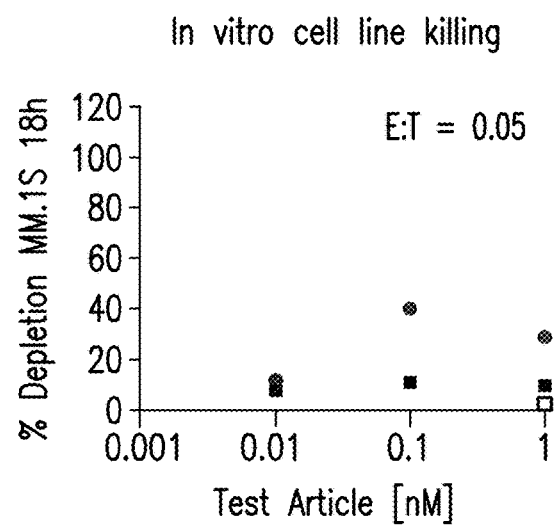
FIGS. 45A and 45B show the in vitro killing of cell lines with the CD16A/BCMA antibody I. CD16A/BCMA antibody I is shown with filled circles, daratumumab ("Dara") is shown with filled squares, and NTx16a, a non-targeted anti-CD16A bispecific antibody, is shown with unfilled squares.
Figure 45B:
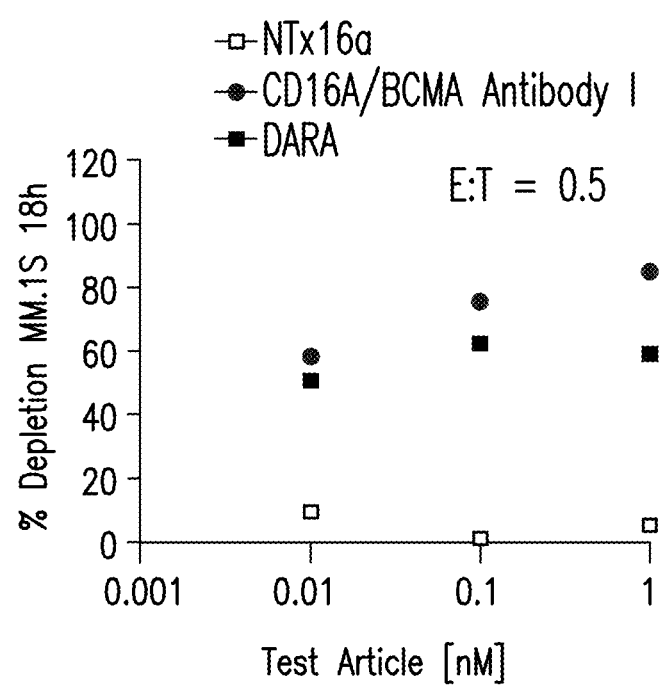
Figure 46A:
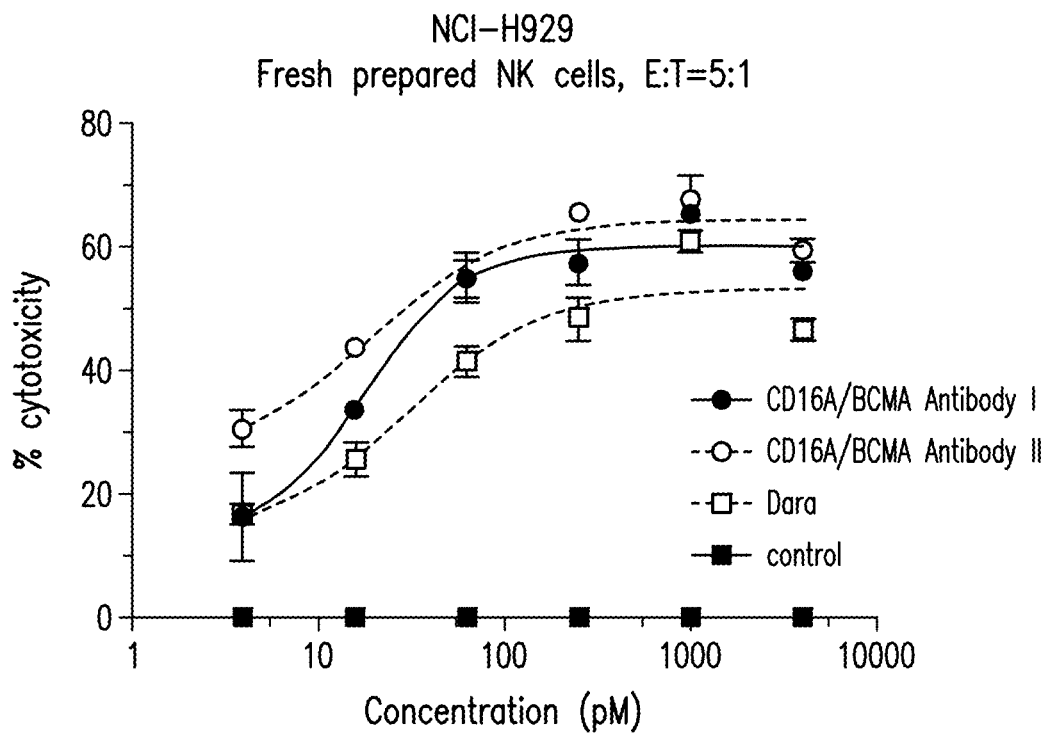
FIGS. 46A-46D show the impact of fresh NK cells on the cytotoxicity of CD16A/BCMA antibody I and CD16A/BCMA antibody II. "Fresh prepared NK cells" represent NK cells that were purified from freshly isolated PBMCs the same day. "2nd day NK cells" represent NK cells that were purified from PBMCs isolated on day one and cultured in RPMI media overnight.
Figure 46B:
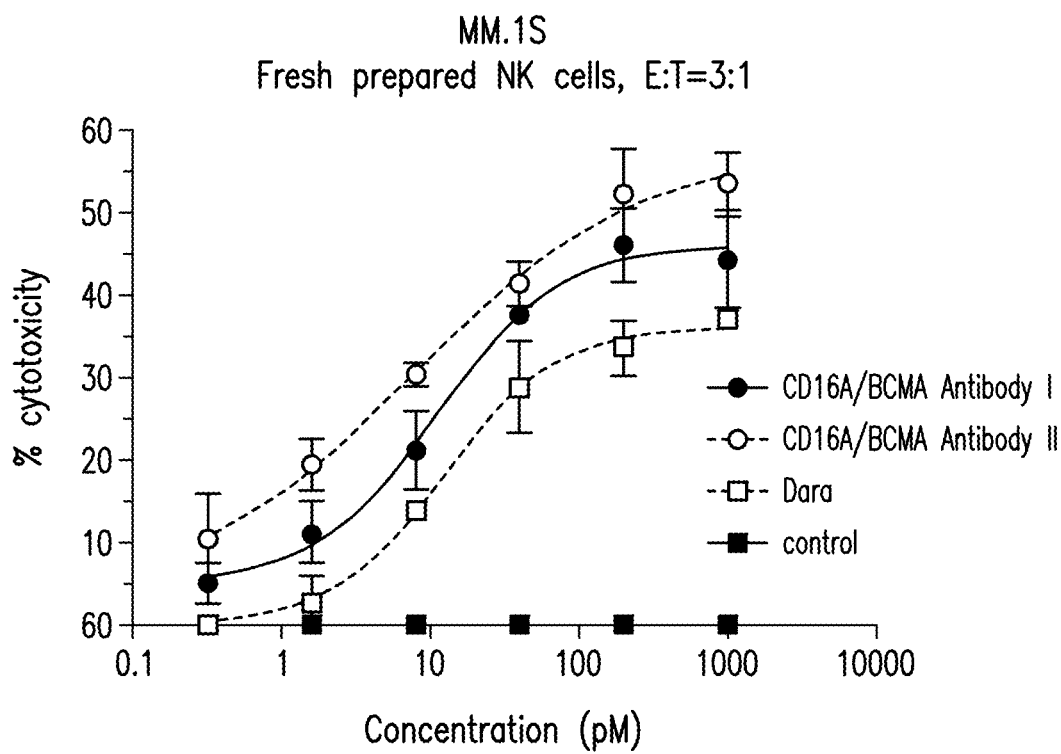
Figure 46C:
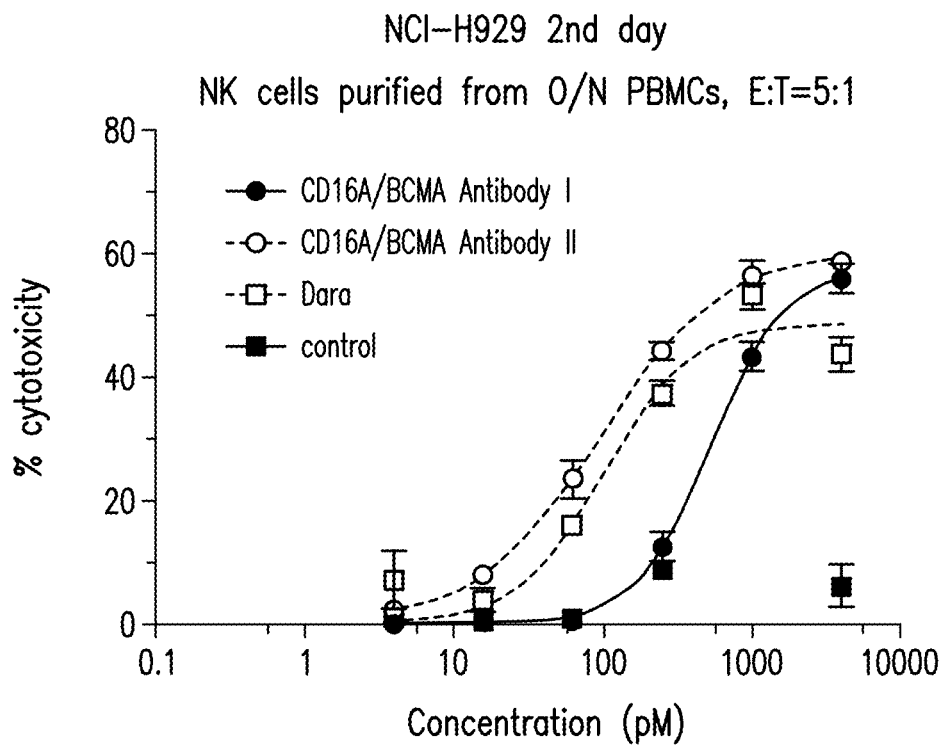
Figure 46D:
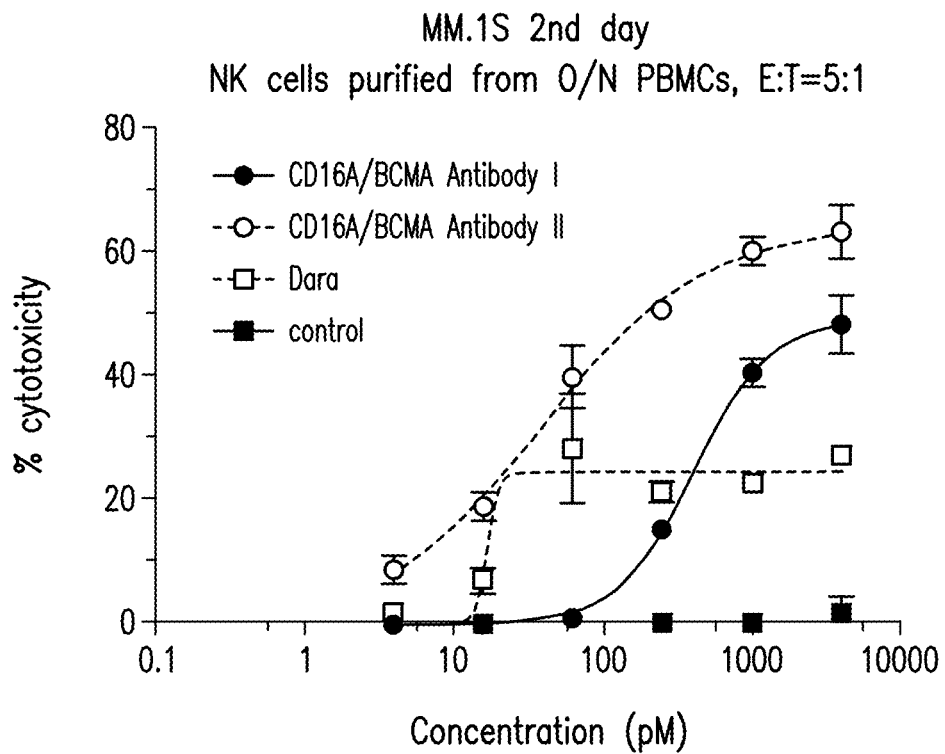

The NK/tumor E:T ratios in the bone marrow of R/R MM patients in phase I study of DFRF4539A are shown in FIG. 44. The in vitro cell line killing data of CD16A/BCMA antibody I shown in FIGS. 45A and 45B indicate that CD16A/BCMA antibody I is effective at the E:T ratios found in DFRF4539A phase I population.

8.10. Fresh NK Cells Impact Cytotoxicity

Cytotoxicity of CD16A/BCMA antibody I and CD16A/BCMA antibody II on fresh NK cells was compared with second day NK cells. Fresh NK cells were NK cells that were purified from freshly isolated PBMCs the same day. Second ($2^{nd}$) day NK cells were NK cells that were purified from PBMCs isolated on day one and cultured in RPMI media overnight. The results are shown in FIGS. 46A, 46B, 46C, and 46D. As shown in FIGS. 46A, 46B, 46C, and 46D, fresh NK cells showed higher cytotoxicity than second day NK cells.

Example 9—Use of CD16A/BCMA Binding Antibodies for Treating Multiple Myeloma

Multiple myeloma ("MM") is malignancy of plasma cells. About 56,000 new cases of MM are diagnosed per year across the U.S. and Europe. Although overall survival is improving, areas of high unmet need remain, including: those relapsed/refractory to available therapies, and those exhibiting high-risk first-line ("1L") disease. Three therapeutic classes have transformed MM therapy and form the backbone of current standard of care ("SOC") including, in certain instances, classes employed across multiple lines of treatment: (1) immunomodulators ("IMiDs", e.g., lenalidomide)—multiple potential MOA including anti-proliferative effects, augmentation of adaptive and innate immune system); (2) proteasome inhibitors (e.g. bortezomib); and (3) daratumumab (an anti-CD38 antibody, whose ADCC, CDC, and apoptosis are triggered by crosslinking of CD38).

NK cells have been widely used in immunotherapies. A balance of activating and inhibitory receptor signals regulate NK cell activation and cytotoxicity, e.g., inhibitory signals dominate in normal healthy tissues. NK cells have been key effectors in Fc-mediated cancer therapies in multiple myeloma, e.g., daratumumab and elotuzumab (an anti-SLAMF7 antibody). NK cell activation and tumor killing can occur through the following mechanisms of action ("MOAs"): (a) loss of MHC class I on tumor cells (e.g., to avoid a T-cell response); (b) overexpression of stress ligands by damaged cells ligating activating NK cell receptors (NKG2D, NKp30, NKp44, NKp46 and DNAM-1), and (c) activation of NK cells by tumor-associated antigen (TAA)-specific therapeutic antibodies binding via their Fc region to the activating receptor CD16A (FcγRIIIa). NK cell engagers mimic MOA (c), yet, as discussed herein, employ a MOA that is distinct from that of daratumumab. An NK engager of the present disclosure that does not recruit NK cells via a conventional Fc-CD16A interaction has potential for treating MM patients, especially second-line ("2L") patients, in combination with SOC. Moreover, a large population of 2L and third-line ("3L") patients are expected to be daratumumab-refractory upon relapse, yet would be expected to be responsive (due to the difference in MOA) to the NK cell engagers, e.g., CD16A/BCMA antibodies I and III, disclosed herein.

The presently disclosed CD16A antigen binding proteins (e.g., CD16A/BCMA antibodies I and III) are NK cell engagers that bind CD16A. CD16A is constitutively expressed on about 95% of NK cells and macrophages and is an NK cell activating receptor.

CD16A/BCMA antibodies I, II and III bind to B-cell maturation antigen (BCMA). As discussed herein, BCMA is a member of the TNF-receptor superfamily and plays a role in the long-term cell survival of plasma cells (O'Connor, JEM 2004; 199(1):91-98). BCMA is expressed in normal plasma cells and up-regulated and high prevalence in multiple myeloma. BCMA is a well-validated target for R/R multiple myeloma immunotherapy, including BCMA-targeted chimeric antigen receptor (CAR) T cell therapy, and BCMA antibody-drug conjugate (ADC) therapy.

Figure 47:
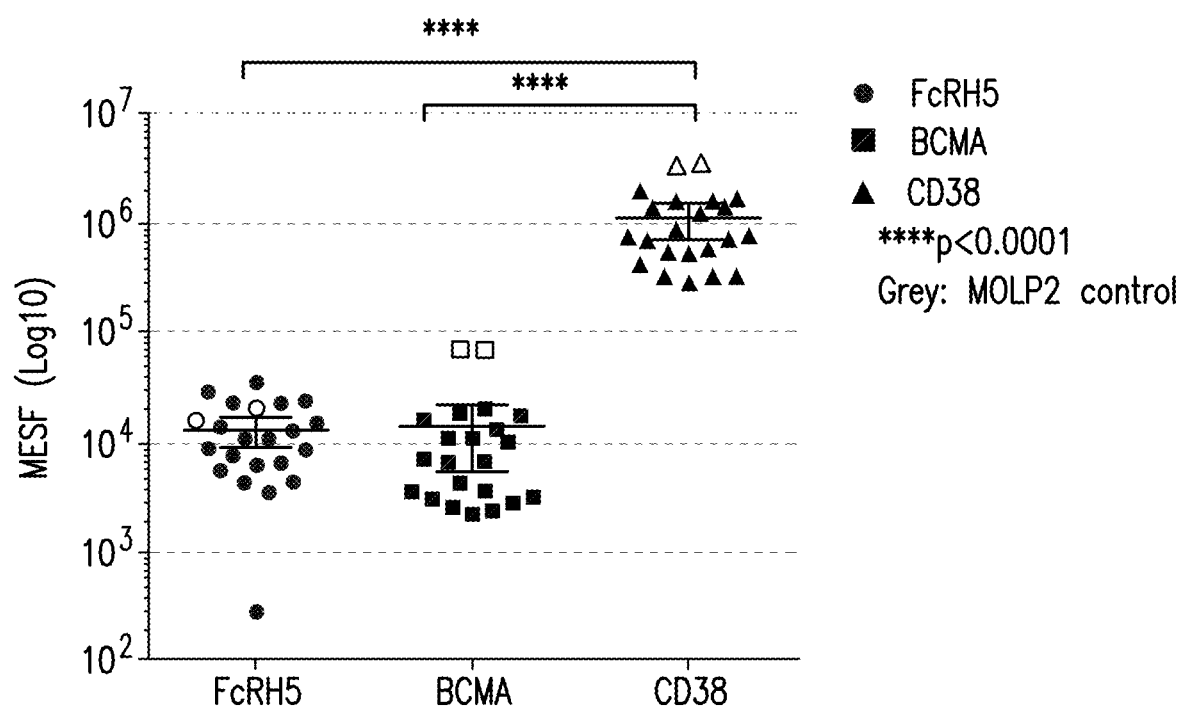
FIG. 47 shows expression of FcRH5, BCMA, and CD38 in frozen primary myeloma myeloma bone marrow mononuclear cells (BMMCs). Frozen primary myeloma bone marrow mononuclear cells (BMMCs) from 20 donors and control (myeloma cell line MOLP-2) were assessed for FcRH5, BCMA (Biolegend 19F2), CD38 cell surface expression. Briefly, BMMCs were thawed, washed with sterile PBS, then resuspended to a final concentration of $1\times10^{\char`\^}6$ cells/mL. BMMCs were stained with viability and myeloma markers (CD45, CD319, CD138, CD38, BCMA, FcRH5). After fixing the cells and washing, the cells were read on the Canto II. Analysis of FcRH5, BCMA, and CD38 was performed in FlowJo by selecting Live/Singlets/CD45−/CD319+ cells (myeloma cells). The MESF (Log10) values for FcRH5, BCMA, and CD38 were plotted in the statistical plotting software Prism.

The expression levels of BCMA, CD38, and FcRH5 in frozen primary myeloma bone marrow mononuclear cells (BMMC) were measure and the results are shown in FIG. 47. As shown in FIG. 47, frozen primary myeloma bone marrow mononuclear cells (BMMCs) from 20 donors and control (myeloma cell line MOLP-2) were assessed for FcRH5, BCMA (Biolegend 19F2), CD38 cell surface expression. Briefly, BMMCs were thawed, washed with sterile PBS, then resuspended to a final concentration of 1×10^6 cells/mL. BMMCs were stained with viability and myeloma markers (CD45, CD319, CD138, CD38, BCMA, FcRH5). After fixing the cells and washing, the cells were read on the Canto II. Analysis of FcRH5, BCMA, and CD38 was performed in FlowJo by selecting Live/Singlets/CD45−/CD319+ cells (myeloma cells). The MESF (Log10) values for FcRH5, BCMA, and CD38 were plotted in the statistical plotting software Prism.

Figure 48A:
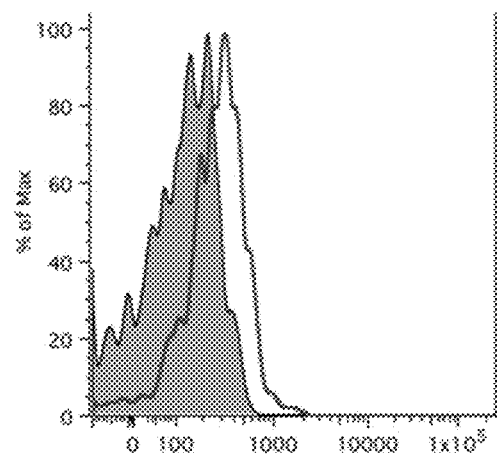
FIGS. 48A and 48B show BCMA expression on normal human plasma cells and primary MM cells.
Figure 48B:
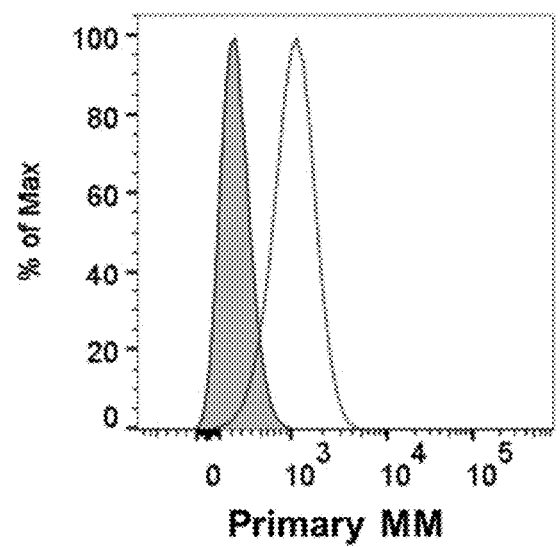
Figure 49A:
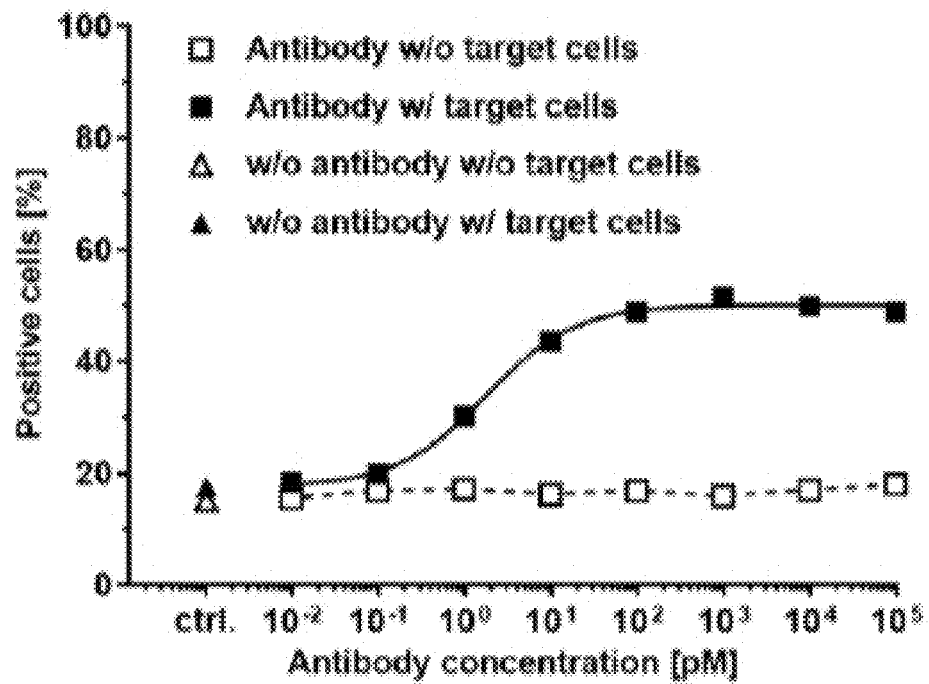
FIGS. 49A-49F show NK cell activation and induction of IFN-γ release by ROCK engagers were strictly dependent on presence of target cells.
Figure 49B:
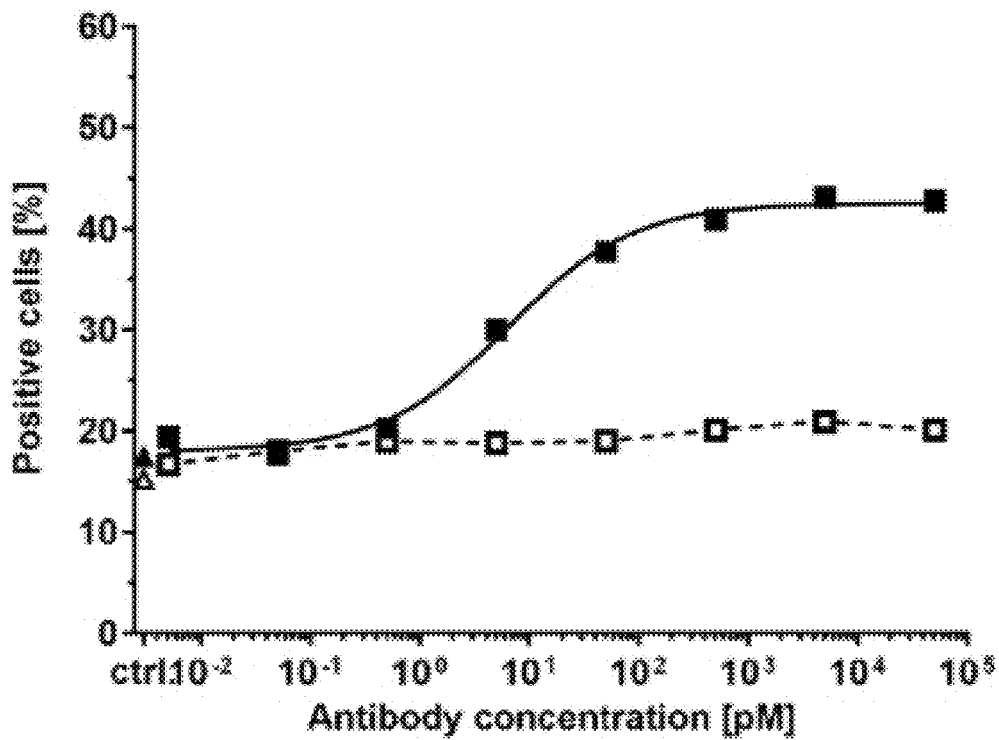
Figure 49C:
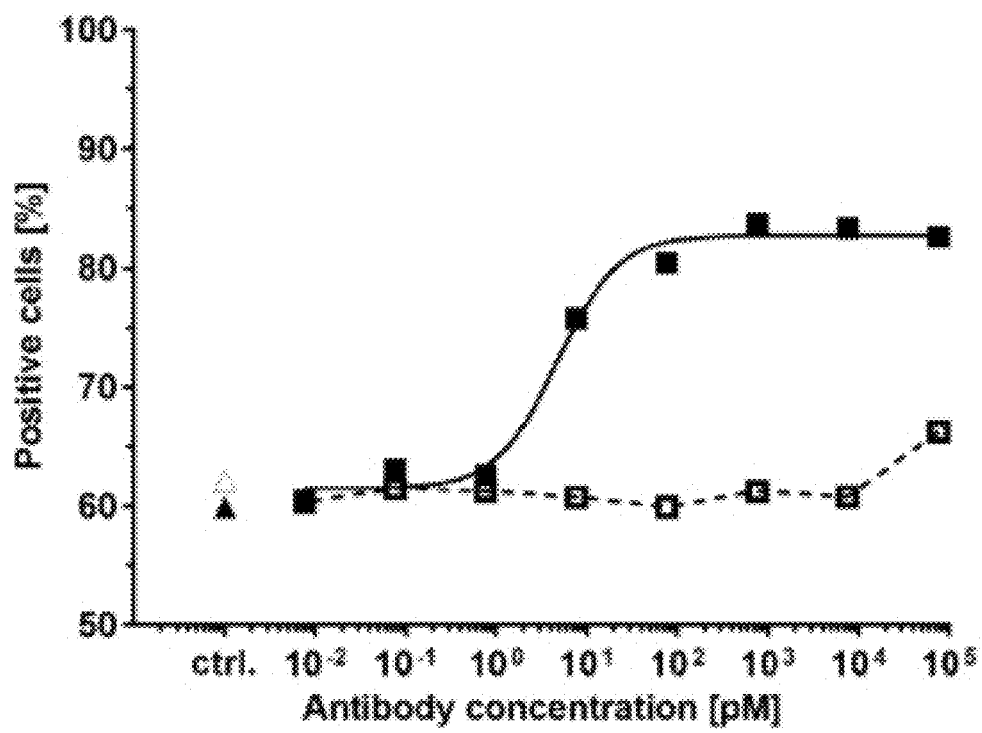
Figure 49D:
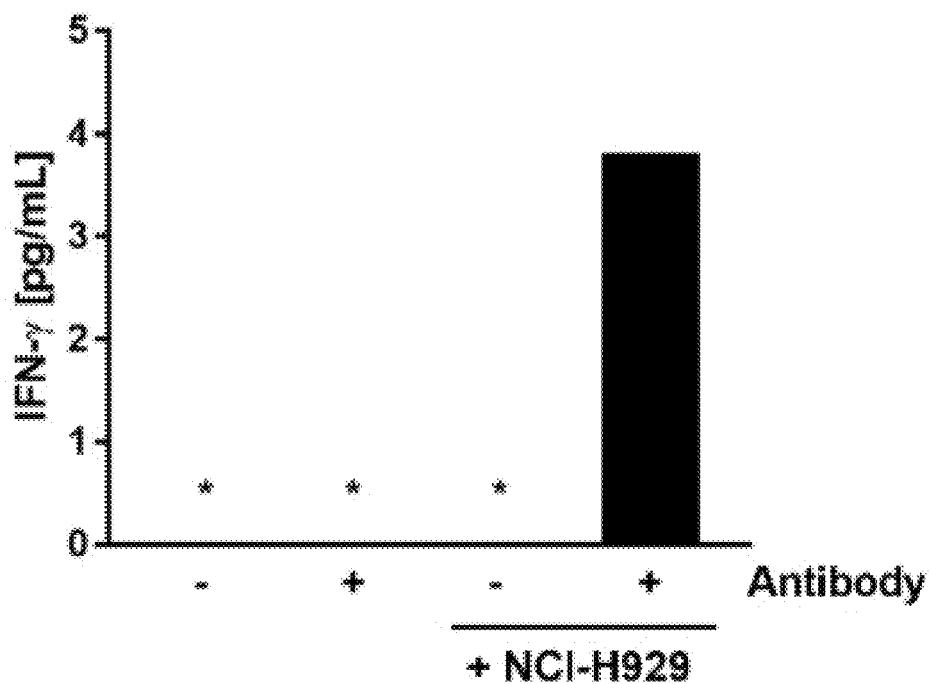
Figure 49E:
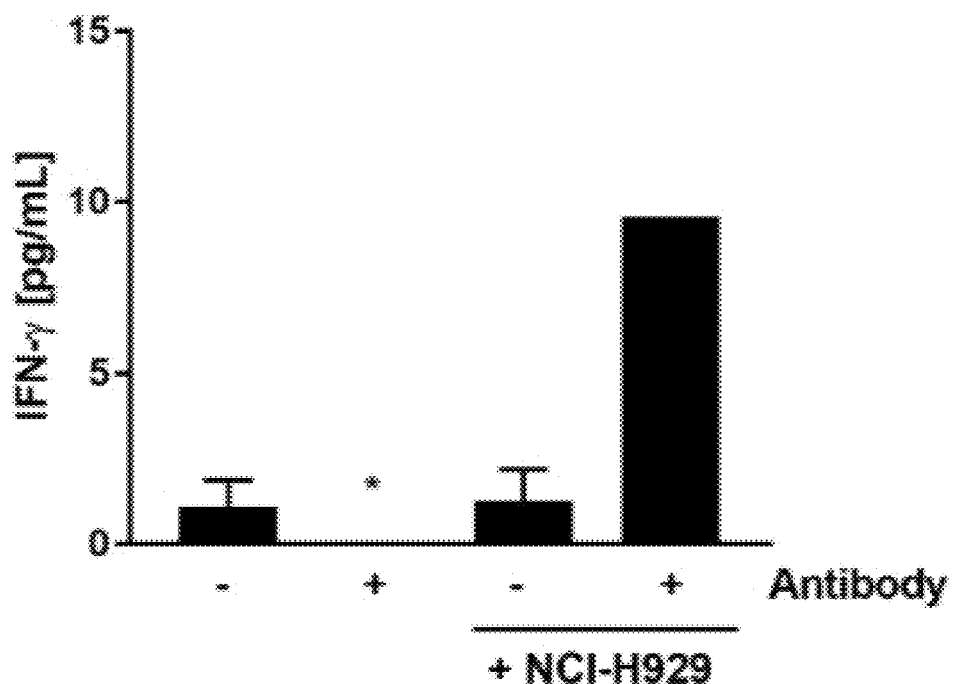
Figure 49F:
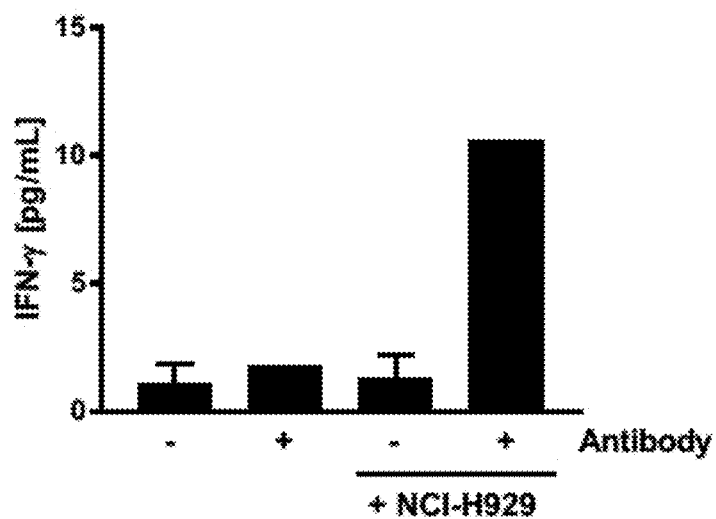

As shown in FIGS. 48A and 48B, BCMA is expressed in normal human plasma cells (FIG. 48A) and is upregulated and found at a high prevalence in MM (FIG. 48B). The primary MM cells used in the experiments shown in FIG. 48B are frozen primary myeloma BMMC which were stained and gated according to the protocol described above for FIG. 47 and then the % of Max was plotted in FlowJo. The grey shaded peak in FIG. 48B is the Fluorescence Minus One (FMO) control and the other peak is the BCMA expression. CD16A/BCMA antibody I exhibited similar results as the anti-BCMA antibody tested.

While BCMA targeted CAR-T cell therapy and CD3/BCMA bispecific antibody have shown impressive anti-MM activity, they have also been associated with significant instances of cytokine release syndrome ("CRS"). The MOA of the presently disclosed CD16A antigen binding proteins (e.g., CD16A/BCMA antibody I), which are NK engagers, enables differentiation from such CRS-associated therapies. For example, favorable safety profile and absence of CRS enable the presently disclosed CD16A antigen binding proteins (e.g., CD16A/BCMA antibody I) to combine with either SOC or other immunotherapies in MM (e.g., cytokines (e.g., IL-15 and IL-12, as shown herein (see, e.g., FIGS. 42A and 42B). The NK-cell based approach disclosed herein can also synergize with T-cell therapies and checkpoint inhibitor therapies (e.g., CD3 bispecific antibodies, anti-PD-1 antibodies (e.g., nivolumab, pembrolizumab), anti-TIGIT antibodies, anti-PD-L1 antibodies (e.g., atezolizumab), anti-VEGF antibodies (e.g., bevacizumab), FcRH5/CD3 bispecific antibodies, etc.).

In view of the foregoing, one or more of the following criteria are used for selecting a NK cell engager for use in treating multiple myeloma:
- the NK cell engager is capable of binding to two targets: CD16A on NK cells, and BCMA on multiple myeloma cells,
- the NK cell engager is at least bivalent for CD16A, e.g., comprises at least two CD16A antigen-binding moieties,
- the NK cell engager is a NK cell bispecific antibody that is not cross-reactive with CD16B, by can be cross-reactive with CD16A from non-human primates,
- the NK cell engager is potent and prevalent, and possesses target-dependent in vitro killing of BCMA+ tumor cells and primary myeloma (e.g., ≥ about 60% cells killed and an $EC_{50} \leq 5$ nM),
- the NK cell engager does not significantly kill NK cells, e.g., reduces or avoids NK cell fratricide,
- the NK cell engager has an acceptable safety profile, e.g., has an in vitro cytokine release profile better than other T-cell engagers (e.g., the NK cell engager lacks CRS), adverse events are monitorable, manageable, and reversible,
- the NK cell engager can be administered to a multiple myeloma subject intravenously, and
- the NK cell engager requires an administrated frequency of once-weekly (QW) or less.

In connection with the instantly described selection strategy, the following Pharmacodynamics (PD) biomarkers can be used: serum M protein and free light chain (FLC), decrease of monoclonal plasma cells, NK cell activation and recruitment in post-treatment bone marrow samples, and peripheral NK cell activation. Although the instantly described selection strategy can include a diagnostic, no diagnostics are necessarily needed based on the high prevalence of BMCA in multiple myeloma.

Certain CD16A/BCMA antigen binding proteins (e.g., CD16A/BCMA antibody I and CD16A/BCMA antibody III) meet the above-described criteria.

In summary, the presently disclosed CD16A/BCMA antigen binding proteins (e.g., CD16A/BCMA antibody I and CD16A/BCMA antibody III) can be used for treating multiple myeloma to achieve durable remissions with favorable safety profiles.

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

Sequence Summary:

| SEQ ID | Sequence |
|---|---|
| 1 | VH CD16A (LSIV21)<br>QVQLVQSGAEVKKPGESLKVSCKASGYTFTSYYMHWVRQAP<br>GQGLEWMGIINPSGGSTSYAQKFQGRVTMTRDTSTSTVYMEL<br>SSLRSEDTAVYYCARGSAYYYDFADYWGQGTLVTVSS |
| 2 | VL CD16A (LSIV21/P2C-47)<br>SYVLTQPSSVSVAPGQTATISCGGHNIGSKNVHWYQQRPGQSP<br>VLVIYQDNKRPSGIPERFSGSNSGNTATLTISGTQAMDEADYY<br>CQVWDNYSVLFGGGTKLTVL |
| 3 | VH CD16A (P2C-47)<br>QVQLVQSGAEVKKPGESLKVSCKASGYTFTSYYMHWVRQAP<br>GQGLEWMGAIEPMYGSTSYAQKFQGRVTMTRDTSTSTVYME<br>LSSLRSEDTAVYYCARGSAYYYDFADYWGQGTLVTVSS |
| 4 | VH CD16A (ABC1163)<br>QVQLVQSGAEVKKPGESLKVSCKASGYTFTNYYMQWVRQAP<br>GQGLEWMGVINPGGGSTSYAQKFQGRVTMTRDTSTSTVYME<br>LSSLRSEDTAVYYCARGSAYYYDFADYWGQGTLVTVSS |
| 5 | VL CD16A (ABC1163)<br>SYVLTQPSSVSVAPGQTARITCGGHNIGSQSVHWYQQKPGQA<br>PVLVIYQDSKRPSGIPERFSGSNSGNTATLTISGTQAMDEADYY<br>CQVWDNYSVVFGGGTKLTVL |
| 6 | VH CD16A (ABC1165)<br>QVQLVQSGAEVKKPGESLKVSCKASGYSFSDFYIQWVRQAPG<br>QGLEWMGIINPGGASTTYAQKFQGRVTMTRDTSTSTVYMELS<br>SLRSEDTAVYYCARGSAYYYDFADYWGQGTLVTVSS |

| SEQ ID | Sequence |
|---|---|
| 7 | VL CD16A (ABC1165)<br>SYVLTQPSSVSVAPGQTARITCGGYNIGRQSVHWYQQKPGQA<br>PVLVIYQDSKRPSGIPERFSGSNSGNTATLTISGTQAMDEADYY<br>CQVWDNYTVVFGGGTKLTVL |
| 8 | VH CD16A (ABC1192)<br>QVQLVQSGAEVKKPGESLKVSCKASGYTFSSYYMHWVRQAP<br>GQGLEWMGAIEPRGVRISYAQKFQGRVTMTRDTSTSTVYMEL<br>SSLRSEDTAVYYCARGSAYYYDFADYWGQGTLVTVSS |
| 9 | VL CD16A (ABC1192)<br>SYVLTQPSSVSVAPGQTARITCGGHNIGSTNVHWYQQKPGQA<br>PVLVIYQDSKRPSGIPERFSGSNSGNTATLTISGTQAMDEADYY<br>CQVWDNYSVQFGGGTKLTVL |
| 10 | VH CD16A (ABC1197)<br>QVQLVQSGAEVKKPGESLKVSCKASGYTFTNYYMQWVRQAP<br>GQGLEWMGIINPSGGVTSYAQKFQGRVTMTRDTSTSTVYMEL<br>SSLRSEDTAVYYCARGSAYYYDFADYWGQGTLVTVSS |
| 11 | VL CD16A (ABC1197)<br>SYVLTQPSSVSVAPGQTARITCGGNNIGSKSVHWYQQKPGQA<br>PVLVIYQDKKRPSGIPERFSGSNSGNTATLTISGTQAMDEADY<br>YCQVWDDYIVLFGGGTKLTVL |
| 12 | VH CD16A (ABC1199)<br>QVQLVQSGAEVKKPGESLKVSCKASGYTFTNYYMHWVRQAP<br>GQGLEWMGVIEPDGGRRTYAQKFQGRVTMTRDTSTSTVYME<br>LSSLRSEDTAVYYCARGSAYYYDFADYWGQGTLVTVSS |
| 13 | VL CD16A (ABC1199)<br>EIVLTQSPATLSLSPGERATLSCRGHQGVSGDVHWYQQKPGQ<br>APRLLIYQANKRASGIPARFSGSGSGTEFTLTISSLEPEDFAVYY<br>CQQWDNYSVTFGQGTKVEIK |
| 14 | VH HSA<br>EVQLLESGGGLVQPGGSLRLSCAVSGIDLSNYAINWVRQAPG<br>KGLEWIGIIWASGTTFYATWAKGRFTISRDNSKNTVYLQMNSL<br>RAEDTAVYYCARTVPGYSTAPYFDLWGQGTLVTVSS |
| 15 | VL HSA<br>DIQMTQSPSSVSASVGDRVTITCQSSPSVWSNFLSWYQQKPGK<br>APKLLIYEASKLTSGVPSRFSGSGSGTDFTLTISSLQPEDFATYY<br>CGGGYSSISDTTFGGGTKVEIK |
| 16 | Linker L1<br>GGSGGS |
| 17 | Linker L2<br>GGSGGSGGSGGSGGSGGS |
| 18 | Linker L3<br>GGSGGSGGSGGSGGSGGSGGS |
| 19 | Connector<br>GGGGS |
| 20 | Connector<br>GGGGSGGGGS |
| 21 | Connector<br>GGGGSGGGGSGGGGSGGGGS |
| 22 | Connector<br>GGGGSGGGGSGGGGSGGGGSGGGGSGGGGS |
| 23 | hinge<br>EPKSCDKTHTCPPCP |
| 24 | middle.hinge<br>DKTHTCPPCP |
| 25 | Human IgG1 CH1, CH2 and CH3 heavy chain constant domain with silencing mutation-1:<br>ASTKGPSVFPLAPSSKSTSGGTAALGCLVKDYFPEPVTVSWNS |

| SEQ ID | Sequence |
|---|---|
| | GALTSGVHTFPAVLQSSGLYSLSSVVTVPSSSLGTQTYICNVNH<br>KPSNTKVDKKVEPKSCDKTHTCPPCPAPEFEGGPSVFLFPPKPK<br>DTLMISRTPEVTCVVVAVSHEDPEVKFNWYVDGVEVHNAKT<br>KPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSRW<br>QQGNVFSCSVMHEALHNHYTQKSLSLSPG |
| 26 | Human IgG1 CH1, CH2 and CH3 heavy chain constant domain (wild-type)<br>ASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKKVEPKSCDKTHTCPPCPAPELLGGPSVFLFPPKPK<br>DTLMISRTPEVTCVVVDVSHEDPEVKFNWYVDGVEVHNAKT<br>KPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSRW<br>QQGNVFSCSVMHEALHNHYTQKSLSLSPG |
| 27 | Human lambda light chain constant domain<br>GQPKAAPSVTLFPPSSEELQANKATLVCLISDFYPGAVTVAWK<br>ADSSPVKAGVETTTPSKQSNNKYAASSYLSLTPEQWKSHRSYS<br>CQVTHEGSTVEKTVAPTECS |
| 28 | Human Kappa light chain constant domain<br>RTVAAPSVFIFPPSDEQLKSGTASVVCLLNNFYPREAKVQWKV<br>DNALQSGNSQESVTEQDSKDSTYSLSSTLTLSKADYEKHKVY<br>ACEVTHQGLSSPVTKSFNRGEC |
| 29 | CH2-CH3 heavy chain constant domain with silencing mutation-1:<br>APEFEGGPSVFLFPPKPKDTLMISRTPEVTCVVVAVSHEDPEVK<br>FNWYVDGVEVHNAKTKPREEQYNSTYRVVSVLTVLHQDWL<br>NGKEYKCKVSNKALPAPIEKTISKAKGQPREPQVYTLPPSREE<br>MTKNQVSLTCLVKGFYPSDIAVEWESNGQPENNYKTTPPVLD<br>SDGSFFLYSKLTVDKSRWQQGNVFSCSVMHEALHNHYTQKSL<br>SLSPG |
| 30 | Monomeric CH2-CH3 heavy chain constant domain with silencing mutation-1<br>APEFEGGPSVFLFPPKPKDTLMISRTPEVTCVVVAVSHEDPEVK<br>FNWYVDGVEVHNAKTKPREEQYNSTYRVVSVLTVLHQDWL<br>NGKEYKCKVSNKALPAPIEKTISKAKGQPREPQVYTKPPSRDE<br>LTKNQVSLSCLVKGFYPSDIAVEWESNGQPENNYKTTVPVLDS<br>DGSFRLASYLTVDKSRWQQGNVFSCSVMHEALHNHYTQKSL<br>SLSP |
| 31 | Knob-chain, CH2-CH3 heavy chain constant domain with silencing mutation-1<br>APEFEGGPSVFLFPPKPKDTLMISRTPEVTCVVVAVSHEDPEVK<br>FNWYVDGVEVHNAKTKPREEQYNSTYRVVSVLTVLHQDWL<br>NGKEYKCKVSNKALPAPIEKTISKAKGQPREPQVYTLPPSREE<br>MTKNQVSLYCLVKGFYPSDIAVEWESNGQPENNYKTTPPVLD<br>SDGSFFLYSKLTVDKSRWQQGNVFSCSVMHEALHNHYTQKSL<br>SLSPG |
| 32 | Hole-chain, CH2-CH3 heavy chain constant domain with silencing mutation-1<br>APEFEGGPSVFLFPPKPKDTLMISRTPEVTCVVVAVSHEDPEVK<br>FNWYVDGVEVHNAKTKPREEQYNSTYRVVSVLTVLHQDWL<br>NGKEYKCKVSNKALPAPIEKTISKAKGQPREPQVYTLPPSREE<br>MTKNQVSLTCLVKGFYPSDIAVEWESNGQPENNYKTTPPVLD<br>SDGSFFLTSKLTVDKSRWQQGNVFSCSVMHEALHNHYTQKSL<br>SLSPG |
| 33 | CH1 heavy chain constant domain<br>ASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKKV |
| 34 | Human lambda light chain constant domain with point-mutation at the C-terminus<br>GQPKAAPSVTLFPPSSEELQANKATLVCLISDFYPGAVTVAWK<br>ADSSPVKAGVETTTPSKQSNNKYAASSYLSLTPEQWKSHRSYS<br>CQVTHEGSTVEKTVAPTESS |

| SEQ ID | Sequence |
|---|---|
| 35 | Human kappa light chain constant domain with point-mutation at the C-terminus<br>RTVAAPSVFIFPPSDEQLKSGTASVVCLLNNFYPREAKVQWKV<br>DNALQSGNSQESVTEQDSKDSTYSLSSTLTLSKADYEKHKVY<br>ACEVTHQGLSSPVTKSFNRGES |
| 36 | CH2-CH3 heavy chain constant domain (wild-type)<br>APELLGGPSVFLFPPKPKDTLMISRTPEVTCVVVDVSHEDPEVK<br>FNWYVDGVEVHNAKTKPREEQYNSTYRVVSVLTVLHQDWL<br>NGKEYKCKVSNKALPAPIEKTISKAKGQPREPQVYTLPPSREE<br>MTKNQVSLTCLVKGFYPSDIAVEWESNGQPENNYKTTPPVLD<br>SDGSFFLYSKLTVDKSRWQQGNVFSCSVMHEALHNHYTQKSL<br>SLSPG |
| 37 | BCMA VH<br>QVQLVQSGAEVKTPGEPLKISCKGSGYSFTDSWIGWVRQMPG<br>KGLEWMGIIYAGDSDARYSPSFQGQVTISADTSTSTVYLQWSS<br>LKASDTAMYYCARNFGDHWGQGTLVTVSS |
| 38 | BCMA VL<br>SYELTQSPSVSVAPGQTARIFCGGDNIGSKNVHWYQQKPGQA<br>PVLVIYRDSNRPSGIPERFSGANSENTATLTISRAQAGDEADYY<br>CQVWDSRTYVFGTGTKLTVL |
| 39 | BCMA scFv<br>QVQLVQSGAEVKTPGEPLKISCKGSGYSFTDSWIGWVRQMPG<br>KGLEWMGIIYAGDSDARYSPSFQGQVTISADTSTSTVYLQWSS<br>LKASDTAMYYCARNFGDHWGQGTLVTVSSGGSGGSGGSGGS<br>GGSGGSSYELTQSPSVSVAPGQTARIFCGGDNIGSKNVHWYQ<br>QKPGQAPVLVIYRDSNRPSGIPERFSGANSENTATLTISRAQAG<br>DEADYYCQVWDSRTYVFGTGTKLTVLAAAGSHHHHHH |
| 40 | VH EGFR<br>QVQLQESGPGLVKPSETLSLTCTVSGGSVSSGSYYWSWIRQPP<br>GKGLEWIGYIYYSGSTNYNPSLKSRVTISVDTSKNQFSLKLSSV<br>TAADTAVYYCARNPISIPAFDIWGQGTMVTVSS |
| 41 | VL EGFR<br>QPVLTQPPSVSVAPGKTARITCGGNNIGSKSVHWYQQKPGQA<br>PVLVIYYDSDRPSGIPERFSGSNSGNTATLTISRVEAGDEADYY<br>CQVWDTSSDHVLFGGGTKLTVL |
| 42 | HCDR1 EGFR<br>GGSVSSGSYY |
| 43 | HCDR2 EGFR<br>IYYSGST |
| 44 | HCDR3 EGFR<br>ARNPISIPAFDI |
| 45 | LCDR1 EGFR<br>NIGSKS |
| 46 | LCDR2 EGFR<br>YDS |
| 47 | LCDR3 EGFR<br>QVWDTSSDHVL |
| 48 | Human CD16A<br>GMRTEDLPKAVVFLEPQWYRVLEKDSVTLKCQGAYSPEDNST<br>QWFHNESLISSQASSYFIDAATVDDSGEYRCQTNLSTLSDPVQ<br>LEVHIGWLLLQAPRWVFKEEDPIHLRCHSWKNTALHKVTYLQ<br>NGKGRKYFHHNSDFYIPKATLKDSGSYFCRGLFGSKNVSSETV<br>NITITQGLAVSTISSFFPPGYQ |
| 49 | Cynomolgus CD16A<br>GMRAEDLPKAVVFLEPQWYRVLEKDRVTLKCQGAYSPEDNS<br>TRWFHNESLISSQTSSYFIAAARVNNSGEYRCQTSLSTLSDPVQ<br>LEVHIGWLLLQAPRWVFKEEESIHLRCHSWKNTLLHKVTYLQ<br>NGKGRKYFHQNSDFYIPKATLKDSGSYFCRGLIGSKNVSSETV<br>NITITQDLAVSSISSFFPPGYQ |

| SEQ ID | Sequence |
|---|---|
| 50 | HCDR1 CD16A<br>GYTFTSYY |
| 51 | HCDR2 CD16A<br>IEPMYGST |
| 52 | HCDR3 CD16A<br>ARGSAYYYDFADY |
| 53 | LCDR1 CD16A<br>NIGSKN |
| 54 | LCDR2 CD16A<br>QDN |
| 55 | LCDR3 CD16A<br>QVWDNYSVL |
| 56 | HCDR2 CD16A<br>INPSGGST |
| 57 | C-terminal sequence of CD16A<br>SFFPPGYQ |
| 58 | His-tag<br>HHHHHH |
| 59 | C-Tag<br>EPEA |
| 60 | Linker L4<br>GGSGGSGGS |
| 61 | scFv-IgAb_I BCMA/CD16a Polypeptide chain 1:<br>EVQLLESGGGLVQPGGSLRLSCAASGFTFSNYDMAWVRQAPG<br>KGLEWVSSISTRGDITSYRDSVKGRFTISRDNSKNTLYLQMNS<br>LRAEDTAVYYCARQDYYTDYMGFAYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPSN<br>TKVDKKVEPKSCDKTHTCPPCPAPEFEGGPSVFLFPPKPKDTL<br>MISRTPEVTCVVVAVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSDIA<br>VEWESNGQPENNYKTTPPVLDSDGSFFLYSKLTVDKSRWQQG<br>NVFSCSVMHEALHNHYTQKSLSLSPGGGGSGGGGSGGGGSG<br>GGGSGGGGSGGGGSSYVLTQPSSVSVAPGQTATISCGGHNIGS<br>KNVHWYQQRPGQSPVLVIYQDNKRPSGIPERFSGSNSGNTATL<br>TISGTQAMDEADYYCQVWDNYSVLFGGGTKLTVLGGSGGSG<br>GSGGSGGSGGSGGSQVQLVQSGAEVKKPGESLKVSCKASGYT<br>FTSYYMHWVRQAPGQGLEWMGAIEPMYGSTSYAQKFQGRVT<br>MTRDTSTSTVYMELSSLRSEDTAVYYCARGSAYYYDFADYW<br>GQGTLVTVSS |
| 62 | scFv-IgAb_I BCMA/CD16a Polypeptide chain 2:<br>AIQMTQSPSSLSASVGDRVTITCRASEDIYNGLAWYQQKPGKA<br>PKLLIYGASSLQDGVPSRFSGSGSGTEFTLTISSLQPEDEATYYC<br>AGPHKYPLTFGGGTKVEIKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGEC |
| 63 | KiH-scDb-Fc BCMA/CD16a Polypeptide chain 1:<br>DKTHTCPPCPAPEFEGGPSVFLFPPKPKDTLMISRTPEVTCVVV<br>AVSHEDPEVKFNWYVDGVEVHNAKTKPREEQYNSTYRVVSV<br>LTVLHQDWLNGKEYKCKVSNKALPAPIEKTISKAKGQPREPQ<br>VYTLPPSREEMTKNQVSLTCLVKGFYPSDIAVEWESNGQPENN<br>YKTTPPVLDSDGSFFLTSKLTVDKSRWQQGNVFSCSVMHEAL<br>HNHYTQKSLSLSPGGGGSGGGGSSYVLTQPSSVSVAPGQTA<br>TISCGGHNIGSKNVHWYQQRPGQSPVLVIYQDNKRPSGIPERFS<br>GSNSGNTATLTISGTQAMDEADYYCQVWDNYSVLFGGGTKL<br>TVLGGSGGSQVQLVQSGAEVKKPGESLKVSCKASGYTFTSYY<br>MHWVRQAPGQGLEWMGAIEPMYGSTSYAQKFQGRVTMTRD<br>TSTSTVYMELSSLRSEDTAVYYCARGSAYYYDFADYWGQGT<br>LVTVSSGGSGGSGGSGGSGGSGGSSYVLTQPSSVSVAPGQTAT<br>ISCGGHNIGSKNVHWYQQRPGQSPVLVIYQDNKRPSGIPERFS<br>GSNSGNTATLTISGTQAMDEADYYCQVWDNYSVLFGGGTKL |

| SEQ ID | Sequence |
|---|---|
| | TVLGGSGGSQVQLVQSGAEVKKPGESLKVSCKASGYTFTSYY<br>MHWVRQAPGQGLEWMGAIEPMYGSTSYAQKFQGRVTMTRD<br>TSTSTVYMELSSLRSEDTAVYYCARGSAYYYDFADYWGQGT<br>LVTVSSAAAGSHHHHHH |
| 64 | KiH-scDb-Fc BCMA/CD16a Polypeptide chain 2:<br>EVQLLESGGGLVQPGGSLRLSCAASGFTFSNYDMAWVRQAPG<br>KGLEWVSSISTRGDITSYRDSVKGRFTISRDNSKNTLYLQMNS<br>LRAEDTAVYYCARQDYYTDYMGFAYWGQGTLVTVSSGGGG<br>SGGGGSGGGGSAIQMTQSPSSLSASVGDRVTITCRASEDIYNG<br>LAWYQQKPGKAPKLLIYGASSLQDGVPSRFSGSGSGTEFTLTIS<br>SLQPEDEATYYCAGPHKYPLTFGGGTKVEIKDKTHTCPPCPAP<br>EFEGGPSVFLFPPKPKDTLMISRTPEVTCVVVAVSHEDPEVKFN<br>WYVDGVEVHNAKTKPREEQYNSTYRVVSVLTVLHQDWLNG<br>KEYKCKVSNKALPAPIEKTISKAKGQPREPQVYTLPPSREEMT<br>KNQVSLYCLVKGFYPSDIAVEWESNGQPENNYKTTPPVLDSD<br>GSFFLYSKLTVDKSRWQQGNVFSCSVMHEALHNHYTQKSLSL<br>SPG |
| 65 | BCMA VH-2<br>EVQLLESGGGLVQPGGSLRLSCAASGFTFSNYDMAWVRQAPG<br>KGLEWVSSISTRGDITSYRDSVKGRFTISRDNSKNTLYLQMNS<br>LRAEDTAVYYCARQDYYTDYMGFAYWGQGTLVTVSS |
| 66 | BCMA VL-2<br>AIQMTQSPSSLSASVGDRVTITCRASEDIYNGLAWYQQKPGKA<br>PKLLIYGASSLQDGVPSRFSGSGSGTEFTLTISSLQPEDEATYYC<br>AGPHKYPLTFGGGTKVEIK |
| 67 | HCDR1 BCMA-2<br>NYDMA |
| 68 | HCDR2 BCMA-2<br>SISTRGDITSYRDSVKG |
| 69 | HCDR3 BCMA-2<br>QDYYTDYMGFAY |
| 70 | LCDR1 BCMA-2<br>RASEDIYNGLA |
| 71 | LCDR2 BCMA-2<br>GASSLQD |
| 72 | LCDR3 BCMA-2<br>AGPHKYPLT |
| 73 | HCDR1 CD16A-2 (P2C-47)<br>SYYMH |
| 74 | HCDR2 CD16A-2 (P2C-47)<br>AIEPMYGSTSYAQKFQG |
| 75 | HCDR3 CD16A-2 (P2C-47)<br>GSAYYYDFADY |
| 76 | LCDR1 CD16A-2 (LSIV21/P2C-47)<br>GGHNIGSKNVH |
| 77 | LCDR2 CD16A-2 (LSIV21/P2C-47)<br>QDNKRPS |
| 78 | LCDR3 CD16A-2 (LSIV21/P2C-47)<br>QVWDNYSVL |
| 79 | CH2 HEAVY CHAIN CONSTANT DOMAIN WITH SILENCING MUTATION-1:<br>APEFEGGPSVFLFPPKPKDTLMISRTPEVTCVVVAVSHEDPEVK<br>FNWYVDGVEVHNAKTKPREEQYNSTYRVVSVLTVLHQDWL<br>NGKEYKCKVSNKALPAPIEKTISKAK |
| 80 | CH3 HEAVY CHAIN CONSTAN TDOMAIN-1<br>GQPREPQVYTLPPSREEMTKNQVSLTCLVKGFYPSDIAVEWES<br>NGQPENNYKTTPPVLDSDGSFFLTSKLTVDKSRWQQGNVFSC<br>SVMHEALHNHYTQKSLSLSPG |

| SEQ ID | Sequence |
|---|---|
| 81 | CH3 HEAVY CHAIN CONSTANT DOMAIN-2<br>GQPREPQVYTLPPSREEMTKNQVSLYCLVKGFYPSDIAVEWES<br>NGQPENNYKTTPPVLDSDGSFFLYSKLTVDKSRWQQGNVFSC<br>SVMHEALHNHYTQKSLSLSPG |
| 82 | HCDR1 CD16A-3 (ABC1163):<br>GYTFTNYY |
| 83 | HCDR2 CD16A-3 (ABC1163):<br>INPGGGST |
| 52 | HCDR3 CD16A-3 (ABC1163):<br>ARGSAYYYDFADY |
| 84 | LCDR1 CD16A-3 (ABC1163):<br>NIGSQS |
| 85 | LCDR2 CD16A-3 (ABC1163):<br>QDS |
| 86 | LCDR3 CD16A-3 (ABC1163):<br>QVWDNYSVV |
| 87 | HCDR1 CD16A-4 (ABC1165):<br>GYSFSDFY |
| 88 | HCDR2 CD16A-4 (ABC1165):<br>INPGGAST |
| 52 | HCDR3 CD16A-4 (ABC1165):<br>ARGSAYYYDFADY |
| 89 | LCDR1 CD16A-4 (ABC1165):<br>NIGRQS |
| 85 | LCDR2 CD16A-4 (ABC1165):<br>QDS |
| 90 | LCDR3 CD16A-4 (ABC1165):<br>QVWDNYTVV |
| 91 | HCDR1 CD16A-5 (ABC1192):<br>GYTFSSYY |
| 92 | HCDR2 CD16A-5 (ABC1192):<br>IEPRGVRI |
| 52 | HCDR3 CD16A-5 (ABC1192):<br>ARGSAYYYDFADY |
| 93 | LCDR1 CD16A-5 (ABC1192):<br>NIGSTN |
| 85 | LCDR2 CD16A-5 (ABC1192):<br>QDS |
| 94 | LCDR3 CD16A-5 (ABC1192):<br>QVWDNYSVQ |
| 82 | HCDR1 CD16A-6 (ABC1197):<br>GYTFTNYY |
| 95 | HCDR2 CD16A-6 (ABC1197):<br>INPSGGVT |
| 52 | HCDR3 CD16A-6 (ABC1197):<br>ARGSAYYYDFADY |
| 96 | LCDR1 CD16A-6 (ABC1197):<br>NIGSKS |
| 97 | LCDR2 CD16A-6 (ABC1197):<br>QDK |
| 98 | LCDR3 CD16A-6 (ABC1197):<br>QVWDDYIVL |

| SEQ ID | Sequence |
|---|---|
| 82 | HCDR1 CD16A-7 (ABC1199):<br>GYTFTNYY |
| 99 | HCDR2 CD16A-7 (ABC1199):<br>IEPDGGRR |
| 52 | HCDR3 CD16A-7 (ABC1199):<br>ARGSAYYYDFADY |
| 100 | LCDR1 CD16A-7 (ABC1199):<br>QGVSGD |
| 101 | LCDR2 CD16A-7 (ABC1199):<br>QAN |
| 102 | LCDR3 CD16A-7 (ABC1199):<br>QQWDNYSVT |
| 50 | HCDR1 CD16A-8:<br>GYTFTSYY |
| 103 | HCDR2 CD16A-8:<br>IEPSGGST |
| 52 | HCDR3 CD16A-8:<br>ARGSAYYYDFADY |
| 53 | LCDR1 CD16A-8:<br>NIGSKN |
| 54 | LCDR2 CD16A-8:<br>QDN |
| 104 | LCDR3 CD16A-8:<br>QVWDSYSVL |
| 50 | HCDR1 CD16A-9:<br>GYTFTSYY |
| 103 | HCDR2 CD16A-9:<br>IEPSGGST |
| 52 | HCDR3 CD16A-9:<br>ARGSAYYYDFADY |
| 53 | LCDR1 CD16A-9:<br>NIGSKN |
| 54 | LCDR2 CD16A-9:<br>QDN |
| 105 | LCDR3 CD16A-9:<br>QVWDNYNVL |
| 106 | HUMAN IGG1 CH1, CH2 AND CH3 HEAVY CHAIN CONSTANT DOMAIN WITH SILENCING MUTATION-2:<br>ASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKKVEPKSCDKTHTCPPCPAPELLGGPSVFLFPPKPK<br>DTLMISRTPEVTCVVVDVSHEDPEVKFNWYVDGVEVHNAKT<br>KPREEQYGSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSRW<br>QQGNVFSCSVMHEALHNHYTQKSLSLSPG |
| 107 | CH2-CH3 HEAVY CHAIN CONSTANT DOMAIN WITH SILENCING MUTATION-2:<br>APELLGGPSVFLFPPKPKDTLMISRTPEVTCVVVDVSHEDPEVK<br>FNWYVDGVEVHNAKTKPREEQYGSTYRVVSVLTVLHQDWL<br>NGKEYKCKVSNKALPAPIEKTISKAKGQPREPQVYTLPPSREE<br>MTKNQVSLTCLVKGFYPSDIAVEWESNGQPENNYKTTPPVLD<br>SDGSFFLYSKLTVDKSRWQQGNVFSCSVMHEALHNHYTQKSL<br>SLSPG |

| SEQ ID | Sequence |
|---|---|
| 108 | CH2 HEAVY CHAIN CONSTANT DOMAIN WITH SILENCING MUTATION-2:<br>APELLGGPSVFLFPPKPKDTLMISRTPEVTCVVVDVSHEDPEVK<br>FNWYVDGVEVHNAKTKPREEQYGSTYRVVSVLTVLHQDWL<br>NGKEYKCKVSNKALPAPIEKTISKAK |
| 109 | CH3 HEAVY CHAIN CONSTANT DOMAIN-3:<br>GQPREPQVYTLPPSREEMTKNQVSLTCLVKGFYPSDIAVEWES<br>NGQPENNYKTTPPVLDSDGSFFLYSKLTVDKSRWQQGNVFSC<br>SVMHEALHNHYTQKSLSLSPG |
| 110 | HUMAN IGG1 CH1, CH2 AND CH3 HEAVY CHAIN CONSTANT DOMAIN WITH SILENCING MUTATION-3:<br>ASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKKVEPKSCDKTHTCPPCPAPEAAGGPSVFLFPPKP<br>KDTLMISRTPEVTCVVVDVSHEDPEVKFNWYVDGVEVHNAK<br>TKPREEQYNSTYRVVSVLTVLHQDWLNGKEYKCKVSNKALP<br>APIEKTISKAKGQPREPQVYTLPPSREEMTKNQVSLTCLVKGF<br>YPSDIAVEWESNGQPENNYKTTPPVLDSDGSFFLYSKLTVDKS<br>RWQQGNVFSCSVMHEALHNHYTQKSLSLSPG |
| 111 | CH2-CH3 HEAVY CHAIN CONSTANT DOMAIN WITH SILENCING MUTATION-3:<br>APEAAGGPSVFLFPPKPKDTLMISRTPEVTCVVVDVSHEDPEV<br>KFNWYVDGVEVHNAKTKPREEQYNSTYRVVSVLTVLHQDW<br>LNGKEYKCKVSNKALPAPIEKTISKAKGQPREPQVYTLPPSREE<br>MTKNQVSLTCLVKGFYPSDIAVEWESNGQPENNYKTTPPVLD<br>SDGSFFLYSKLTVDKSRWQQGNVFSCSVMHEALHNHYTQKSL<br>SLSPG |
| 112 | CH2 HEAVY CHAIN CONSTANT DOMAIN WITH SILENCING MUTATION-3:<br>APEAAGGPSVFLFPPKPKDTLMISRTPEVTCVVVDVSHEDPEV<br>KFNWYVDGVEVHNAKTKPREEQYNSTYRVVSVLTVLHQDW<br>LNGKEYKCKVSNKALPAPIEKTISKAK |
| 113 | CDR-H1 BCMA (BCMA-1):<br>GFTFSNYD |
| 114 | CDR-H2 BCMA (BCMA-1):<br>ISTRGDIT |
| 115 | CDR-H3 BCMA (BCMA-1):<br>ARQDYYTDYMGFAY |
| 116 | CDR-L1 BCMA (BCMA-1):<br>EDIYNG |
| 117 | CDR-L2 BCMA (BCMA-1):<br>GAS |
| 118 | CDR-H1 BCMA (BCMA-2):<br>GFTFSNFD |
| 119 | CDR-H2 BCMA (BCMA-2):<br>ITTGGGDT |
| 120 | CDR-H3 BCMA (BCMA-2):<br>VRHGYYDGYHLFDYWG |
| 121 | CDR-L1 BCMA (BCMA-2):<br>QGISNN |
| 122 | CDR-L2 BCMA (BCMA-2):<br>YTS |
| 123 | CDR-L3 BCMA (BCMA-2):<br>QQFTSLPYT |
| 124 | VH BCMA (BCMA-2):<br>EVQLVESGGGLVQPGGSLRLSCAASGFTFSNFDMAWVRQAPG<br>KGLVWVSSITTGGGDTYYADSVKGRFTISRDNAKSTLYLQMD<br>SLRSEDTAVYYCVRHGYYDGYHLFDYWGQGTLVTVSS |

| SEQ ID | Sequence |
|---|---|
| 125 | VL BCMA (BCMA-2):<br>DIQMTQSPSSLSASVGDRVTITCRANQGISNNLNWYQQKPGKA<br>PKPLIYYTSNLQSGVPSRFSGSGSGTDYTLTISSLQPEDFATYYC<br>QQFTSLPYTFGQGTKLEIK |
| 126 | TandAb (BCMA-A1_T):<br>EVQLLESGGGLVQPGGSLRLSCAASGFTFSNYDMAWVRQAPG<br>KGLEWVSSISTRGDITSYRDSVKGRFTISRDNSKNTLYLQMNS<br>LRAEDTAVYYCARQDYYTDYMGFAYWGQGTLVTVSSGGGSG<br>GSGGSGGSSYVLTQPSSVSVAPGQTATISCGGHNIGSKNVHWY<br>QQRPGQSPVLVIYQDNKRPSGIPERFSGSNSGNTATLTISGTQA<br>MDEADYYCQVWDNYSVLFGGGTKLTVLGGSQVQLVQSGAE<br>VKKPGESLKVSCKASGYTFTSYYMHWVRQAPGQGLEWMGAI<br>EPMYGSTSYAQKFQGRVTMTRDTSTSTVYMELSSLRSEDTAV<br>YYCARGSAYYYDFADYWGQGTLVTVSSGGSGGSGGSGGSAI<br>QMTQSPSSLSASVGDRVTITCRASEDIYNGLAWYQQKPGKAP<br>KLLIYGASSLQDGVPSRFSGSGSGTEFTLTISSLQPEDEATYYC<br>AGPHKYPLTFGGGTKVEIK |
| 127 | Db-Fc (CD16-2-BCMA-1):<br>SYVLTQPSSVSVAPGQTATISCGGHNIGSKNVHWYQQRPGQSP<br>VLVIYQDNKRPSGIPERFSGSNSGNTATLTISGTQAMDEADYY<br>CQVWDNYSVLFGGGTKLTVLGGSGGSQVQLVQSGAEVKKPG<br>ESLKVSCKASGYTFTSYYMHWVRQAPGQGLEWMGAIEPMYG<br>STSYAQKFQGRVTMTRDTSTSTVYMELSSLRSEDTAVYYCAR<br>GSAYYYDFADYWGQGTLVTVSSGGGGSGGGGSDKTHTCPPC<br>PAPEFEGGPSVFLFPPKPKDTLMISRTPEVTCVVVAVSHEDPEV<br>KFNWYVDGVEVHNAKTKPREEQYNSTYRVVSVLTVLHQDW<br>LNGKEYKCKVSNKALPAPIEKTISKAKGQPREPQVYTLPPSREE<br>MTKNQVSLTCLVKGFYPSDIAVEWESNGQPENNYKTTPPVLD<br>SDGSFFLYSKLTVDKSRWQQGNVFSCSVMHEALHNHYTQKSL<br>SLSPGGGGGSGGGGSEVQLLESGGGLVQPGGSLRLSCAASGFT<br>FSNYDMAWVRQAPGKGLEWVSSISTRGDITSYRDSVKGRFTIS<br>RDNSKNTLYLQMNSLRAEDTAVYYCARQDYYTDYMGFAYW<br>GQGTLVTVSSGGGGSGGGGSGGGGSAIQMTQSPSSLSASVGD<br>RVTITCRASEDIYNGLAWYQQKPGKAPKLLIYGASSLQDGVPS<br>RFSGSGSGTEFTLTISSLQPEDEATYYCAGPHKYPLTFGGGTKV<br>EIK |
| 128 | scDb-mFc (CD16-2-BCMA-1):<br>EVQLLESGGGLVQPGGSLRLSCAASGFTFSNYDMAWVRQAPG<br>KGLEWVSSISTRGDITSYRDSVKGRFTISRDNSKNTLYLQMNS<br>LRAEDTAVYYCARQDYYTDYMGFAYWGQGTLVTVSSGGGG<br>SGGGGSGGGGSAIQMTQSPSSLSASVGDRVTITCRASEDIYNG<br>LAWYQQKPGKAPKLLIYGASSLQDGVPSRFSGSGSGTEFTLTIS<br>SLQPEDEATYYCAGPHKYPLTFGGGTKVEIKGGGGSGGGGSA<br>PEFEGGPSVFLFPPKPKDTLMISRTPEVTCVVVAVSHEDPEVKF<br>NWYVDGVEVHNAKTKPREEQYNSTYRVVSVLTVLHQDWLN<br>GKEYKCKVSNKALPAPIEKTISKAKGQPREPQVYTKPPSRDEL<br>TKNQVSLSCLVKGFYPSDIAVEWESNGQPENNYKTTVPVLDS<br>DGSFRLASYLTVDKSRWQQGNVFSCSVMHEALHNHYTQKSL<br>SLSPGGGGSGGGGSSYVLTQPSSVSVAPGQTATISCGGHNIGSK<br>NVHWYQQRPGQSPVLVIYQDNKRPSGIPERFSGSNSGNTATLT<br>ISGTQAMDEADYYCQVWDNYSVLFGGGTKLTVLGGSGGSQV<br>QLVQSGAEVKKPGESLKVSCKASGYTFTSYYMHWVRQAPGQ<br>GLEWMGAIEPMYGSTSYAQKFQGRVTMTRDTSTSTVYMELSS<br>LRSEDTAVYYCARGSAYYYDFADYWGQGTLVTVSSGGSGGS<br>GGSGGSGGSGGSSYVLTQPSSVSVAPGQTATISCGGHNIGSKN<br>VHWYQQRPGQSPVLVIYQDNKRPSGIPERFSGSNSGNTATLTIS<br>GTQAMDEADYYCQVWDNYSVLFGGGTKLTVLGGSGGSQVQ<br>LVQSGAEVKKPGESLKVSCKASGYTFTSYYMHWVRQAPGQG<br>LEWMGAIEPMYGSTSYAQKFQGRVTMTRDTSTSTVYMELSSL<br>RSEDTAVYYCARGSAYYYDFADYWGQGTLVTVSS |
| 129 | Linker L5<br>GGSGGSGGSGGS |
| 130 | Linker L6<br>GGS |

What is claimed is:

1. A multi specific antigen-binding protein comprising:
   a) two B cell maturation antigen (BCMA) antigen-binding moieties each comprising a Fab fragment and an Fc portion and wherein each Fab fragment comprises: a heavy chain variable region comprising a CDR1 consisting of the amino acid sequence set forth in SEQ ID NO:67, a CDR2 consisting of the amino acid sequence set forth in SEQ ID NO:68, and a CDR3 consisting of the amino acid sequence set forth in SEQ ID NO:69; and a light chain variable region comprising a CDR1 consisting of the amino acid sequence set forth in SEQ ID NO:70, a CDR2 consisting of the amino acid sequence set forth in SEQ ID NO:71, and a CDR3 consisting of the amino acid sequence set forth in SEQ ID NO:72, and
   b) two CD16A antigen-binding moieties each in the format of a single chain variable fragment (scFv) comprising: a heavy chain variable region comprising a CDR1 consisting of the amino acid sequence set forth in SEQ ID NO:73, a CDR2 consisting of the amino acid sequence set forth in SEQ ID NO:74, and a CDR3 consisting of the amino acid sequence set forth in SEQ ID NO:75; and a light chain variable region comprising a CDR1 consisting of the amino acid sequence set forth in SEQ ID NO:76, a CDR2 consisting of the amino acid sequence set forth in SEQ ID NO:77, and a CDR3 consisting of the amino acid sequence set forth in SEQ ID NO:78, wherein the variable region at the N-terminus of each of the two scFvs is the light chain variable region,
   wherein the N-terminus of the first of the two scFvs is fused to the C-terminus of the Fc portion of the first of the two BCMA binding moieties and the N-terminus of the second of the two scFvs is fused to the C-terminus of the Fc portion of the second of the two BCMA binding moieties.

2. The multispecific antigen-binding protein of claim 1, comprising an Fc portion mutation selected from the group consisting of (a) C220S, C229S, E233P, L234A, L234V, L234F, L235A, L235E, P238S, D265A, N297A, N297Q, and P331S, or (b) L234A, L234V, L234F, L235A, L235E, P238S, and D265A, according to the Kabat EU numbering.

3. The multispecific antigen-binding protein of claim 1, wherein the two CD16A antigen-binding moieties each comprise:
 a heavy chain variable region comprising the amino acid sequence set forth in SEQ ID NO: 3; and/or a light chain variable region comprising the amino acid sequence set forth in SEQ ID NO: 2.

4. The multispecific antigen-binding protein of claim 1, wherein the protein is a tetramer comprising a first polypeptide chain consisting of the amino acid sequence set forth in SEQ ID NO: 61, and a second polypeptide chain consisting of the amino acid sequence set forth in SEQ ID NO: 62.

5. The multispecific antigen-binding protein of claim 1, wherein the two BCMA antigen-binding moieties each comprise: a heavy chain variable region comprising the amino acid sequence set forth in SEQ ID NO: 65 and/or a light chain variable region comprising the amino acid sequence set forth in SEQ ID NO: 66.

6. A pharmaceutical composition comprising a multispecific antigen-binding protein comprising two CD16A antigen-binding moieties, wherein each CD16A antigen-binding moiety is in the format of a single chain variable fragment (scFv), and two B cell maturation antigen (BCMA) antigen-binding moieties, wherein each BCMA antigen-binding moiety comprises an Fab fragment and an Fc portion, wherein:
 (i) the two CD16A antigen-binding moieties each comprise:
  (a) a heavy chain variable region comprising a CDR1 consisting of the amino acid sequence set forth in SEQ ID NO:73, a CDR2 consisting of the amino acid sequence set forth in SEQ ID NO:74, and a CDR3 consisting of the amino acid sequence set forth in SEQ ID NO:75; and
  (b) a light chain variable region comprising a CDR1 consisting of the amino acid sequence set forth in SEQ ID NO:76, a CDR2 consisting of the amino acid sequence set forth in SEQ ID NO:77, and a CDR3 consisting of the amino acid sequence set forth in SEQ ID NO:78; wherein the variable region at the N-terminus of each of the two scFvs is the light chain variable region;
  (c) wherein the N-terminus of the first of the two scFvs is fused to the C-terminus of the Fc portion of the first of the two BCMA binding moieties and the N-terminus of the second of the two scFvs is fused to the C-terminus of the Fc portion of the second of the two BCMA binding moieties; and
 (ii) the two BCMA antigen-binding moieties each comprise:
  (a) a heavy chain variable region comprising a CDR1 consisting of the amino acid sequence set forth in SEQ ID NO:67, a CDR2 consisting of the amino acid sequence set forth in SEQ ID NO:68, and a CDR3 consisting of the amino acid sequence set forth in SEQ ID NO:69; and
  (b) a light chain variable region comprising a CDR1 consisting of the amino acid sequence set forth in SEQ ID NO:70, a CDR2 consisting of the amino acid sequence set forth in SEQ ID NO:71, and a CDR3 consisting of the amino acid sequence set forth in SEQ ID NO:72;
and a pharmaceutically acceptable carrier.

7. A bispecific antigen-binding protein comprising two CD16A antigen-binding moieties each in the format of a single chain variable fragment (scFv) and two B cell maturation antigen (BCMA)-targeting moieties each comprising an Fab fragment and an Fc portion, wherein the N-terminus of the first of the two scFvs is fused to the C-terminus of the first of the two BCMA-targeting moieties, and the N-terminus of the second of the two scFvs is fused to the C-terminus of the second of the two BCMA-targeting moieties wherein:
 (i) the two CD16A antigen-binding moieties each comprise:
  (a) a heavy chain variable region comprising a CDR1 consisting of the amino acid sequence set forth in SEQ ID NO:73; a CDR2 consisting of the amino acid sequence set forth in SEQ ID NO:74; and a CDR3 consisting of the amino acid sequence set forth in SEQ ID NO:75, and
  (b) a light chain variable region comprising a CDR1 consisting of the amino acid sequence set forth in SEQ ID NO:76; a CDR2 consisting of the amino acid sequence set forth in SEQ ID NO:77; and a CDR3 consisting of the amino acid sequence set forth in SEQ ID NO:78; wherein the variable region at the N-terminus of each of the two scFvs is the light chain variable region; and
 (ii) the two BCMA antigen-binding moieties each comprise:
  (a) a heavy chain variable region comprising a CDR1 consisting of the amino acid sequence set forth in SEQ ID NO:67; a CDR2 consisting of the amino acid sequence set forth in SEQ ID NO:68; and a CDR3 consisting of the amino acid sequence set forth in SEQ ID NO:69, and
  (ii) a light chain variable region comprising a CDR1 consisting of the amino acid sequence set forth in SEQ ID NO:70; a CDR2 consisting of the amino acid sequence set forth in SEQ ID NO:71; and a CDR3 consisting of the amino acid sequence set forth in SEQ ID NO:72.

8. The bispecific antigen-binding protein of claim 7, wherein:
 (i) the two CD16A antigen-binding moieties each comprise a heavy chain variable region comprising the amino acid sequence set forth in SEQ ID NO: 3;
 (ii) the two CD16A antigen-binding moieties each comprise a light chain variable region comprising the amino acid sequence set forth in SEQ ID NO: 2;
 (iii) the two BCMA antigen-binding moieties each comprise a heavy chain variable region comprising the amino acid sequence set forth in SEQ ID NO: 65;
 (iv) the two BCMA antigen-binding moieties each comprise a light chain variable region comprising the amino acid sequence set forth in SEQ ID NO: 66;
 (v) the two CD16A antigen-binding moieties each comprise a heavy chain variable region comprising the amino acid sequence set forth in SEQ ID NO: 3 and a light chain variable region comprising the amino acid sequence set forth in SEQ ID NO: 2;
 (vi) the two BCMA antigen-binding moieties each comprise a heavy chain variable region comprising the amino acid sequence set forth in SEQ ID NO: 65 and a light chain variable region comprising the amino acid sequence set forth in SEQ ID NO: 66; and/or (vii) the two CD16A antigen-binding moieties each comprise a heavy chain variable region comprising the amino acid sequence set forth in SEQ ID NO: 3 and a light chain variable region comprising the amino acid sequence set forth in SEQ ID NO: 2; and the two BCMA antigen-binding moieties each comprise a heavy chain variable region comprising the amino acid sequence set forth in SEQ ID NO: 65 and a light chain variable region comprising the amino acid sequence set forth in SEQ ID NO: 66.

9. The pharmaceutical composition of claim 6, wherein the bispecific antigen-binding protein comprises an Fc portion mutation selected from the group consisting of (a) C220S, C229S, E233P, L234A, L234V, L234F, L235A, L235E, P238S, D265A, N297A, N297Q, and P331S, or (b) L234A, L234V, L234F, L235A, L235E, P238S, and D265A, according to the Kabat EU numbering.

10. The pharmaceutical composition of claim 6, wherein the two CD16A antigen-binding moieties each comprise: a heavy chain variable region comprising the amino acid sequence set forth in SEQ ID NO: 3; and/or a light chain variable region comprising the amino acid sequence set forth in SEQ ID NO: 2.

11. The pharmaceutical composition of claim 6, wherein the two BCMA antigen-binding moieties each comprise: a heavy chain variable region comprising the amino acid sequence set forth in SEQ ID NO: 65 and/or a light chain variable region comprising the amino acid sequence set forth in SEQ ID NO: 66.

12. The pharmaceutical composition of claim 6, wherein the bispecific antigen-binding protein is a tetramer comprising a first polypeptide chain consisting of the amino acid sequence set forth in SEQ ID NO: 61, and a second polypeptide chain consisting of the amino acid sequence set forth in SEQ ID NO: 62.

13. The bispecific antigen-binding protein of claim 7, comprising an Fc portion mutation selected from the group consisting of (a) C220S, C229S, E233P, L234A, L234V, L234F, L235A, L235E, P238S, D265A, N297A, N297Q, and P331S, or (b) L234A, L234V, L234F, L235A, L235E, P238S, and D265A, according to the Kabat EU numbering.

14. The bispecific antigen-binding protein of claim 7, wherein the bispecific antigen-binding protein is a tetramer comprising a first polypeptide chain consisting of the amino acid sequence set forth in SEQ ID NO: 61, and a second polypeptide chain consisting of the amino acid sequence set forth in SEQ ID NO: 62.

* * * * *